US011299522B2

(12) United States Patent
Haefner et al.

(10) Patent No.: US 11,299,522 B2
(45) Date of Patent: Apr. 12, 2022

(54) METHOD OF PRODUCING PROTEINS IN FILAMENTOUS FUNGI WITH DECREASED CLR2 ACTIVITY

(71) Applicant: BASF SE, Ludwigshafen am Rhein (DE)

(72) Inventors: Stefan Haefner, Speyer (DE); Andreas Thywissen, Heidelberg (DE); Holger Hartmann, Mannheim (DE); Nico Boehmer, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 122 days.

(21) Appl. No.: 15/779,595

(22) PCT Filed: Dec. 2, 2016

(86) PCT No.: PCT/EP2016/079526
§ 371 (c)(1),
(2) Date: May 29, 2018

(87) PCT Pub. No.: WO2017/093450
PCT Pub. Date: Jun. 8, 2017

(65) Prior Publication Data
US 2020/0308235 A1 Oct. 1, 2020

(30) Foreign Application Priority Data
Dec. 2, 2015 (EP) ..................................... 15197497

(51) Int. Cl.
| *C12P 21/00* | (2006.01) |
| *C12N 9/14* | (2006.01) |
| *C12N 1/15* | (2006.01) |
| *C07K 14/37* | (2006.01) |
| *C12N 9/16* | (2006.01) |
| *C12N 9/24* | (2006.01) |
| *C12N 15/80* | (2006.01) |

(52) U.S. Cl.
CPC ............... *C07K 14/37* (2013.01); *C12N 9/16* (2013.01); *C12N 9/2491* (2013.01); *C12N 15/80* (2013.01); *C12Y 301/03008* (2013.01); *C12Y 302/01025* (2013.01)

(58) Field of Classification Search
None
See application file for complete search history.

(56) References Cited

U.S. PATENT DOCUMENTS

| 10,519,474 B2 | 12/2019 | Wang et al. |
| 10,597,429 B2 | 3/2020 | Haefner et al. |
| 2012/0005812 A1 | 1/2012 | Corzatt |
| 2015/0376663 A1 | 12/2015 | Schroeder et al. |
| 2016/0298160 A1 | 10/2016 | Hoff et al. |
| 2016/0348082 A1 | 12/2016 | Krawczyk et al. |
| 2016/0355829 A1 | 12/2016 | Schroeder et al. |
| 2016/0362696 A1 | 12/2016 | Krawczyk et al. |
| 2017/0166937 A1 | 6/2017 | Krawczyk et al. |
| 2017/0369835 A1 | 12/2017 | Hoff et al. |
| 2018/0030418 A1 | 2/2018 | Costa et al. |

FOREIGN PATENT DOCUMENTS

| EP | 0635574 A1 | 1/1995 |
| WO | 9846772 A2 | 10/1998 |
| WO | 0020555 A2 | 4/2000 |
| WO | 2008073914 A2 | 6/2008 |
| WO | 2010107303 A2 | 9/2010 |
| WO | 2012048334 A2 | 4/2012 |
| WO | 2013022594 A1 | 2/2013 |
| WO | 2013048661 A1 | 4/2013 |
| WO | 2015092576 A1 | 6/2015 |
| WO | 2015092599 A1 | 6/2015 |
| WO | 2015135980 A1 | 9/2015 |
| WO | 2015169919 A1 | 11/2015 |
| WO | 2015177674 A1 | 11/2015 |
| WO | 2016030373 A1 | 3/2016 |
| WO | 2016193350 A2 | 12/2016 |
| WO | 2017093450 A1 | 6/2017 |

OTHER PUBLICATIONS

Uzbas et al., Appl. Microbiol. Biotechnol. 93:1601-1608, 2012 (Year: 2012).*
Coradetti et al., Microbiologyopen 2:595-609, 2013 (Year: 2013).*
Wang et al., J. Ind. Microbiol. Biotechnol. 42:1233-1241, Jul. 2015 (Year: 2015).*
Davis Rowland H et al: "P Nature Reviews | Genetics vol. 3 | May 2002 | 7 Neurospora: a model of model microbes", Nature Reviews, Jan. 1, 2002, pp. 7-13, XP055710238.
Galagan James E et al: "The genome sequence of the filamentous fungus Neurospora crassa", Nature, vol. 422, No. 6934, Apr. 24, 2003 (Apr. 24, 2003), pp. 859-868, XP002504380, ISSN: 0028-0836, DOI: 10.1038/NATURE01554.
Hinz Sandra W A et al: "Hemicellulase production in Chrysosporium lucknowense C1", Journal of Cereal Science, Academic Press Ltd, GB, vol. 50, No. 3, Nov. 1, 2009 (Nov. 1, 2009), pp. 318-323, XP002593773, ISSN: 0733-5210, DOI: 10.1016/J.JCS.2009.07.005.
Aramayo Rodolfo et al: "Neurospora crassa, a Model System for Epigenetics Research", Cold Spring Harbor Perspectives in Biology, vol. 5, No. 10, Oct. 1, 2013 (Oct. 1, 2013), pp. a017921-a017921, XP055710272, DOI: 10.1101/cshperspect.a017921.

(Continued)

Primary Examiner — David Steadman
(74) Attorney, Agent, or Firm — Armstrong Teasdale LLP

(57) ABSTRACT

The present invention relates to a method of producing a recombinant polypeptide a filamentous fungus which is genetically modified to decrease or eliminate the activity of cellulase regulator 2 (CLR2) and to express said recombinant polypeptide. The method further relates to a filamentous fungus *Myceliophthora thermophila*, which is genetically modified to decrease or eliminate the activity of CLR2 and the use of this filamentous fungus in the production of a recombinant polypeptide.

7 Claims, 5 Drawing Sheets
Specification includes a Sequence Listing.

(56) References Cited

OTHER PUBLICATIONS

Roche Christine M et al: "Neurospora crassa: Looking back and looking forward at a model microbe", American Journal of Botany, Dec. 1, 2014 (Dec. 1, 2014), pp. 2022-2035, XP055710280, DOI: 10.3732/ajb.1400377.

Matsakas Leonidas et al: "Evaluation of Myceliopthora thermophila as an Enzyme Factory for the Production of Thermophilic Cellulolytic Enzymes", Bioresources, vol. 10, Jan. 2015, pp. 5140-5158, XP055710284.

International Search Report and Written Opinion for International Application No. PCT/EP2016/079526, dated Feb. 15, 2017, 14 pages.

Myceliophthora thermophila strain leading to isolates which produce low amounts of endogenous cellulase and proteases. Visser et al. (2011) pp. 214-223.

\* cited by examiner

SEQUENCE LISTING

<160> NUMBER OF SEQ ID NOS: 37

<210> SEQ ID NO 1
<211> LENGTH: 2508
<212> TYPE: DNA
<213> ORGANISM: artificial
<220> FEATURE:
<223> OTHER INFORMATION: clr2 cDNA

<400> SEQUENCE: 1

| | | | | | |
|---|---|---|---|---|---|
| atggcaccaa | ccatcccagt | gcccacacag | ggcggcatgt | tccatacctt | tcaaggagtt | 60 |
| accccacgca | agacatccac | ggattcacag | gacagcacca | agaccaacgg | gtcaggcacc | 120 |
| gctaagagga | taaccacacc | acacgcctgt | gccgagtgca | agcggcgcaa | gatccgctgc | 180 |
| gatggccagc | aaccatgcgg | ccagtgcctc | tccagcaggg | cacccaagcg | gtgtttctat | 240 |
| gacaagcacc | ggcagcgggt | gattccctct | cgcaagaccc | tcgaagccct | gtcgcagtca | 300 |
| ctcgaagaat | gccggtccat | cctgaagcgg | ctgtacccca | accatgaggt | ccaggccttg | 360 |
| ctgcccctgt | cacggcaaga | gctcctcaac | ctcttggaca | ggcccgtcat | agatacctcg | 420 |
| attggcggct | tgccatcacc | gcccatcaac | acctcgccca | tctcggacct | cggctcgccc | 480 |
| atgatgccca | agtccgagag | catcctggag | cagcttccgt | cgagggacac | cgaatgggac | 540 |
| gaggagcgga | ggggccggga | tccgatccct | gccgaggccg | acgacatcaa | cgccctctcg | 600 |
| ctctcggttg | accggcaaac | gtcctacctg | ggcgcctcgt | ccatcaaggc | cgccctgatg | 660 |
| gtcatgctca | aggtgcagcc | cagcctgcgc | acaccttgg | ccgcgcccct | gagcggtgtc | 720 |
| gagatctcgc | acaacttccc | cgccatccgg | cagaagccgt | cggggaccca | gaaagaaggc | 780 |
| cagcggatcc | cctggtcctg | gaaggggcag | accctgatcg | acgcctactt | caagcgcatc | 840 |
| cacgtcttca | tccccatgct | cgacgagagc | accttccggg | ccgactacct | cgaggggcag | 900 |
| cgcaccgacg | cgccctggct | cgcgctcctc | aacatggtgt | tcgccatggg | cagcatcgcc | 960 |
| gccatgaagt | cggacgacta | caaccacgtc | aactactaca | accgcgccat | ggagcacctg | 1020 |
| cccatggacg | ccttcggcag | cagccacatc | gagacggtgc | aggcgctcgc | cctcatcggc | 1080 |
| ggctactacc | tccactacat | caaccgcccc | aacatggcca | acgcggtcct | cggcgccgcc | 1140 |
| atccgcatgg | ccagcgccct | cggcctgcac | cgcgagtccc | tcgtccagtc | gagcagcgac | 1200 |
| atcgtcgcgg | ccgagacccg | ccgccgcacc | tggtggtccc | tcttctgcct | cgacacgtgg | 1260 |
| gccaccacga | ccatgggccg | cccgtccttc | ggccgctggg | gccccgccat | caacgtccgc | 1320 |
| ccgcccgagt | tcggcatcaa | cgggaaccgc | gactcgtccc | agcacgccgg | catcctgccc | 1380 |
| ctgatcgaga | acatcaagtt | ctgcaagatc | gccacccaga | tccaggacat | gctcgccatc | 1440 |
| agccccctcc | tccgcaccga | ggaccgctgc | cacctggacg | cccagctcgt | ctcgtggtac | 1500 |
| aactcgctcc | cctggctcct | gcgcaccacc | gaccccctgcg | ccgagccgct | ctacatggcg | 1560 |
| cgctgcatca | tgaagtggcg | ctaccagaac | ctgcgcatgc | tcctgcaccg | gcccgtcctc | 1620 |
| ctctcgctcg | cctcgtccgg | cctgaacccg | cacacccagg | cctgcgacgc | cgacctggcc | 1680 |
| gccatcgagg | tctgccgcga | gctcgccgcc | cagaccatcg | acgacatcgc | gcgcgagtgg | 1740 |
| gcccgcaacc | agatgagtgg | gtggaacgcc | gtctggttcc | tctaccaggc | cgccatggtg | 1800 |
| cccctcgtca | gcgtcttccg | gcaatgggc | aacccgcgcg | tgcccgagtg | gctcaagcag | 1860 |
| atcgaggccg | tcctcgacct | gctcgagatc | atggaggagt | ggtcgctggc | cgcccgccgc | 1920 |
| tcgcgtgagg | tcgtctggcg | catgtacgag | gccgcccgcc | agctcgtcga | gcagcagcgc | 1980 |
| gccagcgcct | ccccgagcat | ccaggtgctc | gccggcggcg | ccaccgccga | cggcatgctc | 2040 |

```
atgcccagcc ccggcgccgc cgaggctgcc ggcatgcaca tgagcccat cggcctggag      2100 cccgtcgacg ggctcggcct catgggcctc ctcgaccagg gcggcctgtg gggggatttg     2160
gacggcatgt actggaccca gccgggcggg ccatcccccc ctcccgcacc gttaaccccg     2220
caacaacaac aacaccaaca gcaacaacaa caacaacaac aacaaccgcc gcacattagc     2280
ctcggcagcc ccgtggatga gtcggcatgc atggcggcgg cggcggcggc ggcggcggaa     2340
tttgccgcct accacagccc cgtcgtcacc acggccggcg gcgcgtcgc cagcccgcac      2400 gacaccaacg gcatggtcca cgccgttgac tacagcggcc tcatgggcca tcctcaccaa     2460
cctcctcatc cccaccagca gggcatggag tttggctacg tccagtga                 2508

<210> SEQ ID NO 2
<211> LENGTH: 8570
<212> TYPE: DNA
<213> ORGANISM: Myceliophthora thermophila

<400> SEQUENCE: 2
ttattcaacc gcaggagtgt actccataca ctagataaca cactatcaag gagacgttca      60
ttagggcaca tgatggttga tcttctaacc tcagatagcg gtagcgattc cgtttcaatt     120
ctcgtgccca tgcgcggcaa gaaaacaaaa ccaagtcatg tcaccagttg accaaccaag     180
atgatgatca agaaccacag acaacccgat gccatcctgc cgccaaattt ctggtcgaaa     240
cgctgggaaa gggacctgcc actcccagga cgttgcgtca caaggcacg cggcggttcc      300 gaaatgacag gacgcaaaac ggcacaaacc gaagactggc cggcatccgt cgtgagttcg     360
aggcccagcg aacgaaccac tgacgtgagc attccgaccg aaagggatag gcgagaggag     420
aaggaacagt gtggaccagg aaagactccg tttcgcaact gaaccttccc ttgccgcgcg     480
gaattggggg acgctcgagg gtggagaggc ggctcggccg gctcccacca gcccacgggt     540
ccctgacgac gcgcagtcat gtgccttgtc agaagccgaa gttgccattg gcttcatata     600
tcccatgcag ccatcttccc gcagctcgac tccggcgccc cgcagtacca cagcggagca     660
tcaggccaga actttgagtt ctctcatggt tcggccgtga tcgtctcaaa aggccgtccg     720
gtacgatgcg tacgcctttc tttcgtgagt gcggtcggtt ggagagggg gttagattag      780 tgaccgcatc cgggagcgtc gcaggaaccg tccgtgtcta agttcataca tacatacctt     840
acatacacat gcacgcccgt aatgaaggcc ctggtgaccg acgggaacac ggactggagt     900
gctgcgtcac caccagacgc accgactccc cattaggcgc gacacgcctg cttcggccgc     960
ccgccatgcc gcctgctcgc ccaaacttgc caaaagattt ggaggcaggc gctcgagctt    1020
cccggtgtga acgtggagc tgagagccta agacccacac caccaccacc ccggactttt    1080 attttaccc tgtctgccct gatcgaaggg gcgccaaccg gcaggatccc tggcgctcgc     1140
cgttgagcaa agccggacac caatcagacg accaaggcgc gaccgtcctc cccacaaccc    1200
gccttggcac actggcaccc tggatcgagg cgcctttggg gccgacggtc cctcttttcca   1260 gtcctccccc aacgccatct ccaccgttct ccaattccct cctcgcctcg aaggcgcccc    1320 ctctcccctcc cggcctagac tccaacgcgc gacagaaata gtggtacgat ttgcgacgcg    1380
tggagccgtc cctctcatct cgcatccctc actttctcga cgacggcatc acaggggatg     1440
ggacgagcgg caaagctttc catagccaaa agctggtggt cgaccgacgt caggagaatg    1500
ggattgctgt cttgccaatc tcccaaaagt ggcaatgcgg gtctcctgca ggcagcgctc    1560
tcgcctgtta cactactttc acggcctcgg catccgatac tcgactgcaa catcatcagg    1620
```

```
gtattcggct aggcagtcta gtgtagtagt acacaaagtc ttcgattgct ttccgcggga    1680
cagggttcga gagagactcc agtacactac aacgcagccc cacgtgtagc gtcatgggcc    1740
accgctggct gacgttcacg tacttacata cctaggtaca tacaccattc cgtacggata    1800
catcaggtaa tgtatgtaca tacgtggcgc aggtacgcag tacgtacata tcaaccttgc    1860
ttgcatagca cgggccgatg aggtatgtac ggacgtactt cgtacttacg cggtagtggg    1920
gggaaggcca cacatctgat agcttcctct ctccattccc tcatgcaccc agaccctggc    1980
gctgaaacgc cgccgctcag aagccgccca ctggctgcag acttgaacct aacttttttt    2040
tctttgtttt cacttcacca cccctccccc tccccctccc cttccgccct gtccctcttc    2100
gccttcccac cctctttgca agtcgagctg cgctacggga tggcgggcgg cggtgaccta    2160
tactgggcct gacactaata tgcaaaccca ggtacctgcg gttcactctg cccgtttgct    2220
tgtacatacc ttagtgagca gcaggcatgg accctgctga tgtctcgtgt ttagctgatg    2280
ccagactcac gagtgtggac ggcattgacc acggcgggtg cgcccctcct ctcttcaccc    2340
agcagcagga tattcgagat tacctcatgc gcttgttcgt gccttgatca agcaaggtct    2400
gctggggttg cgtaccatgg caaattacag tggcatggct gggggaacgg gaattgcccc    2460
cagtcccgcg caagcgcccg ttacgccagt tgctgcactc cccagctaca gagtagtgta    2520
gtagcgtagt agatctacta cggtaaggga ggcccgcaga gaaacttgtt ctccacttcg    2580
ggaccggcct gggcagccga ccatctttcc caatttcgct ctctcccac actttccgag     2640 agccccatcc acaactccaa gctgcagagc atcaacgtag atatataagt ctgcatctgc    2700
tccccatgtt tccgcctcgc accgtcattg cccaatgtct atctttacca ttgtggctgc    2760
tggtccccat ccgccgtcac ggttttcat gtacaacaac aacaagtttc tgtaaattca     2820
tcagcctcgt cacgaccttc acacgactcg ggcgtcacta cttgggccgg cccccaacat    2880
ctcacagaca aggaaagaaa agagaagaga gagagagaga gagagaaaga aagactcgga    2940
gagccagtga tacccccttga tacccccctt tcggtcctca aaagagtctt ccaacccgcc    3000
atggcaccaa ccatcccagt gcccacacag ggcggcatgt tccatacctt tcaaggagtt    3060
accccacgca agacatccac ggattcacag gacagcacca agaccaacgg gtcaggcacc    3120
gctaagagga taaccacacc acacgcctgt gccgagtgca agcggcgcaa gatgtaagtt    3180
gtggaacaac agcgttcgga actgacacgg ggactgaccg aggtcttgtt cgcagccgct    3240
gcgatggcca gcaaccatgc ggccagtgcc tctccagcag ggcacccaag cggtgtttct    3300
atgacaagca ccggcagcgg gtgattccct ctcgcaagac cctcgaagcc ctgtcgcagt    3360
cactcgaaga atgccggtcc atcctgaagc ggctgtaccc caaccatgag gtccaggcct    3420
tgctgcccct gtcacggcaa gagctcctca acctcttgga caggcccgtc atagatacct    3480
cgattggcgg cttgccatca ccgcccatca acacctcgcc catctcggac ctcggctcgc    3540
ccatgatgcc caagtccgag agcatcctgg agcagcttcc gtcgagggac accgaatggg    3600
acgaggagcg gaggggccgg gatccgatcc ctgccgagcc cgacgacatc aacgccctct    3660
cgctctcggt tgaccggcaa acgtcctacc tgggcgcctc gtccatcaag gccgccctga    3720
tggtcatgct caaggtgcag cccagcctgc ggcacacctt ggccgcgccc ctgagcggtg    3780
tcgagatctc gcacaacttc cccgccatcc ggcagaagcc gtcgggacc cagaaagaag     3840 gccagcggat ccctggtcc tggaaggggc agaccctgat cgacgcctac ttcaagcgca     3900
tccacgtctt catccccatg ctcgacgaga gcacttccg ggccgactac ctcgaggggc     3960
agcgcaccga cgcgccctgg ctcgcgctcc tcaacatggt gttcgccatg ggcagcatcg    4020
```

```
ccgccatgaa gtcggacgac tacaaccacg tcaactacta caaccgcgcc atggagcacc    4080
tgcccatgga cgccttcggc agcagccaca tcgagacggt gcaggcgctc gccctcatcg    4140
gcggctacta cctccactac atcaaccgcc caacatggcc caacgcggtc ctcggcgccg    4200
ccatccgcat ggccagcgcc ctcggcctgc accgcgagtc cctcgtccag tcgagcagcg    4260
acatcgtcgc ggccgagacc cgccgccgca cctggtggtc cctcttctgc ctcgacacgt    4320
gggccaccac gaccatgggc cgcccgtcct cggccgctg gggccccgcc atcaacgtcc    4380
gcccgcccga gttcggcatc aacgggaacc gcgactcgtc ccagcacgcc ggcatcctgc    4440
ccctgatcga gaacatcaag ttctgcaaga tcgccaccca gatccaggac atgctcgcca    4500 tcagcccccct cctccgcacc gaggaccgct gccacctgga cgcccagctc gtctcgtggt    4560
acaactcgct ccccctggct ctgcgcacca ccgaccccctg cgccgagccg ctctacatgg    4620
cgcgctgcat catgaagtgg cgctaccaga acctgcgcat gctcctgcac cggcccgtcc    4680
tcctctcgct cgcctcgtcc ggcctgaacc cgcacaccca ggcctgcgac gccgacctgg    4740
ccgccatcga ggtctgccgc gagctcgccg cccagaccat cgacgacatc gcgcgcgagt    4800
gggcccgcaa ccagatgagt gggtggaacg ccgtctggtt cctctaccag gccgccatgg    4860
tgcccctcgt cagcgtcttc cggcaatggg gcaacccgcg cgtgcccgag tggctcaagc    4920
agatcgaggc cgtcctcgac ctgctcgaga tcatggagga gtggtcgctg gccgcccgcc    4980
gctcgcgtga ggtcgtctgg cgcatgtacg aggccgcccg ccagctcgtc gagcagcagc    5040
gcgccagcgc ctccccgagc atccaggtgc tcgccggcgg cgccaccgcc gacggcatgc    5100
tcatgcccag ccccggcgcc gccgaggctg ccggcatgca catgagcccc atcggcctgg    5160
agcccgtcga cgggctcggc ctcatgggcc tcctcgacca gggcggcctg tgggggatt    5220 tggacggcat gtactggacc cagccgggcg ggccatcccc ccctcccgca ccgttaaccc    5280
cgcaacaaca caacaccaa cagcaacaac aacaacaaca caacaaccg ccgcacatta    5340 gcctcggcag ccccgtggat gagtcggcat gcatggcggc ggcggcggcg gcggcggcgg    5400
aatttgccgc ctaccacagc cccgtcgtca ccacggccgg cggcggcgtc gccagcccgc    5460
acgacaccaa cggcatggtc cacgccgttg actacagcgg cctcatgggc catcctcacc    5520
aacctcctca tccccaccag cagggcatgg agtttggcta cgtccagtga acccactcct    5580
ccctcggccg cccccctccct ccactactac caaccactga ggcgggcaag gtagcagcat    5640
ctcgggctcg aattttttt tcattcttca ttcctcttct tgttcttccc tcttgggcag    5700
acgcttatga tgatacgttt gctccctact ttttttcct cttcgtcttc tccttttttt    5760
ttcttctctt ttgccctata ccctcgcct acctgggtag tagtcttggg aataggactg    5820 ttcggccga aatgggtggg tggcattctt ccccggaaaa atgtgggtg cagcacagag    5880 ggaacaaagc tggaaaggaa aggggatga atgtgacgtc tcttatttaa gtgtcggtgt    5940
gtgtgtgtgt gtgtgtgtgt gtgtgtgtgt gtgtgtgtgt gtgtgtgtgt gagggtgtgt    6000
ggttcgggag ttttggggta ttgtacatac accctaccct ttttttcct ttactctctc    6060 tctcatgatg acgggctggg ttctcgctcg atggatgacg gatataccag gaaggttttt    6120
tttttttgct cacgacccat gtatgtgtat gtacatgcat tcgctacttg ttcaggtttg    6180
gcaggaaagg ggtggggagg cgcggaattg gcagggcacg gcaaggggga acaaaagaga    6240
tggggaggga aaggggggaaa gggggatttc tgcggtgtgc actggaaaag gcgcggttct    6300
gttctcagtc taccattgcc cgtctatact tttggcaaaa tcaacttttg gtgtcctcaa    6360
```

```
ccattgcacc tgcttggctc acctgctttc tgaaaactcg gggtaatggg cggcttgaga    6420
ttgggtaggc aaaattggcg tgtggtcccg attgtgttgg tggaatgtcc cgaaatggta    6480
aggcacattc aactaggcaa ggagggtata acaggctggg ccttgtatgt atgtatgtat    6540
gtactgtaaa gtactagtaa ctaactagtt aactcggtgc tcacttttca ctggctggat    6600
gatttttatt cgagccacga ccctgcgagt tactcctccc ttacccttcc cctctctgtt    6660
tctctccgac ctgcagcaga aggcacgatg caggacgcgt tcccacagct catgttggat    6720
ggtcttgact gcatgtgatg gtgtccgtac caaccccgg acattcgtgg aaggcttcgc     6780
gaagagttct agcgtaacgg cgacatccaa tgaggatgtg ccgccgctga agggcgggct    6840
ggaaccggcc ttttcgctca tcgggatcat cgctgtcgtg gcatgtatgt acatatatgt    6900
atactacggt gctctatggt gtatgtattt gtgtgatata ctgtactata tgtatgtatg    6960
tacctaggta tggacgtgca cttttaacat gagcatttac cggcgctcaa ccgttttttt    7020
gtgtacatac ttctcaatgc ttagtttcgt cggcaagcag gcgggcaagg gtgggaagtc    7080
ggttgcggtg agcgcgaagg tgccctctga ccaaaggatc cggctttcca ctcgggttca    7140
cctttcaaat gcaaagggag gggaaaaaac accgctagat tcactcagcc cgttgacggc    7200
ggccgaatgt gacctgtcgc gtcctcacga agatccggg tggtgggtcg cgatggcaag    7260
ctggatgcta gggccgacgc gccagagcgc caagcggtgc ttggaccttg gctttactc    7320
gtcgcgctg tgatctgcga gcacacctcc accatggctt cctctccgtg attgtttctc    7380
cagtgtacga agtaccatct tttgatgtgg cagggaaaag aagcctcctc tgtttgggct    7440
acggcagccc tggaaaagaa aaggtttgag tgtcatcctt ggcgtcgtcc tcggtgtttg    7500
ttttgtaatc tttagttatg tactgtactg tatccataca tagtgtacag gcacgtctcg    7560
ggcactttcg ttttcggatc cgggatccgg ggatgagctt gagcccgcca accctgatga    7620
gcagccgcca accacaaatc gtcgagggga cggcataaac gttttgatgt cctgggaaga    7680
cgcacatgcc cagtcacgat ttaccccgga ccctctgcat ctcgagccca ctcatcgagg    7740
ggatcatggc gacgtagtag tcaagctcag ggctcagatc cgacgagagc gttcatccag    7800
cggccgcggc atccgatgta ggtgaaaaaa cgggtttcct gaagcggagc aggggagcca    7860
aaacggcaaa aaccgattgg gtggcagaat tgcttcggga tttcgcatcg aagttcgctt    7920
ggcaatctgg atccgcggcc cgtcgcgcag gttgtgtcac aaatgaacgg ttgcgtgtaa    7980
ttacagtacc ggtacctgta cttgcttcct gagcatgttg tcggcgtctt ggcaccagaa    8040
gaactcggat gcgagcgtac cggtactttg gcgtacctt gctctccaag agcggggact     8100
cctgcaagtg atgttggaga gtgcggggta atatgcaccc cagctctgtg acctgggggc    8160
agaaaattgg cgatgcgggg acaagatcca tccactcagt tcgcgactgc agagtcaaac    8220
cacctgacct ttctagccga aggtgatgga gaaggcaacg caacaggctc gccttttccg    8280
tacactactg tggtactctg aacgccccgc tgcttcggga cggtaacata atccggcgag    8340
agcaaccgac cacagggttc cctgggacac ttgattcggg ttcagcagtg gatcgagaat    8400
tgtggagtac tgtaactacc tgaatgtgac cacctccgca gttcctgta gtgtactgtg     8460
tatgtatgta tgtacatccg tacgtatgaa ctacagtaac caagagacct gacaggcgcg    8520
cattcatgtt ccctccctct cctattcaac ccttggcggt catcaaccga                8570
```

<210> SEQ ID NO 3
<211> LENGTH: 835
<212> TYPE: PRT
<213> ORGANISM: Myceliophthora thermophila

<400> SEQUENCE: 3

```
Met Ala Pro Thr Ile Pro Val Pro Thr Gln Gly Gly Met Phe His Thr
1               5                   10                  15

Phe Gln Gly Val Thr Pro Arg Lys Thr Ser Thr Asp Ser Gln Asp Ser
                20                  25                  30

Thr Lys Thr Asn Gly Ser Gly Thr Ala Lys Arg Ile Thr Thr Pro His
            35                  40                  45

Ala Cys Ala Glu Cys Lys Arg Lys Ile Arg Cys Asp Gly Gln Gln
        50                  55                  60

Pro Cys Gly Gln Cys Leu Ser Ser Arg Ala Pro Lys Arg Cys Phe Tyr
65                  70                  75                  80

Asp Lys His Arg Gln Arg Val Ile Pro Ser Arg Lys Thr Leu Glu Ala
                85                  90                  95

Leu Ser Gln Ser Leu Glu Glu Cys Arg Ser Ile Leu Lys Arg Leu Tyr
            100                 105                 110

Pro Asn His Glu Val Gln Ala Leu Leu Pro Leu Ser Arg Gln Glu Leu
        115                 120                 125

Leu Asn Leu Leu Asp Arg Pro Val Ile Asp Thr Ser Ile Gly Gly Leu
130                 135                 140

Pro Ser Pro Pro Ile Asn Thr Ser Pro Ile Ser Asp Leu Gly Ser Pro
145                 150                 155                 160

Met Met Pro Lys Ser Glu Ser Ile Leu Glu Gln Leu Pro Ser Arg Asp
                165                 170                 175

Thr Glu Trp Asp Glu Glu Arg Arg Gly Arg Asp Pro Ile Pro Ala Glu
            180                 185                 190

Ala Asp Asp Ile Asn Ala Leu Ser Leu Ser Val Asp Arg Gln Thr Ser
        195                 200                 205

Tyr Leu Gly Ala Ser Ser Ile Lys Ala Ala Leu Met Val Met Leu Lys
210                 215                 220

Val Gln Pro Ser Leu Arg His Thr Leu Ala Ala Pro Leu Ser Gly Val
225                 230                 235                 240

Glu Ile Ser His Asn Phe Pro Ala Ile Arg Gln Lys Pro Ser Gly Thr
                245                 250                 255

Gln Lys Glu Gly Gln Arg Ile Pro Trp Ser Trp Lys Gly Gln Thr Leu
            260                 265                 270

Ile Asp Ala Tyr Phe Lys Arg Ile His Val Phe Ile Pro Met Leu Asp
        275                 280                 285

Glu Ser Thr Phe Arg Ala Asp Tyr Leu Glu Gly Gln Arg Thr Asp Ala
290                 295                 300

Pro Trp Leu Ala Leu Leu Asn Met Val Phe Ala Met Gly Ser Ile Ala
305                 310                 315                 320

Ala Met Lys Ser Asp Asp Tyr Asn His Val Asn Tyr Asn Arg Ala
                325                 330                 335

Met Glu His Leu Pro Met Asp Ala Phe Gly Ser Ser His Ile Glu Thr
            340                 345                 350

Val Gln Ala Leu Ala Leu Ile Gly Gly Tyr Tyr Leu His Tyr Ile Asn
        355                 360                 365

Arg Pro Asn Met Ala Asn Ala Val Leu Gly Ala Ile Arg Met Ala
370                 375                 380

Ser Ala Leu Gly Leu His Arg Glu Ser Leu Val Gln Ser Ser Ser Asp
385                 390                 395                 400

Ile Val Ala Ala Glu Thr Arg Arg Arg Thr Trp Trp Ser Leu Phe Cys
```

```
                    405                 410                 415
Leu Asp Thr Trp Ala Thr Thr Thr Met Gly Arg Pro Ser Phe Gly Arg
                420                 425                 430

Trp Gly Pro Ala Ile Asn Val Arg Pro Glu Phe Gly Ile Asn Gly
            435                 440                 445

Asn Arg Asp Ser Ser Gln His Ala Gly Ile Leu Pro Leu Ile Glu Asn
        450                 455                 460

Ile Lys Phe Cys Lys Ile Ala Thr Gln Ile Gln Asp Met Leu Ala Ile
465                 470                 475                 480

Ser Pro Leu Leu Arg Thr Glu Asp Arg Cys His Leu Asp Ala Gln Leu
                485                 490                 495

Val Ser Trp Tyr Asn Ser Leu Pro Trp Leu Leu Arg Thr Thr Asp Pro
            500                 505                 510

Cys Ala Glu Pro Leu Tyr Met Ala Arg Cys Ile Met Lys Trp Arg Tyr
        515                 520                 525

Gln Asn Leu Arg Met Leu Leu His Arg Pro Val Leu Leu Ser Leu Ala
        530                 535                 540

Ser Ser Gly Leu Asn Pro His Thr Gln Ala Cys Asp Ala Asp Leu Ala
545                 550                 555                 560

Ala Ile Glu Val Cys Arg Glu Leu Ala Ala Gln Thr Ile Asp Asp Ile
                565                 570                 575

Ala Arg Glu Trp Ala Arg Asn Gln Met Ser Gly Trp Asn Ala Val Trp
            580                 585                 590

Phe Leu Tyr Gln Ala Ala Met Val Pro Leu Val Ser Val Phe Arg Gln
        595                 600                 605

Trp Gly Asn Pro Arg Val Pro Glu Trp Leu Lys Gln Ile Glu Ala Val
        610                 615                 620

Leu Asp Leu Leu Glu Ile Met Glu Glu Trp Ser Leu Ala Ala Arg Arg
625                 630                 635                 640

Ser Arg Glu Val Val Trp Arg Met Tyr Glu Ala Ala Arg Gln Leu Val
                645                 650                 655

Glu Gln Gln Arg Ala Ser Ala Ser Pro Ser Ile Gln Val Leu Ala Gly
            660                 665                 670

Gly Ala Thr Ala Asp Gly Met Leu Met Pro Ser Pro Gly Ala Ala Glu
        675                 680                 685

Ala Ala Gly Met His Met Ser Pro Ile Gly Leu Glu Pro Val Asp Gly
        690                 695                 700

Leu Gly Leu Met Gly Leu Leu Asp Gln Gly Gly Leu Trp Gly Asp Leu
705                 710                 715                 720

Asp Gly Met Tyr Trp Thr Gln Pro Gly Gly Pro Ser Pro Pro Pro Ala
                725                 730                 735

Pro Leu Thr Pro Gln Gln Gln His Gln Gln Gln Gln Gln Gln Gln Gln
            740                 745                 750

Gln Gln Gln Pro Pro His Ile Ser Leu Gly Ser Pro Val Asp Glu Ser
        755                 760                 765

Ala Cys Met Ala Ala Ala Ala Ala Ala Ala Glu Phe Ala Ala Tyr
        770                 775                 780

His Ser Pro Val Val Thr Thr Ala Gly Gly Val Ala Ser Pro His
785                 790                 795                 800

Asp Thr Asn Gly Met Val His Ala Val Asp Tyr Ser Gly Leu Met Gly
                805                 810                 815

His Pro His Gln Pro Pro His Pro His Gln Gln Gly Met Glu Phe Gly
            820                 825                 830
```

Tyr Val Gln
      835

<210> SEQ ID NO 4
<211> LENGTH: 36
<212> TYPE: PRT
<213> ORGANISM: Myceliophthora thermophila

<400> SEQUENCE: 4

Cys Ala Glu Cys Lys Arg Arg Lys Ile Arg Cys Asp Gly Gln Gln Pro
1               5                   10                  15

Cys Gly Gln Cys Leu Ser Ser Arg Ala Pro Lys Arg Cys Phe Tyr Asp
            20                  25                  30

Lys His Arg Gln
        35

<210> SEQ ID NO 5
<211> LENGTH: 2859
<212> TYPE: DNA
<213> ORGANISM: artificial
<220> FEATURE:
<223> OTHER INFORMATION: xyr1 cDNA

<400> SEQUENCE: 5

| | | | | | |
|---|---|---|---|---|---|
| atgttgtcta | acccgcttca | ccggttttca | ccttatcaca | tccctcaac | tacgctgctg | 60 |
| tcgaacggcc | atgttccggg | cggccacctt | cacgcggccg | gacttgactc | gctcgcccct | 120 |
| ggctctcact | acgctctcca | gcaactccag | cagcatgtcg | gcgtccacac | ccccaccc | 180 |
| gctcggactg | gccctcaacc | gaagcatagg | caacatcctt | atgggcctgc | cgccagatct | 240 |
| tcggggcag | ctggaccgat | tcggaggagg | atcagcaggg | cctgcgatca | gtgcaaccag | 300 |
| ctaaggacca | aatgcgacgg | ccaacatcca | tgcgctcatt | gcattgagtt | ccaactgggc | 360 |
| tgcgagtaca | tccgagagcg | caagaagcgt | ggcaaggcat | ccaggaaaga | ccttgcacag | 420 |
| caagccgccg | cccaagccgc | tgcccaagca | gctcagaacg | gccagaagac | cgagaattca | 480 |
| acgacggaga | atacaaagcc | gcggagaac | cggaacgata | caccgagcaa | caccaagcct | 540 |
| gtcttgacgg | ttaacaccga | ccagccacca | gcgttggaca | agaacgtgac | cgatgtacca | 600 |
| gaggatccta | atctgaggga | gcagaggaca | gggagcatcg | aggccttggg | cgacatgagc | 660 |
| gcccatccgg | cacccatgtc | ggctcacccc | ggggcgattg | agcgagaaca | cctcgacaac | 720 |
| ccgacagcac | tggaccttaa | cggatatggt | tccgttcact | cagcgtatga | ccgccaaatg | 780 |
| ggcgcacaca | tgatgaacgg | cccacctcat | gcgccctacg | gccaaaacca | gggcaacatg | 840 |
| tccagttacc | cagagctccc | atatgctctg | caaacgcaga | gcccgacggg | ttatcccgca | 900 |
| aatgccgcga | atgggttccg | cctcgccaac | agccctctcg | gccctattc | gatgggtgga | 960 |
| gaggcccat | cgccgggcgg | atggatgaac | atgtcatcgc | cgcccccca | gtttgcttcg | 1020 |
| catatgccgc | agaacgggta | taaccgttcg | cagctccggt | acccagtcct | ggagcccctt | 1080 |
| gttccccatc | tgggcaacat | catccctctg | tcgctcgcgt | gcgacctcat | cgacctctac | 1140 |
| ttcgcgagct | catcctcggc | ccagatgcac | ccaatgtcgc | cttatgtcct | cggattcgtc | 1200 |
| ttccggaagc | ggtcgttcct | ccacccgacc | aagccgcgac | agtgccagcc | ggctctcctg | 1260 |
| gccagcatgc | tatgggttgc | tgcacagaca | agcgacgctc | ctttcctgac | gagtgtccct | 1320 |
| tcggcccgtg | gcaagatttg | ccagaagctc | ctggagttga | cggtcagcct | tctcaagccg | 1380 |
| ctcatccaca | cgccctcgga | ggaggcatcg | cctgtctcga | gccccatcgt | ggatggcgtt | 1440 |

```
gccctcggcg gccttggcgt cgcactgccc gggtccatca gcatggatgc cctcaccagc   1500
gagtcgggcg ctttcggcgc ggccggttct ctggacgacg tggtcaccta catccacctt   1560
gcgacggtcg tgtcggcgag cgagtacaag ggagccagtc tgcgttggtg gaatgccgcg   1620
tggtcgcttg ctcgcgagct caagctcggg cgcgagttgc ctcagaacgc gccggcgagt   1680
cgccagggtg gagccgccga aatggaaggc gagggcaatg gtgccgagat gaccattccc   1740
ggcgtgatca cggaagagga acgcgaggag aggcggcgga tctggtggct cgtctacatt   1800
gtcgaccgcc atctcgccct gctacaaac cgcccgctct tcctgctcga catcgagtgc   1860
gaacacctct accagcccat ggatgatacc gattaccaga acggtaactt ccgtgcctac   1920
acaaccgacc cgaacgttct cggttcggat accgagggaa aacgcacccg ggtcaagggc   1980
ccctcgttcg tgtgcagcgg ccacagcatc tttggctact tcctcccact aatgaccatc   2040
ctcggcgaaa tcgtagatct tacgcacgcc aaaaaccacc ctcgcttcgg cgtcgggttc   2100
cgttcgtctc gcgagtggga tgaccaaacg gccgagatca cccgccacct tgacatgtac   2160
gagcagagcc tgaaggagtt tgagaagcga cacctcagca tcaacgcgca agcccaggca   2220
gcagacgaga aggcggccga ggcggccggc gtccctacgg ctaatgctaa cgacctcccg   2280 ggcaccccett cgggtcacag cgtgcacagc gtgcacacca cgtcgagccg catgacggag   2340
agcgacatcc agaccgcat cgtcgtggcc tacggcactc atgtcatgca cgtgcttcac   2400
atcctcctca ccggcaagtg ggatcccatc aacctcctcg acgacaacga cctctggatc   2460
agcagccagg ggttcatcac ggcgaccggc cacgcggtca cgcagccga ggccatcagc   2520 aacattctcg agtacgaccc cgggctcgag ttcatgccct tcttcttcgg catctacctc   2580
ctccagggct cgttcctgct gctgctcatt gccgacaagc tgcagctcga ggcgtcgccg   2640
agcgtggtga aggcctgcga gaccatcatc cgcgcgcatg aggcgtgtgt ggtgacgctc   2700
aataccgagt atcagcgcaa ctttagccga gtcatgcgca gtgctctcgc tcaggtacgg   2760
ggccgcgtgc ccgaggacct tggcgagcag caccagcgta ggagggaact cctcgcgcta   2820
tacaggtgga cgggcgatgg taccggtctg gcgctgtag                          2859

<210> SEQ ID NO 6
<211> LENGTH: 9016
<212> TYPE: DNA
<213> ORGANISM: Myceliophthora thermophila

<400> SEQUENCE: 6
agcggactag caactggaaa cgcaccgcag ctggggtcgg cttgttctgg aatgccagga     60
gttcggtgcc attgctatgg agtgtcgctt tgccatttta caaatttgct ggttctcaat    120
gcaattagaa attgcggggc atctcgccac ctgttctcgt gactcaacca cctgtcgtgc    180 ctgccttta caggactttc cctgaatagc cttcagtcga gatcagtccc gatttccatg    240
tcggacgatc tcactttctt tggcgctgtt gcctggcgcg ggcgtgatca ggaacactgg    300
catagtagtc tccatgtttc gagagcattg ctccttccta gtttgcaga acttaggctg     360 ggaggccaaa acttgaagac caataacatt cactgtgtgg aagtgtggat tccactaaaa    420
cgaagttgtg gttactccg tgcttcgtac taagttctct gtaaattctc ggtgcaacat    480
cacgtacaac gggactggct tggcgtagcc cacttcgttc aggccgctgc tgccatatgc    540
cgctctcgtc gacaaagtcc gatgctgagc gcgggcgaat cccttgaaaa ctggcctcca    600
ccgatcgacc tcgaacaagc tctctttggg atctcgacta cacacgcc cccaggtgct     660 ttcggcaatg cctccgacaa acatggaaac ttcgcttcgt gcttccgtcc ccagacgcat    720
```

```
aacagcaggc acatataatc cgtacactac acacaccacc attgcaacga aataacaggc      780
gtcttatagc gcggcggatc gggatggtca cgaccatctg cgtttgaggg ttccatctgc      840
ccagaaacag tccactgctt ggttaacgca cggcaagcat aggcgaccag ggggctctac      900
ccccagacgc acactgggtg ccggctggag cagcagggcc catcgtctcg actgcctcga      960
gcaatcagca gtcataccga atatggagtg attaagcaac cgaaaagatg cccagctga      1020 tccggtttgg ctccgacccc aacttttctc ccagcggtga cgggtacccc gcccagcacc     1080
catggctgcg actccatggg gagatgatgg ggaagcctcg gggcccctct tctcgctact     1140
cgcaactcca ccggccgaca gggatagcac agtccacaac cgccggcaac gaacaagccc     1200
tggcttcgct gcggctcctg gcgcgttcat cgttccgcat caacctgtca caccatctac     1260
cacccactgc gcctatacac tcaaatgaag gatccggata gatgtgttgt atacgtctgt     1320
atggactatg tacacacgta cacatgacgg aggcagggtg cgcaggaagc aatggagcgc     1380
cggtcaaaag tgatcctaaa ccagtctgaa aagggagcgt cagacgcatg gcctcgcgcc     1440
cagtttgtgc tagaggaaaa acaaaaccct cttgaatgtc tggctgctga ttaacaagtg     1500
ccgcggtatt agtgggcacg ttcaggacag cgtacaagta gtggtgcgct ttgatgtccc     1560
ccatgctgtg ccgatgcgct ggaggacaag gggctttggc aatccatgct actccacgac     1620
tccgtacttg gtagtgtatt gtaccaaatc cgtacacaca ctacaagacg aggatggtgg     1680
agttccattg cactttctcc accatgaccg ctgtctggac ccctgccaga gtggcaaccc     1740
ttgttcaaca gttcttcgca gcgtgccggc gggacaagca gaggcccata tatcctcagc     1800
aggccctgac gaggcggact ctccagagcc cgctgttgct aactctttca gctagcacta     1860
cccgccccgc gctctcacac ggtacttctc tgctctccat agacgcccct tcccgccggc     1920
ttatattgcc ctcgcaatat atccttgata ctcgatattg tgctggacca ggagccgtcg     1980
cctccttgcc accaatcgcg tctagttaca tccacgagca ttatcgcgcg tcttctgttg     2040
tggatgtgcg ccaagccgac ctccagactc gccagaaagt actttgagag gcaggaatag     2100
cgcgcatatt taccgattcg ctcacttgtt cgaatcgggc atcccttggt ccttttggcg     2160
ccccgggccc ctcttaagca ctatacggca catcgccctg aggctcagac caggagagca     2220
gcgcttcatc gatagacgga caaccgggaa gcatctggtg tgtgcagcga aggccttcat     2280
ctgaatttca gggttcaagg ggctcggaaa ggacttacaa gaaacggccg acccaacggt     2340
ctctggcaac gaggactggc caagcgctct cttgccatcc gaccccgtat cccgtacgtt     2400
gatggttccc tcttccctgc cctccacgtt ctccttctcc cgcgccccc cttgccggcc      2460 ggtccgctgt ccctcgtcca tccagacacc cctccccct tcccctcct tcaccccct       2520 tcaccccct tcccttccc ttaacccga catgcgctgc tggtgcttca tcctccgtgc        2580
agtgagttga ctgtggcacc cgttcgccca catccgcgca gatcagcttc cagcgctttg     2640
gtgtctgtca atgctattct cgcatctccc taaatctaat gcctgctact gaccttaccc     2700 caggggaag ctcactcaac tccgtctgac tgccgttcct ccaatcagga cccggcagct      2760
tagcaccggc ggagcttgaa tatagatacc tcccgctccc catcgccgct gtcgacgggt     2820
tcccacctgt ggtgtctgtt ctcctgttca gacgcaccct cgcttcaacc aactgccgc      2880 actcgctcga agccggccgt cttcatatgt tctaagttag ggtcttgacg accccatctc     2940
catctaatct taaccacaac ataacctcat tcaaaatcat atctccatct ccggtccaag     3000
atgttgtcta acccgcttca ccggttttca ccttatcaca tcccctcaac tacgctgctg     3060
```

```
tcgaacggcc atgttccggg cggccacctt cacgcggccg gacttgactc gctcgcccct    3120
ggctctcact acgctctcca gcaactccag cagcatgtcg gcgtccacac ccccacctc     3180 gctcggactg gccctcaacc gaagcatagg caacatcctt atgggcctgc cgccagatct    3240 tcggggggcag ctggaccgat tcggaggagg atcagcaggg cctgcgatca gtgcaaccag   3300
ctaaggacca aatgcgacgg ccaacatcca tgcgctcatt gcattggtga gatcacttcg    3360
cgaatgtccc agggtgcaat gaccttttct aacctttggt agagttccaa ctgggctgcg    3420
agtacatccg agagcgcaag aagcgtggca aggcatccag gaaagacctt gcacagcaag    3480
ccgccgccca agccgctgcc caagcagctc agaacggcca gaagaccgag aattcaacga    3540
cggagaatac aaagcccgcg agaaccggaa acgatacacc gagcaacacc aagcctgtct    3600
tgacggttaa caccgaccag ccaccagcgt tggacaagaa cgtgaccgat gtaccagagg    3660
atcctaatct gagggagcag aggacaggga gcatcgaggc cttgggcgac atgagcgccc    3720
atccggcacc catgtcggct caccccgggg cgattgagcg agaacacctc gacaacccga    3780
cagcactgga ccttaacgga tatggttccg ttcactcagc gtatgaccgc caaatgggcg    3840
cacacatgat gaacgcccca cctcatgcgc cctacggccc aaaccagggc aacatgtcca    3900
gttacccaga gctcccatat gctctgcaaa cgcagagccc gacgggttat cccgcaaatg    3960
ccgcgaatgg gttccgcctc gccaacagcc ctctcggccc ctattcgatg ggtggagagg    4020
ccccatcgcc gggcggatgg atgaacatgt catcgccgcc cccccagttt gcttcgcata    4080
tgccgcagaa cgggtataac cgttcgcagc tccggtaccc agtcctggag ccccttgttc    4140
cccatctggg caacatcatc cctctgtcgc tcgcgtgcga cctcatcgac ctctacttcg    4200
cgagctcatc ctcggcccag atgcacccaa tgtcgcctta tgtcctcgga ttcgtcttcc    4260
ggaagcggtc gttcctccac ccgaccaagc cgcgacagtg ccagccggct ctcctggcca    4320
gcatgctatg ggttgctgca cagacaagcg acgctccttt cctgacgagt gtcccttcgg    4380
cccgtggcaa gatttgccag aagctcctgg agttgacggt cagccttctc aagccgctca    4440
tccacacgcc ctcggaggag gcatcgcctg tctcgagccc catcgtggat ggcgttgccc    4500
tcggcggcct tggcgtcgca ctgcccgggt ccatcagcat ggatgccctc accagcgagt    4560
cgggcgcttt cggcgcggcc ggttctctgg acgacgtggt cacctacatc caccttgcga    4620
cggtcgtgtc ggcgagcgag tacaagggag ccagtctgcg ttggtggaat gccgcgtggt    4680
cgcttgctcg cgagctcaag ctcgggcgcg agttgcctca gaacgcgccg gcgagtcgcc    4740
agggtggagc cgccgaaatg gaaggcgagg caatggtgc cgagatgacc attcccggcg     4800
tgatcacgga agaggaacgc gaggagaggc ggcggatctg gtggctcgtc tacattgtcg    4860
accgccatct cgcccctctgc tacaaccgcc cgctcttcct gctcgacatc gagtgcgaac   4920
acctctacca gcccatggat gataccgatt accagaacgg taacttccgt gcctacacaa    4980
ccgacccgaa cgttctcggt tcggataccg agggaaaacg cacccgggtc aagggccccct  5040 cgttcgtgtg cagcggccac agcatctttg gctacttcct cccactaatg accatcctcg    5100
gcgaaatcgt agatcttacg cacgccaaaa accaccctcg cttcggcgtc gggttccgtt    5160
cgtctcgcga gtgggatgac caaacggccg agatcacccg ccaccttgac atgtacgagc    5220
agagcctgaa ggagtttgag aagcgacacc tcagcatcaa cgcgcaagcc caggcagcag    5280
acgagaaggc ggccgaggcg gccggcgtcc ctacggctaa tgctaacgac ctcccgggca    5340
cccctcgggg tcacagcgtg cacagcgtgc acaccacgtc gagccgcatg acggagagcc    5400
acatccagac ccgcatcgtc gtggcctacg gcactcatgt catgcacgtg cttcacatcc    5460
```

```
tcctcaccgg caagtgggat cccatcaacc tcctcgacga caacgacctc tggatcagca    5520
gccaggggtt catcacggcg accggccacg cggtcagcgc agccgaggcc atcagcaaca    5580
ttctcgagta cgaccccggg ctcgagttca tgcccttctt cttcggcatc tacctcctcc    5640
agggctcgtt cctgctgctg ctcattgccg acaagctgca gctcgaggcg tcgccgagcg    5700
tggtgaaggc ctgcgagacc atcatccgcg cgcatgaggc gtgtgtggtg acgctcaata    5760
ccgagtatca ggtatgtaca tgttaaccca atcaaatcaa aatcactctg gtggtggtgg    5820
cctcgaggaa acataaacag atgctaactc gctattttt tcacccaaac agcgcaactt    5880
tagccgagtc atgcgcagtg ctctcgctca ggtacgggc gcgtgcccg aggaccttgg    5940 cgagcagcac cagcgtagga gggaactcct cgcgctatac aggtggacgg gcgatggtac    6000
cggtctggcg ctgtagaaaa agggcctgac cggttatttc cacttgttac tcctcgtgtg    6060
taaccgtggg tttggctgtg tcttttcag ccccgcccgg atttcccgca tctctctatt    6120
ctgttctcta cagccacaca caacgggttc gtcggttggc atttcaattg ttttttcccc    6180
ccttataacc ggcgatgctt cttctcggct ggcgtttgat ggcttgatgg cttttcattt    6240
gggctttggg aaggtgttt cagggttgtt cccaaaaaaa aataaccgaa aaggcaaagg    6300
gggttcactg gggggtcttt ggaaggttgg cggatatcgg ccgatgagag attcccttac    6360
aggacggaca agtggggatg gtttggagga ggtagaacat gagcagatgg ggacgatttt    6420
tgatggctcc ttcaacgacg acggaacgga ccccgacatg actcactcta tggatgaggg    6480
agattgtgtg gcggtgctgg gtcttgagcg atatattga cggtttctgt tttagacgcc    6540
gtttggcatt gaggttttt ttttttttt gttgggttgc tgtgattttc tctttggata    6600
cctcagttct tctggctttt ggaaggggcc ctggaagttc ttttgtttct tctgtcgact    6660
gttggctagg ggggacactc tgggaacctg tactgcgaac aatactgtgt agatatcatg    6720
tttttgtata cggattaggt agtgatgata caccgtatga cttacatgac cccggactga    6780
gcctgctcgt cttatttct tacatagcct gccagatgtg ttagccgggc tcgccgccgg    6840
tctagtcaac gttttctctc gcacggcagt caattctcgc cgcccgggcc gcattcagca    6900
ttggattggt tttagctca tcagctccat gtctgacaca actctacacc tcagaagcat    6960
cgaaccggag gagctttcga tcgcatttca catggccgac ccagcaattc gttcgttgac    7020
aatagcaaca acagtgcatt cttccacagg tagatcctca tgaacagctg gtgacagata    7080
tctgtttggt tttcatgatc ccggatggtt tcttgacgtt tactcgtcgt gccgccgtca    7140
actcaacact tcgccggccg accacgggaa agtgacgggc gaacatattc gagtcccttg    7200
tgtgggaaga atcgttcatg ttcttaccaa tgctgaccct gtctggggac acattggtcc    7260
ggtagtatcc tgctctgggc gaccttgaaa caagcaggcc aagatatggc ccatgactct    7320
atcgtgcgca ttcaactcgg ggtcgccact gtgattatgt ccgccggttc ttaaagggag    7380
cttctcaaag tcgtggcgga tgagctattc gtccaacaag aagatatggg aggccaccaa    7440
caaggacatg ctcctcaaag catatcgagc atcaagcagc aatcaggggc gccgactttg    7500
tcctcggcgt cgggctcagg agccgccctc gtgactgcca acgatccatt cgagaacaaa    7560 gaaccccgc aaagccaggg ctgggcattt gcgtggaggg atgcgaggca tcgccaccga    7620
cgagacggcc gtctccatca agagttggac caatgagggt gtatgcccg tcgaatagcg    7680 agcaagacac gccgttgcgt cgaacccgag atgtctggat cggcgacggc gatgaagatg    7740
cgaaaaaact ggttaggcga cgcgggcgtg cgcggaggag actggcctag tagatagagg    7800
```

```
caaaaggcct ggcgggaatg aggtggtgac gtcgaccgat attctggacg gttcccctga    7860
agcaggtcgg gggcttaggg cggtaagtcg tcgtatatag cgaagtcaga gagagtgtgg    7920
ccgttgtttg tccgaggagg cggcggccag ccaccaacca agtctccagc cacactctcc    7980
tcaaccgctc atccattggt cacctcagag agattatcct cttccccccc ccccccccc    8040 cccctctttc tctctcaaac cccctagcc tccagatccg ccatcttctc gtccatcctc    8100
ctcgccgcct cctcttccgc atcatccgcc tcggcggcgc caccaccccg ggggcgcgc    8160 actaccacga cctcgatccc cctcctcctc agctcgtcct cgacatcgcg gcgggtgacc    8220
atgcccctct ctgcgccgcg catgatgcgc gcgagatcgg cgcgcatctt gcggcccag    8280 ccgtcgaggc tgcgcatgcc gacgacgagg aagccgagct cctcgcggtc gacgtcgaag    8340
acctcccacc actcgcactc gggcatcttg gcgccgacgt cgcgggcggc gttgtagacg    8400
gccgcgacgg ccagcgcgtt gggctggctg gtcaggtaca gcatctgggg cgagagcagg    8460
gcggcgttga ggtaggcgac cgcccggctg ccgatgcgct cccgcggggc cacggccagg    8520
aagtcgagcg cctgcaggta cgtgacggcc agcgggtggg gcagggcgac gtgggtgtcg    8580
aaggcgaggg cgtagagcgc gcgggcctcg agcgcgagga cgcgggcgtg aaggcgtgg    8640 taggcggact cggacaggta gtagctggcc ggctcgttgg ccggggggcgg ggcggtcggc    8700 ggctggaaga gcgagctgga cggggagagg aggtaggcgt agacgttggc caggtcgcgc    8760
ggggaccgtg ggtgggccga gagcttggcg gtcaggtaga ctgttgcggc cgagacgtcc    8820
tgtttagata gtgggcgttg gggagggag acacgccccg gcccattcta tcagtcgtcc    8880
tagtcccggt aggtgggttg cgtgaggata aagcgaagaa agggcgaaaa agagcgtacg    8940
ctgaactcat gagacatcat gggctcgacg agccagtatc gcgcaagaag cacgttggcc    9000
tgcgccgtga cggact                                                   9016
```

<210> SEQ ID NO 7
<211> LENGTH: 952
<212> TYPE: PRT
<213> ORGANISM: Mycelophthora thermophila

<400> SEQUENCE: 7

Met Leu Ser Asn Pro Leu His Arg Phe Ser Pro Tyr His Ile Pro Ser
1               5                   10                  15

Thr Thr Leu Leu Ser Asn Gly His Val Pro Gly Gly His Leu His Ala
            20                  25                  30

Ala Gly Leu Asp Ser Leu Ala Pro Gly Ser His Tyr Ala Leu Gln Gln
        35                  40                  45

Leu Gln Gln His Val Gly Val His Thr Pro His Leu Ala Arg Thr Gly
    50                  55                  60

Pro Gln Pro Lys His Arg Gln His Pro Tyr Gly Pro Ala Ala Arg Ser
65                  70                  75                  80

Ser Gly Ala Ala Gly Pro Ile Arg Arg Arg Ile Ser Arg Ala Cys Asp
                85                  90                  95

Gln Cys Asn Gln Leu Arg Thr Lys Cys Asp Gly Gln His Pro Cys Ala
            100                 105                 110

His Cys Ile Glu Phe Gln Leu Gly Cys Glu Tyr Ile Arg Glu Arg Lys
        115                 120                 125

Lys Arg Gly Lys Ala Ser Arg Lys Asp Leu Ala Gln Ala Ala Ala
    130                 135                 140

Gln Ala Ala Ala Gln Ala Ala Gln Asn Gly Gln Lys Thr Glu Asn Ser
145                 150                 155                 160

-continued

```
Thr Thr Glu Asn Thr Lys Pro Ala Glu Asn Arg Asn Asp Thr Pro Ser
            165                 170                 175

Asn Thr Lys Pro Val Leu Thr Val Asn Thr Asp Gln Pro Pro Ala Leu
            180                 185                 190

Asp Lys Asn Val Thr Asp Val Pro Glu Asp Pro Asn Leu Arg Glu Gln
            195                 200                 205

Arg Thr Gly Ser Ile Glu Ala Leu Gly Asp Met Ser Ala His Pro Ala
        210                 215                 220

Pro Met Ser Ala His Pro Gly Ala Ile Glu Arg Glu His Leu Asp Asn
225                 230                 235                 240

Pro Thr Ala Leu Asp Leu Asn Gly Tyr Gly Ser Val His Ser Ala Tyr
            245                 250                 255

Asp Arg Gln Met Gly Ala His Met Met Asn Gly Pro Pro His Ala Pro
            260                 265                 270

Tyr Gly Pro Asn Gln Gly Asn Met Ser Ser Tyr Pro Glu Leu Pro Tyr
        275                 280                 285

Ala Leu Gln Thr Gln Ser Pro Thr Gly Tyr Pro Ala Asn Ala Ala Asn
        290                 295                 300

Gly Phe Arg Leu Ala Asn Ser Pro Leu Gly Pro Tyr Ser Met Gly Gly
305                 310                 315                 320

Glu Ala Pro Ser Pro Gly Gly Trp Met Asn Met Ser Ser Pro Pro Pro
            325                 330                 335

Gln Phe Ala Ser His Met Pro Gln Asn Gly Tyr Asn Arg Ser Gln Leu
            340                 345                 350

Arg Tyr Pro Val Leu Glu Pro Leu Val Pro His Leu Gly Asn Ile Ile
        355                 360                 365

Pro Leu Ser Leu Ala Cys Asp Leu Ile Asp Leu Tyr Phe Ala Ser Ser
370                 375                 380

Ser Ser Ala Gln Met His Pro Met Ser Pro Tyr Val Leu Gly Phe Val
385                 390                 395                 400

Phe Arg Lys Arg Ser Phe Leu His Pro Thr Lys Pro Arg Gln Cys Gln
            405                 410                 415

Pro Ala Leu Leu Ala Ser Met Leu Trp Val Ala Ala Gln Thr Ser Asp
            420                 425                 430

Ala Pro Phe Leu Thr Ser Val Pro Ser Ala Arg Gly Lys Ile Cys Gln
        435                 440                 445

Lys Leu Leu Glu Leu Thr Val Ser Leu Leu Lys Pro Leu Ile His Thr
450                 455                 460

Pro Ser Glu Glu Ala Ser Pro Val Ser Ser Pro Ile Val Asp Gly Val
465                 470                 475                 480

Ala Leu Gly Gly Leu Gly Val Ala Leu Pro Gly Ser Ile Ser Met Asp
            485                 490                 495

Ala Leu Thr Ser Glu Ser Gly Ala Phe Gly Ala Ala Gly Ser Leu Asp
            500                 505                 510

Asp Val Val Thr Tyr Ile His Leu Ala Thr Val Val Ser Ala Ser Glu
        515                 520                 525

Tyr Lys Gly Ala Ser Leu Arg Trp Trp Asn Ala Ala Trp Ser Leu Ala
530                 535                 540

Arg Glu Leu Lys Leu Gly Arg Glu Leu Pro Gln Asn Ala Pro Ala Ser
545                 550                 555                 560

Arg Gln Gly Gly Ala Ala Glu Met Glu Gly Gly Asn Gly Ala Glu
            565                 570                 575
```

```
Met Thr Ile Pro Gly Val Ile Thr Glu Glu Arg Glu Arg Arg
                575                 580                 585                 590

Arg Ile Trp Trp Leu Val Tyr Ile Val Asp Arg His Leu Ala Leu Cys
            595                 600                 605

Tyr Asn Arg Pro Leu Phe Leu Leu Asp Ile Glu Cys Glu His Leu Tyr
        610                 615                 620

Gln Pro Met Asp Asp Thr Asp Tyr Gln Asn Gly Asn Phe Arg Ala Tyr
625                 630                 635                 640

Thr Thr Asp Pro Asn Val Leu Gly Ser Asp Thr Glu Gly Lys Arg Thr
                645                 650                 655

Arg Val Lys Gly Pro Ser Phe Val Cys Ser Gly His Ser Ile Phe Gly
            660                 665                 670

Tyr Phe Leu Pro Leu Met Thr Ile Leu Gly Glu Ile Val Asp Leu Thr
        675                 680                 685

His Ala Lys Asn His Pro Arg Phe Gly Val Gly Phe Arg Ser Ser Arg
    690                 695                 700

Glu Trp Asp Asp Gln Thr Ala Glu Ile Thr Arg His Leu Asp Met Tyr
705                 710                 715                 720

Glu Gln Ser Leu Lys Glu Phe Glu Lys Arg His Leu Ser Ile Asn Ala
                725                 730                 735

Gln Ala Gln Ala Ala Asp Glu Lys Ala Ala Glu Ala Ala Gly Val Pro
            740                 745                 750

Thr Ala Asn Ala Asn Asp Leu Pro Gly Thr Pro Ser Gly His Ser Val
        755                 760                 765

His Ser Val His Thr Thr Ser Ser Arg Met Thr Glu Ser Asp Ile Gln
    770                 775                 780

Thr Arg Ile Val Val Ala Tyr Gly Thr His Val Met His Val Leu His
785                 790                 795                 800

Ile Leu Leu Thr Gly Lys Trp Asp Pro Ile Asn Leu Leu Asp Asp Asn
                805                 810                 815

Asp Leu Trp Ile Ser Ser Gln Gly Phe Ile Thr Ala Thr Gly His Ala
            820                 825                 830

Val Ser Ala Ala Glu Ala Ile Ser Asn Ile Leu Glu Tyr Asp Pro Gly
        835                 840                 845

Leu Glu Phe Met Pro Phe Phe Phe Gly Ile Tyr Leu Leu Gln Gly Ser
    850                 855                 860

Phe Leu Leu Leu Leu Ile Ala Asp Lys Leu Gln Leu Glu Ala Ser Pro
865                 870                 875                 880

Ser Val Val Lys Ala Cys Glu Thr Ile Ile Arg Ala His Glu Ala Cys
                885                 890                 895

Val Val Thr Leu Asn Thr Glu Tyr Gln Arg Asn Phe Ser Arg Val Met
            900                 905                 910

Arg Ser Ala Leu Ala Gln Val Arg Gly Arg Val Pro Glu Asp Leu Gly
        915                 920                 925

Glu Gln His Gln Arg Arg Glu Leu Leu Ala Leu Tyr Arg Trp Thr
    930                 935                 940

Gly Asp Gly Thr Gly Leu Ala Leu
945                 950

<210> SEQ ID NO 8
<211> LENGTH: 2127
<212> TYPE: DNA
<213> ORGANISM: artificial
<220> FEATURE:
<223> OTHER INFORMATION: clr1 cDNA
```

<400> SEQUENCE: 8

```
atgtcgccct cctccaacgg cgactcgccc cactcggtca cggccaccat gactactgct      60
gccgcagccg cgccacggt cgtcaggcag tacccgccgc tgccgaattg ggacttcacc      120
gtcgagatac cctctccgca gcagctctct gccggcgcca acggcgccaa cacgatcaag      180
tctccgaact cgctcaaggc ggcaacacgg actccgaact tcagccggga aggcatcctc      240
ggctcggccc agaaagcccg caacctatcg cagtcgtcgg ataacaggcc cgagacgatc      300
acgaacggca ttcccaagtc tgcgagtgaa gagggcgtta atccgctcaa gaggagaaat      360
acagatgccg ccgtcgatta tcctaggcgg agagcgacca ttgcctgcga agtctgccgc      420
tcgagaaagt cacgatgtga cggtacgaaa ccgaaatgca agctctgcac agagcttggt      480
gcagagtgca tttatcgcga gcccggcatc aagctcgacg cggggggataa gctcatcctg      540
gagcgcctta acaggattga gagccttctg cagatgaacc tggttgccaa ccaaggaaac      600
ggtatcaact gtctcacga ctcgccaaac atgagcaatg gaaccgccct gagcggggat      660
aacctcctgg tgcgggaccc gagcagcaat tttgtctccg tcatcccag cggcggcctg      720
gggacctggt cggcaaactc gacaaacatc tcaactatgc caaaggtgca caccaacgcc      780
gccctccacc ttctgcaatg gccgctgatc cgcgacttgg tctcgcggcc gtatgaccct      840
caaattctcc tccagcttga aatggcccgc gaaccgctgc actcgctcgc gaagacgccc      900
tgcgtcgact tgtccaacac gaatgcgtac atcgaggcgt actttgaccg agtcaatgtg      960
tggtacgcct gcgtcaaccc atacacctgg cggagccact accggatcgc tctatccaac     1020
ggcttcaggg agggtccaga aagctgcatt gtacttctcg tcttggcgct cgggcaggcg     1080
agcttgagag gcagcatatc caggatcgtc ccgcacgagg accccccggg ccttcagtac     1140
ttcacggccg cttggtcatt gctcccgggc atgatgactt ccaacagcgt cctggccgcc     1200
cagtgccacc tgctcgcggc cgcctacctc ttctacctgg tgcggccact ggaggcctgg     1260
aacttgctct gcaccacaag tacgaaactg cagctcctgc tcatgacgcc gaaccgagtt     1320
cctccggacc agcgagagct tatcgagcga atctactgga acgccctgct cttcgagagc     1380
gacttgctcg cagagttgga tctaccccac tctggcgtcg tcgcgtttga ggagaatgtg     1440
ggcttgccct gcggtttcga gggggatgaa caggaggcag tcgggcgaga cgagctatgg     1500
tacttcttgg ccgaaatcgc gctccgccga ttgctgaacc gggtcagcca actcatttac     1560
tccaaggact cgatggcctc gacgaccagt ctcgagccgg tggttgccga gctggatttc     1620
cagctgacgc agtggtacga aagcctgccg gtgcccctgc aattcccatt tacgcgcacc     1680
atgttaccgg atccggtgca gacggtgttg aggctgcgct tcttcgcatg ccggaccatc     1740
atctaccgcc cgtacatcct cgcggtcctg acaacgaac aggccatatt ggaccccgcg     1800
gtgcgggagg cctgtaccaa gtgcctagaa gcctccatcc ggcaattgga gcacattacc     1860
gcgcatcacg ccggacacat gccttacctc tggcaaggtg cgctttccat cgtgtcgcag     1920
accctgctcg tcatgggtgc cacaatgtca ccgtcgctgt ctaccatcct ctggagcctc     1980
gtcccccacc gcgaggcaat cgaccaaatc atcaacgacg tggtcatgga aattgaacgc     2040
tacgccgttc tttctcccag cctcagcctt tccgctgaaa tcatcaaaga agctgaggtc     2100
cggcgccgga ctttcctgag cggttga                                           2127
```

<210> SEQ ID NO 9
<211> LENGTH: 8245
<212> TYPE: DNA

<213> ORGANISM: Myceliophthora thermophila

<400> SEQUENCE: 9

```
gcctgggacc gctaacacta ttttgcgtag ggaccattat tagcacttca gttgcgctga      60
gcgtacagtt caggaccgat gcgctccact aatgcacacc aactacggag tgcccacgca     120
aggcttactt ccttgggagt tgttgtctc ggacatcgtt cttgttggcg gtctccgtga      180
cgatatagat ggtatagccg gcggtaggac acaccgacct aactacctag gtaaggaatg     240
catctgagac ggctctgttc ctaccacata ctgcggcggt gtcagggtcc gctcggttac     300
ccgaaatagg acacggcttg ctcgacaggc caggtaccac agactcgctt gcggtggcga     360
tcttagggtg gatcgtggtg ctcacgaggt cttgtgcccc aacaagaaag gaaggagtcc     420
tcatttgcgg cggaagcagt cgattctgtg tgcagagacg gagagcaccc gtattcacat     480
gaccctcaag ctgtcgtttg catgttcagt atggatacat acaaatttaa ctgcgtgcct     540
gtgcatgacg gaagggcggc ggcagcgtct cgaataact accggctgtc tcagtccccg     600
tcacccgaaa atcaggtcag ggctcaacat gcagtggaag ccagccatac caggcagagg     660
gattggatgt cgcgcgtgcg cagatacata ctatgtagta cggtgcacaa cacggcatac     720
ccggagggtg cagcctgtcc ccgcgcttgc tgcttcgagc gatgatcttg tcctgccatc     780
ctgcagctag tgtcttggac aatcagacga aaagcgccca gtgcggtgtg tgtgtggggg     840
tgggccgccg cttctcgaag ccttcgaccc gtcttccaag ggaccatgtt gccggacgat     900
gcgggaaacc cgagccttgg tctgacgtgg ttcagcagcc aagagattgc taatgcaggt     960
agcgtcaagc ggctgccgaa tttatgctaa aagaaaagga tgaaaggttt gctgaggctt    1020
cacctagcca tgttgcggac ttgctcctgc gtgcattgaa gaaaatgcag ctccttttca    1080
atgggtgttt ccatctcgag cgggtagaag gcgttctcct gccaccgagg tggcatattc    1140
ttctatagag gttgcttaga actgttgaga tttactaccg ctaccgcact ccaagcaaaa    1200
caagagacgc gagcgctgtc gtggttgttg tccgctgcaa ctaccagtgt tcgttagtca    1260
aggggtgatt cattcgaagg actgcggcgt ggcaggcgct cgacgccatt cacacctatc    1320
atcatgccat actagtactt gtatttccta tcgcccagag gataggtac gcgaggtctt     1380
ttagcgccca agcccgcccg tcaacacacc accgttgct gagcgacatg atcggcggac     1440
caaggatgtc acctagagga ggttggatgg aatgctcgga cctctacatg gatagggccg    1500
gcttctcttt gcagttctcg cttccaccac tcaccaatcc cttcgcgagc tgaaaggctc    1560
acttctgtgt tacgaaacga atccagaatt gggacccgac gatgagacgg tgaattatgg    1620
gaaataatgt ccttaaactc ggcgacgtaa cttcgaaggg aagacaggag agttgactga    1680
tggcagcggg aagctgcgga cctcgacccc aaaaaaaagt ggcccagtga tcgctgcgag    1740
cggttcgaat cggaaacccc accccgcgt ttttttggtt ggcatgctct ccttcatttg      1800
cttctctccg cacacccaaa cttcctgacc caccatttct catgccggcc tggcctgggc    1860
gtgccatttt cgccctctgc aaccgaggta gctaatgtga aaaacaccac ttcgtacata    1920
cctctactgt gtacactacg gcggtagtat cagcagtcgg tggctcgttg cccatttgcc    1980
aacaatgaca cggccgcccc ctgatcgcgt tgtgcagctc cccagaattt tcaagggcgt    2040
ggcaggtctt tcgtgatagc tatttggtct ggtggagaag gaccacagtt gtttcggttt    2100
ggcgcgcgaa ccattgcagt ctctttttgg ccccacccct actccgaagt gtactagtac    2160
tatgtagtgt aggcatctcc acgttcggag cagggcgaga gacaaaaacc caggagaaaa    2220
gcgacatttg aagcacccca caatgcatct tctttcgaag cgtccatgca accctcggca    2280
```

```
agggcctttc gtgcgcaacc gcagtcgtct cctcaccccg gtcggcacta gtgcattcta    2340
cccctgctcc ccgccgcccg ccctccgtta gactatggca ggcttttccccg gcttccttct   2400 cagttaacag gtccaggcgc ctcccccccgc agagactcgc cgttttcgtt agcacagtac    2460
aagtgcctac cccagacacg cgccagccct tgcctgctgt ggttcagggt acattggttc    2520
acggacagcg gccgcgcccc ctgattggag tccccagctc gtctcgcaaa ggctgtaccc    2580
cgttgtgggg gatgggagac atatgaatcc gtcaccttcc ggtccccaaa atcccggcgc    2640
agcttcccac ccaattcccc taccaagccc tttccgcccg aacctgacgc accacgcacc    2700
atcgcctgcg ccaaaccagt catccggcac tggctcttcg gtcctgtcgg tagcggcacg    2760
ataatgcgac ttcgactgcg agccgcgggt cctagtgttt tcggtgcttg cggcgtctga    2820
atcgtcgcac ttcggtgctg gagcagccgc cgacgttgct gaccggtcgt ccaaatcgaa    2880
gaaacaaaag acctaaaaaa aaaaaaaaaa aagaatcgtc gacgacttcc ctgtctccaa    2940
acttgtggac acgctaaaag gcccccgtc cgcctggtgt cgcggtctgc agagctcagc    3000
atgtcgccct cctccaacgg cgactcgccc cactcggtca cggccaccat gactactgct    3060
gccgcagccg cgccacggt cgtcaggcag taccccgccgc tgccgaattg ggacttcacc    3120
gtcgagatac cctctccgca gcagctctct gccggcgcca acggcgccaa cacgatcaag    3180
tctccgaact cgctcaaggc ggcaacacgg actccgaact tcagccggga aggcatcctc    3240
ggctcggccc agaaagcccg caacctatcg cagtcgtcgg ataacaggcc cgagacgatc    3300
acgaacggca ttcccaagtc tgcgagtgaa gagggcgtta atccgctcaa gaggagaaat    3360
acagatgccg ccgtcgatta tcctaggcgg agagcgacca ttgccgtacg ttggaatcgc    3420
aacggaaccg tgtttccccc gatactgact agtcggtagt gcgaagtctg ccgctcgaga    3480
aagtcacgat gtgacggtac gaaaccgaaa tgcaagctct gcacagagct tggtgcagag    3540
tgcatttatc gcgagcccgg catcaagctc gacgcggggg ataagctcat cctggagcgc    3600
cttaacagga ttgagagcct tctgcagatg aacctggttg ccaaccaagg aaacggtatc    3660
aacttgtctc acgactcgcc aaacatgagc aatggaaccg ccctgagcgg ggataacctc    3720
ctggtgcggg acccgagcag caattttgtc tccgtcatcc ccagcggcgg cctggggacc    3780
tggtcggcaa actcgacaaa catctcaact atgccaaagg tgcacaccaa cgccgccctc    3840
caccttctgc aatggccgct gatccgcgac ttggtctcgc ggccgtatga ccctcaaatt    3900
ctcctccagc ttgaaatggc ccgcgaaccg ctgcactcgc tcgcgaagac gccctgcgtc    3960
gacttgtcca acacgaatgc gtacatcgag gcgtactttg accgagtcaa tgtgtggtac    4020
gcctgcgtca acccatacac ctggcggagc cactaccgga tcgctctatc caacggcttc    4080 agggaggggtc cagaaagctg cattgtactt tcgtcttgg cgctcgggca ggcgagcttg    4140
agaggcagca tatccaggat cgtcccgcac gaggaccccc cgggccttca gtacttcacg    4200
gccgcttggt cattgctccc gggcatgatg acttccaaca gcgtcctggc cgcccagtgc    4260
cacctgctcg cggccgccta cctcttctac ctggtgcggc cactggaggc ctggaacttg    4320
ctctgcacca caagtacgaa actgcagctc ctgctcatga cgccgaaccg agttcctccg    4380
gaccagcgag agcttatcga gcgaatctac tggaacgccc tgctcttcga gagcgacttg    4440
ctcgcagagt tggatctacc ccactctggc gtcgtcgcgt ttgaggagaa tgtgggcttg    4500
ccctgcggtt tcgaggggga tgaacaggag gcagtcgggc gagacgagct atggtacttc    4560
ttggccgaaa tcgcgctccg ccgattgctg aaccgggtca gccaactcat ttactccaag    4620
```

-continued

```
gactcgatgg cctcgacgac cagtctcgag ccggtggttg ccgagctgga tttccagctg      4680
acgcagtggt acgaaagcct gccggtgccc ctgcaattcc catttacgcg caccatgtta      4740
ccggatccgg tgcagacggt gttgaggctg cgcttcttcg catgccggac catcatctac      4800
cgcccgtaca tcctcgcggt cctggacaac gaacaggcca tattggaccc cgcggtgcgg      4860
gaggcctgta ccaagtgcct agaagcctcc atccggcaat ggagcacat taccgcgcag       4920
taagtgtcct gcccgcatct cctattggtc ggcgcccctc ccaatctaac caattgaccg      4980
cagtcacgcc ggacacatgc cttacctctg gcaaggtgcg cttttccatcg tgtcgcagac     5040
cctgctcgtc atgggtgcca caatgtcacc gtcgctgtct accatcctct ggagcctcgt      5100
cccccaccgc gaggcaatcg accaaatcat caacgacgtg gtcatggaaa ttgaacgcta      5160
cgccgttctt tctcccagcc tcagcctttc cgctgaaatc atcaaagaag ctgaggtccg      5220
gcgccggact ttcctgagcg gttgatccat tgcacatcca gtgcgaacgc ctaacgtccc      5280
gcccagagct tcctgccagg acacttgttc taaggcatcg acgatgcacg ctaccaacag      5340
tcaaacatca cgcgatagcc ccggcatccc tgaccggcac cctcgcaacc aagtgctggg      5400
gcacagcgga ggtttcggcg gtctacgaca tcagctgcga aactgcgcgc ctggttttcc      5460
tgtgagccgg tttccgtgct caagatgtgg acaaaagagc tggcacgtcg gaaaagcaca      5520
cacggatgct tcccctgtct ccctgtccct gttcctgaaa agtgggctg gcagtttcaa       5580
gtgggaagtg tgtccggcca aaacgcagac tgctgagcat ctgcaggctt ggttctgggg      5640
ttgcacactc tgtttgccgc agcgagtcac aatttggcct cttgttgagc aaggctgcgg      5700
atgacctttg gggtgcggag aagccggccc gagctgccgc ttcccaccttt tccattcccc     5760
gctccccgca ttctcttctt gatgcgctcc ctgctcggga cataatccga acggggacgc      5820
gttcctcttt ttttttgttg catcttagcc ctccggggct ggttcctaac gtcaagtacg      5880
aaaacttgga gggggggggt tcaaaatcgg catgggatac accgaccacc gtttggcgtt      5940
gggatggagt gcctttgtga ggacatgcta gctacgtttc ggatgtttca gttgcattt       6000
cattgcggta ctatctcatt aagatgctgg atatatcccc gggcttatac cattcaatat      6060
gtattcaagg gtatggtgat cgagccgtat gagttacgtt gcctgaaaaa aaaaaaaaaa      6120
acaatctccc caaattccat ccgttgtact ggtgaaccgt ttaggtcgtg atcgaatctc      6180
ctgaacaact ggtgatggtc tttgcgtcca tgagatcaag ccacaacaat gaggcccgtc      6240
ggcggcattt gggtcctata tctggtcatg gcttaagtgg ttcgcttcct ctgcctgtat      6300
gatccatctc ggcccaccac aacggtgcag catggcgggg cgtgctgctc gaacaagatt      6360
ccttatatcc cctttcgaaa gaagaaaga tactacgaag gaaatcgcga tgatccttt        6420
aacacatttc atgtcgtgta ctatggaagc ctaccaccac tttaacctgt aggtacccga      6480
tttggtgcag atgtggaagt actaggtatg taccccaggt ttttccctttg tggcgccttc     6540
tcttacccac tttctcaccc caagttttc tccttctccc cctcgtttc ccatctcacc        6600
ggggcccgtc ctccgacgcc atatgcaagg gccggaacga tcgccgagca tagccacggc     6660
cgcacttatt tgtacgggaa gcggaacggt ggttggggg ccagcagggt gggtggggag       6720
ggttggtgag agtcggatgg cctcgatggg gaggaacttg atcggagaag tgtttccatc      6780
aaaaatcaac gggggtgcac tctcggtgga cttccccaaa tgagcataag cgcatttatc     6840
cttttctctt cctttgtctc gtttctgctt cgtcctggtc aagatcggat tgaacgcgg       6900
ggcttagtgc tagcgcgcaa ttccgcacgc ttctattctc tcttcgccgt tggttctctt     6960
ccatcggcag aagcgggcgg ggcgggtttt ggggggggg gggagcaaca cgcccaaaag      7020
```

```
cgcccagacc tgccatctgc cacatcacac attcccatcc cgtccatcat cgtatactgc    7080
agtagttatt ataacttggc agttattgac tcccggttcc ttacccgagt cactaatcgt    7140
gcaatggtgg cgaggcgcat agttgtttct ttgagccaaa cgcattaccc caagactttg    7200
ttgagcggat tgagttatcc acaaaacagc tcatccgtac ccttagtcag actgatggaa    7260
tcggcggatg agcccgaagc agctctcgcc cgaccggggg tggctgaccg tgtatgcaca    7320
atacgaaatc ctacaggtac ttgcggtagt tatgtcatcc gtgcgcagta cgaaccttgg    7380
gtccagagta ggtagtgtca caaaagccca taggcagggg tgcgcttctc gacgcattct    7440
cgaagcatat cctgcaggtt ccaattccct gcggtacata aggtacatac aaacgctatc    7500
tccatggcaa tctggcccgc gggaataaag gacggacacg gacgccgagg agaacgggta    7560
agtgggttcg caggagcttc gaatcgctcg aatcattatt agcgtgtgcc gtgtcctcca    7620
catggtcgtg gatgacaatc gcttacaaag ccccccaggggt ggaagggggg gggggggaat    7680
ggccccccgt gtttgtcgac tttgccgtgg cccgaacggc agcccacgcg gaccgttctg    7740
ggttgtgcag gatgccgaga tcgcttgca aaccgcgcgt ctctcctttg atcatttcaa    7800
atcccaaatc ttcagaaagg ctcggtttcc tgccaccgta gcccctccaa atcgtgtgtt    7860
ttctttctat cctcggtagt agttatttca ctttgttttt atcttcttga accgacaagc    7920
cgtgggtggt tcgtaattgc cagtgaagtg aagtcctaag atgccgtcta ggcgtcttca    7980
actcggaagc ccgcatactc gtatatttgc aagagacttg gattaaattc aagttgcgta    8040
tgtgcctgtt gacgcccaag aaatcgggat caggtacagg tttcacggcc gtcggttgca    8100
cagcatggct cgatcggcgg cccatggtcg gcctgctcgg agtgggtacc cttggagcgc    8160
cctgcgttcg gtttatcggc ggagtcgtcc ataggtgcaa gtcatccccg acaggatggc    8220
gatagttatc ccaattggca ggtat                                           8245
```

<210> SEQ ID NO 10
<211> LENGTH: 708
<212> TYPE: PRT
<213> ORGANISM: Myceliphthora thermophila

<400> SEQUENCE: 10

Met Ser Pro Ser Ser Asn Gly Asp Ser Pro His Ser Val Thr Ala Thr
1               5                   10                  15

Met Thr Thr Ala Ala Ala Gly Ala Thr Val Val Arg Gln Tyr Pro
            20                  25                  30

Pro Leu Pro Asn Trp Asp Phe Thr Val Glu Ile Pro Ser Pro Gln Gln
        35                  40                  45

Leu Ser Ala Gly Ala Asn Gly Ala Asn Thr Ile Lys Ser Pro Asn Ser
    50                  55                  60

Leu Lys Ala Ala Thr Arg Thr Pro Asn Phe Ser Arg Glu Gly Ile Leu
65                  70                  75                  80

Gly Ser Ala Gln Lys Ala Arg Asn Leu Ser Gln Ser Ser Asp Asn Arg
                85                  90                  95

Pro Glu Thr Ile Thr Asn Gly Ile Pro Lys Ser Ala Ser Glu Glu Gly
            100                 105                 110

Val Asn Pro Leu Lys Arg Arg Asn Thr Asp Ala Ala Val Asp Tyr Pro
        115                 120                 125

Arg Arg Arg Ala Thr Ile Ala Cys Glu Val Cys Arg Ser Arg Lys Ser
    130                 135                 140

Arg Cys Asp Gly Thr Lys Pro Lys Cys Lys Leu Cys Thr Glu Leu Gly

-continued

```
              145                 150                 155                 160
Ala Glu Cys Ile Tyr Arg Glu Pro Gly Ile Lys Leu Asp Ala Gly Asp
                          165                 170                 175
Lys Leu Ile Leu Glu Arg Leu Asn Arg Ile Glu Ser Leu Leu Gln Met
                          180                 185                 190
Asn Leu Val Ala Asn Gln Gly Asn Gly Ile Asn Leu Ser His Asp Ser
                          195                 200                 205
Pro Asn Met Ser Asn Gly Thr Ala Leu Ser Gly Asp Asn Leu Leu Val
        210                 215                 220
Arg Asp Pro Ser Ser Asn Phe Val Ser Val Ile Pro Ser Gly Gly Leu
225                 230                 235                 240
Gly Thr Trp Ser Ala Asn Ser Thr Asn Ile Ser Thr Met Pro Lys Val
                  245                 250                 255
His Thr Asn Ala Ala Leu His Leu Leu Gln Trp Pro Leu Ile Arg Asp
                  260                 265                 270
Leu Val Ser Arg Pro Tyr Asp Pro Gln Ile Leu Leu Gln Leu Glu Met
                  275                 280                 285
Ala Arg Glu Pro Leu His Ser Leu Ala Lys Thr Pro Cys Val Asp Leu
                  290                 295                 300
Ser Asn Thr Asn Ala Tyr Ile Glu Ala Tyr Phe Asp Arg Val Asn Val
305                 310                 315                 320
Trp Tyr Ala Cys Val Asn Pro Tyr Thr Trp Arg Ser His Tyr Arg Ile
                  325                 330                 335
Ala Leu Ser Asn Gly Phe Arg Glu Gly Pro Glu Ser Cys Ile Val Leu
                  340                 345                 350
Leu Val Leu Ala Leu Gly Gln Ala Ser Leu Arg Gly Ser Ile Ser Arg
                  355                 360                 365
Ile Val Pro His Glu Asp Pro Pro Gly Leu Gln Tyr Phe Thr Ala Ala
                  370                 375                 380
Trp Ser Leu Leu Pro Gly Met Met Thr Ser Asn Ser Val Leu Ala Ala
385                 390                 395                 400
Gln Cys His Leu Leu Ala Ala Ala Tyr Leu Phe Tyr Leu Val Arg Pro
                  405                 410                 415
Leu Glu Ala Trp Asn Leu Leu Cys Thr Thr Ser Thr Lys Leu Gln Leu
                  420                 425                 430
Leu Leu Met Thr Pro Asn Arg Val Pro Pro Asp Gln Arg Glu Leu Ile
                  435                 440                 445
Glu Arg Ile Tyr Trp Asn Ala Leu Leu Phe Glu Ser Asp Leu Leu Ala
                  450                 455                 460
Glu Leu Asp Leu Pro His Ser Gly Val Val Ala Phe Glu Glu Asn Val
465                 470                 475                 480
Gly Leu Pro Cys Gly Phe Glu Gly Asp Glu Gln Glu Ala Val Gly Arg
                  485                 490                 495
Asp Glu Leu Trp Tyr Phe Leu Ala Glu Ile Ala Leu Arg Arg Leu Leu
                  500                 505                 510
Asn Arg Val Ser Gln Leu Ile Tyr Ser Lys Asp Ser Met Ala Ser Thr
                  515                 520                 525
Thr Ser Leu Glu Pro Val Ala Glu Leu Asp Phe Gln Leu Thr Gln
                  530                 535                 540
Trp Tyr Glu Ser Leu Pro Val Pro Leu Gln Phe Pro Phe Thr Arg Thr
545                 550                 555                 560
Met Leu Pro Asp Pro Val Gln Thr Val Leu Arg Leu Arg Phe Phe Ala
                  565                 570                 575
```

```
Cys Arg Thr Ile Ile Tyr Arg Pro Tyr Ile Leu Ala Val Leu Asp Asn
            580                 585                 590
Glu Gln Ala Ile Leu Asp Pro Ala Val Arg Glu Ala Cys Thr Lys Cys
        595                 600                 605
Leu Glu Ala Ser Ile Arg Gln Leu Glu His Ile Thr Ala His His Ala
    610                 615                 620
Gly His Met Pro Tyr Leu Trp Gln Gly Ala Leu Ser Ile Val Ser Gln
625                 630                 635                 640
Thr Leu Leu Val Met Gly Ala Thr Met Ser Pro Ser Leu Ser Thr Ile
                645                 650                 655
Leu Trp Ser Leu Val Pro His Arg Glu Ala Ile Asp Gln Ile Ile Asn
            660                 665                 670
Asp Val Val Met Glu Ile Glu Arg Tyr Ala Val Leu Ser Pro Ser Leu
        675                 680                 685
Ser Leu Ser Ala Glu Ile Ile Lys Glu Ala Glu Val Arg Arg Arg Thr
    690                 695                 700
Phe Leu Ser Gly
705

<210> SEQ ID NO 11
<211> LENGTH: 1191
<212> TYPE: DNA
<213> ORGANISM: artificial
<220> FEATURE:
<223> OTHER INFORMATION: alp1 cDNA

<400> SEQUENCE: 11
atgcacttct ccaccgctct cctggccttc ctgcccgccg ccctcgcggc ccctactgcc      60
gagaccctcg acaagcgcgc cccgatcctg actgctcgcg ctggccaggt cgtcccgggc     120
aagtacatca tcaagctccg cgacggagcc agcgacgatg tccttgaggc cgccatcggc     180
aagctccgct ccaaggccga ccacgtctac cgcggcaagt tcaggggctt tgccggcaag     240
ctcgaggatg acgtccttga cgccatccgt cttctccccg aagtcgagta cgtcgaggag     300
gaggccatct tcaccatcaa cgcgtacacc tcgcagtcca acgcccctg gggccttgcg     360
cgcctctcgt ccaagaccgc gggctccacc acctacacct acgacaccag cgccggcgag     420
ggcacctgtg cctatgtgat cgacacgggc atctacacta gccactccga cttcggcggc     480
cgtgccactt cgccgccaa cttcgtcgac agctctaaca ccgatggcaa cggccacggc     540
acccacgtcg ccggcaccat cggcggcacc acgtacggtg ttgccaagaa gaccaagctc     600
tacgccgtca aggttctcgg ctccgacggc tctggcacca cttctggtgt cattgctggc     660
atcaacttcg tcgctgacga cgcgcccaag cgcagctgcc ccaagggcgt cgtcgccaac     720
atgtcgctcg gcggtagcta ctcggcctcc atcaacaacg ccgccgccgc cctcgtcagg     780
tcgggcgtct cctggccgt cgccgccggc aacgagaacc agaacgccgc caactcgtcg     840
cccgcctccg aggcgtccgc ctgcaccgtc ggcgccaccg acaggaacga cgccaaggcc     900
agctactcca actacggcag cgtcgtcgat atccaggccc ccggctccaa catcctgagc     960
acctggatcg gcagcacctc tgctaccatg cactctcaga acaccatctc gggtacctcg    1020
atggcctccc ccacattgc cggcctcggt gcctacctcc tggccctcga gggctccaag    1080
acccctgccg agctctgcaa ctacatcaag tcgaccggca acgccgccat cactggcgtt    1140
cccagcggca ccaccaaccg catcgccttc aacggcaacc ctctgcctg a              1191
```

<210> SEQ ID NO 12
<211> LENGTH: 11547
<212> TYPE: DNA
<213> ORGANISM: Myceliophthora thermophila

<400> SEQUENCE: 12

```
acagaaacgt ggcacgagtg ggtaaatgac ttcgttcatc aggaccctaa ccgggtccgg      60
tttggcctcc accggttaca actgcgggag ctttgtgagg gcgtcaaaca ttttgttcgg     120
ctcacaaaca aggacgagct tccgaacgag ttgctgaagc tcccgggcag tgacaagatc     180
tcgatagccc gagttctctt gcacggcatg ctggcaaact tcgttatctc ggaagcgttc     240
aagtctccgt tttgggtgtt tgatgccatt gctgtcaacg cttacgagtt agagagcccg     300
actgttccgc gactcgactc catgtcgccg gtcgggtttc ggatggacct aaccgcgtgg     360
aagaatttca atgttgcgcc accgcgcgat gtcaaacctc tcggcctaa ccctgttcct     420 aacgaccgcc tagctggacc gcaagatggg cgtcagcttc cccgactagt caccttaata     480
caaccgccca atctttctac gaaccctgcg atgagtttgc ttggtcgaga gctaccgtcg     540
cggcaggcaa tattagagag cctctaccag atcttatcag agggtaggcc acttctctcc     600
ctctcaccac gccatctctc tgccttcagc tcgtgctaag tagtattacg atagtcgcag     660
gcggtggtta cgcgactgaa tggcgtgcct ctttgatcaa ggcattctgc gtgggtggca     720
tgagttccga gctcgatagt acttcccctgg caagcgagtc tcgcgccttg ccgaagcca     780 ggttcaggca cgctggaagg ctcaaggaca gctttctgag aggtactgcc cggttccttc     840
tccgagatca ggaagcggcg ggcatcgagg agctcgagag ccgtcttatg caagagatcg     900
atgctgcgct gcggttctca tgtcaactct ggtgtcgcca ggacacccctt cgggtgtgcg     960 gtctcgacga gcttgcggaa acggcgctca aagccgctag cgaccatatg cggttgtatc    1020
aagtccaggc gccactccat atcgagcctg ccggtaatac gctcgaatcc cagaccgaac    1080
cccgtggatc ccatgacggc cattccgtga tcatggttat tcaaccctcg gtcggcgcaa    1140
gcgcaaacac caaagccggc aagccaagca aggacttcaa aggcgacacc aaggtttgga    1200
ccaaggctag cgttctcgtg gcagcccccc ccccccccc ccagccgctt gtgcggcagc    1260
gctcggcacc tctgcaaaag gtcaccatcc tcgcaggccc cagcacgtgt tcaacccccg    1320 atttcttcc cagcccgcgc ttccgtcaac gccatcgtcg gcacacctag tcctcttgcc    1380
gcgcatccgg taccgcccga ggatgctcaa gagacgcat taactgtgct ccccagcata    1440
gcttttcggg acatgccacg cccgctggtc aggtaaccga caatgctgcc tctgccgccg    1500
ccaccgccgc cctctttctc ggattttttgg tggcttcacg aaatgatcgg acatatacat    1560
gccgcttctc tctggaagaa ggaatacctg acgcttctgc cttgatggtc gccgtctttt    1620
tgggaacaaa ggcgtgttga agaaaactta ggttgcgcgg tctgaaactc aagtttctcc    1680
aaacctcgtc ttcccccgat tggagcattg gattcgagtc gatcgttgct tgaaaaaaaa    1740
cttggttgcc aaatattagt actacgggta ctggatatg ccgactcttt gatggcatag    1800
cagctcgaac acgaaggccg gagagtgcag tggctaatca ccgtcgtgca atggttctca    1860
gctgatcaac tgtcttgaaa gttgagcacc gaatcatatc gaggacaggt gccgaaggga    1920
tctggaaata ctacctcggt cttacatttc ggtccgacca gtggtattct gatctccgct    1980
cggaccaact gcacgcctac gtcaggctaa taagtttcaa ttcaggcgtt cagatgactg    2040
agaaaggcac gtagcattac ttgaggtgag cgaagtaaat ctacggcaag gatggtactt    2100
tatccaaagc aggcacacga ctcaaacgtt aattacttgc taagtgtcgc ggaaggggcg    2160
```

```
gaatccttgg gcccgtcaac aaacagcaag acaatgcgac ggttcagagc tggagatccc    2220
gtgtcccacc cggagataat caatgcgcat cactgccgct tcggtctctc aggagctagg    2280
cagccgtcgc ttacatgatc aggagcggcc attgaggaat gacaccttct tcccaaagag    2340
cattgttgta actgacatgt aacgcatcgc ggcccaagac atctcgcggc tgcctagtgg    2400
tctgggccag gtcgcacgca acgggcagtc atgctggatt tggcagctgg tgaggtttgc    2460
gcccgcatag caatggggcg atgagaaggc gcaatcgctc acccaaagca tgagcaacag    2520
gaattctgct tgctcattgc tgattgctca ctgcgcactt tattagcgag ggcaacaagg    2580
aaatgcagct gccaatgccg tgcgatccct cggtttcgcg gctatggcga gtagcgtgcg    2640
agggcggcag ggggaggggg cggtggccct cagatcgaaa gggagagaga gagggcgggc    2700
caagatgtga cttgaccgtt acttgatccg gaaggccacc agataaggcc cggcagatga    2760
cccatgctag gcggaacagc gggctgcgga tgcgccgtac gcgatcgatt tcagtggggt    2820
ttctctgctt gggggaacac agatcacgtt agggagagtt ggcgacaatg caggaaccga    2880
gcttttcggg tattcatctt ctgtctgtca gatctttgtg agatgtaact ggctatcttt    2940
ttggctggat gctggcggtc agcaatgggt cgacctgtct tgagtcaaat ccaacccgtc    3000 ggattttgg cttgggtttc tgcagtaacc gggtaagtaa cctggtttag ggaacaggaa    3060
aggtggatga gggtggcatt acacgtgtac ttgcgcttgg cttcgacata gtaataactg    3120
tagtaatccg tacgataata ctccgtagat gaaagcgttt caaggacgt ggcagggta    3180 ggggaagggg attaactaca catgtgggca ggagcccgat ctggaatctc gctgcaccgc    3240
ccacttttct gccacagtgc taccggacta ctcgctaggg tagtgtactg taggtagcta    3300
ggtcgtgact gtaacctacc ttagtcgcag cacccaaccg gatactaact atgtattcac    3360
tcttgccaaa cttgctcaca aaacacttta gtacgcagag ttactttgca ctcgcatgga    3420
aattcccctc cccccacggc cagacttgga ccaaggaaaa gagataccac ctgccgaacg    3480
tggctctcgc tccagcattt cgagagcgta cctcagccaa ccactcggct ccccgtgtcg    3540
agcgatcggc acttgcggcc tttgcaatgc cccatccttg aactccacca aataggctac    3600
caccacacca cccctccatt tcttgttcct cggcttcctc gctcgaggta ccgatccagg    3660
gtgggccgat tgcgatggtg ccattgctgc ccttgctttg gcttcaccta ggcgatgtca    3720
cgttcagata tagtccgcag gctttacccc agatcctctg attgccgatc tcggccatga    3780
cctctggttg tttcacaagc acacagggtc agtcgccccc gttgcgcctc tgtacagtct    3840
gtacagacct tctcagctga atgtttccga gactagagac taaaatctga atcactttgg    3900
cccagagaga gggttcgcga agtcccacac acccttctag aaggagagac cagagccacg    3960
aaacatgaag cctgatcgct tatttttttt ttttttttttt ggccccggag tgcccgcggt    4020
cacggtactt tggggttatg acaggctgtt tgacttccat ggataatccc ctttaattat    4080
ttaggctgac cactcaccgg acctgtttcg cctgtgcaac ttcaccagtc ggaggtcatg    4140
ctcaaattgt cagtcagata ctttatacat actctgtgta caacatacca caacacacac    4200
gcacacacat agaaagtaca tacatgctgg atcggaaccc accacgcctt gtacatacac    4260
ccacacaccc ctcccacac ccctcttccc ggcacttttc gcgccagaga tcgtcgcctt    4320
tgccccttag gcaagttcac ccgttatgtt aggtaaccct ctcgacgggg ccgcctgcgg    4380
atgttggcgc atgcttgaca cgcccggtcg tgcggcgttg ctagtcctcg aaagtcaggt    4440
attgcacccg gaacccctga tcacaagcac ttgatcacgg cggagcacc cgcgcgcctg    4500 aacgggaccc cagccaatgc cggaccagag gccgaagcgg gaaggtgtct tgctttctgg    4560
```

```
cctgcccttt tctttcaaca atgggcaata cgggtcagcg aaaccCttcc tagtcctcgc    4620
agcaaactcg agctgctatc agattcccgg gaagcggcct gccacagccg ctcaacccgg    4680
ccttggcatg ccaggcggc cctttcatgt gtcgaaagcg gcaggtcatc agcacagatc    4740
tcgagggtgg gaaagagagg gggggagggg gcgatgctgg ggcgatgctg cttggagccg    4800
catccgggga gggggccctg ctgttcatcc atatccagga tgatgcgaga ttgaagcaag    4860
ataaataaca cggcttcccc ctcccctttc gatccggacc agaccatcgt ctccaacacc    4920
ccaaagtcga tccgacaagt cccaatccac cccgcccgcc cctccctccg tcgccgtccc    4980
ggtcttccga tttcgtcaag atgcacttct ccaccgctct cctggccttc ctgcccgccg    5040
ccctcgcggc ccctactgcc gagaccctcg acaagcgcgc cccgatcctg actgctcgcg    5100
ctggccaggt cgtcccgggc aagtacatca tcaagctccg cgacggagcc agcgacgatg    5160
tccttgaggc cgccatcggc aagctccgct ccaaggccga ccacgtctac cgcggcaagt    5220
tcagggcctt gccggcaag ctcgaggatg acgtccttga cgccatccgt cttctccccg    5280
aagtgagtcc gcgtcccgga agaaatagag gcgagcgggg gagagagtga agggcgaaaa    5340
gagccgtgtt ttgttaaccg cttgtctttt ctttctctct tgcaataggt cgagtacgtc    5400
gaggaggagg ccatcttcac catcaacgcg tacacctcgc agtccaacgc ccctggggc    5460
cttgcgcgcc tctcgtccaa gaccgcgggc tccaccacct acacctacga caccagcgcc    5520
ggcgagggca cctgtgccta tgtgatcgac acgggcatct acactagcca ctccgtatgt    5580
ctcgcggtta cctcccCttt cggaagaagg ggcatccata tgctgacccc tcctgatcac    5640
aggacttcgg cggccgtgcc actttcgccg ccaacttcgt cgacagctct aacaccgatg    5700
gcaacggcca cggcacccac gtcgccggca ccatcggcgg caccacgtac ggtgttgcca    5760
agaagaccaa gctctacgcc gtcaaggttc tcggctccga cggctctggc accacgtatg    5820
cctcgcaccc gcgcacccgc acacccgccc ggccgttatc ttctgactga cattcctctt    5880
tctcctctct agttctggtg tcattgctgg catcaacttc gtcgctgacg acgcgcccaa    5940
gcgcagctgc cccaagggcg tcgtcgccaa catgtcgctc ggcggtagct actcggcctc    6000
catcaacaac gccgccgccg ccctcgtcag gtcgggcgtc ttcctggccg tcgccgccgg    6060
caacgagaac cagaacgccg ccaactcgtc gcccgcctcc gaggcgtccg cctgcaccgt    6120
cggcgccacc gacaggaacg acgccaaggc cagctactcc aactacgca gcgtcgtcga    6180
tatccaggcc cccggctcca acatcctgag cacctggatc ggcagcacct ctgctaccgt    6240
aagccccccc tccccccccc cacccccagc ctttggcgac attcccgccc cgtatttatt    6300
tctccggggt ggggagaaa caaaacaaaa tagctaacat gagatgcact ctcagaacac    6360
catctcgggt acctcgatgg cctccccca cattgccggc ctcggtgcct acctcctggc    6420
cctcgagggc tccaagaccc ctgccgagct ctgcaactac atcaagtcga ccggcaacgc    6480
cgccatcact ggcgttccca gcggcaccac caaccgcatc gccttcaacg gcaacccctc    6540
tgcctgaatt gtttcccgcg atccgggaca aaatgggca tgagcacttc ctgcacctct    6600
tcttattcta gaggattcgg gagtggggag ccggcaaaaa aaggaggtgg tggaggagga    6660
ggaggaggag ataacggccg gggtcttctc cgagcgaatg agggctgcat attctcttgt    6720
tcatttttt ggttcatgtc tattatggtt ttacgcattt tattctagtt gggacagagt    6780
cacgatgcgg gtccgagggg cgccgatcgg ggttcctgcc cacctcccca gcgtctaaat    6840
aactttcata gacgaggaaa tgatgagatc tcatgagcgg accgcgaagg cctggactga    6900
```

```
cttctatcgt gactaattat gtgaatcatg agggcggaat gagagagatg atatgtcaga    6960
atacgcatac ttaaggtgca attgctggcg ggcaattgcg gcgtcacttt tgcttttcga    7020
catgatatca tgtctcctta atccaagtag ttaataatta gtctataaat aatttgtcta    7080
taattttgtc tattgcctga agaaataagc gattttgcaa attctggtat gtagagtaca    7140
ggtcaagtat tggagaggaa ggaaggaagc ggtatgtttc tcatattgac aagtgacagg    7200
agcaagcttc ttcctagaat cttagcaagg aaatgttgaa aattaagaaa gcagaataga    7260
aacaaggact aatagagcaa tttattgact caatcaatcg ttaattatga gtcgaagata    7320
ggttctcaaa acttttttcaa attagttttg ggaggacatg cccgagccat gtaaaacggg    7380
cgaggtacct cggtatgtta atgggggttgc gtaatgcttg gctgtcgagg atactagtaa    7440
ttgtatcgtg tttgtcagaa tacctactta ggtgcaattg ctggaagcag caattgcggc    7500
gtcgcttttg cagtttcaca gtgttgaaga ggtgagggca acatgtatc gcatatcttg     7560
ggggtcggtt taccaagaga gatatcatat ctaaccccta agagatgtgt attaaccctg    7620
gaagactaca tccacaaaaa ggaggcaaat cctgtgtaat tgacgcacga gtcttggggc    7680
actgaatgtt tggcagatac ataatgaaca tcccattgcc acttcattta tccggtctcc    7740
gatgcttagt cgtggtcttg ttacgttgtg cagctctcat catgattcca ccattcatag    7800
agttttcacc taggctaata ctctgtacgc agcacaaacg gcgcccggtg tgacaaatta    7860
tcagtctaag gaaagatccg ctacttactt tgtaggggat gtatgaatga cctcggacaa    7920
ttggcagtcg ggtatgctac gttccagata gccataacta atgcttgaga agcgacacct    7980
gtcaggctct gatgttgtgg gaagggatgc caatggacct actcaggtgg tggaaattca    8040
tcgtttccac cacctgagtg tgtccgaccc ttagggatgc aagatgcgag tgtcaacctc    8100
ttggtgttcc gaaatggccg ctcgcttata ccctcggtgg cgcgtgttaa tccgagttgg    8160
cggacgctaa gctcccatta ttaatagttc tctaacacaa ctcctctcaa ttcaatagca    8220
tgcttatcat agcagcactt cagcagcacc ctgatttgta ggaaccgaca ctggtgtttg    8280
atgccgaggg taatcagttc ctgttagaca tagtattcga aagtactggc gtaggctgct    8340
actctagcac tatgacttgc tgttcccttt ccagcgcctc gagatcttga accacttcct    8400
cggcactctc atattccatc cgccagcact tcattgtgat agcactgcag gcgtgcttgt    8460
cttcgggaaa ggcccccttt cgaaatctgt cttccacctt tcataccac ccttcttctc     8520
cgtgaacgat atcgggatat acggcgtgcc ccatcatgat gaagtagaaa gtacacccta    8580
gcgcaaagag gtcggtcttg atgtctgcgt cgaacgggtc gtttcgcgga gcagagaatt    8640
tgcacgactc agcgctccag ccgtcgacga gcactttgcc gtcggccgat aaatgcctcc    8700
cttggaagtc ggagagcttt atatggaggt gttcgtcgag aagtagattc gttggctgga    8760
tgtcgcaatg gaggactcgc cggctatgaa tccacgcgac agcctccgca gcctcgcggc    8820
accaggccag ccgctgcttg acggaaggag ggggtttgcc ggattcaagc atatactcgg    8880
caatattacc gttagtggcg cgttctagat aaagccccgt gtctgtaaag cctttgcatg    8940
ctataatgcg cttatgcggt ccgatgattt ctaggagctt cttctctgcc tcaagccggg    9000
tcatgtcacc gccgggggcg agtggatatt ttaatacagt cgagtcgtcg acctcgccaa    9060
taaaggcgct gcctcccgag gctagaactc gcttcacctc cggggggacag tagtgttggt    9120
aaacaacaac agatggtgct ttgtcgttcg acatgatgag ctgtcagaa tgtctaggta     9180
ttgtgttgtt gatggacatt ggcgaaggtt ttaggagggg actttcgaac cgaaataaga    9240
gccgacgaat gcttataagg cggtgtgttt ggatgcctgc gaggtgaggt gtggctgggc    9300
```

```
caatcagtgg cgagggtgct cgcagactcc atgttcacga atttctcaaa cctgcttact   9360
catctgggat ttggcccgcg gggttccatt aagcggtctg tgccaagaag cgtgctattc   9420
ttaatctacc tcactaggga atgtcaaacc ggtggtgaag agcctcctgt ctctgccatc   9480
tactgtgtac atgtcaattg cagggaacca aaatcgtgga gttgaacctc tccttccctt   9540
tcttcctaat cagaagacta ccggatttga gttggccacc acccaacggt ggcttggccc   9600
agatgctgtt agaatctcaa tctccattga cgaccatgtc ggtttacttc agctaagcac   9660
tcacctcgag acgtcgatgg ccttttaaca cttttgggcac acatggccgg gggtcctcat   9720
ggttgtgcta ccataatgga cgtccttgta tccggtgtag agaggaccac caggattcga   9780
gcactgaaca aacgagatgt cttctaccac atgcttcggc gttgcggtgc agttctggta   9840
ggtcttgcga gcaatccggc gttcgcaccc acaggccatg atttgtgcgt tctccagcaa   9900
aggagaataa ccaggcgaga tagatggtaa agtgctgttg gctgtggctc ttcgagtgtt   9960
tgtggaaagg ggccagttgc ttgaggagcc tggcctcgaa actctacgtt ccaggagcga  10020
gggaagggct ctttatatag gcaaggaagg aaattccaac acgatttctg gtggcattca  10080
tgattaccag gctgtcaaga cgcgaaccag ctttggttcg ccgagtgtat gctaaggcaa  10140
gaacctacat tcaggcaacc atccctctac accattgcta cattattgct ctaagctatc  10200
aggcctcgct tgccgaggct attacgcagg ccggcaaggc atccacgtgc aatgaagtc   10260
gagagagagc cctgtcaacg aggaaggacc gatgtcgttt cctgcaggca ggctcaccag  10320
ggtcctgtca tgcctttccc cgcccggtca acattagaa tgacgaccac atgttcggtg   10380
caaaagtaca agaccccaac cagggaatgg gagcagagcg aagacgagcg tcgcacagag  10440
tgagtaatga attccatctc aaaagaggta cacacaccta cgggaaggta cctcttgtga  10500
ctcaccagtc ctagcatgca gcgaagcgag gcgactcgcc cacctggcgc cgcttgaggg  10560
gttgtcgaac actgaccaat aggcaaacgt aactgagaga ggggacaagc tgctgccttc  10620
gcaacctgca gatcgcagcc ctgccttggc cccggtgaga ctttctcccg attgtgacca  10680
ctcgatctaa gtctaattta agccatacat accccaaaca cgggcgcgga agtccccgaa  10740
gccaaacgtt tgaggaggaa gttaccacgt cgagaagagc tcgacaatgg aaagggtca   10800
acacgtataa ctccaatgat ctcccccagtg cgttcaacac aaccaacatc gggcttatcg  10860
ggagtcctct acgatcggtt cttctcgaca ctggcacctc tggtttccct gaagatcgca  10920
agggctcgct aaagagacag gaatgccgag cggcgggagg acttacttgt cctgatcggg  10980
atcacagcag gcgatgaggc tgcccacaat tcggaggggc agcgagcgag ctaagagcag  11040
gttaggtacc tgactctaaa gacaaggttc cattaaagaa gagcgctagg gtagggagga  11100
ccagtcatta atgcagcctg cctgcagcct gtttgtggcc tgactgctgc tgcctgcctg  11160
ctcaagtcgg tgtcgctctg tgttggttgt gcagcgagca cagtgcagat cgccatcaac  11220
cctcgccgtt tattcttctg gatcatcgca acctttcgca ccgccctcta ccgcgaccta  11280
tttgcgcact cgccaagaat tccgcttgcg ctcttccccc ccccccccc cttcctcccc  11340
gggccatttc cccgaccacc gatacgatgc ccttctcgcc gccacgcgac acgagggaga  11400
aagatatccg atggcaagcc tctgccaagg tcggatgtcg cgacagcaga cctctgtgga  11460
cagactactg gcagcggttc aacaccatca ccattccgct gcttgatgag gatgcctttt  11520
tttccgacgc cctcgccgcc gagaaag                                      11547
```

<210> SEQ ID NO 13

<211> LENGTH: 396
<212> TYPE: PRT
<213> ORGANISM: Myceliophthora thermophila

<400> SEQUENCE: 13

Met His Phe Ser Thr Ala Leu Leu Ala Phe Leu Pro Ala Ala Leu Ala
1               5                   10                  15

Ala Pro Thr Ala Glu Thr Leu Asp Lys Arg Ala Pro Ile Leu Thr Ala
            20                  25                  30

Arg Ala Gly Gln Val Val Pro Gly Lys Tyr Ile Ile Lys Leu Arg Asp
        35                  40                  45

Gly Ala Ser Asp Asp Val Leu Glu Ala Ala Ile Gly Lys Leu Arg Ser
    50                  55                  60

Lys Ala Asp His Val Tyr Arg Gly Lys Phe Arg Gly Phe Ala Gly Lys
65                  70                  75                  80

Leu Glu Asp Asp Val Leu Asp Ala Ile Arg Leu Leu Pro Glu Val Glu
                85                  90                  95

Tyr Val Glu Glu Glu Ala Ile Phe Thr Ile Asn Ala Tyr Thr Ser Gln
            100                 105                 110

Ser Asn Ala Pro Trp Gly Leu Ala Arg Leu Ser Ser Lys Thr Ala Gly
        115                 120                 125

Ser Thr Thr Tyr Thr Tyr Asp Thr Ser Ala Gly Glu Gly Thr Cys Ala
    130                 135                 140

Tyr Val Ile Asp Thr Gly Ile Tyr Thr Ser His Ser Asp Phe Gly Gly
145                 150                 155                 160

Arg Ala Thr Phe Ala Ala Asn Phe Val Asp Ser Ser Asn Thr Asp Gly
                165                 170                 175

Asn Gly His Gly Thr His Val Ala Gly Thr Ile Gly Gly Thr Thr Tyr
            180                 185                 190

Gly Val Ala Lys Lys Thr Lys Leu Tyr Ala Val Lys Val Leu Gly Ser
        195                 200                 205

Asp Gly Ser Gly Thr Thr Ser Gly Val Ile Ala Gly Ile Asn Phe Val
    210                 215                 220

Ala Asp Asp Ala Pro Lys Arg Ser Cys Pro Lys Gly Val Val Ala Asn
225                 230                 235                 240

Met Ser Leu Gly Gly Ser Tyr Ser Ala Ser Ile Asn Asn Ala Ala Ala
                245                 250                 255

Ala Leu Val Arg Ser Gly Val Phe Leu Ala Val Ala Ala Gly Asn Glu
            260                 265                 270

Asn Gln Asn Ala Ala Asn Ser Ser Pro Ala Ser Glu Ala Ser Ala Cys
        275                 280                 285

Thr Val Gly Ala Thr Asp Arg Asn Asp Ala Lys Ala Ser Tyr Ser Asn
    290                 295                 300

Tyr Gly Ser Val Val Asp Ile Gln Ala Pro Gly Ser Asn Ile Leu Ser
305                 310                 315                 320

Thr Trp Ile Gly Ser Thr Ser Ala Thr Met His Ser Gln Asn Thr Ile
                325                 330                 335

Ser Gly Thr Ser Met Ala Ser Pro His Ile Ala Gly Leu Gly Ala Tyr
            340                 345                 350

Leu Leu Ala Leu Glu Gly Ser Lys Thr Pro Ala Glu Leu Cys Asn Tyr
        355                 360                 365

Ile Lys Ser Thr Gly Asn Ala Ala Ile Thr Gly Val Pro Ser Gly Thr
    370                 375                 380

Thr Asn Arg Ile Ala Phe Asn Gly Asn Pro Ser Ala

<210> SEQ ID NO 14
<211> LENGTH: 1818
<212> TYPE: DNA
<213> ORGANISM: Myceliophthora thermophila

<400> SEQUENCE: 14

```
ctgcagtccc ttacctatgg gctcctagtc tcgttcctct ttttgataga tttgtatttt      60
gcaacgttgc aaaatgagac atttcaatca tatgtagccg ccagctactg ttagcgtact     120
cagcgttgcc caaacggcgg ttttttctggg tagcactgtg ccgcgtgccc ctgagccgtg    180
cgtcgcggaa acccccttaa gtagcaagta tgttaccgcc gagaccgaca atgctgttgg    240
ttacctcgct ggtccatgat tgcaatctag atatcgtgcg gggcttttgc aatcggtttt    300
ccctacccac tttcttcttt tggacacttt ctcttttgga aaatgccgaa atgatgcggc    360
tcgctcacgc cccgaagtcc cgagctgggg ctagatccgt gattgcaacg cggtgcgaac    420
gcgactgggg cagacctcgc tcagccttgg tcgtgccgga atggcgggta cctttaccag    480
gtcgggatca attacatagg atgccatgtg cgtggatttg attgcatcgc tgtcccttt     540
gtatgtgtcc gagagcgaga tatcaacgcg aaaaccggaa tgctcccaac gtcgctctct    600
gttcataggg tctttttttt tcttctgctc catatcatct gtcttgaact aagtgatcat    660
ctgctgtcac gtcccgccca atgattgtaa agaatgataa gtgatgctcg ccggggccag    720
gctctgtgaa agttccctct ttggttgacg atcaggtagc gccaacgttg attgggccgc    780
ccgtaaaatc cgaccctgtc tcctttcgtt gcaagtctcc gcgagaccgt gccaagcatg    840
ttctccggat ccctcaatta cataaggttt ggctccaggg taggtctgga agctacccac    900
ctcggccaag caaccaatca caaccagacc tcgcggcgtt tcgaccttcc tggtttgtct    960
cagggctggc caacgtcctc ccgtggcggg tgcctggtga tcgcaggtcg caggcgagtg   1020
ccgggcacgc ggagccccccg tcaaagcttg acccttcag agctaggttt cattaggcct   1080
tcgaaaacaa cccaaggccc cgtcgcaacc atcacaaccg gccgataacc agatctcggt   1140
aggtccgata aggatccaaa atggtgtcgg ctgacgttgc atgtgcccag gcaggaggat   1200
gatccccagg gttgttgccg gcagctcccg cacgtcgggg agggggaggg ggagggaaa    1260
gccctaacta acgttcgttc tatcacgggc cgaccgggcc atgctttcgg cttgtgagcg   1320
gtggggtcaa gggcaacaag aaatgctaag tgcgggacga agacacgcgg gcatgaggtc   1380
tcagggtgac ctgcgcaaaa ccaagtccca ctcgccatgc ctccagcagc aacgttgccg   1440
tagaagggtc aggggggtttg ttgtagaccc acgaccatgc tgccggcgag cggagggttg   1500
gcttgctaca ggcgctgaag ggtcaactcg gtgcccaaag tggctaccaa gcgtgccatc   1560
aagggaaatg agatgatggt ggctcgtggg caaagaaaag acaagggagg tgactctaga   1620
gagatgctct cgagttcacg ggtataagag cactgtgatc gttcacaaag ccggcgtact   1680
cctctagagc atctatcatc aacatcacca gaaaggtcaa gaccaggtgg ttgccatatc   1740
cagtcgcaaa agagccaaag agcgaaggag cacgaaagca cagcccaatc attccctgct   1800
ttgctacttc ttctccac                                                1818
```

<210> SEQ ID NO 15
<211> LENGTH: 2479
<212> TYPE: DNA
<213> ORGANISM: Myceliophthora thermophila

<400> SEQUENCE: 15

```
tcgaccctga cagagacgta tcacagagga ctgggggtgg ttcaaaatac cagttagtga      60
gaaagacctc tcgatgtgaa agggtaggtg ctccctccaa cttaacacaa aaacgacaca     120
ctaccaaacc tctagaggtg gacaaagcaa ccccgcgtac tccgttccat tcgtagcaca     180
ggacgccaga gaaagcaaac cacaggtcag gaaacacaca accccgggtt tctaggatcg     240
tcggccgtcg tttcacgtat cggctacgga ggttagtaag aatccccgg gtgggggggt      300
tcctcttgtt gaaatgggtg acatttctat gttctgcgca tgctttcagc ccagcagcga     360
gcggctcggg tatgctaggc aatcttggag ctttgatgta cctaggcgcg tgtgataaga     420
acacaacaag gtccacttcc cgtacctacc gcctgtggat cccggttcga ggttggacct     480
gtgcagtaaa gcgcacagct gaggacgatt tgaggacgat tgaggacgga catacctgat     540
gtaggcaacg aaaagcttaa gccggcttct acggggagtc tctccccatc accaaagatc     600
ggaccaccta ggcggctacc gggcatgaga tacgagcagg gggaagcggc gagtgacacg     660
tcgtccgccc atgggacggc tgaagggta atggcagcac cttgacgtcc cttctcgcgg      720
agaggcggga accattgctc tgggaacgga cagctgccgg gtgcgccgat actaacgagg     780
ttccctggaa tatgatggtg gaaccgcgct cgcgaggaag cttggccggc caacccctgt     840
tcccccgaag acctgtcacc gtcgggaact gccgagctcg aaagaccaca gtctccgaat     900
tgatcaactc ctacttatcc catctatgag aggagaacat cgaacgattc tgacccggga     960
actctggaga tgcccatggt gccttccttt agatctggcc atgttccgca tctatctaca    1020
tcagttcagt ctttgccctg ttggtcttgc tagcggcgat gctatgaaaa tctatcaatt    1080
aatggtgtcc tttttcgatg cgagtacact actcatttcg tttccgaatc gccatctctt    1140
cgaccattgc tgaactaatt caatcttagg tagtctgctg ttccttgttt tccatttcct    1200
tgtcttaagt aaaaccaact ggcacacctc gaaacacgct tgacggatgg acagtagaat    1260
tgaccgtgta cgtacatgta ccttgacgtc ctccgaggtt cgacatcagg gttcgtcata    1320
gggagtgaaa cacccgccat gattccgtag ccgcgcgcga agatacgaag cagatatttc    1380
acggacatgg cggagatact tgtttcccgt actaaggtag tcatgtcgga gacatctgaa    1440
cgacagagct ggccaagaga accgaccagt tgccccagga cgatctagac aaaaaaaaga    1500
gagatgagtg ggccactttt gccacaacat cgacggccct gcgaccgccc ccaggcaaac    1560
aaacaaaccg ccgaacaata atacttttgt cattttagga ggagcgttgt atggataaaa    1620
acaacatctc gttgctgcag aatgtggact tcaaacttgc agaaaatggg aggcggattt    1680
gcatgatcgg agggtagttg actcacgccg caggctgcaa atccgtcctc cattattcca    1740
tgaacaactt cgtaaggttg ggctgagcgc caatgcctaa cggaccgggg gccacagcgc    1800
aacgtcccac ttaaaggcca gcgtgacatg ccagttccat accaagtagt ggcaccagag    1860
gcggccaatg ctcagtaagg gcagggaggg aggctcaaac gattggcaaa agagggggct    1920
tgccagttca gttccctgtg cgagcgcgag agggggcagtt tcaaatctgg aggggtgtgt    1980
tgcgctggtc tgaagagaaa gagaagactg tacttaataa ttgttcaaag agtccatcat    2040
cgcgttgcgg actcctctag ctgtatttag agccctatca ttacttgtcg ggtgcgaatc    2100
aaaataccgg gatgcagccc tctggcgatt tgcatgcggt tgtggaggaa gtgaagcctg    2160
aatcgcgggg ctgggcggca aagcacgacg tgaaattcct ggcgaaattc gagggcttgc    2220
cccaccgtgt ttgaagtttt tgtgctgcgt aaccccacca cccgcccttg ccctcccgc    2280
ctgcccataa aaacttcgac ccctcctcaa atcttcttcg attcttcctc ttcacttcct    2340
```

```
tcgtcggcat acctgattca agcaatcacc tgccactttc aagtgcgtat accatcatcg    2400
atacactggt tcttgacaag tacatcgtct ctaactttcc tttttgcagt tttcattaag    2460
cgcaagtcgc cagtttcgt                                                 2479

<210> SEQ ID NO 16
<211> LENGTH: 4241
<212> TYPE: DNA
<213> ORGANISM: artificial
<220> FEATURE:
<223> OTHER INFORMATION: pDB40-amdS-5'

<400> SEQUENCE: 16
ggccgctcga tttaaatctc gagaggcctg acgtcgggcc cggtaccacg cgtcatatga      60
ctagttcgga cctagggata tcgtcgacat cgatgctctt ctgcgttaat taacaattgg     120
gatcctctag acccgggaag ctcagcgtcc aattcgagct ctgtacagtg accggtgact     180
cttcctggca tgcggagaga cggacggacg cagagagaag ggctgagtaa taagcgccac     240
tgcgccagac agctctggcg gctctgaggt gcagtggatg attattaatc cgggaccggc     300
cgcccctccg ccccgaagtg gaaaggctgg tgtgcccctc gttgaccaag aatctattgc     360
atcatcggag aatatggagc ttcatcgaat caccggcagt aagcgaagga gaatgtgaag     420 ccagggggtgt atagccgtcg gcgaaatagc atgccattaa cctaggtaca gaagtccaat     480
tgcttccgat ctggtaaaag attcacgaga tagtaccttc tccgaagtag gtagagcgag     540
tacccggcgc gtaagctccc taattggccc atccggcatc tgtagggcgt ccaaatatcg     600
tgcctctcct gctttgcccg tgtatgaaa ccggaaaggc cgctcaggag ctggccagcg     660
gcgcagaccg ggaacacaag ctggcagtcg acccatccgg tgctctgcac tcgacctgct     720
gaggtccctc agtccctggt aggcagcttt gcccgtctg tccgcccggt gtgtcggcgg     780
ggttgacaag gtcgttgcgt cagtccaaca tttgttgcca tatttcctg ctctccccac     840 cagctgctct tttctttct cttctttc ccatcttcag tatattcatc ttcccatcca     900 agaacctta tttccctaa gtaagtactt tgctacatcc atactccatc cttcccatcc     960
cttattcctt tgaaccttc agttcgagct ttcccacttc atcgcagctt gactaacagc    1020
taccccgctt gagcagacat caccatgcct caatcctggg aagaactggc cgctgataag    1080
cgcgcccgcc tcgcaaaaac catccctgat gaatggaaag tccagacgct gcctgcggaa    1140
gacagcgtta ttgatttccc aaagaaatcg ggatccttt cagaggccga actgaagatc    1200
acagaggcct ccgctgcaga tcttgtgtcc aagctggcgg ccggagagtt gacctcggtg    1260
gaagttacgc tagcattctg taaacgggca gcaatcgccc agcagttagt agggtcccct    1320
ctacctctca gggagatgta acaacgccac cttatgggac tatcaagctg acgctggctt    1380
ctgtgcagac aaactgcgcc cacgagttct tccctgacgc cgctctcgcg caggcaaggg    1440
aactcgatga atactacgca aagcacaaga gacccgttgg tccactccat ggcctcccca    1500
tctctctcaa agaccagctt cgagtcaagg tacaccgttg cccctaagtc gttagatgtc    1560 ccttttttgtc agctaacata tgccaccagg gctacgaaac atcaatgggc tacatctcat    1620
ggctaaacaa gtacgacgaa ggggactcgg ttctgacaac catgctccgc aaagccggtg    1680
ccgtcttcta cgtcaagacc tctgtcccgc agaccctgat ggtctgcgag acagtcaaca    1740
acatcatcgg gcgcaccgtc aacccacgca caagaactg tcgtgcggc ggcagttctg    1800 gtggtgaggg tgcgatcgtt gggattcgtg gtggcgtcat cggtgtagga acggatatcg    1860
gtggctcgat tcgagtgccg gccgcgttca acttcctgta cggtctaagg ccgagtcatg    1920
```

```
ggcggctgcc gtatgcaaag atggcgaaca gcatggaggc ggccgctacg ggatttaaat    1980
cgctagcggg ctgctaaagg aagcggaaca cgtagaaagc cagtccgcag aaacggtgct    2040
gaccccggat gaatgtcagc tactgggcta tctggacaag ggaaaacgca agcgcaaaga    2100
gaaagcaggt agcttgcagt gggcttacat ggcgatagct agactgggcg gttttatgga    2160
cagcaagcga accggaattg ccagctgggg cgccctctgg taaggttggg aagccctgca    2220
aagtaaactg gatggctttc ttgccgccaa ggatctgatg cgcaggggga tcaagatctg    2280
atcaagagac aggatgagga tcgtttcgca tgattgaaca agatggattg cacgcaggtt    2340
ctccggccgc ttgggtggag aggctattcg gctatgactg ggcacaacag acaatcggct    2400
gctctgatgc cgccgtgttc cggctgtcag cgcaggggcg cccggttctt tttgtcaaga    2460
ccgacctgtc cggtgccctg aatgaactgc aggacgaggc agcgcggcta tcgtggctgg    2520
ccacgacggg cgttccttgc gcagctgtgc tcgacgttgt cactgaagcg ggaagggact    2580
ggctgctatt gggcgaagtg ccggggcagg atctcctgtc atctcacctt gctcctgccg    2640
agaaagtatc catcatggct gatgcaatgc ggcggctgca tacgcttgat ccggctacct    2700
gcccattcga ccaccaagcg aaacatcgca tcgagcgagc acgtactcgg atggaagccg    2760
gtcttgtcga tcaggatgat ctggacgaag agcatcaggg gctcgcgcca gccgaactgt    2820
tcgccaggct caaggcgcgc atgcccgacg gcgaggatct cgtcgtgacc catggcgatg    2880
cctgcttgcc gaatatcatg gtggaaaatg gccgcttttc tggattcatc gactgtggcc    2940
ggctgggtgt ggcggaccgc tatcaggaca tagcgttggc tacccgtgat attgctgaag    3000
agcttggcgg cgaatgggct gaccgcttcc tcgtgcttta cggtatcgcc gctcccgatt    3060
cgcagcgcat cgccttctat cgccttcttg acgagttctt ctgagcggga ctctggggtt    3120
cgaaatgacc gaccaagcga cgcccaacct gccatcacga tttcgatt ccaccgccgc    3180
cttctatgaa aggttgggct tcggaatcgt tttccgggac gccggctgga tgatcctcca    3240
gcgcggggat ctcatgctgg agttcttcgc ccacgctagc ggcgcgccgg ccggcccggt    3300
gtgaaatacc gcacagatgc gtaaggagaa aataccgcat caggcgctct tccgcttcct    3360
cgctcactga ctcgctgcgc tcggtcgttc ggctgcggcg agcggtatca gctcactcaa    3420
aggcggtaat acggttatcc acagaatcag gggataacgc aggaaagaac atgtgagcaa    3480
aaggccagca aaaggccagg aaccgtaaaa aggccgcgtt gctggcgttt ttccataggc    3540
tccgcccccc tgacgagcat cacaaaaatc gacgctcaag tcagaggtgg cgaaacccga    3600
caggactata aagataccag gcgtttcccc ctggaagctc cctcgtgcgc tctcctgttc    3660
cgaccctgcc gcttaccgga tacctgtccg cctttctccc ttcgggaagc gtggcgcttt    3720
ctcatagctc acgctgtagg tatctcagtt cggtgtaggt cgttcgctcc aagctgggct    3780
gtgtgcacga accccccgtt cagcccgacc gctgcgcctt atccggtaac tatcgtcttg    3840
agtccaaccc ggtaagacac gacttatcgc cactggcagc agccactggt aacaggatta    3900
gcagagcgag gtatgtaggc ggtgctacag agttcttgaa gtggtggcct aactacggct    3960
acactagaag gacagtattt ggtatctgcg ctctgctgaa gccagttacc ttcggaaaaa    4020
gagttggtag ctcttgatcc ggcaaacaaa ccaccgctgg tagcggtggt ttttttgttt    4080
gcaagcagca gattacgcgc agaaaaaaag gatctcaaga agatcctttg atcttttcta    4140
cggggtctga cgctcagtgg aacgaaaact cacgttaagg gattttggtc atgagattat    4200
caaaaaggat cttcacctag atcctttta aggccggccg c                         4241
```

<210> SEQ ID NO 17
<211> LENGTH: 4076
<212> TYPE: DNA
<213> ORGANISM: artificial
<220> FEATURE:
<223> OTHER INFORMATION: pDB41-amdS-3'

<400> SEQUENCE: 17

| | | | | | |
|---|---|---|---|---|---|
| gatcttgatc | ccctgcgcca | tcagatcctt | ggcggcaaga | aagccatcca | gtttactttg | 60 |
| cagggcttcc | caaccttacc | agagggcgcc | ccagctggca | attccggttc | gcttgctgtc | 120 |
| cataaaaccg | cccagtctag | ctatcgccat | gtaagcccac | tgcaagctac | ctgctttctc | 180 |
| tttgcgcttg | cgttttccct | tgtccagata | gcccagtagc | tgacattcat | ccggggtcag | 240 |
| caccgtttct | gcggactggc | tttctacgtg | ttccgcttcc | tttagcagcc | cgctagcgat | 300 |
| ttaaatcccg | tagcggccgc | aaggggactc | ggttctgaca | accatgctcc | gcaaagccgg | 360 |
| tgccgtcttc | tacgtcaaga | cctctgtccc | gcagaccctg | atggtctgcg | agacagtcaa | 420 |
| caacatcatc | gggcgcaccg | tcaacccacg | caacaagaac | tggtcgtgcg | gcggcagttc | 480 |
| tggtggtgag | ggtgcgatcg | ttgggattcg | tggtggcgtc | atcggtgtag | gaacggatat | 540 |
| cggtggctcg | attcgagtgc | cggccgcgtt | caacttcctg | tacggtctaa | ggccgagtca | 600 |
| tgggcggctg | ccgtatgcaa | agatggcgaa | cagcatggag | ggtcaggaga | cggtgcacag | 660 |
| cgttgtcggg | ccgattacgc | actctgttga | gggtgagtcc | ttcgcctctt | ccttcttttc | 720 |
| ctgctctata | ccaggcctcc | actgtcctcc | tttcttgctt | tttatactat | atacgagacc | 780 |
| ggcagtcact | gatgaagtat | gttagacctc | cgcctcttca | ccaaatccgt | cctcggtcag | 840 |
| gagccatgga | aatacgactc | caaggtcatc | cccatgccct | ggcgccagtc | cgagtcggac | 900 |
| attattgcct | ccaagatcaa | gaacggcggg | ctcaatatcg | gctactacaa | cttcgacggc | 960 |
| aatgtccttc | cacaccctcc | tatcctgcgc | ggcgtggaaa | ccaccgtcgc | cgcactcgcc | 1020 |
| aaagccggtc | acaccgtgac | cccgtggacg | ccatacaagc | acgatttcgg | ccacgatctc | 1080 |
| atctcccata | tctacgcggc | tgacggcagc | gccgacgtaa | tgcgcgatat | cagtgcatcc | 1140 |
| ggcgagccgg | cgattccaaa | tatcaaagac | ctactgaacc | cgaacatcaa | agctgttaac | 1200 |
| atgaacgagc | tctgggacac | gcatctccag | aagtggaatt | accagatgga | gtaccttgag | 1260 |
| aaatggcggg | aggctgaaga | aaaggccggg | aaggaactgg | acgccatcat | cgcgccgatt | 1320 |
| acgcctaccg | ctgcggtacg | gcatgaccag | ttccggtact | atgggtatgc | ctctgtgatc | 1380 |
| aacctgctgg | atttcacgag | cgtggttgtt | ccggttacct | tgcggataa | gaacatcgat | 1440 |
| aagaagaatg | agagtttcaa | ggcggttagt | gagcttgatg | ccctcgtgca | ggaagagtat | 1500 |
| gatccggagg | cgtaccatgg | ggcaccggtt | gcagtgcagg | ttatcggacg | gagactcagt | 1560 |
| gaagagagga | cgttggcgat | tgcagaggaa | gtggggaagt | tgctgggaaa | tgtggtgact | 1620 |
| ccatagctaa | taagtgtcag | atagcaattt | gcacaagaaa | tcaataccag | caactgtaaa | 1680 |
| taagcgctga | agtgaccatg | ccatgctacg | aaagagcaga | aaaaaacctg | ccgtagaacc | 1740 |
| gaagagatat | gacacgcttc | catctctcaa | aggaagaatc | ccttcagggt | tgcgtttcca | 1800 |
| gtctagacac | gtataacggc | acaagtgtct | ctcaccaaat | gggttatatc | tcaaatgtga | 1860 |
| tctaaggatg | gaaagcccag | aatattggct | gggttgatgg | ctgcttcgag | tgcagtctca | 1920 |
| tgctgccaca | ggtgactctg | gatggcccca | taccactcaa | cccatgcgtg | cgaggtcccg | 1980 |
| ggtctagagg | atcccaattg | ttaattaacg | cagaagagca | tcgatgtcga | cgatatccct | 2040 |
| aggtccgaac | tagtcatatg | acgcgtggta | ccgggcccga | cgtcaggcct | ctcgagattt | 2100 |

| aaatcgagcg gccgcggccg gcctttaaaa ggatctaggt gaagatcctt tttgataatc | 2160 |
| tcatgaccaa aatcccttaa cgtgagtttt cgttccactg agcgtcagac cccgtagaaa | 2220 |
| agatcaaagg atcttcttga tccttttttt ttctgcgcgt aatctgctgc ttgcaaacaa | 2280 |
| aaaaaccacc gctaccagcg gtggtttgtt tgccggatca agagctacca actcttttc | 2340 |
| cgaaggtaac tggcttcagc agagcgcaga taccaaatac tgtccttcta gtgtagccgt | 2400 |
| agttaggcca ccacttcaag aactctgtag caccgcctac atacctcgct ctgctaatcc | 2460 |
| tgttaccagt ggctgctgcc agtggcgata agtcgtgtct taccgggttg gactcaagac | 2520 |
| gatagttacc ggataaggcg cagcggtcgg gctgaacggg gggttcgtgc acacagccca | 2580 |
| gcttggagcg aacgacctac accgaactga gatacctaca gcgtgagcta tgagaaagcg | 2640 |
| ccacgcttcc cgaagggaga aaggcggaca ggtatccggt aagcggcagg gtcggaacag | 2700 |
| gagagcgcac gagggagctt ccaggggaa acgcctggta tctttatagt cctgtcgggt | 2760 |
| ttcgccacct ctgacttgag cgtcgatttt tgtgatgctc gtcagggggg cggagcctat | 2820 |
| ggaaaaacgc cagcaacgcg gccttttttac ggttcctggc cttttgctgg ccttttgctc | 2880 |
| acatgttctt tcctgcgtta tcccctgatt ctgtggataa ccgtattacc gcctttgagt | 2940 |
| gagctgatac cgctcgccgc agccgaacga ccgagcgcag cgagtcagtg agcgaggaag | 3000 |
| cggaagagcg cctgatgcgg tatttttctcc ttacgcatct gtgcggtatt tcacaccggg | 3060 |
| ccggccggcg cgccgctagc gtgggcgaag aactccagca tgagatcccc gcgctggagg | 3120 |
| atcatccagc cggcgtcccg gaaaacgatt ccgaagccca acctttcata gaaggcggcg | 3180 |
| gtggaatcga aatctcgtga tggcaggttg ggcgtcgctt ggtcggtcat ttcgaacccc | 3240 |
| agagtcccgc tcagaagaac tcgtcaagaa ggcgatagaa ggcgatgcgc tgcgaatcgg | 3300 |
| gagcggcgat accgtaaagc acgaggaagc ggtcagccca ttcgccgcca agctcttcag | 3360 |
| caatatcacg ggtagccaac gctatgtcct gatagcggtc cgccacaccc agccggccac | 3420 |
| agtcgatgaa tccagaaaag cggccatttt ccaccatgat attcggcaag caggcatcgc | 3480 |
| catgggtcac gacgagatcc tcgccgtcgg catgcgcgc cttgagcctg gcgaacagtt | 3540 |
| cggctggcgc gagcccctga tgctcttcgt ccagatcatc ctgatcgaca agaccggctt | 3600 |
| ccatccgagt acgtgctcgc tcgatgcgat gtttcgcttg gtggtcgaat gggcaggtag | 3660 |
| ccggatcaag cgtatgcagc cgccgcattg catcagccat gatggatact ttctcggcag | 3720 |
| gagcaaggtg agatgacagg agatcctgcc ccggcacttc gcccaatagc agccagtccc | 3780 |
| ttcccgcttc agtgacaacg tcgagcacag ctgcgcaagg aacgcccgtc gtggccagcc | 3840 |
| acgatagccg cgctgcctcg tcctgcagtt cattcagggc accggacagg tcggtcttga | 3900 |
| caaaaagaac cgggcgcccc tgcgctgaca gccgaacac ggcggcatca gagcagccga | 3960 |
| ttgtctgttg tgcccagtca tagccgaata gcctctccac ccaagcggcc ggagaacctg | 4020 |
| cgtgcaatcc atcttgttca atcatgcgaa acgatcctca tcctgtctct tgatca | 4076 |

<210> SEQ ID NO 18
<211> LENGTH: 2406
<212> TYPE: DNA
<213> ORGANISM: artificial
<220> FEATURE:
<223> OTHER INFORMATION: pH305

<400> SEQUENCE: 18
gatttaaatc gagcggccgc ggccggcctt taaaaggatc taggtgaaga tccttttga 60

```
taatctcatg accaaaatcc cttaacgtga gttttcgttc cactgagcgt cagacccgt      120
agaaaagatc aaaggatctt cttgagatcc ttttttctg cgcgtaatct gctgcttgca      180
aacaaaaaaa ccaccgctac cagcggtggt ttgtttgccg gatcaagagc taccaactct     240
ttttccgaag gtaactggct tcagcagagc gcagatacca aatactgtcc ttctagtgta     300
gccgtagtta ggccaccact tcaagaactc tgtagcaccg cctacatacc tcgctctgct     360
aatcctgtta ccagtggctg ctgccagtgg cgataagtcg tgtcttaccg ggttggactc     420
aagacgatag ttaccggata aggcgcagcg gtcgggctga acggggggtt cgtgcacaca     480
gcccagcttg gagcgaacga cctacaccga actgagatac ctacagcgtg agctatgaga     540
aagcgccacg cttcccgaag ggagaaaggc ggacaggtat ccggtaagcg gcagggtcgg     600
aacaggagag cgcacgaggg agcttccagg gggaaacgcc tggtatcttt atagtcctgt     660
cgggtttcgc cacctctgac ttgagcgtcg attttttgtga tgctcgtcag gggggcggag    720
cctatgaaaa aacgccagca acgcggcctt tttacggttc ctggccttt gctggccttt     780
tgctcacatg ttctttcctg cgttatcccc tgattctgtg ataaccgta ttaccgcctt     840
tgagtgagct gataccgctc gccgcagccg aacgaccgag cgcagcgagt cagtgagcga     900
ggaagcggaa gagcgcctga tgcggtattt tctccttacg catctgtgcg gtatttcaca     960
ccggccggc cggcgcgccg ctagcgtggg cgaagaactc cagcatgaga tccccgcgct     1020
ggaggatcat ccagccggcg tcccggaaaa cgattccgaa gcccaacctt tcatagaagg    1080
cggcggtgga atcgaaatct cgtgatggca ggttgggcgt cgcttggtcg gtcatttcga    1140
accccagagt cccgctcaga agaactcgtc aagaaggcga tagaaggcga tgcgctgcga    1200
atcgggagcg gcgataccgt aaagcacgag gaagcggtca gcccattcgc cgccaagctc    1260
ttcagcaata tcacgggtag ccaacgctat gtcctgatag cggtccgcca cacccagccg    1320
gccacagtcg atgaatccag aaaagcggcc attttccacc atgatattcg gcaagcaggc    1380
atcgccatgg gtcacgacga gatcctcgcc gtcgggcatg cgcgccttga gcctggcgaa    1440
cagttcggct ggcgcgagcc cctgatgctc ttcgtccaga tcatcctgat cgacaagacc    1500
ggcttccatc cgagtacgtg ctcgctcgat gcgatgtttc gcttggtggt cgaatgggca    1560
ggtagccgga tcaagcgtat gcagccgccg cattgcatca gccatgatgg atactttctc    1620
ggcaggagca aggtgagatg acaggagatc ctgccccggc acttcgccca atagcagcca    1680
gtcccttccc gcttcagtga caacgtcgag cacagctgcg caaggaacgc ccgtcgtggc    1740
cagccacgat agccgcgctg cctcgtcctg cagttcattc agggcaccgg acaggtcggt    1800
cttgacaaaa agaaccgggc gcccctgcgc tgacagccgg aacacggcgg catcagagca    1860
gccgattgtc tgttgtgccc agtcatagcc gaatagcctc tccacccaag cggccggaga    1920
acctgcgtgc aatccatctt gttcaatcat gcgaaacgat cctcatcctg tctcttgatc    1980
agatcttgat ccctgcgcc atcagatcct tggcggcaag aaagccatcc agtttacttt    2040
gcagggcttc ccaaccttac cagagggcgc cccagctggc aattccggtt cgcttgctgt    2100
ccataaaacc gcccagtcta gctatcgcca tgtaagccca ctgcaagcta cctgctttct    2160
ctttgcgctt gcgttttccc ttgtccagat agcccagtag ctgacattca tccgggtca    2220
gcaccgtttc tgcggactgg cttctacgt gttccgcttc ctttagcagc ccgctagcga    2280
tttaaatccc gggtctagag gatcccaatt gttaattaac gcagaagagc atcgatgtcg    2340
acgatatccc taggtccgaa ctagtcatat gacgcgtggt accgggcccg acgtcaggcc    2400
tctcga                                                                2406
```

<210> SEQ ID NO 19
<211> LENGTH: 10495
<212> TYPE: DNA
<213> ORGANISM: artificial
<220> FEATURE:
<223> OTHER INFORMATION: pGBAAS-1

<400> SEQUENCE: 19

| | | | | | |
|---|---|---|---|---|---|
| ctcgagtagc | aagaagaccc | agtcaatctt | gcatgagcat | gtcacagtcg | aattctgggg | 60 |
| tcacgcggtg | cttgagggcg | aatacggctc | catcggtgag | taacctctct | cttactacca | 120 |
| cggaaacatc | actgacgtaa | ccaggacccg | gcggcttatc | catcatggga | aacaacacct | 180 |
| acaaatccgc | cagaattctc | tcggaagaat | ataacctcta | ctactccgtc | tggtgcgacg | 240 |
| gtgaccacga | gctgtacgat | ctctcagtaa | gtgccaaccg | gttcccgcca | ctatcgtaaa | 300 |
| aacaaaaaat | ctaacaacac | cagacggacc | cctaccaaat | gaacaacatc | tacacccaac | 360 |
| aagacaacat | ccacctccta | agcagacctc | tatccagcgt | gattgatcgt | atcgacgctc | 420 |
| tccttctggt | tctgaaatcc | tgcaagggta | acacatgcat | ccagccgtgg | cgggtcctcc | 480 |
| accccgacgg | gtccgtagag | agcctcaaag | atgcactgca | ggtgaaatac | gattcctttt | 540 |
| acaccaacca | gcccaaggtg | tcgtattcag | tatgtgaacc | cgggtacatc | attgaggctg | 600 |
| aggggcccca | ggtcggattg | cagtatagag | atgggctgag | ttgggaggcg | tggacttgac | 660 |
| gattccgtca | agtatgagta | tgggtacgaa | taatgagcgt | tattgctatg | tattttttata | 720 |
| gatagtttat | ttatatatca | tgactaaact | tgagagccat | ggaatcaatg | aaatgacatg | 780 |
| gcgagtgtag | atcacgatag | tcatagtagc | cgaagtgggc | ggatagccaa | gaataacacc | 840 |
| agaatcagat | aacaggaaca | tcacaaccga | tcacaccata | gataatatcc | aaagaagttt | 900 |
| aaatagccga | gacaaagaga | atagagacaa | gatcatggga | acaagaaagg | tacacccggt | 960 |
| agataaaccc | tgggacgggc | ccgagtcctt | acccatagat | caatcccacg | ggaacaaaac | 1020 |
| caaagtcaac | aaccaccacc | accattacca | caaccgcatc | aatagaaccg | gtgaaaaatg | 1080 |
| acaccatcga | atccttcacc | ctaagtaaag | ccctgtacgt | tgcatatcgc | ttaagcacaa | 1140 |
| aagtagtaga | atagatatga | gcccgcacgc | gcggccaacg | atccaaacta | gccctgacat | 1200 |
| caaagccagc | ggcgattgcg | ccatcaagcc | cccgtctcac | ttcatagtgg | aattgcgggt | 1260 |
| cacctcactg | attgactgtc | tgtctagaca | cactcaccca | cgcatgctgt | ctgtgcccag | 1320 |
| aacgtggact | ttggctctgc | cgagctagag | gatcaaatat | aagtagattg | gatgtaggcc | 1380 |
| cgtatttttt | ttatttcgtg | tgactcggag | attttatgcg | ttgtgttgtt | gggcggaaaa | 1440 |
| agaaatatac | tttctttttg | ttcttttctt | tttctctcta | ttgcttgcct | tggatatccc | 1500 |
| ttgcatacgg | tcggttgctg | attgactaag | ggtgctgtct | tgtgtcactg | aactgctgct | 1560 |
| caacctctgt | ctggtattcc | tgttgtcgtg | atggtgggga | aacagttcga | gttcgaggac | 1620 |
| cagagggatg | gcatcgtgcc | tcccttggag | gaaaagaagg | tcgtcgatga | ggtctatacc | 1680 |
| gataatgatg | ttgcgtcgga | ggagattgtc | aaggactggg | atgataagga | ggagggcaag | 1740 |
| ctgcggagga | agtgagtcgt | cactgttttc | attcactgcc | atataggttc | aagcatatac | 1800 |
| tgactggtat | ataggatcga | tatcatcctc | atccccattc | tcgctctcgc | tttcttcggc | 1860 |
| ctccagattg | atcgcggcaa | tatcagcgca | gctcttacct | ccactatcac | cgaagaccta | 1920 |
| ggtgtcacca | cgaaccaaat | caatattgga | acccagttgc | tttcggctgg | tattgtcatc | 1980 |
| accgagatcc | cgtcaaatat | tatacttcag | cgcatcggtc | cccaggtctg | gttgtcggca | 2040 |

```
cagctgatcg cttggggtct ggttggcaca ttccaggctt ttgtacagtc gtacccggcg    2100
tatctggcca cgaggttgtt gctggggctg ttggagggag ggtttattcc tggtttgtct    2160
ggtcgtgcgc cttggtctat ggtggtagcg ctaacaatgg gtttggtaca ggtgccctgt    2220
actatctctc gacatggtat aaacgtcctg agacgagttt ccggaccact ctgttcttct    2280
atgggcagat gtttgccggt gcgacctcta ggcggccgca agctcagcgt ccaattcgag    2340
ctctgtacag tgaccggtga ctcttttctgg catgcggaga gacggacgga cgcagagaga    2400
agggctgagt aataagcgcc actgcgccag acagctctgg cggctctgag gtgcagtgga    2460
tgattattaa tccgggaccg gccgcccctc cgccccgaag tggaaaggct ggtgtgcccc    2520
tcgttgacca agaatctatt gcatcatcgg agaatatgga gcttcatcga atcaccggca    2580
gtaagcgaag gagaatgtga agccaggggt gtatagccgt cggcgaaata gcatgccatt    2640
aacctaggta cagaagtcca attgcttccg atctggtaaa agattcacga gatagtacct    2700
tctccgaagt aggtagagcg agtacccggc gcgtaagctc cctaattggc ccatccggca    2760
tctgtagggc gtccaaatat cgtgcctctc ctgctttgcc cggtgtatga aaccggaaag    2820
gccgctcagg agctggccag cggcgcagac cgggaacaca agctggcagt cgacccatcc    2880
ggtgctctgc actcgacctg ctgaggtccc tcagtccctg gtaggcagct ttgccccgtc    2940
tgtccgcccg gtgtgtcggc ggggttgaca aggtcgttgc gtcagtccaa catttgttgc    3000
catattttcc tgctctcccc accagctgct ctttttcttt tctctttcttt tcccatcttc    3060
agtatattca tcttcccatc caagaacctt tatttcccct aagtaagtac tttgctacat    3120
ccatactcca tccttcccat cccttattcc tttgaacctt tcagttcgag ctttcccact    3180
tcatcgcagc ttgactaaca gctaccccgc ttgagcagac atcaccatgc ctcaatcctg    3240
ggaagaactg gccgctgata agcgcgcccg cctcgcaaaa accatccctg atgaatggaa    3300
agtccagacg ctgcctgcgg aagacagcgt tattgatttc ccaaagaaat cggggatcct    3360
ttcagaggcc gaactgaaga tcacagaggc ctccgctgca gatcttgtgt ccaagctggc    3420
ggccggagag ttgacctcgg tggaagttac gctagcattc tgtaaacggg cagcaatcgc    3480
ccagcagtta gtagggtccc ctctacctct caggagatg taacaacgcc accttatggg    3540
actatcaagc tgacgctggc ttctgtgcag acaaactgcg cccacgagtt cttccctgac    3600
gccgctctcg cgcaggcaag ggaactcgat gaatactacg caaagcacaa gagacccgtt    3660
ggtccactcc atggcctccc catctctctc aaagaccagc ttcgagtcaa ggtacaccgt    3720
tgcccctaag tcgttagatg tccctttttg tcagctaaca tatgccacca gggctacgaa    3780
acatcaatgg gctacatctc atggctaaac aagtacgacg aagggggactc ggttctgaca    3840
accatgctcc gcaaagccgg tgccgtcttc tacgtcaaga cctctgtccc gcagaccctg    3900
atggtctgcg agacagtcaa caacatcatc gggcgcaccg tcaacccacg caacaagaac    3960
tggtcgtgcg gcggcagttc tggtggtgag ggtgcgatcg ttgggattcg tggtggcgtc    4020
atcggtgtag aacggatat cggtggctcg attcgagtgc cggccgcgtt caacttcctg    4080
tacggtctaa ggccgagtca tgggcggctg ccgtatgcaa agatggcgaa cagcatggag    4140
ggtcaggaga cggtgcacag cgttgtcggg ccgattacgc actctgttga gggtgagtcc    4200
ttcgcctctt ccttctttc ctgctctata ccaggcctcc actgtcctcc tttcttgctt    4260
tttatactat atacgagacc ggcagtcact gatgaagtat gttagacctc cgcctcttca    4320
ccaaatccgt cctcggtcag gagccatgga aatacgactc caaggtcatc cccatgccct    4380
ggcgccagtc cgagtcggac attattgcct ccaagatcaa gaacggcggg ctcaatatcg    4440
```

```
gctactacaa cttcgacggc aatgtccttc cacaccctcc tatcctgcgc ggcgtggaaa    4500
ccaccgtcgc cgcactcgcc aaagccggtc acaccgtgac cccgtggacg ccatacaagc    4560
acgatttcgg ccacgatctc atctcccata tctacgcggc tgacggcagc gccgacgtaa    4620
tgcgcgatat cagtgcatcc ggcgagccgg cgattccaaa tatcaaagac ctactgaacc    4680
cgaacatcaa agctgttaac atgaacgagc tctgggacac gcatctccag aagtggaatt    4740
accagatgga gtaccttgag aaatggcggg aggctgaaga aaaggccggg aaggaactgg    4800
acgccatcat cgcgccgatt acgcctaccg ctgcggtacg gcatgaccag ttccggtact    4860
atgggtatgc ctctgtgatc aacctgctgg atttcacgag cgtggttgtt ccggttacct    4920
ttgcggataa gaacatcgat aagaagaatg agagtttcaa ggcggttagt gagcttgatg    4980
ccctcgtgca ggaagagtat gatccggagg cgtaccatgg ggcaccggtt gcagtgcagg    5040
ttatcggacg gagactcagt gaagagagga cgttggcgat tgcagaggaa gtggggaagt    5100
tgctgggaaa tgtggtgact ccatagctaa taagtgtcag atagcaattt gcacaagaaa    5160
tcaataccag caactgtaaa taagcgctga agtgaccatg ccatgctacg aaagagcaga    5220
aaaaaacctg ccgtagaacc gaagagatat gacacgcttc catctctcaa aggaagaatc    5280
ccttcagggt tgcgtttcca gtctagacac gtataacggc acaagtgtct ctcaccaaat    5340
gggttatatc tcaaatgtga tctaaggatg gaaagcccag aatattggct gggttgatgg    5400
ctgcttcgag tgcagtctca tgctgccaca ggtgactctg gatggcccca taccactcaa    5460
cccatgcgtg cgaggtacca caatcaatcc atttcgctat agttaaagga tggggatgag    5520
ggcaattggt tatatgatca tgtatgtagt gggtgtgcat aatagtagtg aaatggaagc    5580
caagtcatgt gattgtaatc gaccgacgga attgaggata tccggaaata cagacaccgt    5640
gaaagccatg gtctttcctt cgtgtagaag accagacaga cagtccctga tttaccctgc    5700
acaaagcact agaaaattag cattccatcc ttctctgctt gctctgctga tatcactgtc    5760
attcaatgca tagccatgag ctcatcttag atccaagcac gtaattccat agccgaggtc    5820
cacagtggag cagcaacatt ccccatcatt gctttcccca ggggcctccc aacgactaaa    5880
tcaagagtat atctctaccg tccaatagat cgtcttcgct tcaaaatctt tgacaattcc    5940
aagagggtcc ccatccatca aacccagttc aataatagcc gagatgcatg gtggagtcaa    6000
ttaggcagta ttgctggaat gtcggggcca gttccgggtg tcattggcc gcctgtgatg    6060
ccatctgcca ctaaatccga tcattgatcc accgcccacg agggcgtctt tgcttttgc    6120
gcggcgtcca ggttcaactc tctctgcagc tccagtccaa cgctgactga ctagtttacc    6180
tactggtctg atcggctcca tcagagctat ggcgttatcc cgtgccgttg ctgcgcaatc    6240
gctatcttga tcgcaacctt gaactcactc ttgttttaat agtgatcttg gtgacggagt    6300
gtcggtgagt gacaaccaac atcgtgcaag ggagattgat acggaattgt cgctcccatc    6360
atgatgttct tgccggcttt gttggcccta ttcgtgggat cgatgccctc ctgtgcagca    6420
gcaggtactg ctggatgagg agccatcggt ctctgcacgc aaacccaact tcctcttcat    6480
tctcacggat gatcaggatc tccggatgaa ttctccggcg tatatgccgt atacgcaggc    6540
gagaatcaag gaaaaggcta ccgagttctt gaaccatttc gtcactaccg cgctttgctg    6600
tccgtcgcgc gtgagtcttt ggacgggaag acaggctcat aatactaatg tgacggatgt    6660
gaacccgcct tatggtatgg acactgcttc gatcggtctt gattcttcag cgtggttaca    6720
attgctaatg cggcataggc ggatacccca aattcgtcgc tcaaggcttc aacgaaaact    6780
```

```
tcctccccgt ttggctgcag tccgccggtt acaatacctc ctacacgggg aagctgttca   6840
actcgcacag tgtcgctacc tataacgcgc cctttgtgaa cggtttcaat ggctccgact   6900
tcctcctcga cccccacaca tattcctact ggaatgcgac ataccagcga aaccatgagc   6960
ctccgcggag ttacgaggga caatatacta cggatgtgat gaaggagaag gcatcgggat   7020
tgttggcaga tgcgctggac agtgacgcgc cattcttcct gacggtcgcg ccgatcgcac   7080
cgcacacgaa catcgatgtg gaggggctga gcggtgcggg tggaccgaag atgacagagc   7140
cgctgcctgc accgagacat gcgcatttgt ttgctgatgc aaaggtgccg cggacgccta   7200
atttcaatcc ggacaaggtg tgtgatatcc tgacacagtg gtgggacgg gcactgacaa    7260 gagtaggatt ctggtgcggg gtggatccaa accatggaac tacagaacca gaccgtcatc   7320
gactacgaag accatcttta tcgccagcgt ctgcgcactt tgcaagccgt cgatgagatg   7380
gtggatgcgc tgatcacgca gctggaagaa agtgggcaga tcgacaatac ctacatcatt   7440
tacagtgctg ataacggcta ccacattggc catcaccgtc tacccccgg caagacaact    7500 ggctatgaag aggacattcg cgtaccattc tacattcgcg gacctggcat tcctgaggga   7560
aagagcgttg accgtgtaac cacgcacatt gacattgcac ctacactgtt cgagttggct   7620
ggggttccct tgcgagagga ctttgacggg actccgatgc ccgtctcgag agaaagcttg   7680
gcactggccg tcgttttaca acgtcgtgac tgggaaaacc ctggccttac ccaacttaat   7740
cgccttgcag cacatccccc tttcgccagc tggcgtaata gcgaagaggc ccgcaccgat   7800
cgcccttccc aacagttgcg cagcctgaat ggcgaatggg aaattgtaaa cgttaatatt   7860
ttgttaaaat tcgcgttaaa tttttgttaa atcagctcat tttttaacca ataggccgaa   7920
atcggcaaaa tcccttataa atcaaaagaa tagaccgaga tagggttgag tgttgttcca   7980
gtttggaaca agagtccact attaaagaac gtggactcca acgtcaaagg gcgaaaaacc   8040
gtctatcagg gcgatggccc actacgtgaa ccatcaccct aatcaagttt ttggggtcg    8100 aggtgccgta aagcactaaa tcggaaccct aaagggagcc cccgatttag agcttgacgg   8160
ggaaagccgg cgaacgtggc gagaaaggaa gggaagaaag cgaaaggagc gggcgctagg   8220
gcgctggcaa gtgtagcggt cacgctgcgc gtaaccacca caccgccgc gcttaatgcg    8280 ccgctacagg gcgcgtcagg tggcactttt cggggaaatg tgcgcggaac ccctatttgt   8340
ttatttttct aaatacattc aaatatgtat ccgctcatga caataaccc tgataaatg     8400 cttcaataat attgaaaaag gaagagtatg agtattcaac atttccgtgt cgcccttatt   8460
cccttttttg cggcattttg ccttcctgtt tttgctcacc cagaaacgct ggtgaaagta   8520
aaagatgctg aagatcagtt gggtgcacga gtgggttaca tcgaactgga tctcaacagc   8580
ggtaagatcc ttgagagttt tcgccccgaa gaacgttttc caatgatgag cacttttaaa   8640
gttctgctat gtggcgcggt attatcccgt attgacgccg ggcaagacca actcggtcgc   8700
cgcatacact attctcagaa tgacttggtt gagtactcac cagtcacaga aaagcatctt   8760
acggatggca tgacagtaag agaattatgc agtgctgcca taaccatgag tgataacact   8820
gcggccaact tacttctgac aacgatcgga ggaccgaagg agctaaccgc ttttttgcac   8880
aacatggggg atcatgtaac tcgccttgat cgttgggaac cggagctgaa tgaagccata   8940
ccaaacgacg agcgtgacac cacgatgcct gtagcaatgg caacaacgtt gcgcaaacta   9000
ttaactggcg aactacttag tctagcttcc cggcaacaat taatagactg gatggaggcg   9060
gataaagttg caggaccact tctgcgctcg gcccttccgg ctggctggtt tattgctgat   9120
aaatctggag ccggtgagcg tgggtctcgc ggtatcattg cagcactggg gccagatggt   9180
```

-continued

| | | | | | |
|---|---|---|---|---|---|
| aagccctccc | gtatcgtagt | tatctacacg | acggggagtc | aggcaactat | ggatgaacga | 9240 |
| aatagacaga | tcgctgagat | aggtgcctca | ctgattaagc | attggtaact | gtcagaccaa | 9300 |
| gtttactcat | atatacttta | gattgattta | aaacttcatt | tttaatttaa | aaggatctag | 9360 |
| gtgaagatcc | tttttgataa | tctcatgacc | aaaatccctt | aacgtgagtt | ttcgttccac | 9420 |
| tgagcgtcag | accccgtaga | aaagatcaaa | ggatcttctt | gagatccttt | ttttctgcgc | 9480 |
| gtaatctgct | gcttgcaaac | aaaaaaacca | ccgctaccag | cggtggtttg | tttgccggat | 9540 |
| caagagctac | cacctctttt | tccgaaggta | actggcttca | gcagagcgca | gataccaaat | 9600 |
| actgtccttc | tagtgtagcc | gtagttaggc | caccacttca | agaactctgt | agcaccgcct | 9660 |
| acatacctcg | ctctgctaat | cctgttacca | gtggctgctg | ccagtggcga | taagtcgtgt | 9720 |
| cttaccgggt | tggactcaag | acgatagtta | ccggataagg | cgcagcggtc | gggctgaacg | 9780 |
| gggggttcgt | gcacacagcc | cagcttggag | cgaacgacct | acaccgaact | gagatacccta | 9840 |
| cagcgtgagc | attgagaaag | cgccacgctt | cccgaaggga | gaaaggcgga | caggtatccg | 9900 |
| gtaagcggca | gggtcggaac | aggagagcgc | acgagggagc | ttccagggggg | aaacgcctgg | 9960 |
| tatctttata | gtcctgtcgg | gtttcgccac | ctctgacttg | agcgtcgatt | tttgtgatgc | 10020 |
| tcgtcagggg | ggcggagcct | atggaaaaac | gccagcaacg | cggccttttt | acggttcctg | 10080 |
| gccttttgct | ggccttttgc | tcacatgttc | tttcctgcgt | tatccctga | ttctgtggat | 10140 |
| aaccgtatta | ccgcctttga | gtgagctgat | accgctcgcc | gcagccgaac | gaccgagcgc | 10200 |
| agcgagtcag | tgagcgagga | agcggaagag | cgcccaatac | gcaaaccgcc | tctccccgcg | 10260 |
| cgttggccga | ttcattaatg | cagctggcac | gacaggtttc | ccgactggaa | agcgggcagt | 10320 |
| gagcgcaacg | caattaatgt | gagttagctc | actcattagg | caccccaggc | tttacacttt | 10380 |
| atgcttccgg | ctcgtatgtt | gtgtggaatt | gtgagcggat | aacaatttca | cacaggaaac | 10440 |
| agctatgacc | atgattacga | atttaatacg | actcactata | ggggaattgg | agctt | 10495 |

<210> SEQ ID NO 20
<211> LENGTH: 5754
<212> TYPE: DNA
<213> ORGANISM: artificial
<220> FEATURE:
<223> OTHER INFORMATION: pMT121-Clr2-A

<400> SEQUENCE: 20

| | | | | | |
|---|---|---|---|---|---|
| cgatccttac | atacacatgc | acgcccgtaa | tgaaggccct | ggtgaccgac | gggaacacgg | 60 |
| actggagtgc | tgcgtcacca | ccagacgcac | cgactcccca | ttaggcgcga | cacgcctgct | 120 |
| tcggccgccc | gccatgccgc | ctgctcgccc | aaacttgcca | aaagatttgg | aggcaggcgc | 180 |
| tcgagcttcc | cggtgtgaac | ggtggagctg | agagcctaag | acccacacca | ccaccacccc | 240 |
| ggactttttat | tttacccctg | tctgccctga | tcgaagggggc | gccaaccggc | aggatccctg | 300 |
| gcgctcgccg | ttgagcaaag | ccggacacca | atcagacgac | caaggcgcga | ccgtcctccc | 360 |
| cacaacccgc | cttggcacac | tggcaccctg | gatcgaggcg | cctttggggc | cgacggtccc | 420 |
| tctttccagt | cctcccccaa | cgccatctcc | accgttctcc | aattccctcc | tcgcctcgaa | 480 |
| ggcgcccct | ctccctcccg | gcctagactc | caacgcgcga | cagaaatagt | ggtacgattt | 540 |
| gcgacgcgtg | gagccgtccc | tctcatctcg | catccctcac | tttctcgacg | acggcatcac | 600 |
| agggatggg | acgagcggca | aagctttcca | tagccaaaag | ctggtggtcg | accgacgtca | 660 |
| ggagaatggg | attgctgtct | tgccaatctc | ccaaaagtgg | caatgcgggt | ctcctgcagg | 720 |

```
cagcgctctc gcctgttaca ctactttcac ggcctcggca tccgatactc gactgcaaca      780
tcatcagggt attcggctag gcagtctagt gtagtagtac acaaagtctt cgattgcttt      840
ccgcgggaca gggttcgaga gagactccag tacactacaa cgcagcccca cgtgtagcgt      900
catgggccac cgctggctga cgttcacgta cttacatacc taggtacata caccattccg      960
tacggataca tcaggtaatg tatgtacata cgtggcgcag gtacgcagta cgtacatatc     1020
aaccttgctt gcatagcacg ggccgatgag gtatgtacgg acgtacttcg tacttacgcg     1080
gtagtggggg gaaggccaca catctgatag cttcctctct ccattccctc atgcacccag     1140
accctggcgc tgaaacgccg ccgctcagaa gccgcccact ggctgcagac ttgaacctaa     1200
cttttttttc tttgttttca cttcaccacc cctcccccctc cccctcccct ccgccctgt      1260
ccctcttcgc cttcccaccc tctttgcaag tcgagctgcg ctacgggatg gcgggcggcg     1320
gtgacctata ctgggcctga cactaatatg caaacccagg tacctgcggt tcactctgcc     1380
cgtttgcttg tacataccttt agtgagcagc aggcatggac cctgctgatg tctcgtgttt     1440
agctgatgcc agactcacga gtgtggacgg cattgaccac ggcgggtgcg cccctcctct     1500
cttcacccag cagcaggata ttcgagatta cctcatgcgc ttgttcgtgc cttgatcggg     1560
aagctcagcg tccaattcga gctctgtaca gtgaccggtg actctttctg gcatgcggag     1620
agacggacgg acgcagagag aagggctgag taataagcgc cactgcgcca gacagctctg     1680
gcggctctga ggtgcagtgg atgattatta atccgggacc ggccgcccct ccgcccgaa      1740
gtggaaaggc tggtgtgccc ctcgttgacc aagaatctat tgcatcatcg gagaatatgg     1800
agcttcatcg aatcaccggc agtaagcgaa ggagaatgtg aagccagggg tgtatagccg     1860
tcggcgaaat agcatgccat taacctaggt acagaagtcc aattgcttcc gatctggtaa     1920
aagattcacg agatagtacc ttctccgaag taggtagagc gagtaccccgg cgcgtaagct     1980
ccctaattgg cccatccggc atctgtaggg cgtccaaata tcgtgcctct cctgctttgc     2040
ccggtgtatg aaaccggaaa ggccgctcag gagctggcca gcggcgcaga ccgggaacac     2100
aagctggcag tcgacccatc cggtgctctg cactcgacct gctgaggtcc ctcagtccct     2160
ggtaggcagc tttgccccgt ctgtccgccc ggtgtgtcgg cggggttgac aaggtcgttg     2220
cgtcagtcca acatttgttg ccatatttttc ctgctctccc caccagctgc tcttttctttt    2280
tctctttctt ttcccatctt cagtatattc atcttcccat ccaagaacct ttatttcccc     2340
taagtaagta ctttgctaca tccatactcc atccttccca tcccttattc ctttgaacct     2400
ttcagttcga gctttcccac ttcatcgcag cttgactaac agctacccccg cttgagcaga     2460
catcaccatg cctcaatcct gggaagaact ggccgctgat aagcgcgccc gcctcgcaaa     2520
aaccatccct gatgaatgga agtccgagac gctgcctgcg gaagacagcg ttattgattt     2580
cccaaagaaa tcggggatcc tttcagaggc cgaactgaag atcacagagg cctccgctgc     2640
agatcttgtg tccaagctgg cggccggaga gttgacctcg gtggaagtta cgctagcatt     2700
ctgtaaacgg gcagcaatcg cccagcagtt agtagggtcc cctctacctc tcagggagat     2760
gtaacaacgc caccttatgg gactatcaag ctgacgctgg cttctgtgca gacaaactgc     2820
gcccacgagt tcttccctga cgccgctctc gcgcaggcaa gggaactcga tgaatactac     2880
gcaaagcaca agagacccgt tggtccactc catggcctcc ccatctctct caaagaccag     2940
cttcgagtca aggtacaccg ttgcccctaa gtcgttagat gtccctttttt gtcagctaac     3000
atatgccacc agggctacga aacatcaatg ggctacatct catggctaaa caagtacgac     3060
gaaggggact cggttctgac aaccatgctc cgcaaagccg gtgccgtctt ctacgtcaag     3120
```

```
acctctgtcc cgcagaccct gatggtctgc gagacagtca acaacatcat cgggcgcacc    3180
gtcaacccac gcaacaagaa ctggtcgtgc ggcggcagtt ctggtggtga gggtgcgatc    3240
gttgggattc gtggtggcgt catcggtgta ggaacggata tcggtggctc gattcgagtg    3300
ccggccgcgt tcaacttcct gtacggtcta aggccgagtc atgggcggct gccgtatgca    3360
aagatggcga acagcatgga ggcggccgct acgggattta aatcgctagc gggctgctaa    3420
aggaagcgga acacgtagaa agccagtccg cagaaacggt gctgacccc gatgaatgtc      3480
agctactggg ctatctggac aagggaaaac gcaagcgcaa agagaaagca ggtagcttgc    3540
agtgggctta catggcgata gctagactgg gcggttttat ggacagcaag cgaaccggaa    3600
ttgccagctg gggcgccctc tggtaaggtt gggaagccct gcaaagtaaa ctggatggct    3660
ttcttgccgc caaggatctg atggcgcagg ggatcaagat ctgatcaaga gacaggatga    3720
ggatcgtttc gcatgattga acaagatgga ttgcacgcag gttctccggc cgcttgggtg    3780
gagaggctat tcggctatga ctgggcacaa cagacaatcg gctgctctga tgccgccgtg    3840
ttccggctgt cagcgcaggg gcgcccggtt cttttttgtca agaccgacct gtccggtgcc    3900
ctgaatgaac tgcaggacga ggcagcgcgg ctatcgtggc tggccacgac gggcgttcct    3960
tgcgcagctg tgctcgacgt tgtcactgaa gcgggaaggg actggctgct attgggcgaa    4020
gtgccggggc aggatctcct gtcatctcac cttgctcctg ccgagaaagt atccatcatg    4080
gctgatgcaa tgcggcggct gcatacgctt gatccggcta cctgcccatt cgaccaccaa    4140
gcgaaacatc gcatcgagcg agcacgtact cggatggaag ccggtcttgt cgatcaggat    4200
gatctggacg aagagcatca ggggctcgcg ccagccgaac tgttcgccag gctcaaggcg    4260
cgcatgcccg acggcgagga tctcgtcgtg acccatggcg atgcctgctt gccgaatatc    4320
atggtggaaa atggccgctt ttctggattc atcgactgtg gccggctggg tgtggcggac    4380
cgctatcagg acatagcgtt ggctacccgt gatattgctg aagagcttgg cggcgaatgg    4440
gctgaccgct tcctcgtgct ttacggtatc gccgctcccg attcgcagcg catcgccttc    4500
tatcgccttc ttgacgagtt cttctgagcg ggactctggg gttcgaaatg accgaccaag    4560
cgacgcccaa cctgccatca cgagatttcg attccaccgc cgccttctat gaaaggttgg    4620
gcttcggaat cgttttccgg gacgccggct ggatgatcct ccagcgcggg gatctcatgc    4680
tggagttctt cgcccacgct agcggcgcgc cggccggccc ggtgtgaaat accgcacaga    4740
tgcgtaagga gaaaataccg catcaggcgc tcttccgctt cctcgctcac tgactcgctg    4800
cgctcggtcg ttcggctgcg gcgagcggta tcagctcact caaaggcggt aatacggtta    4860
tccacagaat caggggataa cgcaggaaag aacatgtgag caaaaggcca gcaaaggcc    4920
aggaaccgta aaaaggccgc gttgctggcg ttttttccata ggctccgccc cctgacgag    4980
catcacaaaa atcgacgctc aagtcagagg tggcgaaacc cgacaggact ataaagatac    5040
caggcgtttc ccctggaag ctccctcgtg cgctctcctg ttccgaccct gccgcttacc    5100
ggatacctgt ccgcctttct cccttcggga agcgtggcgc tttctcatag ctcacgctgt    5160
aggtatctca gttcggtgta ggtcgttcgc tccaagctgg gctgtgtgca cgaacccccc    5220
gttcagcccg accgctgcgc cttatccggt aactatcgtc ttgagtccaa cccggtaaga    5280
cacgacttat cgccactggc agcagccact ggtaacagga ttagcagagc gaggtatgta    5340
ggcggtgcta cagagttctt gaagtggtgg cctaactacg gctacactag aaggacagta    5400
tttggtatct gcgctctgct gaagccagtt accttcggaa aaagagttgg tagctcttga    5460
```

```
tccggcaaac aaaccaccgc tggtagcggt ggttttttg tttgcaagca gcagattacg    5520
cgcagaaaaa aaggatctca agaagatcct ttgatctttt ctacggggtc tgacgctcag    5580
tggaacgaaa actcacgtta agggatttttg gtcatgagat tatcaaaaag gatcttcacc    5640
tagatccttt taaaggccgg ccgcggccgc tcgatttaaa tctcgagagg cctgacgtcg    5700
ggcccggtac cacgcgtcat atgactagtt cggacctagg gatatcgtcg acat          5754

<210> SEQ ID NO 21
<211> LENGTH: 5708
<212> TYPE: DNA
<213> ORGANISM: artificial
<220> FEATURE:
<223> OTHER INFORMATION: pMT147-Dclr2-B

<400> SEQUENCE: 21
gccatgtaag cccactgcaa gctacctgct ttctctttgc gcttgcgttt tcccttgtcc      60
agatagccca gtagctgaca ttcatccggg gtcagcaccg tttctgcgga ctggcttttct    120 acgtgttccg cttcctttag cagcccgcta gcgatttaaa tccgtagcg gccgcaaggg     180 gactcggttc tgacaaccat gctccgcaaa gccggtgccg tcttctacgt caagacctct    240
gtcccgcaga ccctgatggt ctgcgagaca gtcaacaaca tcatcgggcg caccgtcaac    300
ccacgcaaca agaactggtc gtgcggcggc agttctggtg gtgagggtgc gatcgttggg    360
attcgtggtg gcgtcatcgg tgtaggaacg gatatcggtg gctcgattcg agtgccggcc    420
gcgttcaact tcctgtacgg tctaaggccg agtcatgggc ggctgccgta tgcaaagatg    480
gcgaacagca tggagggtca ggagacggtg cacagcgttg tcgggccgat tacgcactct    540
gttgagggtg agtccttcgc ctcttccttc ttttcctgct ctataccagg cctccactgt    600
cctcctttct tgcttttttat actatatacg agaccggcag tcactgatga agtatgttag    660
acctccgcct cttcaccaaa tccgtcctcg gtcaggagcc atggaaatac gactccaagg    720
tcatccccat gccctggcgc cagtccgagt cggacattat tgcctccaag atcaagaacg    780
gcgggctcaa tatcggctac tacaacttcg acggcaatgt ccttccacac cctcctatcc    840
tgcgcggcgt ggaaaccacc gtcgccgcac tcgccaaagc cggtcacacc gtgaccccgt    900
ggacgccata caagcacgat ttcggccacg atctcatctc ccatatctac gcggctgacg    960
gcagcgccga cgtaatgcgc gatatcagtg catccggcga gccggcgatt ccaaatatca    1020
aagacctact gaacccgaac atcaaagctg ttaacatgaa cgagctctgg gacacgcatc    1080
tccagaagtg gaattaccag atggagtacc ttgagaaatg gcgggaggct gaagaaaagg    1140
ccgggaagga actggacgcc atcatcgcgc cgattacgcc taccgctgcg gtacggcatg    1200
accagttccg gtactatggg tatgcctctg tgatcaacct gctggatttc acgagcgtgg    1260
ttgttccggt tacctttgcg gataagaaca tcgataagaa gaatgagagt ttcaaggcgg    1320
ttagtgagct tgatgccctc gtgcaggaag agtatgatcc ggaggcgtac catggggcac    1380
cggttgcagt gcaggttatc ggacggagac tcagtgaaga gaggacgttg gcgattgcag    1440
aggaagtggg gaagttgctg ggaaatgtgg tgactccata gctaataagt gtcagatagc    1500
aatttgcaca agaaatcaat accagcaact gtaaataagc gctgaagtga ccatgccatg    1560
ctacgaaaga gcagaaaaaa acctgccgta gaaccgaaga gatatgacac gcttccatct    1620
ctcaaaggaa gaatcccttc agggttgcgt ttccagtcta gacacgtata acggcacaag    1680
tgtctctcac caaatgggtt atatctcaaa tgtgatctaa ggatgaaaag cccagaatat    1740
tggctgggtt gatggctgct tcgagtgcag tctcatgctg ccacaggtga ctctggatgg    1800
```

| | |
|---|---|
| ccccatacca ctcaacccat gcgtgcgagg tcccgggtct agaggatccc aattgttaat | 1860 |
| taacgatgga tgacggatat accaggaagg tttttttttt gctcacgacc catgtatgtg | 1920 |
| tatgtacatg cattcgctac ttgttcaggt ttggcaggaa aggggtgggg aggcgcggaa | 1980 |
| ttggcagggc acggcaaagg ggaacaaaag agatggggag ggaaaggggg aaaggggggat | 2040 |
| ttctgcggtg tgcactggaa aaggcgcggt tctgttctca gtctaccatt gcccgtctat | 2100 |
| acttttggca aaatcaactt ttggtgtcct caaccattgc acctgcttgg ctcacctgct | 2160 |
| ttctgaaaac tcggggtaat gggcggcttg agattgggta ggcaaaattg gcgtgtggtc | 2220 |
| ccgattgtgt tggtggaatg tcccgaaatg gtaaggcaca ttcaactagg caaggagggt | 2280 |
| ataacaggct gggccttgta tgtatgtatg tatgtactgt aaagtactag taactaacta | 2340 |
| gttaactcgg tgctcacttt tcactggctg atgattttt attcgagcca cgaccctgcg | 2400 |
| agttactcct cccttacccct tcccctctct gtttctctcc gacctgcagc agaaggcacg | 2460 |
| atgcaggacg cgttcccaca gctcatgttg atggtcttg actgcatgtg atggtgtccg | 2520 |
| taccaaccccc cggacattcg tggaaggctt cgcgaagagt tctagcgtaa cggcgacatc | 2580 |
| caatgaggat gtgccgccgc tgaagggcgg gctggaaccg gccttttcgc tcatcgggat | 2640 |
| catcgctgtc gtggcatgta tgtacatata tgtatactac ggtgctctat ggtgtatgta | 2700 |
| tttgtgtgat atactgtact atatgtatgt atgtacctag gtatggacgt gcacttttaa | 2760 |
| catgagcatt taccggcgct caaccgtttt tttgtgtaca tacttctcaa tgcttagttt | 2820 |
| cgtcggcaag caggcgggca agggtgggaa gtcggttgcg gtgagcgcga aggtgccctc | 2880 |
| tgaccaaagg atccggcttt ccactcgggt tcaccttca aatgcaaagg gaggggaaaa | 2940 |
| aacaccgcta gattcactca gcccgttgac ggcggccgaa tgtgacctgt cgcgtcctca | 3000 |
| cgaaagatcc gggtggtggg tcgcgatggc aagctggatg ctagggccga cgcgccagag | 3060 |
| cgccaagcgg tgcttggacc ttgggcttta ctcgtcgcgg ctgtgatctg cgagcacacc | 3120 |
| tccaccatgg cttcctctcc gtgattgttt ctccagtgta cgaagtacca tcttttgatg | 3180 |
| tggcagggaa aagaagcctc ctctgtttgg gctacggcag ccctggaaaa gaaaaggttt | 3240 |
| gagtgtcatc cttggcgtcg tcctcggtgt ttgttttgta atctttagtt atgtactgta | 3300 |
| ctgtatccat acatagtgta caggcacgtc tcgggcactt tcgttttcgg atccgggatc | 3360 |
| cggggatgag cttgagcccg ccaaccctga tgagcagccg ccaaccacaa atcgtcgagg | 3420 |
| ggacggcata aacgttttga tgtcctggga agacgcacat gcccagtcac gatttacccc | 3480 |
| ggaccctctg catctcgagc ccactcatcg aggggatcat ggcgacgtag tagtcaagct | 3540 |
| ccatatgacg cgtggtaccg ggcccgacgt caggcctctc gagatttaaa tcgagcggcc | 3600 |
| gcggccggcc tttaaaagga tctaggtgaa gatccttttt gataatctca tgaccaaaat | 3660 |
| cccttaacgt gagttttcgt tccactgagc gtcagacccc gtagaaaaga tcaaaggatc | 3720 |
| ttcttgagat cctttttttc tgcgcgtaat ctgctgcttg caaacaaaaa aaccaccgct | 3780 |
| accagcggtg gtttgtttgc cggatcaaga gctaccaact cttttttccga aggtaactgg | 3840 |
| cttcagcaga gcgcagatac caaatactgt ccttctagtg tagccgtagt taggccacca | 3900 |
| cttcaagaac tctgtagcac cgcctacata cctcgctctg ctaatcctgt taccagtggc | 3960 |
| tgctgccagt ggcgataagt cgtgtcttac cgggttggac tcaagacgat agttaccgga | 4020 |
| taaggcgcag cggtcgggct gaacggggggg ttcgtgcaca cagcccagct ggagcgaac | 4080 |
| gacctacacc gaactgagat acctacagcg tgagctatga gaaagcgcca cgcttcccga | 4140 |

| | |
|---|---|
| agggagaaag gcggacaggt atccggtaag cggcagggtc ggaacaggag agcgcacgag | 4200 |
| ggagcttcca gggggaaacg cctggtatct ttatagtcct gtcgggtttc gccacctctg | 4260 |
| acttgagcgt cgattttttgt gatgctcgtc aggggggcgg agcctatgga aaaacgccag | 4320 |
| caacgcggcc ttttttacggt tcctggcctt ttgctggcct tttgctcaca tgttctttcc | 4380 |
| tgcgttatcc cctgattctg tggataaccg tattaccgcc tttgagtgag ctgataccgc | 4440 |
| tcgccgcagc cgaacgaccg agcgcagcga gtcagtgagc gaggaagcgg aagagcgcct | 4500 |
| gatgcggtat tttctcctta cgcatctgtg cggtatttca caccgggccg gccggcgcgc | 4560 |
| cgctagcgtg ggcgaagaac tccagcatga gatccccgcg ctggaggatc atccagccgg | 4620 |
| cgtcccggaa aacgattccg aagcccaacc tttcatagaa ggcggcggtg aatcgaaat | 4680 |
| ctcgtgatgg caggttgggc gtcgcttggt cggtcatttc gaaccccaga gtcccgctca | 4740 |
| gaagaactcg tcaagaaggc gatagaaggc gatgcgctgc gaatcgggag cggcgatacc | 4800 |
| gtaaagcacg aggaagcggt cagcccattc gccgccaagc tcttcagcaa tatcacgggt | 4860 |
| agccaacgct atgtcctgat agcggtccgc cacacccagc cggccacagt cgatgaatcc | 4920 |
| agaaaagcgg ccattttcca ccatgatatt cggcaagcag gcatcgccat gggtcacgac | 4980 |
| gagatcctcg ccgtcgggca tgcgcgcctt gagcctggcg aacagttcgg ctggcgcgag | 5040 |
| cccctgatgc tcttcgtcca gatcatcctg atcgacaaga ccggcttcca tccgagtacg | 5100 |
| tgctcgctcg atgcgatgtt tcgcttggtg gtcgaatggg caggtagccg atcaagcgt | 5160 |
| atgcagccgc cgcattgcat cagccatgat ggatactttc tcggcaggag caaggtgaga | 5220 |
| tgacaggaga tcctgccccg gcacttcgcc caatagcagc cagtcccttc ccgcttcagt | 5280 |
| gacaacgtcg agcacagctg cgcaaggaac gcccgtcgtg gccagccacg atagccgcgc | 5340 |
| tgcctcgtcg tgcagttcat tcagggcacc ggacaggtcg gtcttgacaa aaagaaccgg | 5400 |
| gcgcccctgc gctgacagcc ggaacacggc ggcatcagag cagccgattg tctgttgtgc | 5460 |
| ccagtcatag ccgaatagcc tctccaccca agcggccgga gaacctgcgt gcaatccatc | 5520 |
| ttgttcaatc atgcgaaacg atcctcatcc tgtctcttga tcagatcttg atcccctgcg | 5580 |
| ccatcagatc cttggcggca agaaagccat ccagtttact ttgcagggct tcccaacctt | 5640 |
| accagagggc gccccagctg gcaattccgg ttcgcttgct gtccataaaa ccgcccagtc | 5700 |
| tagctatc | 5708 |

<210> SEQ ID NO 22
<211> LENGTH: 7262
<212> TYPE: DNA
<213> ORGANISM: artificial
<220> FEATURE:
<223> OTHER INFORMATION: pMT189-Dclr2-AB

<400> SEQUENCE: 22

| | |
|---|---|
| acctgctttc tctttgcgct tgcgttttcc cttgtccaga tagcccagta gctgacattc | 60 |
| atccggggtc agcaccgttt ctgcggactg gctttctacg tgttccgctt cctttagcag | 120 |
| cccgctagcg atttaaatcc cgtagcggcc gcaagggggac tcggttctga caaccatgct | 180 |
| ccgcaaagcc ggtgccgtct tctacgtcaa gacctctgtc ccgcagaccc tgatggtctg | 240 |
| cgagacagtc aacaacatca tcgggcgcac cgtcaaccca cgcaacaaga actggtcgtg | 300 |
| cggcggcagt tctggtggtg agggtgcgat cgttgggatt cgtggtggcg tcatcggtgt | 360 |
| aggaacggat atcggtggct cgattcgagt gccggccgcg ttcaacttcc tgtacgtcct | 420 |
| aaggccgagt catgggcggc tgccgtatgc aaagatggcg aacagcatgg agggtcagga | 480 |

```
gacggtgcac agcgttgtcg ggccgattac gcactctgtt gagggtgagt ccttcgcctc    540
ttccttcttt tcctgctcta taccaggcct ccactgtcct cctttcttgc tttttatact    600
atatacgaga ccggcagtca ctgatgaagt atgttagacc tccgcctctt caccaaatcc    660
gtcctcggtc aggagccatg gaaatacgac tccaaggtca tccccatgcc ctggcgccag    720
tccgagtcgg acattattgc ctccaagatc aagaacggcg ggctcaatat cggctactac    780
aacttcgacg gcaatgtcct tccacaccct cctatcctgc gcggcgtgga aaccaccgtc    840
gccgcactcg ccaaagccgg tcacaccgtg accccgtgga cgccatacaa gcacgatttc    900
ggccacgatc tcatctccca tatctacgcg gctgacggca cgccgacgt aatgcgcgat    960 atcagtgcat ccggcgagcc ggcgattcca aatatcaaag acctactgaa cccgaacatc   1020
aaagctgtta acatgaacga gctctgggac acgcatctcc agaagtggaa ttaccagatg   1080
gagtaccttg agaaatggcg ggaggctgaa gaaaaggccg ggaaggaact ggacgccatc   1140
atcgcgccga ttacgcctac cgctgcggta cggcatgacc agttccggta ctatgggtat   1200
gcctctgtga tcaacctgct ggatttcacg agcgtggttg ttccggttac ctttgcggat   1260
aagaacatcg ataagaagaa tgagagtttc aaggcggtta gtgagcttga tgccctcgtg   1320
caggaagagt atgatccgga ggcgtaccat ggggcaccgg ttgcagtgca ggttatcgga   1380
cggagactca gtgaagagag gacgttggcg attgcagagg aagtggggaa gttgctggga   1440
aatgtggtga ctccatagct aataagtgtc agatagcaat ttgcacaaga aatcaatacc   1500
agcaactgta aataagcgct gaagtgacca tgccatgcta cgaaagagca gaaaaaaacc   1560
tgccgtagaa ccgaagagat atgacacgct tccatctctc aaaggaagaa tcccttcagg   1620
gttgcgtttc cagtctagac acgtataacg cacaagtgt ctctcaccaa atgggttata   1680
tctcaaatgt gatctaagga tggaaagccc agaatattgg ctgggttgat ggctgcttcg   1740
agtgcagtct catgctgcca caggtgactc tggatggccc cataccactc aacccatgcg   1800
tgcgaggtcc cgggtctaga ggatcccaat tgttaattaa ccttacatac acatgcacgc   1860
ccgtaatgaa ggccctggtg accgacggga acacggactg gagtgctgcg tcaccaccag   1920
acgcaccgac tccccattag gcgcgacacg cctgcttcgg ccgcccgcca tgccgcctgc   1980
tcgcccaaac ttgccaaaag atttggaggc aggcgctcga gcttcccggt gtgaacggtg   2040
gagctgagag cctaagaccc acaccaccac caccccggac ttttatttta cccctgtctg   2100
ccctgatcga aggggcgcca accggcagga tccctggcgc tcgccgttga gcaaagccgg   2160
acaccaatca gacgaccaag gcgcgaccgt cctccccaca acccgccttg gcacactggc   2220
accctggatc gaggcgcctt tggggccgac ggtccctctt tccagtcctc ccccaacgcc   2280
atctccaccg ttctccaatt ccctcctcgc ctcgaaggcg ccccctctcc ctcccggcct   2340
agactccaac gcgcgacaga aatagtggta cgatttgcga cgcgtggagc cgtccctctc   2400
atctcgcatc cctcactttc tcgacgacgg catcacaggg gatgggacga gcggcaaagc   2460
tttccatagc caaaagctgg tggtcgaccg acgtcaggag aatgggattg ctgtcttgcc   2520
aatctcccaa aagtggcaat gcgggtctcc tgcaggcagc gctctcgcct gttacactac   2580
tttcacggcc tcggcatccg atactcgact gcaacatcat cagggtattc ggctaggcag   2640
tctagtgtag tagtacacaa agtcttcgat tgctttccgc gggacagggt tcgagagaga   2700
ctccagtaca ctacaacgca gccccacgtg tagcgtcatg ggccaccgct ggctgacgtt   2760
cacgtactta catacctagg tacatacacc attccgtacg gatacatcag gtaatgtatg   2820
```

```
tacatacgtg gcgcaggtac gcagtacgta catatcaacc ttgcttgcat agcacgggcc    2880
gatgaggtat gtacggacgt acttcgtact tacgcggtag tggggggaag gccacacatc    2940
tgatagcttc ctctctccat tccctcatgc acccagaccc tggcgctgaa acgccgccgc    3000
tcagaagccg cccactggct gcagacttga acctaactt tttttttctt gttttcactt     3060
caccacccct cccctcccc ctcccttcc gccctgtccc tcttcgcctt cccaccctct      3120
ttgcaagtcg agctgcgcta cgggatggcg ggcggcggtg acctatactg ggcctgacac    3180
taatatgcaa acccaggtac ctgcggttca ctctgcccgt ttgcttgtac ataccttagt    3240
gagcagcagg catggaccct gctgatgtct cgtgtttagc tgatgccaga ctcacgagtg    3300
tggacggcat tgaccacggc gggtgcgccc ctcctctctt cacccagcag caggatattc    3360
gagattacct catgcgcttg ttcgtgcctt gatccgatgg atgacggata taccaggaag    3420
gttttttttt tgctcacgac ccatgtatgt gtatgtacat gcattcgcta cttgttcagg    3480
tttggcagga aaggggtggg gaggcgcgga attggcaggg cacggcaaag gggaacaaaa    3540
gagatgggga gggaaagggg gaaagggga tttctgcggt gtgcactgga aaaggcgcgg     3600
ttctgttctc agtctaccat tgcccgtcta tacttttggc aaaatcaact tttggtgtcc    3660
tcaaccattg cacctgcttg gctcacctgc tttctgaaaa ctcggggtaa tgggcggctt    3720
gagattgggt aggcaaaatt ggcgtgtggt cccgattgtg ttggtggaat gtcccgaaat    3780
ggtaaggcac attcaactag gcaaggaggg tataacaggc tgggccttgt atgtatgtat    3840
gtatgtactg taaagtacta gtaactaact agttaactcg gtgctcactt ttcactggct    3900
ggatgatttt tattcgagcc acgaccctgc gagttactcc tcccttaccc ttcccctctc    3960
tgtttctctc cgacctgcag cagaaggcac gatgcaggac gcgttcccac agctcatgtt    4020
ggatggtctt gactgcatgt gatggtgtcc gtaccaaccc ccggacattc gtggaaggct    4080
tcgcgaagag ttctagcgta acggcgacat ccaatgagga tgtgccgccg ctgaagggcg    4140
ggctggaacc ggccttttcg ctcatcggga tcatcgctgt cgtggcatgt atgtacatat    4200
atgtatacta cggtgctcta tggtgtatgt atttgtgtga tatactgtac tatatgtatg    4260
tatgtaccta ggtatggacg tgcacttta acatgagcat ttaccggcgc tcaaccgttt     4320
ttttgtgtac atacttctca atgcttagtt tcgtcggcaa gcaggcgggc aagggtggga    4380
agtcggttgc ggtgagcgcg aaggtgccct ctgaccaaag gatccggctt tccactcggg    4440
ttcacctttc aaatgcaaag ggaggggaaa aaacaccgct agattcactc agcccgttga    4500
cggcggccga atgtgacctg tcgcgtcctc acgaaagatc cgggtggtgg gtcgcgatgg    4560
caagctggat gctagggccg acgcgccaga gcgccaagcg gtgcttggac cttgggcttt    4620
actcgtcgcg gctgtgatct gcgagcacac ctccaccatg gcttcctctc cgtgattgtt    4680
tctccagtgt acgaagtacc atcttttgat gtggcaggga aaagaagcct cctctgtttg    4740
ggctacggca gccctggaaa agaaaaggtt tgagtgtcat ccttggcgtc gtcctcggtg    4800
tttgttttgt aatctttagt tatgtactgt actgtatcca tacatagtgt acaggcacgt    4860
ctcgggcact ttcgttttcg gatccgggat ccggggatga gcttgagccc gccaaccctg    4920
atgagcagcc gccaaccaca aatcgtcgag gggacggcat aaacgttttg atgtcctggg    4980
aagacgcaca tgcccagtca cgatttaccc cggaccctct gcatctcgag cccactcatc    5040
gaggggatca tggcgacgta gtagtcaagc tccatatgac gcgtggtacc gggcccgacg    5100
tcaggcctct cgagatttaa atcgagcggc cgcggccggc cttaaaagg atctaggtga    5160 agatcctttt tgataatctc atgaccaaaa tcccttaacg tgagttttcg ttccactgag    5220
```

```
cgtcagaccc cgtagaaaag atcaaaggat cttcttgaga tccttttttt ctgcgcgtaa    5280
tctgctgctt gcaaacaaaa aaaccaccgc taccagcggt ggtttgtttg ccggatcaag    5340
agctaccaac tcttttccg aaggtaactg gcttcagcag agcgcagata ccaaatactg    5400
tccttctagt gtagccgtag ttaggccacc acttcaagaa ctctgtagca ccgcctacat    5460
acctcgctct gctaatcctg ttaccagtgg ctgctgccag tggcgataag tcgtgtctta    5520
ccgggttgga ctcaagacga tagttaccgg ataaggcgca gcggtcgggc tgaacggggg    5580
gttcgtgcac acagcccagc ttggagcgaa cgacctacac cgaactgaga tacctacagc    5640
gtgagctatg agaaagcgcc acgcttcccg aagggagaaa ggcggacagg tatccggtaa    5700
gcggcagggt cggaacagga gagcgcacga gggagcttcc agggggaaac gcctggtatc    5760
tttatagtcc tgtcgggttt cgccacctct gacttgagcg tcgatttttg tgatgctcgt    5820
caggggggcg gagcctatgg aaaaacgcca gcaacgcggc ctttttacgg ttcctggcct    5880
tttgctggcc ttttgctcac atgttctttc ctgcgttatc ccctgattct gtggataacc    5940
gtattaccgc ctttgagtga gctgataccg ctcgccgcag ccgaacgacc gagcgcagcg    6000
agtcagtgag cgaggaagcg gaagagcgcc tgatgcggta ttttctcctt acgcatctgt    6060
gcggtatttc acaccgggcc ggccggcgcg ccgctagcgt gggcgaagaa ctccagcatg    6120
agatccccgc gctggaggat catccagccg gcgtcccgga aaacgattcc gaagcccaac    6180
ctttcataga aggcggcggt ggaatcgaaa tctcgtgatg gcaggttggg cgtcgcttgg    6240
tcggtcattt cgaaccccag agtcccgctc agaagaactc gtcaagaagg cgatagaagg    6300
cgatgcgctg cgaatcggga gcggcgatac cgtaaagcac gaggaagcgg tcagcccatt    6360
cgccgccaag ctcttcagca atatcacggg tagccaacgc tatgtcctga tagcggtccg    6420
ccacacccag ccggccacag tcgatgaatc cagaaaagcg gccattttcc accatgatat    6480
tcggcaagca ggcatcgcca tgggtcacga cgagatcctc gccgtcgggc atgcgcgcct    6540
tgagcctggc gaacagttcg gctggcgcga gccctgatg ctcttcgtcc agatcatcct    6600
gatcgacaag accggcttcc atccgagtac gtgctcgctc gatgcgatgt ttcgcttggt    6660
ggtcgaatgg gcaggtagcc ggatcaagcg tatgcagccg ccgcattgca tcagccatga    6720
tggatacttt ctcggcagga gcaaggtgag atgacaggag atcctgcccc ggcacttcgc    6780
ccaatagcag ccagtcccct tcccgcttca gtgacaacgt cgagcacagct gcgcaaggaa    6840 cgcccgtcgt ggccagccac gatagccgcg ctgcctcgtc ctgcagttca ttcagggcac    6900
cggacaggtc ggtcttgaca aaaagaaccg ggcgcccctg cgctgacagc cggaacacgg    6960
cggcatcaga gcagccgatt gtctgttgtg cccagtcata ccgaatagc ctctccaccc    7020 aagcggccgg agaacctgcg tgcaatccat cttgttcaat catgcgaaac gatcctcatc    7080
ctgtctcttg atcagatctt gatccctgc gccatcagat ccttggcggc aagaaagcca    7140
tccagtttac tttgcagggc ttcccaacct taccagaggg cgcccagct ggcaattccg    7200 gttcgcttgc tgtccataaa accgcccagt ctagctatcg ccatgtaagc ccactgcaag    7260
ct                                                                   7262
```

<210> SEQ ID NO 23
<211> LENGTH: 5700
<212> TYPE: DNA
<213> ORGANISM: artificial
<220> FEATURE:
<223> OTHER INFORMATION: pDB45-Dxyr1-A

<400> SEQUENCE: 23

```
ggccgctcga tttaaatctc gagaggcctg acgtcgggcc cggtaccacg cgtcatatga      60
ctagtttccg catcaacctg tcacaccatc taccacccac tgcgcctata cactcaaatg     120
aaggatccgg atagatgtgt tgtatacgtc tgtatggact atgtacacac gtacacatga     180
cggaggcagg gtgcgcagga agcaatggag cgccggtcaa aagtgatcct aaaccagtct     240
gaaaagggag cgtcagacgc atggcctcgc gcccagtttg tgctagagga aaaacaaaac     300
cctcttgaat gtctggctgc tgattaacaa gtgccgcggt attagtgggc acgttcagga     360
cagcgtacaa gtagtggtgc gctttgatgt cccccatgct gtgccgatgc gctggaggac     420
aagggctttt ggcaatccat gctactccac gactccgtac ttggtagtgt attgtaccaa     480
atccgtacac acactacaag acgaggatgg tggagttcca ttgcactttc tccaccatga     540
ccgctgtctg gaccctgcc  agagtggcaa cccttgttca acagttcttc gcagcgtgcc     600
ggcgggacaa gcagaggccc atatatcctc agcaggccct gacgaggcgg actctccaga     660
gcccgctgtt gctaactctt tcagctagca ctacccgccc cgcgctctca cacgtactt      720
ctctgctctc catagacgcc ccttcccgcc ggcttatatt gccctcgcaa tatatccttg     780
atactcgata ttgtgctgga ccaggagccg tcgcctcctt gccaccaatc gcgtctagtt     840
acatccacga gcattatcgc gcgtctcctg ttgtggatgt gcgccaagcc gacctccaga     900
ctcgccagaa agtactttga gaggcaggaa tagcgcgcat atttaccgat cgctcactt      960
gttcgaatcg ggcatccctt ggtccttttg gcgccccggg cccctcttaa gcactatacg    1020
gcacatcgcc ctgaggctca gaccaggaga gcagcgcttc atcgatagac ggacaaccgg    1080
gaagcatctg gtgtgtgcag cgaaggcctt catctgaatt tcagggttca aggggctcgg    1140
aaaggactta caagaaacgg ccgacccaac ggtctctggc aacgaggact ggccaagcgc    1200
tctcttgcca tccgaccccg tatcccgtac gttgatggtt ccctcttccc tgccctccac    1260
gttctccttc tcccgcgccc cccttgccg  gccggtccgc tgtccctcgt ccatccagac    1320
accctccc  ccttcccta accccgacat gcgctgctgg tgcttcatcc tccgtgcagt     1380
gagttgactg tggcacccgt tcgcccacat ccgcgcagat cagcttccag cgctttggtg    1440
tctgtcaatg ctattctcgc atctccctaa atctaatgcc tgctactgac cttaccccag    1500
ggggaagctc actcaactcc gtctgactgc cgttcctcca atcaggaccc ggcagcttag    1560
caccggcgga gcttgaatat agatacctcc cgcgggaagc tcagcgtcca attcgagctc    1620
tgtacagtga ccggtgactc tttctggcat gcggagagac ggacggacgc agagagaagg    1680
gctgagtaat aagcgccact cgccagaca  gctctggcgg ctctgaggtg cagtggatga    1740
ttattaatcc gggaccggcc gcccctccgc cccgaagtgg aaaggctggt gtgcccctcg    1800
ttgaccaaga atctattgca tcatcggaga atatggagct tcatcgaatc accggcagta    1860
agcgaaggag aatgtgaagc caggggtgta tagccgtcgg cgaaatagca tgccattaac    1920
ctaggtacag aagtccaatt gcttccgatc tggtaaaaga ttcacgagat agtaccttct    1980
ccgaagtagg tagagcgagt acccggcgcg taagctccct aattggccca tccggcatct    2040
gtagggcgtc caaatatcgt gcctctcctg ctttgcccgg tgtatgaaac cggaaaggcc    2100
gctcaggagc tggccagcgg cgcagaccgg gaacacaagc tggcagtcga cccatccggt    2160
gctctgcact cgacctgctg aggtcctca  gtcctggta  ggcagctttg ccccgtctgt    2220
ccgcccggtg tgtcggcggg gttgacaagg tcgttgcgtc agtccaacat tgttgccat     2280
attttcctgc tctcccacc  agctgctctt ttcttttctc tttcttttcc catcttcagt    2340
```

```
atattcatct tcccatccaa gaacctttat ttcccctaag taagtacttt gctacatcca   2400
tactccatcc ttcccatccc ttattccttt gaacctttca gttcgagctt tcccacttca   2460
tcgcagcttg actaacagct accccgcttg agcagacatc accatgcctc aatcctggga   2520
agaactggcc gctgataagc gcgcccgcct cgcaaaaacc atccctgatg aatggaaagt   2580
ccagacgctg cctgcggaag acagcgttat tgatttccca agaaatcgg ggatcctttc    2640 agaggccgaa ctgaagatca cagaggcctc cgctgcagat cttgtgtcca agctggcggc   2700
cggagagttg acctcggtgg aagttacgct agcattctgt aaacgggcag caatcgccca   2760
gcagttagta gggtcccctc tacctctcag ggagatgtaa caacgccacc ttatgggact   2820
atcaagctga cgctggcttc tgtgcagaca aactgcgccc acgagttctt ccctgacgcc   2880
gctctcgcgc aggcaaggga actcgatgaa tactacgcaa agcacaagag acccgttggt   2940
ccactccatg gcctccccat ctctctcaaa gaccagcttc gagtcaaggt acaccgttgc   3000
ccctaagtcg ttagatgtcc cttttttgtca gctaacatat gccaccaggg ctacgaaaca   3060
tcaatgggct acatctcatg gctaaacaag tacgacgaag gggactcggt tctgacaacc   3120
atgctccgca aagccggtgc cgtcttctac gtcaagacct ctgtcccgca gaccctgatg   3180
gtctgcgaga cagtcaacaa catcatcggg cgcaccgtca acccacgcaa caagaactgg   3240
tcgtgcggcg gcagttctgg tggtgagggt gcgatcgttg ggattcgtgg tggcgtcatc   3300
ggtgtaggaa cggatatcgg tggctcgatt cgagtgccgg ccgcgttcaa cttcctgtac   3360
ggtctaaggc cgagtcatgg gcggctgccg tatgcaaaga tggcgaacag catggaggcg   3420
gccgctacgg gatttaaatc gctagcgggc tgctaaagga agcggaacac gtagaaagcc   3480
agtccgcaga aacggtgctg accccggatg aatgtcagct actgggctat ctggacaagg   3540
gaaaacgcaa gcgcaaagag aaagcaggta gcttgcagtg ggcttacatg gcgatagcta   3600
gactgggcgt ttttatggac agcaagcgaa ccggaattgc cagctggggc gccctctggt   3660
aaggttggga agccctgcaa agtaaactgg atggctttct tgccgccaag gatctgatgg   3720
cgcaggggat caagatctga tcaagagaca ggatgaggat cgtttcgcat gattgaacaa   3780
gatggattgc acgcaggttc tccggccgct tgggtggaga ggctattcgg ctatgactgg   3840
gcacaacaga caatcggctg ctctgatgcc gccgtgttcc ggctgtcagc gcaggggcgc   3900
ccggttcttt ttgtcaagac cgacctgtcc ggtgccctga tgaactgca ggacgaggca    3960 gcgcggctat cgtggctggc cacgacgggc gttccttgcg cagctgtgct cgacgttgtc   4020
actgaagcgg gaagggactg gctgctattg ggcgaagtgc cggggcagga tctcctgtca   4080
tctcaccttg ctcctgccga gaaagtatcc atcatggctg atgcaatgcg gcggctgcat   4140
acgcttgatc cggctacctg cccattcgac caccaagcga acatcgcat cgagcgagca    4200 cgtactcgga tggaagccgg tcttgtcgat caggatgatc tggacgaaga gcatcagggg   4260
ctcgcgccag ccgaactgtt cgccaggctc aaggcgcgca tgcccgacgg cgaggatctc   4320
gtcgtgaccc atggcgatgc ctgcttgccg aatatcatgg tggaaaatgg ccgcttttct   4380
ggattcatcg actgtggccg gctgggtgtg gcggaccgct atcaggacat agcgttggct   4440
acccgtgata ttgctgaaga gcttggcggc gaatgggctg accgcttcct cgtgctttac   4500
ggtatcgccg ctcccgattc gcagcgcatc gccttctatc gccttcttga cgagttcttc   4560
tgagcgggac tctggggttc gaaatgaccg accaagcgac gcccaacctg ccatcacgag   4620
atttcgattc caccgccgcc ttctatgaaa ggttgggctt cggaatcgtt ttccgggacg   4680
```

```
ccggctggat gatcctccag cgcggggatc tcatgctgga gttcttcgcc cacgctagcg    4740
gcgcgccggc cggcccggtg tgaaataccg cacagatgcg taaggagaaa ataccgcatc    4800
aggcgctctt ccgcttcctc gctcactgac tcgctgcgct cggtcgttcg gctgcggcga    4860
gcggtatcag ctcactcaaa ggcggtaata cggttatcca cagaatcagg gataacgca     4920
ggaaagaaca tgtgagcaaa aggccagcaa aaggccagga accgtaaaaa ggccgcgttg    4980
ctggcgtttt tccataggct ccgcccccct gacgagcatc acaaaaatcg acgctcaagt    5040
cagaggtggc gaaacccgac aggactataa agataccagg cgtttccccc tggaagctcc    5100
ctcgtgcgct ctcctgttcc gaccctgccg cttaccggat acctgtccgc ctttctccct    5160
tcgggaagcg tggcgctttc tcatagctca cgctgtaggt atctcagttc ggtgtaggtc    5220
gttcgctcca agctgggctg tgtgcacgaa ccccccgttc agcccgaccg ctgcgcctta    5280
tccggtaact atcgtcttga gtccaacccg gtaagacacg acttatcgcc actggcagca    5340
gccactggta acaggattag cagagcgagg tatgtaggcg gtgctacaga gttcttgaag    5400
tggtggccta actacggcta cactagaagg acagtatttg gtatctgcgc tctgctgaag    5460
ccagttacct tcggaaaaag agttggtagc tcttgatccg gcaaacaaac caccgctggt    5520
agcggtggtt tttttgtttg caagcagcag attacgcgca gaaaaaaagg atctcaagaa    5580
gatcctttga tcttttctac ggggtctgac gctcagtgga acgaaaactc acgttaaggg    5640
attttggtca tgagattatc aaaaaggatc ttcacctaga tccttttaaa ggccggccgc    5700
```

<210> SEQ ID NO 24
<211> LENGTH: 7086
<212> TYPE: DNA
<213> ORGANISM: artificial
<220> FEATURE:
<223> OTHER INFORMATION: pDB58-Dxyr1-AB

<400> SEQUENCE: 24

```
gatcttgatc ccctgcgcca tcagatcctt ggcggcaaga agccatcca gtttactttg      60
cagggcttcc aaccttacc agagggcgcc ccagctggca attccggttc gcttgctgtc     120
cataaaaccg cccagtctag ctatcgccat gtaagcccac tgcaagctac ctgctttctc    180
tttgcgcttg cgttttccct tgtccagata gcccagtagc tgacattcat ccggggtcag    240
caccgttttct gcggactggc tttctacgtg ttccgcttcc tttagcagcc cgctagcgat    300
ttaaatcccg tagcggccgc aaggggactc ggttctgaca accatgctcc gcaaagccgg    360
tgccgtcttc tacgtcaaga cctctgtccc gcagaccctg atggtctgcg agacagtcaa    420
caacatcatc gggcgcaccg tcaacccacg caacaagaac tggtcgtgcg gcggcagttc    480
tggtggtgag ggtgcgatcg ttgggattcg tggtggcgtc atcggtgtag gaacggatat    540
cggtggctcg attcgagtgc cggccgcgtt caacttcctg tacggtctaa ggccgagtca    600
tgggcggctg ccgtatgcaa agatggcgaa cagcatggag ggtcaggaga cggtgcacag    660
cgttgtcggg ccgattacgc actctgttga gggtgagtcc ttcgcctctt ccttcttttc    720
ctgctctata ccaggcctcc actgtcctcc tttcttgctt tttatactat atacgagacc    780
ggcagtcact gatgaagtat gttagacctc cgcctcttca ccaaatccgt cctcggtcag    840
gagccatgga aatacgactc caaggtcatc cccatgccct ggcgccagtc cgagtcggac    900
attattgcct ccaagatcaa gaacggcggg ctcaatatcg gctactacaa cttcgacggc    960
aatgtccttc acacccctcc tatcctgcgc ggcgtggaaa ccaccgtcgc cgcactcgcc   1020
aaagccggtc acaccgtgac cccgtggacg ccatacaagc acgatttcgg ccacgatctc   1080
```

```
atctcccata tctacgcggc tgacggcagc gccgacgtaa tgcgcgatat cagtgcatcc    1140
ggcgagccgg cgattccaaa tatcaaagac ctactgaacc cgaacatcaa agctgttaac    1200
atgaacgagc tctgggacac gcatctccag aagtggaatt accagatgga gtaccttgag    1260
aaatggcggg aggctgaaga aaaggccggg aaggaactgg acgccatcat cgcgccgatt    1320
acgcctaccg ctgcggtacg gcatgaccag ttccggtact atgggtatgc ctctgtgatc    1380
aacctgctgg atttcacgag cgtggttgtt ccggttacct tgcggataa gaacatcgat    1440 aagaagaatg agagtttcaa ggcggttagt gagcttgatg ccctcgtgca ggaagagtat    1500
gatccggagg cgtaccatgg ggcaccggtt gcagtgcagg ttatcggacg gagactcagt    1560
gaagagagga cgttggcgat tgcagaggaa gtggggaagt tgctgggaaa tgtggtgact    1620
ccatagctaa taagtgtcag atagcaattt gcacaagaaa tcaataccag caactgtaaa    1680
taagcgctga agtgaccatg ccatgctacg aaagagcaga aaaaaacctg ccgtagaacc    1740
gaagagatat gacacgcttc catctctcaa aggaagaatc ccttcagggt tgcgtttcca    1800
gtctagacac gtataacggc acaagtgtct ctcaccaaat gggttatatc tcaaatgtga    1860
tctaaggatg gaaagcccag aatattggct ggggttgatgg ctgcttcgag tgcagtctca    1920
tgctgccaca ggtgactctg gatggcccca taccactcaa cccatgcgtg cgaggtcccg    1980
ggtctagagg atcccaattg ttaattaacg cagaagagca tcgatgtcga cgatatccct    2040
aggtccgaac tagtttccgc atcaacctgt cacaccatct accacccact gcgcctatac    2100
actcaaatga aggatccgga tagatgtgtt gtatacgtct gtatggacta tgtacacacg    2160
tacacatgac ggaggcaggg tgcgcaggaa gcaatggagc gccggtcaaa agtgatccta    2220
aaccagtctg aaaagggagc gtcagacgca tggcctcgcg cccagtttgt gctagaggaa    2280
aaacaaaacc ctcttgaatg tctggctgct gattaacaag tgccgcggta ttagtgggca    2340
cgttcaggac agcgtacaag tagtggtgcg ctttgatgtc ccccatgctg tgccgatgcg    2400
ctggaggaca aggggctttg gcaatccatg ctactccacg actccgtact tggtagtgta    2460
ttgtaccaaa tccgtacaca cactacaaga cgaggatggt ggagttccat tgcactttct    2520
ccaccatgac cgctgtctgg accccctgcca gagtggcaac ccttgttcaa cagttcttcg    2580
cagcgtgccg gcgggacaag cagaggccca tatatcctca gcaggccctg acgaggcgga    2640
ctctccagag cccgctgttg ctaactcttt cagctagcac taccgccc gcgctctcac    2700 acggtacttc tctgctctcc atagacgccc cttcccgccg gcttatattg ccctcgcaat    2760
atatccttga tactcgatat tgtgctggac caggagccgt cgcctccttg ccaccaatcg    2820
cgtctagtta catccacgag cattatcgcg cgtctcctgt tgtggatgtg cgccaagccg    2880
acctccagac tcgccagaaa gtactttgag aggcaggaat agcgcgcata tttaccgatt    2940
cgctcacttg ttcgaatcgg gcatcccttg gtccttttgg cgccccgggc ccctcttaag    3000
cactatacgc cacatcgccc tgaggctcag accaggagag cagcgcttca tcgatagacg    3060
gacaaccggg aagcatctgg tgtgtgcagc gaaggccttc atctgaattt cagggttcaa    3120
ggggctcgga aaggacttac aagaaacggc cgacccaacg gtctctggca acgaggactg    3180
gccaagcgct ctcttgccat ccgacccgt atcccgtacg ttgatggttc cctcttccct    3240
gccctccacg ttctccttct cccgcgcccc cccttgccgg ccggtccgct gtccctcgtc    3300
catccagaca cccctccccc cttcccttaa cccgacatg cgctgctggt gcttcatcct    3360
ccgtgcagtg agttgactgt ggcacccgtt cgcccacatc cgcgcagatc agcttccagc    3420
```

```
gctttggtgt ctgtcaatgc tattctcgca tctccctaaa tctaatgcct gctactgacc      3480 ttacccccagg gggaagctca ctcaactccg tctgactgcc gttcctccaa tcaggacccg     3540
gcagcttagc accggcggag cttgaatata gatacctccc gcaaaaaggg cctgaccggt      3600
tatttccact tgttactcct cgtgtgtaac cgtgggtttg gctgtgtctt tttcagcccc      3660
gcccggattt cccgcatctc tctattctgt tctctacagc cacacacaac gggttcgtcg      3720
gttggcattt caattgtttt tcccccccctt ataaccggcg atgcttcttc tcggctggcg     3780
tttgatggct tgatggcttt tcatttgggc tttgggaagg tgttttcagg gttgttccca      3840
aaaaaaaata accgaaaagg caaagggggt tcactggggg gtctttggaa ggttggcgga     3900
tatcggccga tgagagattc ccttacagga cggacaaggt gggatggttt ggaggaggta      3960
gaacatgagc agatggggac gattttttgat ggctccttca acgacgacgg aacggacccc    4020
gacatgactc actctatgga tgaggagat tgtgtggcgg tgctgggtct tgagcgatat       4080
atttgacggt tctgttttta gacgccgttt ggcattgagg ttttttttttt ttttttgttg     4140 ggttgctgtg attttctctt tggataccctc agttcttctg gcttttggaa ggggcccctgg   4200 aagttcttt gtttcttctg tcgactgttg gctagggggg acactctggg aacctgtact      4260
gcgaacaata ctgtgtagat atcatgtttt tgtatacgga ttaggtagtg atgatacacc     4320
gtatgactta catgaccccg gactgagcct gctcgtctta ttttcttaca tagcctgcca     4380
gatgtgttag ccgggctcgc cgccggtcta gtcaacgttt tctctcgcac ggcagtcaat     4440
tctcgccgcc cgggccgcat tcagcattgg attggttttt agctcatcag ctccatgtct     4500
gacacaactc tacacctcag aagcatcgaa ccggaggagc tttcgatcgc atttcacatg    4560
gccgacccag caattcgttc gttgacaata gcaacaacag tgcattcttc cacaggtaga    4620
tcctcatgaa cagctggtga cagatatctg tttggttttc atgatcccgg atggtttctt    4680
gacgtttact cgtcgtgccg ccgtcaactc aacacttcgc cggccgacca cgggaaagtg    4740
acgggcgaac atattcgagt cccttgtgtg ggaagaatcg ttcatgttct taccaatgct     4800
gaccctgtct ggggacacat tggtccggta gtatcctgct ctgggcgacc ttgaaacaag    4860
caggccaaga tatggcccat gactctatcg tgcgcattca actcggggtc gccactgtga    4920
ttatgtccgc cggttcttaa agggagcttc tcaaagtcgt ggcggatgag ctattcgtcc    4980
aacaagaaga tatgggaggc caccaacaag gacatgctcc tcaaagcata tcgagcatca    5040
agcagcaatc aggggcgccg actttgtcct cggcgtcggg ctcaggagcc gccctcgtga    5100
ctcgagattt aaatcgagcg gccgcggccg gcctttaaaa ggatctaggt gaagatcctt    5160
tttgataatc tcatgaccaa aatcccttaa cgtgagtttt cgttccactg agcgtcagac    5220
cccgtagaaa agatcaaagg atcttcttga gatccttttt ttctgcgcgt aatctgctgc    5280
ttgcaaacaa aaaaccacc gctaccagcg gtggtttgtt tgccggatca agagctacca    5340 actcttttc cgaaggtaac tggcttcagc agagcgcaga taccaaatac tgtccttcta     5400
gtgtagccgt agttaggcca ccacttcaag aactctgtag caccgcctac atacctcgct    5460
ctgctaatcc tgttaccagt ggctgctgcc agtggcgata agtcgtgtct taccgggttg    5520
gactcaagac gatagttacc ggataaggcg cagcggtcgg gctgaacggg gggttcgtgc    5580
acacagccca gcttggagcg aacgacctac accgaactga gatacctaca gcgtgagcta    5640
tgagaaagcg ccacgcttcc cgaagggaga aaggcggaca ggtatccggt aagcggcagg    5700
gtcggaacag gagagcgcac gagggagctt ccaggggaaa acgcctggta tctttatagt    5760
cctgtcgggt ttcgccacct ctgacttgag cgtcgatttt tgtgatgctc gtcagggggg    5820
```

```
cggagcctat ggaaaaacgc cagcaacgcg gccttttac ggttcctggc cttttgctgg    5880
ccttttgctc acatgttctt tcctgcgtta tcccctgatt ctgtggataa ccgtattacc    5940
gcctttgagt gagctgatac cgctcgccgc agccgaacga ccgagcgcag cgagtcagtg    6000
agcgaggaag cggaagagcg cctgatgcgg tattttctcc ttacgcatct gtgcggtatt    6060
tcacaccggg ccggccggcg cgccgctagc gtgggcgaag aactccagca tgagatcccc    6120
gcgctggagg atcatccagc cggcgtcccg gaaaacgatt ccgaagccca acctttcata    6180
gaaggcggcg gtggaatcga aatctcgtga tggcaggttg ggcgtcgctt ggtcggtcat    6240
ttcgaacccc agagtcccgc tcagaagaac tcgtcaagaa ggcgatagaa ggcgatgcgc    6300
tgcgaatcgg gagcggcgat accgtaaagc acgaggaagc ggtcagccca ttcgccgcca    6360
agctcttcag caatatcacg ggtagccaac gctatgtcct gatagcggtc cgccacaccc    6420
agccggccac agtcgatgaa tccagaaaag cggccatttt ccaccatgat attcggcaag    6480
caggcatcgc catgggtcac gacgagatcc tcgccgtcgg catgcgcgc cttgagcctg    6540
gcgaacagtt cggctggcgc gagcccctga tgctcttcgt ccagatcatc ctgatcgaca    6600
agaccggctt ccatccgagt acgtgctcgc tcgatgcgat gtttcgcttg gtggtcgaat    6660
gggcaggtag ccggatcaag cgtatgcagc cgccgcattg catcagccat gatggatact    6720
ttctcggcag gagcaaggtg agatgacagg agatcctgcc ccggcacttc gcccaatagc    6780
agccagtccc ttcccgcttc agtgacaacg tcgagcacag ctgcgcaagg aacgcccgtc    6840
gtggccagcc acgatagccg cgctgcctcg tcctgcagtt cattcagggc accggacagg    6900
tcggtcttga caaaaagaac cgggcgcccc tgcgctgaca gccggaacac ggcggcatca    6960
gagcagccga ttgtctgttg tgcccagtca tagccgaata gcctctccac ccaagcggcc    7020
ggagaacctg cgtgcaatcc atcttgttca atcatgcgaa acgatcctca tcctgtctct    7080
tgatca                                                              7086

<210> SEQ ID NO 25
<211> LENGTH: 12155
<212> TYPE: DNA
<213> ORGANISM: artificial
<220> FEATURE:
<223> OTHER INFORMATION: pDalp-1-amdS
<220> FEATURE:
<221> NAME/KEY: misc_feature
<222> LOCATION: (2481)..(2481)
<223> OTHER INFORMATION: n is a, c, g, or t
<220> FEATURE:
<221> NAME/KEY: misc_feature
<222> LOCATION: (5963)..(5963)
<223> OTHER INFORMATION: n is a, c, g, or t

<400> SEQUENCE: 25
ctaaattgta agcgttaata ttttgttaaa attcgcgtta aattttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttgggt cgaggtgccg taaagcacta aatcggaacc ctaaagggag     300
ccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
```

```
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gccccccctc gaggtcgacg gtatcgataa gcttgctcct gtcacttgtc aatatgagaa    720
acataccgct tccttccttc ctctccaata cttgacctgt actctacata ccagaatttg    780
caaaatcgct tatttcttca ggcaatagac aaaattatag acaaattatt tatagactaa    840
ttattaacta cttggattaa ggagacatga tatcatgtcg aaaagcaaaa gtgacgccgc    900
aattgcccgc cagcaattgc accttaagta tgcgtattct gacatatcat ctctctcatt    960
ccgccctcat gattcacata attagtcacg atagaagtca gtccaggcct tcgcggtccg   1020
ctcatgagat ctcatcattt cctcgtctat gaaagttatt tagacgctgg ggaggtgggc   1080
aggaaccccg atcggcgccc ctcggacccg catcgtgact ctgtcccaac tagaataaaa   1140
tgcgtaaaac cataatagac atgaaccaaa aaatgaaca agagaatatg cagccctcat   1200
tcgctcggag aagaccccgg ccgttatctc ctcctcctcc tcctcaccca cctccttttt   1260
ttgccggctc cccactcccg aatcctctag aataagaaga ggtgcaggaa gtgctcatgc   1320
cccattttgt cccggatcgc gggaaacaat tcaggcagag gggttgccgt tgaaggcgat   1380
gcggttggtg gtgccgctgg gaacgccagt gatggcggcg ttgccggtcg acttgatgta   1440
gttgcagagc tcggcagggg tcttggagcc ctcgagggcc aggaggtagg caccgaggcc   1500
ggcaatgtgg ggggaggcca tcgaggtacc cgagatggtg ttctgagagt gcatctcatg   1560
ttagctattt tgttttgttt ctcccccacc ccggagaaat aaatacgggg cgggaatgtc   1620
gccaaaggct gggggtgggt gggggagggg ggggcttacg gtagcagagg tgctgccgat   1680
ccaggtgctc aggatgttgg agccggggc ctggatatcg acgacgctgc cgtagttgga   1740
gtagctggcc ttggcgtcgt tcctgtcggt ggcgccgacg gtgcaggcgg acgcctcgga   1800
ggcgggcgac gagttggcgg cgttctggtt ctcgttgccg gcggcgacgg ccaggaagac   1860
gcccgacctg acgagggcgg cggcggcgtt gttgatggag gccgagtagc taccgccgag   1920
cgacatgttg gcgacgacgc ccttggggca gctgcgcttg ggcgcgtcgt cagcgacgaa   1980
gttgatgcca gcaatgacac cagaactaga gaggagaaag aggaatgtca gtcagaagat   2040
aacggccggg cggtgtgcg ggtgcgcggg tgcgaggcat acgtggtgcc agagccgtcg   2100
gagccgagaa ccttgacggc gtagagcttg gtcttcttgg caacaccgta cgtggtgccg   2160
ccgatggtgc cggcgacgtg ggtgccgtgg ccgttgccat cggtgttaga gctgtcgacg   2220
aagttggcgg cgaaagtggc acggccgccg aagtcctgtg atcaggaggg gtcagcatac   2280
gaaacgacca agaagatcac ggtcgtcacc cagttcctca agaactcggc cggcgagctc   2340
tccgagatca agcggttcta cgtccagaac ggcaaggtca tccccaactc cgagtccacc   2400
atcccgggcg tcgagggcaa ctccatcacc caggactggt gcgaccgcca gaaggccgcc   2460
ttcggcgacg tgaccgactt ncaggacaag ggcggcatgg tccagatggg caaggccctc   2520
gcggggccca tggtcctcgt catgtccatc tgggacgacc acgccgtcaa catgctctgg   2580
ctcgactcca cctggcccat cgacggcgcc ggcaagccgg gcgccgagcg cggtgcctgc   2640
cccaccacct cgggcgtccc cgctgaggtc gaggccgagg cccccaactc caacgtcatc   2700
ttctccaaca tccgcttcgg ccccatcggc tccaccgtct ccggcctgcc cgacggcggc   2760
agcggcaacc ccaacccgcc cgtcagctcg tccaccccgg tccctcctc gtccaccaca   2820 tcctccggtt cctccggccc gactggcggc acgggtgtcg ctaagcacta tctagatcta   2880
```

```
cgccaggacc gagcaagccc agatgagaac cgacgcagat ttccttggca cctgttgctt    2940
cagctgaatc ctggcaatac gagatacctg ctttgaatat tttgaatagc tcgcccgctg    3000
gagagcatcc tgaatgcaag taacaaccgt agaggctgac acggcaggtg ttgctaggga    3060
gcgtcgtgtt ctacaaggcc agacgtcttc gcggttgata tatatgtatg tttgactgca    3120
ggctgctcag cgacgacagt caagttcgcc ctcgctgctt gtgcaataat cgcagtgggg    3180
aagccacacc gtgactccca tctttcagta aagctctgtt ggtgtttatc agcaatacac    3240
gtaatttaaa ctcgttagca tggggctgat agcttaatta ccgtttacca gtgccgcggt    3300
tctgcagctt ccttggccc gtaaaattcg gcgaagccag ccaatcacca gctaggcacc    3360
agctaaaccc tataattagt ctcttatcaa caccatccgc tcccccggga tcaatgagga    3420
gaatgagggg gatgcgggc taagaagcc tacataaccc tcatgccaac tcccagttta    3480
cactcgtcga gccaacatcc tgactataag ctaacacaga atgcctcaat cctgggaaga    3540
actggccgct gataagcgcg cccgcctcgc aaaaaccatc cctgatgaat ggaaagtcca    3600
gacgctgcct gcggaagaca gcgttattga tttcccaaag aaatcgggga tcctttcaga    3660
ggccgaactg aagatcacag aggcctccgc tgcagatctt gtgtccaagc tggcggccgg    3720
agagttgacc tcggtggaag ttacgctagc attctgtaaa cgggcagcaa tcgcccagca    3780
gttagtaggg tcccctctac ctctcaggga gatgtaacaa cgccacctta tgggactatc    3840
aagctgacgc tggcttctgt gcagacaaac tgcgcccacg agttcttccc tgacgccgct    3900
ctcgcgcagg caagggaact cgatgaatac tacgcaaagc acaagagacc cgttggtcca    3960
ctccatggcc tccccatctc tctcaaagac cagcttcgag tcaaggtaca ccgttgcccc    4020
taagtcgtta gatgtcccct tttgtcagct aacatatgcc accagggcta cgaaacatca    4080
atgggctaca tctcatggct aaacaagtac gacgaagggg actcggttct gacaaccatg    4140
ctccgcaaag ccggtgccgt cttctacgtc aagacctctg tcccgcagac cctgatggtc    4200
tgcgagacag tcaacaacat catcgggcgc accgtcaacc cacgcaacaa gaactggtcg    4260
tgcggcggca gttctggtgg tgagggtgcg atcgttggga ttcgtggtgg cgtcatcggt    4320
gtaggaacgg atatcggtgg ctcgattcga gtgccggccg cgttcaactt cctgtacggt    4380
ctaaggccga gtcatgggcg gctgccgtat gcaaagatgg cgaacagcat ggagggtcag    4440
gagacggtgc acagcgttgt cgggccgatt acgcactctg ttgagggtga gtccttcgcc    4500
tcttccttct tttcctgctc tataccaggc ctccactgtc ctcctttctt gctttttata    4560
ctatatacga gaccggcagt cactgatgaa gtatgttaga cctccgcctc ttcaccaaat    4620
ccgtcctcgg tcaggagcca tggaaatacg actccaaggt catccccatg ccctggcgcc    4680
agtccgagtc ggacattatt gcctccaaga tcaagaacgg cgggctcaat atcggctact    4740
acaacttcga cggcaatgtc cttccacacc ctcctatcct gcgcggcgtg gaaaccaccg    4800
tcgccgcact cgccaaagcc ggtcacaccg tgacccgtg gacgccatac aagcacgatt    4860
tcggccacga tctcatctcc catatctacg cggctgacgg cagcgccgac gtaatgcgcg    4920
atatcagtgc atccggcgag ccggcgattc caaatatcaa agacctactg aacccgaaca    4980
tcaaagctgt taacatgaac gagctctggg acacgcatct ccagaagtgg aattaccaga    5040
tggagtacct tgagaaatgg cgggaggctg aagaaaaggc cgggaaggaa ctggacgcca    5100
tcatcgcgcc gattacgcct accgctgcgg tacggcatga ccagttccgg tactatgggt    5160
atgcctctgt gatcaacctg ctggatttca cgagcgtggt tgttccggtt acctttgcgg    5220
```

```
ataagaacat cgataagaag aatgagagtt tcaaggcggt tagtgagctt gatgccctcg    5280
tgcaggaaga gtatgatccg gaggcgtacc atggggcacc ggttgcagtg caggttatcg    5340
gacggagact cagtgaagag aggacgttgg cgattgcaga ggaagtgggg aagttgctgg    5400
gaaatgtggt gactccatag ctaataagtg tcagatagca atttgcacaa gaaatcaata    5460
ccagcaactg taaataagcg ctgaagtgac catgccatgc tacgaaagag cagaaaaaaa    5520
cctgccgtag aaccgaagag atatgacacg cttccatctc tcaaggaag aatcccttca     5580 gggttgcgtt tccagtctag acacgtataa cggcacaagt gtctctcacc aaatgggtta    5640
tatctcaaat gtgatctaag gatggaaagc ccagaatatt ggctgggttg atggctgctt    5700
cgagtgcagt ctcatgctgc cacaggtgac tctggatggc cccataccac tcaacccatg    5760
gtaccacgac caagaagatc acggtcgtca cccagttcct caagaactcg gccggcgagc    5820
tctccgagat caagcggttc tacgtccaga acggcaaggt catccccaac tccgagtcca    5880
ccatcccggg cgtcgagggc aactccatca cccaggactg gtgcgaccgc cagaaggccg    5940
ccttcggcga cgtgaccgac ttncaggaca agggcggcat ggtccagatg gcaaggccc     6000 tcgcggggcc catggtcctc gtcatgtcca tctgggacga ccacgccgtc aacatgctct    6060
ggctcgactc cacctggccc atcgacgcg ccggcaagcc gggcgccgag cgcggtgcct     6120
gccccaccac ctcgggcgtc cccgctgagg tcgaggccga ggcccccaac tccaacgtca    6180
tcttctccaa catccgcttc ggccccatcg gctccaccgt ctccggcctg cccgacggcg    6240
gcagcggcaa ccccaacccg cccgtcagct cgtccacccc ggtcccctcc tcgtccacca    6300
catcctccgg ttcctccggc ccgactggcg gcacgggtgt cgctaagcac tattcgggga    6360
atctgatagc agctcgagtt tgctgcgagg actaggaagg gtttcgctga cccgtattgc    6420
ccattgttga agaaaaggg caggccagaa agcaagacac cttcccgctt cggcctctgg      6480
tccggcattg gctggggtcc cgttcaggcg cgcgggtgct cccgccgtga tcaagtgctt    6540
gtgatcaggg gttccgggtg caatacctga ctttcgagga ctagcaacgc cgcacgaccg    6600
ggcgtgtcaa gcatgcgcca acatccgcag gcggccccgt cgagagggtt acctaacata    6660
acgggtgaac ttgcctaagg ggcaaaggcg acgatctctg cgcgaaaag tgccgggaag     6720 aggggtgtgg ggagggtgt gtgggtgtat gtacaaggcg tggtgggttc cgatccagca    6780
tgtatgtact ttctatgtgt gtgcgtgtgt gttgtggtat gttgtacaca gagtatgtat    6840
aaagtatctg actgacaatt tgagcatgac ctccgactgg tgaagttgca caggcgaaac    6900
aggtccggtg agtggtcagc ctaaataatt aaagggatt atccatggaa gtcaaacagc      6960
ctgtcataac cccaaagtac cgtgaccgcg ggcactccgg ggccaaaaaa aaaaaaaaa     7020 ataagcgatc aggcttcatg tttcgtggct ctggtctctc cttctagaag ggtgtgtggg    7080
acttcgcgaa ccctctctct gggccaaagt gattcagatt ttagtctcta gtctcggaaa    7140
cattcagctg agaaggtctg tacagactgt acagaggcgc aacggggcg actgaccctg      7200 tgtgcttgtg aaacaaccag aggtcatggc cgagatcggc aatcagagga tctgggtaa      7260 agcctgcgga ctatatctga acgtgacatc gcctaggtga agccaaagca agggcagcaa    7320
tggcaccatc gcaatcggcc caccctggat cggtacctcg agcgaggaag ccgaggaaca    7380
agaaatggag gggtggtgtg gtggtagcct atttggtgga gttcaaggat ggggcattgc    7440
aaaggccgca agtgccgatc gctcgacacg gggagccgag tggttggctg aggtacgctc    7500
tcgaaatgct ggagcgagag ccacgttcgg caggtggtat ctcttttcct tggtccaagt    7560
ctggccgtgg ggggagggga atttccatgc gagtgcaaag taactctgcg tactaaagtg    7620
```

-continued

```
ttttgtgagc aagtttggca agagtgaata catagttagt atccggttgg gtgctgcgac    7680
taaggtaggt tacagtcacg acctagctac ctacagtaca ctaccctagc gagtagtccg    7740
gtagcactgt ggcagaaaag tgggcggtgc agcgagattc cagatcgggc tcctgcccac    7800
atgtgtagtt aatccccttc ccctacccct gccacgtccc ttgaaacgct ttcatctacg    7860
gagtattatc gtacggatta ctacagttat tactatgtcg aagccaagcg caagtacacg    7920
tgtaatgcca ccctcatcca cctttcctgt tccctaaacc aggttactta cccgttact     7980
gcagaaaccc aagccaaaaa tccgacgggt tggatttgac tcaagacagg tcgacccatt    8040
gctgaccgcc agcatccagc caaaagata gccagttaca tctcacaaag atctgacaga     8100
cagaagatga atacccgaaa agctcggttc ctgcattgtc gccaactctc cctaacgtga    8160
tctgtgttcc cccaagcaga gaaacccccac tgaaatcgat cgcgtacggc gcatccgcag   8220
cccgctgttc cgcctagcat gggtcatctg ccgggcctta tctggtggcc ttccggatca    8280
agtaacggtc aagtcacatc ttggcccgcc ctctctctct ccctttcgat ctgagggcca    8340
ccgcccctc ccctgccgc cctcgcacgc tactcgccat agccgcgaaa ccgagggatc      8400
gcacggcatt ggcagctgca tttccttgtt gccctcgcta ataaagtgcg cagtgagcaa    8460
tcagcaatga gcaagcagaa ttcctgttgc tcatgctttg ggtgagcgat gcgccttct     8520
catcgcccca ttgctatgcg ggcgcaaacc tcaccagctg ccaaatccag catgactgcc    8580
cgttgcgtgc gacctggccc agaccactag gcagccgcga gatgtcttgg gccgcgatgc    8640
gttacatgtc agttcaaaca atgctctttg gaagaaggt gtcattcctc aatggccgct     8700
cctgatcatg taagcgacgg ctgcctagct cctgagagac cgaagcggca gtgatgcgca    8760
ttgattatct ccgggtggga cacgggatct ccagctctga accgtcgcat tgtcttgctg    8820
tttgttgacg ggcccaagga ttccgcccct tccgcgacac ttagcaagta attaacgttt    8880
gagtcgtgtg cctgctttgg ataaagtacc atccttgccg tagatttact tcgctcacct    8940
caagtaatgc tacgtgcctt tctcagtcat ctgaacgcct gaattgaaac ttattagcct    9000
gacgtaggcg tgcagttggt ccgagcggag atcagaatac cactggtcgg accgaaatgt    9060
aagaccgagg tagtatttcc agatcccttc ggcacctgtc ctcgatatga ttcggtgctc    9120
aactttcaag acagttgatc agctgagaac cattgcacga cggtgattag ccactgcact    9180
ctccggcctt cgtgttcgag ctgctatgcc atcaaagagt cggcatatcc cagtacccgt    9240
agtactaata tttggcaacc aagttttttt tcaagcaacg atcgactcga atccaatgct    9300
ccaatcgggg gaagacgagg tttggagaaa cttgagtttc agaccgcgca acctaagttt    9360
ctttcaacac gcctttgttc ccaaaagacg gcggaccatc aaggcagaag cgtcaggtat    9420
tctccttttcc agagagaagc ggcatgtata tgtccgatca tttcgtgaag ccaccaaaaa    9480
tccgagaaag agggcggcgg tggcggcggc agaggcagca ttgtcggtta cctgaccagc    9540
gggcgtggca tgtcccgaaa agctatgctg gggagcacag ttaatgccgt ctcttgagca    9600
tcctcgggcg gtaccggatg cgcggcaaga ggactaggtg tgccgacgat ggcgttgacg    9660
gaagcgcggg ctgggaagaa aatcgggggt tgaacacgtg ctggggcctg cgaggatggt    9720
gacctttgc agaggtgccg agcgctgccg cacaagcggc tggggggggg gggggggggc     9780
tgccacgaga acgctagcct tggtccaaac cttggtgtcg cctttgaagt ccttgcttgg    9840
cttgccggct ttggtgtttg cgcttgcgcc gaccgagggt tgaataacca tgatcacgga    9900
atggccgtca tgggatccac tagttctaga gcggccgcca ccgcggtgga gctccagctt    9960
```

```
ttgttcccctt tagtgagggt taattgcgcg cttggcgtaa tcatggtcat agctgtttcc    10020
tgtgtgaaat tgttatccgc tcacaattcc acacaacata cgagccggaa gcataaagtg    10080
taaagcctgg ggtgcctaat gagtgagcta actcacatta attgcgttgc gctcactgcc    10140
cgctttccag tcgggaaacc tgtcgtgcca gctgcattaa tgaatcggcc aacgcgcggg    10200
gagaggcggt ttgcgtattg ggcgctcttc cgcttcctcg ctcactgact cgctgcgctc    10260
ggtcgttcgg ctgcggcgag cggtatcagc tcactcaaag gcggtaatac ggttatccac    10320
agaatcaggg gataacgcag gaaagaacat gtgagcaaaa ggccagcaaa aggccaggaa    10380
ccgtaaaaag gccgcgttgc tggcgttttt ccataggctc cgcccccctg acgagcatca    10440
caaaaatcga cgctcaagtc agaggtggcg aaacccgaca ggactataaa gataccaggc    10500
gtttccccct ggaagctccc tcgtgcgctc tcctgttccg accctgccgc ttaccggata    10560
cctgtccgcc tttctccctt cgggaagcgt ggcgctttct catagctcac gctgtaggta    10620
tctcagttcg gtgtaggtcg ttcgctccaa gctgggctgt gtgcacgaac cccccgttca    10680
gcccgaccgc tgcgccttat ccggtaacta tcgtcttgag tccaacccgg taagacacga    10740
cttatcgcca ctggcagcag ccactggtaa caggattagc agagcgaggt atgtaggcgg    10800
tgctacagag ttcttgaagt ggtggcctaa ctacggctac actagaagga cagtatttgg    10860
tatctgcgct ctgctgaagc cagttacctt cggaaaaaga gttggtagct cttgatccgg    10920
caaacaaacc accgctggta gcggtggttt ttttgtttgc aagcagcaga ttacgcgcag    10980
aaaaaaagga tctcaagaag atcctttgat cttttctacg gggtctgacg ctcagtggaa    11040
cgaaaactca cgttaaggga ttttggtcat gagattatca aaaaggatct tcacctagat    11100
ccttttaaat taaaaatgaa gttttaaatc aatctaaagt atatatgagt aaacttggtc    11160
tgacagttac caatgcttaa tcagtgaggc acctatctca gcgatctgtc tatttcgttc    11220
atccatagtt gcctgactcc ccgtcgtgta gataactacg atacgggagg gcttaccatc    11280
tggccccagt gctgcaatga taccgcgaga cccacgctca ccggctccag atttatcagc    11340
aataaaccag ccagccggaa gggccgagcg cagaagtggt cctgcaactt tatccgcctc    11400
catccagtct attaattgtt gccgggaagc tagagtaagt agttcgccag ttaatagttt    11460
gcgcaacgtt gttgccattg ctacaggcat cgtggtgtca cgctcgtcgt ttggtatggc    11520
ttcattcagc tccggttccc aacgatcaag gcgagttaca tgatccccca tgttgtgcaa    11580
aaaagcggtt agctccttcg gtcctccgat cgttgtcaga agtaagttgg ccgcagtgtt    11640
atcactcatg gttatggcag cactgcataa ttctcttact gtcatgccat ccgtaagatg    11700
cttttctgtg actggtgagt actcaaccaa gtcattctga atagtgta tgcggcgacc    11760 gagttgctct tgcccggcgt caatacggga taataccgcg ccacatagca gaactttaaa    11820
agtgctcatc attggaaaac gttcttcggg gcgaaaactc tcaaggatct taccgctgtt    11880
gagatccagt tcgatgtaac ccactcgtgc acccaactga tcttcagcat cttttacttt    11940
caccagcgtt tctgggtgag caaaaacagg aaggcaaaat gccgcaaaaa agggaataag    12000
ggcgacacgg aaatgttgaa tactcatact cttccttttt caatattatt gaagcattta    12060
tcagggttat tgtctcatga gcggatacat atttgaatgt atttagaaaa ataaacaaat    12120 agggggttccg cgcacatttc cccgaaaagt gccac                              12155
```

<210> SEQ ID NO 26
<211> LENGTH: 5152
<212> TYPE: DNA
<213> ORGANISM: artificial
<220> FEATURE:
<223> OTHER INFORMATION: pMT123-DKu70-A

<400> SEQUENCE: 26

| | | | | | |
|---|---|---|---|---|---:|
| ctgaagccag | ttaccttcgg | aaaaagagtt | ggtagctctt | gatccggcaa | acaaaccacc | 60 |
| gctggtagcg | gtggtttttt | tgtttgcaag | cagcagatta | cgcgcagaaa | aaaggatct | 120 |
| caagaagatc | ctttgatctt | ttctacgggg | tctgacgctc | agtggaacga | aaactcacgt | 180 |
| taagggattt | tggtcatgag | attatcaaaa | aggatcttca | cctagatcct | tttaaaggcc | 240 |
| ggccgcggcc | gctcgattta | aatctcgagt | acatgtcctc | ggtgagcggg | ttcgcgtagc | 300 |
| ggaaggcgac | atagggcata | tgcggtgccg | tctcgggcga | gatcttatcg | aggattttgc | 360 |
| acatctcggc | gcactggtgc | tcggaccact | tgcggatggg | tgagccgccg | ccgatggccg | 420 |
| catattgttg | ctggatcttg | ggcgtgcgcc | gcttggagag | gagcgggccg | atgtagccct | 480 |
| ggagccggcc | gagagggatg | agatcgccat | cggactggag | gtgaaacaaa | gcgttaggcg | 540 |
| atcggtccgg | gcggccgtat | tttggagcac | cggggggggg | gggggttaac | tcacgaatag | 600 |
| tctgctgagg | aagtcgccca | cttcatcggt | cgtcgatggg | ccgcccatgt | tgagaaacac | 660 |
| catagccgtt | gggccccgcc | cagagtcttg | ggtgactgga | tgaaccggcg | tcgcgagcca | 720 |
| tcgtgcctgt | tgtgcagaag | gttttgccag | cctatgaggc | cggagtggcc | gcatggcggc | 780 |
| cgggagacga | agcgccatct | cgaagcgaaa | cacgggaatc | cgaggcgagt | cgcagtaaa | 840 |
| aaagaaaaa | aaaatgaaa | agaagcgct | gttagtcgtt | gcagtaaaaa | agataaacaa | 900 |
| gaacaaacgg | gattgagaca | atccctaggg | ccatctatca | atttattcgc | aatgcgtcag | 960 |
| aggaaactga | cgataccttg | gtttcagaca | gtggcgaacg | gaacaggagg | ccagatcaca | 1020 |
| ctccgcccgc | gactttcgcg | gcaactcggc | ggcggtacga | tcaaaggccg | actttgccat | 1080 |
| cttggcatcg | gcgttgacct | tgcagatcgg | ccggatccc | ttttggccaa | tcgcaaatgt | 1140 |
| tcaattgcac | agcttgcctt | gtcgtctgcg | tcacatgttc | tggcgttagg | caggcgcgtc | 1200 |
| agcctagcat | cacgtcgcgt | cgcacctgca | ccttcaaagc | ccgttggtca | gcttcggcac | 1260 |
| gaacatgccc | aacttctcgc | ccaaagccag | agggaagctc | agcgtccaat | tcgagctctg | 1320 |
| tacagtgacc | ggtgactctt | tctggcatgc | ggagagacga | acggacgcag | agagaagggc | 1380 |
| tgagtaataa | gcgccactgc | gccagacagc | tctggcggct | ctgaggtgca | gtggatgatt | 1440 |
| attaatccgg | gaccggccgc | ccctccgccc | gaagtggaa | aggctggtgt | gcccctcgtt | 1500 |
| gaccaagaat | ctattgcatc | atcggagaat | atggagcttc | atcgaatcac | cggcagtaag | 1560 |
| cgaaggagaa | tgtgaagcca | gggggtgtata | gccgtcggcg | aaatagcatg | ccattaacct | 1620 |
| aggtacagaa | gtccaattgc | ttccgatctg | gtaaagatt | cacgagatag | taccttctcc | 1680 |
| gaagtaggta | gagcgagtac | ccggcgcgta | agctccctaa | ttggcccatc | cggcatctgt | 1740 |
| agggcgtcca | aatatcgtgc | ctctcctgct | ttgcccggtg | tatgaaaccg | gaaaggccgc | 1800 |
| tcaggagctg | gccagcggcg | cagaccggga | acacaagctg | gcagtcgacc | catccggtgc | 1860 |
| tctgcactcg | acctgctgag | gtccctcagt | ccctggtagg | cagcttttgcc | ccgtctgtcc | 1920 |
| gcccggtgtg | tcggcggggt | tgacaaggtc | gttgcgtcag | tccaacattt | gttgccatat | 1980 |
| tttcctgctc | tccccaccag | ctgctctttt | cttttctctt | tcttttccca | tcttcagtat | 2040 |
| attcatcttc | ccatccaaga | acctttattt | ccctaagta | agtactttgc | tacatccata | 2100 |
| ctccatcctt | cccatccctt | attcctttga | acctttcagt | tcgagctttc | ccacttcatc | 2160 |
| gcagcttgac | taacagctac | cccgcttgag | cagacatcac | catgcctcaa | tcctgggaag | 2220 |

```
aactggccgc tgataagcgc gcccgcctcg caaaaaccat ccctgatgaa tggaaagtcc    2280
agacgctgcc tgcggaagac agcgttattg atttcccaaa gaaatcgggg atcctttcag    2340
aggccgaact gaagatcaca gaggcctccg ctgcagatct tgtgtccaag ctggcggccg    2400
gagagttgac ctcggtggaa gttacgctag cattctgtaa acgggcagca atcgcccagc    2460
agttagtagg gtcccctcta cctctcaggg agatgtaaca acgccacctt atgggactat    2520
caagctgacg ctggcttctg tgcagacaaa ctgcgcccac gagttcttcc ctgacgccgc    2580
tctcgcgcag gcaagggaac tcgatgaata ctacgcaaag cacaagagac ccgttggtcc    2640
actccatggc ctccccatct ctctcaaaga ccagcttcga gtcaaggtac accgttgccc    2700
ctaagtcgtt agatgtccct ttttgtcagc taacatatgc caccagggct acgaaacatc    2760
aatgggctac atctcatggc taaacaagta cgacgaaggg gactcggttc tgacaaccat    2820
gctccgcaaa gccggtgccg tcttctacgt caagacctct gtcccgcaga ccctgatggt    2880
ctgcgagaca gtcaacaaca tcatcgggcg caccgtcaac ccacgcaaca gaactggtc     2940 gtgcggcggc agttctggtg gtgagggtgc gatcgttggg attcgtggtg gcgtcatcgg    3000
tgtaggaacg gatatcggtg gctcgattcg agtgccggcc gcgttcaact tcctgtacgg    3060
tctaaggccg agtcatgggc ggctgccgta tgcaaagatg gcgaacagca tggaggcggc    3120
cgctacggga tttaaatcgc tagcgggctg ctaaaggaag cggaacacgt agaaagccag    3180
tccgcagaaa cggtgctgac cccggatgaa tgtcagctac tgggctatct ggacaaggga    3240
aaacgcaagc gcaaagagaa agcaggtagc ttgcagtggg cttacatggc gatagctaga    3300
ctgggcggtt ttatggacag caagcgaacc ggaattgcca gctggggcgc cctctggtaa    3360
ggttgggaag ccctgcaaag taaactggat ggctttcttg ccgccaagga tctgatggcg    3420
caggggatca agatctgatc aagagacagg atgaggatcg tttcgcatga ttgaacaaga    3480
tggattgcac gcaggttctc cggccgcttg ggtggagagg ctattcggct atgactgggc    3540
acaacagaca atcggctgct ctgatgccgc cgtgttccgg ctgtcagcgc aggggcgccc    3600
ggttcttttt gtcaagaccg acctgtccgg tgccctgaat gaactgcagg acgaggcagc    3660
gcggctatcg tggctggcca cgacgggcgt tccttgcgca gctgtgctcg acgttgtcac    3720
tgaagcggga agggactggc tgctattggg cgaagtgccg gggcaggatc tcctgtcatc    3780
tcaccttgct cctgccgaga aagtatccat catggctgat gcaatgcggc ggctgcatac    3840
gcttgatccg gctacctgcc cattcgacca ccaagcgaaa catcgcatcg agcgagcacg    3900
tactcggatg gaagccggtc ttgtcgatca ggatgatctg gacgaagagc atcaggggct    3960
cgcgccagcc gaactgttcg ccaggctcaa ggcgcgcatg cccgacggcg aggatctcgt    4020
cgtgacccat ggcgatgcct gcttgccgaa tatcatggtg gaaaatggcc gcttttctgg    4080
attcatcgac tgtggccggc tgggtgtggc ggaccgctat caggacatag cgttggctac    4140
ccgtgatatt gctgaagagc ttggcggcga atgggctgac cgcttcctcg tgctttacgg    4200
tatcgccgct cccgattcgc agcgcatcgc cttctatcgc cttcttgacg agttcttctg    4260
agcgggactc tggggttcga aatgaccgac caagcgacgc ccaacctgcc atcacgagat    4320
ttcgattcca ccgccgcctt ctatgaaagg ttgggcttcg aatcgttttt ccgggacgcc    4380
ggctggatga tcctccagcg cggggatctc atgctggagt tcttcgccca cgctagcggc    4440
gcgccggccg gcccggtgtg aaataccgca cagatgcgta aggagaaaat accgcatcag    4500
gcgctcttcc gcttcctcgc tcactgactc gctgcgctcg gtcgttcggc tgcggcgagc    4560
ggtatcagct cactcaaagg cggtaatacg gttatccaca gaatcagggg ataacgcagg    4620
```

-continued

| | |
|---|---|
| aaagaacatg tgagcaaaag gccagcaaaa ggccaggaac cgtaaaaagg ccgcgttgct | 4680 |
| ggcgttttc cataggctcc gccccctga cgagcatcac aaaaatcgac gctcaagtca | 4740 |
| gaggtggcga acccgacag gactataaag ataccaggcg tttccccctg gaagctccct | 4800 |
| cgtgcgctct cctgttccga ccctgccgct taccggatac ctgtccgcct ttctcccttc | 4860 |
| gggaagcgtg gcgctttctc atagctcacg ctgtaggtat ctcagttcgg tgtaggtcgt | 4920 |
| tcgctccaag ctgggctgtg tgcacgaacc ccccgttcag cccgaccgct gcgccttatc | 4980 |
| cggtaactat cgtcttgagt ccaacccggt aagacacgac ttatcgccac tggcagcagc | 5040 |
| cactggtaac aggattagca gagcgaggta tgtaggcgt gctacagagt tcttgaagtg | 5100 |
| gtggcctaac tacggctaca ctagaaggac agtatttggt atctgcgctc tg | 5152 |

<210> SEQ ID NO 27
<211> LENGTH: 6131
<212> TYPE: DNA
<213> ORGANISM: artificial
<220> FEATURE:
<223> OTHER INFORMATION: pMT124-DKu70-AB

<400> SEQUENCE: 27

| | |
|---|---|
| tcttgttcaa tcatgcgaaa cgatcctcat cctgtctctt gatcagatct tgatcccctg | 60 |
| cgccatcaga tccttggcgg caagaaagcc atccagttta ctttgcaggg cttcccaacc | 120 |
| ttaccagagg gcgccccagc tggcaattcc ggttcgcttg ctgtccataa aaccgcccag | 180 |
| tctagctatc gccatgtaag cccactgcaa gctacctgct ttctctttgc gcttgcgttt | 240 |
| tcccttgtcc agatagccca gtagctgaca ttcatccggg gtcagcaccg tttctgcgga | 300 |
| ctggctttct acgtgttccg cttcctttag cagcccgcta gcgatttaaa tcccgtagcg | 360 |
| gccgcaaggg gactcggttc tgacaaccat gctccgcaaa gccggtgccg tcttctacgt | 420 |
| caagacctct gtcccgcaga ccctgatggt ctgcgagaca gtcaacaaca tcatcgggcg | 480 |
| caccgtcaac ccacgcaaca agaactggtc gtgcggcggc agttctggtg gtgagggtgc | 540 |
| gatcgttggg attcgtggtg gcgtcatcgg tgtaggaacg gatatcggtg gctcgattcg | 600 |
| agtgccggcc gcgttcaact tcctgtacgg tctaaggccg agtcatgggc ggctgccgta | 660 |
| tgcaaagatg gcgaacagca tggagggtca ggagacggtg cacagcgttg tcgggccgat | 720 |
| tacgcactct gttgagggtg agtccttcgc ctcttccttc ttttcctgct ctataccagg | 780 |
| cctccactgt cctcctttct tgcttttat actatatacg agaccggcag tcactgatga | 840 |
| agtatgttag acctccgcct cttcaccaaa tccgtcctcg gtcaggagcc atggaaatac | 900 |
| gactccaagg tcatccccat gccctggcgc cagtccgagt cggacattat tgcctccaag | 960 |
| atcaagaacg gcgggctcaa tatcggctac tacaacttcg acggcaatgt ccttccacac | 1020 |
| cctcctatcc tgcgcggcgt ggaaaccacc gtcgccgcac tcgccaaagc cggtcacacc | 1080 |
| gtgacccgt ggacgccata caagcacgat ttcggccacg atctcatctc ccatatctac | 1140 |
| gcggctgacg gcagcgccga cgtaatgcgc gatatcagtg catccggcga gccggcgatt | 1200 |
| ccaaatatca aagacctact gaaccccgaac atcaaagctg ttaacatgaa cgagctctgg | 1260 |
| gacacgcatc tccagaagtg gaattaccag atggagtacc ttgagaaatg gcgggaggct | 1320 |
| gaagaaaagg ccgggaagga actggacgcc atcatcgcgc cgattacgcc taccgctgcg | 1380 |
| gtacggcatg accagttccg gtactatggg tatgcctctg tgatcaacct gctggatttc | 1440 |
| acgagcgtgg ttgttccggt taccttgcg gataagaaca tcgataagaa gaatgagagt | 1500 |

```
ttcaaggcgg ttagtgagct tgatgccctc gtgcaggaag agtatgatcc ggaggcgtac    1560
catggggcac cggttgcagt gcaggttatc ggacggagac tcagtgaaga gaggacgttg    1620
gcgattgcag aggaagtggg gaagttgctg ggaaatgtgg tgactccata gctaataagt    1680
gtcagatagc aatttgcaca agaaatcaat accagcaact gtaaataagc gctgaagtga    1740
ccatgccatg ctacgaaaga gcagaaaaaa acctgccgta gaaccgaaga gatatgacac    1800
gcttccatct ctcaaaggaa gaatcccttc agggttgcgt ttccagtcta gacacgtata    1860
acggcacaag tgtctctcac caaatggggtt atatctcaaa tgtgatctaa ggatggaaag    1920
cccagaatat tggctgggtt gatggctgct cgagtgcag tctcatgctg ccacaggtga    1980
ctctggatgg ccccatacca ctcaacccat gcgtgcgagg tcccgtacat gtcctcggtg    2040
agcgggttcg cgtagcggaa ggcgacatag ggcatatgcg gtgccgtctc gggcgagatc    2100
ttatcgagga ttttgcacat ctcggcgcac tggtgctcgg accacttgcg gatgggtgag    2160
ccgccgccga tggccgcata ttgttgctgg atcttgggcg tgcgccgctt ggagaggagc    2220
gggccgatgt agccctggag ccggccgaga gggatgagat cgccatcgga ctggaggtga    2280
aacaaagcgt taggcgatcg gtccgggcgg ccgtattttg gagcaccggg gggggggggg    2340
gttaactcac gaatagtctg ctgaggaagt cgcccacttc atcggtcgtc gatgggccgc    2400
ccatgttgag aaacaccata gccgttgggc cccgcccaga gtcttgggtg actggatgaa    2460
ccggcgtcgc gagccatcgt gcctgttgtg cagaaggttt tgccagccta tgaggccgga    2520
gtggccgcat ggcggccggg agacgaagcg ccatctcgaa gcggaacacg ggaatccgag    2580
gcgagttcgc agtaaaaaaa gaaaaaaaa atgaaaaga agcgctgtta gtcgttgcag    2640 taaaaagat aaacaagaac aaacgggatt gagacaatcc ctagggccat ctatcaattt    2700
attcgcaatg cgtcagagga aactgacgat accttggttt cagacagtgg cgaacggaac    2760
aggaggccag atcacactcc gcccgcgact ttcgcggcaa ctcggcggcg gtacgatcaa    2820
aggccgactt tgccatcttg gcatcggcgt tgacctttgca gatcggccgg gatccctttt    2880
ggccaatcgc aaatgttcaa ttgcacagct tgccttgtcg tctgcgtcac atgttctggc    2940
gttaggcagg cgcgtcagcc tagcatcacg tcgcgtcgca cctgcacctt caaagcccgt    3000
tggtcagctt cggcacgaac atgcccaact tctcgcccaa agccagagga gaacatatga    3060
tcttgaaacg gtttcttatt ctttggaatg tgtgtattgc agtcggtacg aagtatattc    3120
tgtaatgatg ctacttcgtc agggacatgc ccttcccatg gtttagcgtt gctcaaaaca    3180
cgttgttatc cgagatgctc tggagctgaa gttccaaggc gttttttggag agagattgcg    3240 gaactccaaa cataaggtag agagagatat tcctcagtcc gcactaaaca aggtccctgt    3300
ttaatagtta cacagcaatg gagatccatg cactcccgca cgtctggatg cacccaccct    3360
tgctgctctc tcggccccgc tttggtctcc ttccactcat tgccagttct gactggttcg    3420
caacaacgca tgtcctcgta cgtccgcacg cagccactcc actttacaat agaaactaaa    3480
gatacccgct tggcaaagcg acacgacgac gcgacggaga tactggtggt ttgtcgcgcc    3540
gtcctgtttt ctgatccaaa cgacagcctt gtcatggaga ctctgacctc tgcattctga    3600
agccaagcga atgagcgcag gcgacccgac ctacttgaaa gagaacgagc ggcaatggag    3660
gctctgctgg gcaccggcca gtcgaacccg acctgcggtt cgctggccga cctccaggag    3720
caactccggc atcttcttca gagtcgcgtg accgaaactc gcgccgaaca tatttcggtg    3780
gcattcgaag tccgagcgac cgcgattttt gacatccctg tgaccggcgt cgaaaatgac    3840
ctgctcggga accccctcgaa catcgacccg tcgctgggcg ggtcacggtc gagcgctgct    3900
```

```
gcgccagcca tcaacggtag tgcgggacag ccgacccgac gagtcagcgc catcgacgcc    3960
ctgatcaacc agcccgtgga cgacccggtg ttgcagactg cgattgccag gcagatcata    4020
tcgtcggtgg gcgaggccga ctcgagcaac tgggcagtgc ggcaggtctc gcgcgctgag    4080
cagagttgga cgtttgccta catctgcaag gattcctggg aggcctggaa ccgtcaggcg    4140
tcgaagacac tagtcatatg acgcgtggta ccgggcccga cgtcaggcct ctcgagattt    4200
aaatcgagcg gccgcggccg gcctttaaaa ggatctaggt gaagatcctt tttgataatc    4260
tcatgaccaa aatcccttaa cgtgagtttt cgttccactg agcgtcagac cccgtagaaa    4320
agatcaaagg atcttcttga gatccttttt ttctgcgcgt aatctgctgc ttgcaaacaa    4380
aaaaaccacc gctaccagcg gtggtttgtt tgccggatca agagctacca actctttttc    4440
cgaaggtaac tggcttcagc agagcgcaga taccaaatac tgtccttcta gtgtagccgt    4500
agttaggcca ccacttcaag aactctgtag caccgcctac atacctcgct ctgctaatcc    4560
tgttaccagt ggctgctgcc agtggcgata agtcgtgtct taccgggttg gactcaagac    4620
gatagttacc ggataaggcg cagcggtcgg gctgaacggg gggttcgtgc acacagccca    4680
gcttggagcg aacgacctac accgaactga gatacctaca gcgtgagcta tgagaaagcg    4740
ccacgcttcc cgaagggaga aaggcggaca ggtatccggt aagcggcagg gtcggaacag    4800
gagagcgcac gagggagctt ccaggggaa acgcctggta tctttatagt cctgtcgggt    4860
ttcgccacct ctgacttgag cgtcgatttt tgtgatgctc gtcaggggg cggagcctat    4920 ggaaaaacgc cagcaacgcg gccttttac ggttcctggc cttttgctgg ccttttgctc    4980
acatgttctt cctgcgtta tccctgat ctgtggataa ccgtattacc gcctttgagt    5040
gagctgatac cgctcgccgc agccgaacga ccgagcgcag cgagtcagtg agcgaggaag    5100
cggaagagcg cctgatgcgg tatttctcc ttacgcatct gtgcggtatt tcacaccggg    5160
ccggccggcg cgccgctagc gtgggcgaag aactccagca tgagatcccc gcgctggagg    5220
atcatccagc cggcgtcccg gaaaacgatt ccgaagccca acctttcata gaaggcggcg    5280
gtggaatcga aatctcgtga tggcaggttg ggcgtcgctt ggtcggtcat ttcgaacccc    5340
agagtcccgc tcagaagaac tcgtcaagaa ggcgatagaa ggcgatgcgc tgcgaatcgg    5400
gagcggcgat accgtaaagc acgaggaagc ggtcagccca ttcgccgcca agctcttcag    5460
caatatcacg ggtagccaac gctatgtcct gatagcggtc cgccacaccc agccggccac    5520
agtcgatgaa tccagaaaag cggccatttt ccaccatgat attcggcaag caggcatcgc    5580
catgggtcac gacgagatcc tcgccgtcgg gcatgcgcgc cttgagcctg gcgaacagtt    5640
cggctggcgc gagcccctga tgctcttcgt ccagatcatc ctgatcgaca gaccggcttt    5700
ccatccgagt acgtgctcgc tcgatgcgat gtttcgcttg gtggtcgaat gggcaggtag    5760
ccggatcaag cgtatgcagc cgccgcattg catcagccat gatggatact ttctcggcag    5820
gagcaaggtg agatgacagg agatcctgcc ccggcacttc gcccaatagc agccagtccc    5880
ttcccgcttc agtgacaacg tcgagcacag ctgcgcaagg aacgcccgtc gtggccagcc    5940
acgatagccg cgctgcctcg tcctgcagtt cattcagggc accggacagg tcggtcttga    6000
caaaaagaac cgggcgcccc tgcgctgaca gccggaacac ggcggcatca gagcagccga    6060
ttgtctgttg tgcccagtca tagccgaata gcctctccac ccaagcggcc ggagaacctg    6120
cgtgcaatcc a                                                         6131

<210> SEQ ID NO 28
```

```
<211> LENGTH: 1059
<212> TYPE: DNA
<213> ORGANISM: artificial
<220> FEATURE:
<223> OTHER INFORMATION: mannanase engineered variant DNA

<400> SEQUENCE: 28
gccagccgct tcgtcaccat cagcggcacc cagttcaaca tcgacggcaa ggtcggctac      60
ttcgccggca ccaactgcta ctggtgcagc tacctcacca ccacgccga cgtcgacagc     120
accttcagcc acatcagcag cagcggcctc aaggtcgtcc gcgtctgggg cttcaacgac    180
gtcaacaccc agccccccc gggccagatc tggttccaga agctcagcgc caccggcagc     240
accatcaaca ccggcgccga cggcctccag accctcgact acgtcgtccg gtcggccgag    300
cagcacaacc tcaagctcat catcccttc gtcaactact ggtcggacta cggcggcatc     360
aacgcctacg tcaacgcctt cggcggcaac gccaccacct ggtacaccaa cacggccgcc    420
cagacccagt accgcaagta cgtccaggcc gtcgtcagcc gctacgccaa cagcaccgcc    480
atcttcgcct gggagctggg caacgagccc cgctgccacg gctgcagcac cgacgtcatc    540
caccagtggg ccaccagcgt cagccagtac gtcaagagcc tcgactcgaa ccacctcgtc    600
tcgctcggcg acgagggctt cggcctcagc accggcgacg gcacctaccc ctacacctac    660
ggcgagggca cggacttcgc caagaacgtc cagatcaagt cgctcgactt cggcaccttc    720
cacctctacc ccgacagctg gggcacgaac tacacctggg gcaacggctg gatccgcacc    780
cacgccgccg cctgcctggc cgccggcaag ccctgcgtcc tcgaggagta cggcgcccgc    840
caggacccct gcaccaacga ggccccctgg cagaccacca gcctcaccac cgcggcatg     900
ggcggcgata tgttctggca gtggggcgac acgttcgcca acggcgccca gagcaacagc    960
gacccgtaca ccgtctggta caacagcagc tcgtggcagt gcctcgtcaa gaaccacgtc   1020
gacgccatca acggcggcac caccaccccc ccgccctaa                         1059

<210> SEQ ID NO 29
<211> LENGTH: 352
<212> TYPE: PRT
<213> ORGANISM: artificial
<220> FEATURE:
<223> OTHER INFORMATION: engineered mannanase variant protein

<400> SEQUENCE: 29

Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Tyr Leu
            20                  25                  30

Thr Asn His Ala Asp Val Asp Ser Thr Phe Ser His Ile Ser Ser Ser
        35                  40                  45

Gly Leu Lys Val Val Arg Val Trp Gly Phe Asn Asp Val Asn Thr Gln
    50                  55                  60

Pro Pro Gly Gln Ile Trp Phe Gln Lys Leu Ser Ala Thr Gly Ser
65                  70                  75                  80

Thr Ile Asn Thr Gly Ala Asp Gly Leu Gln Thr Leu Asp Tyr Val Val
                85                  90                  95

Arg Ser Ala Glu Gln His Asn Leu Lys Leu Ile Ile Pro Phe Val Asn
            100                 105                 110

Tyr Trp Ser Asp Tyr Gly Gly Ile Asn Ala Tyr Val Asn Ala Phe Gly
        115                 120                 125

Gly Asn Ala Thr Thr Trp Tyr Thr Asn Thr Ala Ala Gln Thr Gln Tyr
```

```
                130              135                 140
Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys His Gly Cys Ser
                165                 170                 175

Thr Asp Val Ile His Gln Trp Ala Thr Ser Val Ser Gln Tyr Val Lys
                180                 185                 190

Ser Leu Asp Ser Asn His Leu Val Ser Leu Gly Asp Glu Gly Phe Gly
                195                 200                 205

Leu Ser Thr Gly Asp Gly Thr Tyr Pro Tyr Thr Tyr Gly Glu Gly Thr
                210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
                245                 250                 255

Trp Ile Arg Thr His Ala Ala Ala Cys Leu Ala Ala Gly Lys Pro Cys
                260                 265                 270

Val Leu Glu Glu Tyr Gly Ala Arg Gln Asp Pro Cys Thr Asn Glu Ala
                275                 280                 285

Pro Trp Gln Thr Thr Ser Leu Thr Thr Arg Gly Met Gly Gly Asp Met
                290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Trp Gln Cys Leu Val
                325                 330                 335

Lys Asn His Val Asp Ala Ile Asn Gly Gly Thr Thr Pro Pro
                340                 345                 350

<210> SEQ ID NO 30
<211> LENGTH: 6875
<212> TYPE: DNA
<213> ORGANISM: artificial
<220> FEATURE:
<223> OTHER INFORMATION: pChi1-manT
<220> FEATURE:
<221> NAME/KEY: misc_feature
<222> LOCATION: (3138)..(3138)
<223> OTHER INFORMATION: n is a, c, g, or t

<400> SEQUENCE: 30
gtcccttacc tatgggctcc tagtctcgtt cctcttttg atagatttgt attttgcaac        60
gttgcaaaat gagacatttc aatcatatgt agccgccagc tactgttagc gtactcagcg       120
ttgcccaaac ggcggttttt ctgggtagca ctgtgccgcg tgcccctgag ccgtgcgtcg       180 cggaaaccc cttaagtagc aagtatgtta ccgccgagac cgacaatgct gttggttacc       240
tcgctggtcc atgattgcaa tctagatatc gtgcggggct tttgcaatcg gttttcccta      300
cccactttct tcttttggac actttctctt ttggaaaatg ccgaaatgat gcggctcgct      360
cacgccccga agtcccgagc tggggctaga tccgtgattg caacgcggtg cgaacgcgac      420
tggggcagac ctcgctcagc cttggtcgtg ccggaatggc gggtaccttt accaggtcgg      480
gatcaattac ataggatgcc atgtgcgtgg atttgattgc atcgctgtcc cttttgtatg      540
tgtccgagag cgagatatca acgcgaaaac cggaatgctc caacgtcgc tctctgttca      600 tagggtcttt ttttttcttc tgctccatat catctgtctt gaactaagtg atcatctgct      660
gtcacgtccc gcccaatgat tgtaaagaat gataagtgat gctcgccggg gccaggctct      720
```

```
gtgaaagttc cctctttggt tgacgatcag gtagcgccaa cgttgattgg gccgcccgta    780
aaatccgacc ctgtctcctt tcgttgcaag tctccgcgag accgtgccaa gcatgttctc    840
cggatccctc aattacataa ggtttggctc cagggtaggt ctggaagcta cccacctcgg    900
ccaagcaacc aatcacaacc agacctcgcg gcgtttcgac cttcctggtt tgtctcaggg    960
ctggccaacg tcctcccgtg gcgggtgcct ggtgatcgca ggtcgcaggc gagtgccggg   1020
cacgcggagc ccccgtcaaa gcttgaccct ttcagagcta ggtttcatta ggccttcgaa   1080
aacaacccaa ggccccgtcg caaccatcac aaccggccga taaccagatc tcggtaggtc   1140
cgataaggat ccaaaatggt gtcggctgac gttgcatgtg cccaggcagg aggatgatcc   1200
ccagggttgt tgccggcagc tcccgcacgt cggggagggg gaggggggagg ggaaagccct   1260 aactaacgtt cgttctatca cgggccgacc gggccatgct ttcggcttgt gagcggtggg   1320
gtcaagggca acaagaaatg ctaagtgcgg gacgaagaca cgcgggcatg aggtctcagg   1380
gtgacctgcg caaaaccaag tcccactcgc catgcctcca gcagcaacgt tgccgtagaa   1440
gggtcagggg gtttgttgta gacccacgac catgctgccg gcgagcggag ggttggcttg   1500
ctacaggcgc tgaagggtca actcggtgcc caaagtggct accaagcgtg ccatcaaggg   1560
aaatgagatg atggtggctc gtgggcaaag aaaagacaag ggaggtgact ctagagagat   1620
gctctcgagt tcacgggtat aagagcactg tgatcgttca caaagccggc gtactcctct   1680
agagcatcta tcatcaacat caccagaaag gtcaagacca ggtggttgcc atatccagtc   1740
gcaaaagagc caaagagcga aggagcacga agcacagcc caatcattcc ctgctttgct   1800
acttcttctc caccatgtac gccaagttcg cgaccctcgc cgcccttgtg gctggcgccg   1860
ctgctcagaa cgccagccgc ttcgtcacca tcagcggcac ccagttcaac atcgacggca   1920
aggtcggcta cttcgccggc accaactgct actggtgcag ctacctcacc aaccacgccg   1980
acgtcgacag caccttcagc cacatcagca gcagcggcct caaggtcgtc cgcgtctggg   2040
gcttcaacga cgtcaacacc cagccccccc cgggccagat ctggttccag aagctcagcg   2100
ccaccggcag caccatcaac accggcgccg acggcctcca gaccctcgac tacgtcgtcc   2160
ggtcggccga gcagcacaac ctcaagctca tcatcccctt cgtcaactac tggtcggact   2220
acggcggcat caacgcctac gtcaacgcct tcggcggcaa cgccaccacc tggtacacca   2280
acacggccgc ccagacccag taccgcaagt acgtccaggc cgtcgtcagc cgctacgcca   2340
acagcaccgc catcttcgcc tgggagctgg gcaacgagcc ccgctgccac ggctgcagca   2400
ccgacgtcat ccaccagtgg gccaccagcg tcagccagta cgtcaagagc ctcgactcga   2460
accacctcgt ctcgctcggc gacgagggct tcggcctcag caccggcgac ggcacctacc   2520
cctacaccta cggcgagggc acggacttcg ccaagaacgt ccagatcaag tcgctcgact   2580
tcggcacctt ccacctctac cccgacagct ggggcacgaa ctacacctgg ggcaacggct   2640
ggatccgcac ccacgccgcc gcctgcctgg ccgccggcaa gccctgcgtc ctcgaggagt   2700
acggcgcccg ccaggacccc tgcaccaacg aggcccctg gcagaccacc agcctcacca   2760
cccgcggcat gggcggcgat atgttctggg cagtggggcga cacgttcgcc aacggcgccc   2820
agagcaacag cgaccgtac accgtctggt acaacagcag ctcgtggcag tgcctcgtca   2880
agaaccacgt cgacgccatc aacggcggca ccaccacccc ccgccctaa gaattcggat   2940 cctaagtaag taaacgaacc tctctgaagg aggttctgag acacgcgcga ttcttctgta   3000
tatagtttta tttttcactc tggagtgctt cgctccacca gtacataaac cttttttttc   3060
acgtaacaaa atggcttctt ttcagaccat gtgaaccatc ttgatgcctt gacctcttca   3120
```

```
gttctcactt taacgtantt cgcgttagtc tgtatgtccc agttgcatgt agttgagata    3180
aatacccctg gaagtgggtc tgggcctttg tgggacggag ccctctttct gtggtctgga    3240
gagcccgctc tctaccgcct accttcttac cacagtacac tactcacaca ttgctgaact    3300
gacccatcat accgtacttt atcctgttaa ttcgtggtgc tgtcgactat tctatttgct    3360
caaatggaga gcacattcat cggcgcaggg atacacggtt tatggacccc aagagtgtaa    3420
ggactattat tagtaatatt atatgcctct aggcgcctta acttcaacag gcagcacta    3480
ctaatcaact tttggtagac ccaattacaa cgaccatac gtgccggaaa ttttgggatt    3540
ccgtccgctc tccccaacca agctagaaga ggcaacgaac agccaatccc ggtgctaatt    3600
aaattatatg gttcattttt tttaaaaaaa ttttttcttc ccattttcct ctcgcttttc    3660
tttttcgcat cgtagttgat caaagtccaa gtcaagcgag ctatttgtgc tatagctcgg    3720
tggctataat cagtacagct tagagaggct gtaaaggtat gataccacag cagtattcgc    3780
gctataagcg gcactcctag actaattgtt acggtctaca gaagtaggta ataaaagcgt    3840
taattgttct aaatactaga ggcacttaga gaagctatct aaatatatat tgaccctagc    3900
ttattatccc tattagtaag ttagttagct ctaacctata gatagatgca tgcggccgca    3960
ggtaccaggc aattcgccct atagtgagtc gtattacgcg cgctcactgg ccgtcgtttt    4020
acaacgtcgt gactgggaaa accctggcgt tacccaactt aatcgccttg cagcacatcc    4080
ccctttcgcc agctggcgta atagcgaaga ggcccgcacc gatcgccctt cccaacagtt    4140
gcgcagcctg aatggcgaat gggacgcgcc ctgtagcggc gcattaagcg cggcgggtgt    4200
ggtggttacg cgcagcgtga ccgctacact tgccagcgcc ctagcgcccg ctcctttcgc    4260
tttcttccct tcctttctcg ccacgttcgc cggctttccc cgtcaagctc taaatcgggg    4320
gctcccttta gggttccgat ttagtgcttt acggcacctc gaccccaaaa aacttgatta    4380
gggtgatggt tcacgtagtg gccatcgcc ctgatagacg ttttttcgcc ctttgacgtt    4440
ggagtccacg ttctttaata gtggactctt gttccaaact ggaacaacac tcaaccctat    4500
ctcggtctat tcttttgatt tataagggat tttgccgatt tcggcctatt ggttaaaaaa    4560
tgagctgatt taacaaaaat ttaacgcgaa ttttaacaaa atattaacgc ttacaattta    4620
ggtggcactt ttcggggaaa tgtgcgcgga accctatt gtttattttt ctaaatacat    4680
tcaaatatgt atccgctcat gagacaataa ccctgataaa tgcttcaata atattgaaaa    4740
aggaagagta tgagtattca acatttccgt gtcgccctta ttcccttttt tgcggcattt    4800
tgccttcctg tttttgctca cccagaaacg ctggtgaaag taaaagatgc tgaagatcag    4860
ttgggtgcac gagtgggtta catcgaactg gatctcaaca gcggtaagat ccttgagagt    4920
tttcgccccg aagaacgttt tccaatgatg agcacttta aagttctgct atgtggcgcg    4980
gtattatccc gtattgacgc cgggcaagag caactcggtc gccgcataca ctattctcag    5040
aatgacttgg ttgagtactc accagtcaca gaaaagcatc ttacgatgg catgacagta    5100
agagaattat gcagtgctgc cataaccatg agtgataaca ctgcggccaa cttacttctg    5160
acaacgatcg gaggaccgaa ggagctaacc gcttttttgc acaacatggg gatcatgta    5220
actcgccttg atcgttggga accggagctg aatgaagcca taccaaacga cgagcgtgac    5280
accacgatgc ctgtagcaat ggcaacaacg ttgcgcaaac tattaactgg cgaactactt    5340
actctagctt cccggcaaca attaatagac tggatgagg cggataaagt tgcaggacca    5400
cttctgcgct cggccttcc ggctggctgg tttattgctg ataaatctgg agccggtgag    5460
```

| | |
|---|---|
| cgtgggtctc gcggtatcat tgcagcactg gggccagatg gtaagccctc ccgtatcgta | 5520 |
| gttatctaca cgacggggag tcaggcaact atggatgaac gaaatagaca gatcgctgag | 5580 |
| ataggtgcct cactgattaa gcattggtaa ctgtcagacc aagtttactc atatatactt | 5640 |
| tagattgatt taaaacttca ttttttaattt aaaaggatct aggtgaagat ccttttttgat | 5700 |
| aatctcatga ccaaaatccc ttaacgtgag ttttcgttcc actgagcgtc agaccccgta | 5760 |
| gaaaagatca aaggatcttc ttgagatcct ttttttctgc gcgtaatctg ctgcttgcaa | 5820 |
| acaaaaaaac caccgctacc agcggtggtt tgtttgccgg atcaagagct accaactctt | 5880 |
| tttccgaagg taactggctt cagcagagcg cagataccaa atactgtcct tctagtgtag | 5940 |
| ccgtagttag gccaccactt caagaactct gtagcaccgc ctacatacct cgctctgcta | 6000 |
| atcctgttac cagtggctgc tgccagtggc gataagtcgt gtcttaccgg gttggactca | 6060 |
| agacgatagt taccggataa ggcgcagcgg tcgggctgaa cggggggttc gtgcacacag | 6120 |
| cccagcttgg agcgaacgac ctacaccgaa ctgagatacc tacagcgtga gctatgagaa | 6180 |
| agcgccacgc ttcccgaagg agaaaggcg gacaggtatc cggtaagcgg cagggtcgga | 6240 |
| acaggagagc gcacgaggga gcttccaggg ggaaacgcct ggtatcttta tagtcctgtc | 6300 |
| gggtttcgcc acctctgact tgagcgtcga ttttgtgat gctcgtcagg gggcggagc | 6360 |
| ctatggaaaa acgccagcaa cgcggccttt ttacggttcc tggccttttg ctggccttt | 6420 |
| gctcacatgt tctttcctgc gttatcccct gattctgtgg ataaccgtat taccgccttt | 6480 |
| gagtgagctg ataccgctcg ccgcagccga acgaccgagc gcagcgagtc agtgagcgag | 6540 |
| gaagcggaag agcgcccaat acgcaaaccg cctctccccg cgcgttggcc gattcattaa | 6600 |
| tgcagctggc acgacaggtt tcccgactgg aaagcgggca gtgagcgcaa cgcaattaat | 6660 |
| gtgagttagc tcactcatta ggcaccccag gctttacact ttatgcttcc ggctcgtatg | 6720 |
| ttgtgtggaa ttgtgagcgg ataacaattt cacacaggaa acagctatga ccatgattac | 6780 |
| gccaagcgcg caattaaccc tcactaaagg gaacaaaagc tggagctcca ccgcggtggc | 6840 |
| ggccgctcta gaactagtgg atcccccggg ctgca | 6875 |

<210> SEQ ID NO 31
<211> LENGTH: 1245
<212> TYPE: DNA
<213> ORGANISM: artificial
<220> FEATURE:
<223> OTHER INFORMATION: phytase variant DNA

<400> SEQUENCE: 31

| | |
|---|---|
| agcgaaaccg aaccttccgg atatcagctg gagaaggtgg tcattctctc gcgtcacggt | 60 |
| gtccgagccc ccaccaagat gacacagacg atgcgcgatg tcactcctca tcagtggcct | 120 |
| gagtggcccg tgaagctcgg ctacatcact cctcgtggag aacacctcat cagcctgatg | 180 |
| ggcggttct ataggaacg gttccagcag caggggattgc ttcccaacga cacctgtccg | 240 |
| accccccgacg ccgtctacgt gtggaccgac gttaaccagc gtaccgcaa gactggagag | 300 |
| gctttcctcg ccggtcttgc gcctcagtgt gatctggcca tccaccacca gcagaacatc | 360 |
| acgcaggctg acccgctgtt tcacccggtc aaggccggta tctgttcgat gaacaagtct | 420 |
| cagacctatg cggctgtcga aagcaggct ggcggcccta ttgagacgct aaaccagcgc | 480 |
| taccaggccg aactggcatt gatgtcctct gtgttggatt tccccaagtc cccatattgc | 540 |
| cagcagcata acatcggcaa actgtgcgac ttttcacagg ctatgcctag ccgcctcaac | 600 |
| atctccgatg acgggaatga ggtgcaactc gaaggcgccg tcggtcttc ctccacgctc | 660 |

```
gccgagatct tcctactgga atacgctcag ggtatgcctg tggtcgcctg gggcaacatt    720
cacaacgaga gccagtggaa gagcctcctt aacttgcaca acgcccattt caacctgatg    780
cacagaacgc cctacattgc caagcaccag ggaaccccctt tacttcaggc tatcagcaac   840
gctctcaacc caaatgcaac tgagtcgaag ctccccgata tctctcccga caacaagatc    900
cttttcattg ccggccacga caccaacatc gcaaacatcg gaggcatgtt gggtatgaac    960
tggactctcc cgggccagcc agacaatact ccgcccggcg gtggactggt tttcgaactc   1020
tggcagaacc cggataacca tcagcagtac gttgcggtga agatgatcta ccagaccatg   1080
gaccagctgc gcaattccga gaagctggac ttgaagagca accctgctgg gatcgtcccc   1140
attgagatcg aaggttgcga gaacatcggt accgacaagc tgtgccagct ggatactttt   1200
cagaagcgtg ttgcccaggt cattgagccc gcgtgccaaa tctaa                   1245
```

<210> SEQ ID NO 32
<211> LENGTH: 414
<212> TYPE: PRT
<213> ORGANISM: artificial
<220> FEATURE:
<223> OTHER INFORMATION: phytase variant protein

<400> SEQUENCE: 32

```
Ser Glu Thr Glu Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Asn Asp Thr Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Thr Gln Ala Asp Pro Leu Phe His
        115                 120                 125

Pro Val Lys Ala Gly Ile Cys Ser Met Asn Lys Ser Gln Thr Tyr Ala
    130                 135                 140

Ala Val Glu Lys Gln Ala Gly Gly Pro Ile Glu Thr Leu Asn Gln Arg
145                 150                 155                 160

Tyr Gln Ala Glu Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Asn Glu Ser Gln Trp Lys Ser Leu Leu Asn Leu His Asn Ala His
                245                 250                 255
```

```
Phe Asn Leu Met His Arg Thr Pro Tyr Ile Ala Lys His Gln Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Gly Gly Met Leu Gly Met Asn
305                 310                 315                 320

Trp Thr Leu Pro Gly Gln Pro Asp Asn Thr Pro Gly Gly Gly Leu
            325                 330                 335

Val Phe Glu Leu Trp Gln Asn Pro Asp Asn His Gln Gln Tyr Val Ala
        340                 345                 350

Val Lys Met Ile Tyr Gln Thr Met Asp Gln Leu Arg Asn Ser Glu Lys
    355                 360                 365

Leu Asp Leu Lys Ser Asn Pro Ala Gly Ile Val Pro Ile Glu Ile Glu
    370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys Gln Ile
            405                 410

<210> SEQ ID NO 33
<211> LENGTH: 7799
<212> TYPE: DNA
<213> ORGANISM: artificial
<220> FEATURE:
<223> OTHER INFORMATION: pMT873

<400> SEQUENCE: 33
aggctgcgca actgttggga agggcgatcg gtgcgggcct cttcgctatt acgccagctg      60
gcgaaagggg gatgtgctgc aaggcgatta agttgggtaa cgccagggtt ttcccagtca     120
cgacgttgta aaacgacggc cagtgagcgc gcgtaatacg actcactata gggcgaattg     180
gagctccacc gcggtggcgg ccgctctaga actagtggat cccccgggct gcaggaattc     240
gatggtctcc atattcgacc ctgacagaga cgtatcacag aggactgggg gtggttcaaa     300
ataccagtta gtgagaaaga cctctcgatg tgaaagggta ggtgctccct ccaacttaac     360
acaaaaacga cacactacca aacctctaga ggtggacaaa gcaaccccgc gtactccgtt     420
ccattcgtag cacaggacgc cagagaaagc aaaccacagg tcaggaaaca cacaaccccg     480
ggtttctagg atcgtcggcc gtcgtttcac gtatcggcta cggaggttag taagaatccc     540
ccgggtgggg gggttcctct tgttgaaatg ggtgacattt ctatgttctg cgcatgcttt     600
cagcccagca gcgagcggct cgggtatgct aggcaatctt ggagctttga tgtacctagg     660
cgcgtgtgat aagaacacaa caaggtccac ttcccgtacc taccgcctgt ggatcccggt     720
tcgaggttgg acctgtgcag taaagcgcac agctgaggac gatttgagga cgattgagga     780
cggacatacc tgatgtaggc aacgaaaagc ttaagccggc ttctacgggg agcttctccc     840
catcaccaaa gatcggacca cctaggcggc taccgggcat gagatacgag caggggaag      900
cggcgagtga cacgtcgtcc gcccatggga cggctgaagg ggtaatggca gcaccttgac     960
gtcccttctc gcggagaggc gggaaccatt gctctgggaa cggacagctg ccgggtgcgc    1020
cgatactaac gaggttccct ggaatatgat ggtggaaccg cgctcgcgag gaagcttggc    1080
cggccaaccc ctgttccccc gaagacctgt caccgtcggg aactgccgag ctcgaaagac    1140
cacagtctcc gaattgatca actcctactt atcccatcta tgagaggaga acatcgaacg    1200
```

```
attctgaccc gggaactctg gagatgccca tggtgccttc ctttagatct ggccatgttc   1260
cgcatctatc tacatcagtt cagtctttgc cctgttggtc ttgctagcgg cgatgctatg   1320
aaaatctatc aattaatggt gtcctttttc gatgcgagta cactactcat ttcgtttccg   1380
aatcgccatc tcttcgacca ttgctgaact aattcaatct taggtagtct gctgttcctt   1440
gttttccatt tccttgtctt aagtaaaacc aactggcaca cctcgaaaca cgcttgacgg   1500
atggacagta gaattgaccg tgtacgtaca tgtaccttga cgtcctccga ggttcgacat   1560
cagggttcgt cataggagt gaaacacccg ccatgattcc gtagccgcgc gcgaagatac    1620
gaagcagata tttcacggac atggcggaga tacttgtttc ccgtactaag gtagtcatgt   1680
cggagacatc tgaacgacag agctggccaa gagaaccgac cagttgcccc aggacgatct   1740
agacaaaaaa aagagagatg agtgggccac ttttgccaca acatcgacgg ccctgcgacc   1800
gcccccaggc aaacaaacaa accgccgaac aataatactt ttgtcatttt aggaggagcg   1860
ttgtatggat aaaacaaca tctcgttgct gcagaatgtg gacttcaaac ttgcagaaaa     1920
tgggaggcgg atttgcatga tcggagggta gttgactcac gccgcaggct gcaaatccgt   1980
cctccattat tccatgaaca acttcgtaag gttgggctga cgccaatgc ctaacggacc    2040
gggggccaca gcgcaacgtc ccacttaaag gccagcgtga catgccagtt ccataccaag   2100
tagtggcacc agaggcggcc aatgctcagt aagggcaggg agggaggctc aaacgattgg   2160
caaaagagg ggcttgccag ttcagttccc tgtgcgagcg cgagaggggc agtttcaaat    2220
ctggagggt gtgttgcgct ggtctgaaga gaaagagaag actgtactta ataattgttc    2280
aaagagtcca tcatcgcgtt gcggactcct ctagctgtat ttagagccct atcattactt   2340
gtcgggtgcg aatcaaaata ccgggatgca gccctctggc gatttgcatg cggttgtgga   2400
ggaagtgaag cctgaatcgc ggggctgggc ggcaaagcac gacgtgaaat tcctggcgaa   2460
attcgagggc ttgccccacc gtggttgaag tttttgtgct gcgtaacccc accaacccgc   2520
cttgcccctc ccgcctgccc ataaaaactt cgacccctcc tcaaatcttc ttcgattctt   2580
cctcttcact tccttgtcg gcatacctga ttcaagcaat cacctgccac tttcaagtgc    2640
gtataccatc atcgatacac tggttcttga caagtacatc gtctctaact ttccttttg    2700
cagttttcat taagcgcaag tcgccagttt cgtatatcct gctttgctac ttcttctcca   2760
ccatggtgac tccctctctg aagaaggcag ctctggctgc cctgtccctc ttcccgctcc   2820
tctccctggc tagcgaaacc gaaccttccg gatatcagct ggagaaggtg gtcattctct   2880
cgcgtcacgg tgtccgagcc cccaccaaga tgacacagac gatgcgcgat gtcactcctc   2940
atcagtggcc tgagtggccc gtgaagctcg gctacatcac tcctcgtgga aacacctca    3000
tcagcctgat gggcggtttc tatagggaac ggttccagca gcagggattg cttcccaacg   3060
acacctgtcc gacccccgac gccgtctacg tgtggaccga cgttaaccag cgtacccgca   3120
agactggaga ggctttcctc gccggtcttg cgcctcagtg tgatctggcc atccaccacc   3180
agcagaacat cacgcaggct gacccgctgt ttcacccggt caaggccggt atctgttcga   3240
tgaacaagtc tcagacctat gcggctgtcg agaagcaggc tggcggccct attgagacgc   3300
taaaccagcg ctaccaggcc gaactggcat tgatgtcctc tgtgttggat ttccccaagt   3360
ccccatattg ccagcagcat aacatcggca aactgtgcga cttttcacag gctatgccta   3420
gccgcctcaa catctccgat gacgggaatg aggtgcaact cgaaggcgcc gtcggtcttt   3480
cctccacgct cgccgagatc ttcctactgg aatacgctca gggtatgcct gtggtcgcct   3540
```

| | |
|---|---|
| ggggcaacat tcacaacgag agccagtgga agagcctcct taacttgcac aacgcccatt | 3600 |
| tcaacctgat gcacagaacg ccctacattg ccaagcacca gggaaccccct ttacttcagg | 3660 |
| ctatcagcaa cgctctcaac ccaaatgcaa ctgagtcgaa gctccccgat atctctcccg | 3720 |
| acaacaagat ccttttcatt gccggccacg acaccaacat cgcaaacatc ggaggcatgt | 3780 |
| tgggtatgaa ctggactctc ccgggccagc cagacaatac tccgcccggc ggtggactgg | 3840 |
| ttttcgaact ctggcagaac ccggataacc atcagcagta cgttgcggtg aagatgatct | 3900 |
| accagaccat ggaccagctg cgcaattccg agaagctgga cttgaagagc aaccctgctg | 3960 |
| ggatcgtccc cattgagatc gaaggttgcg agaacatcgg taccgacaag ctgtgccagc | 4020 |
| tggatacttt tcagaagcgt gttgcccagg tcattgagcc cgcgtgccaa atctaatagc | 4080 |
| acgaacctct ctgaaggagg ttctgagaca cgcgcgattc ttctgtatat agttttatt | 4140 |
| ttcactctgg agtgcttcgc tccaccagta cataaacctt ttttcacgt aacaaaatgg | 4200 |
| cttcttttca gaccatgtga accatcttga tgccttgacc tcttcagttc tcactttaac | 4260 |
| gtagttcgcg tttgtctgta tgtcccagtt gcatgtagtt gagataaata cccctggaag | 4320 |
| tgggtctggg cctttgtggg acggagccct ctttctgtgg tctggagagc ccgctctcta | 4380 |
| ccgcctacct tcttaccaca gtacactact cacacattgc tgaactgacc catcataccg | 4440 |
| tactttatcc tgttaattcg tggtgctgtc gactattcta tttgctcaaa tggagagcac | 4500 |
| attcatcggc gcagggatac acggtttatg acccccaaga gtgtaaggac tattattagt | 4560 |
| aatattatat gcctctaggc gccttaactt caacaggcga gcactactaa tcaacttttg | 4620 |
| gtagacccaa ttcaaaacga ccatacgtgc cggaaatttt gggattccgt ccgctctccc | 4680 |
| caaccaagct agaagaggca acgaacagcc aatcccggtg ctaattaaat tatatggttc | 4740 |
| atttttttaa aaaaatttt tcttcccatt ttcctctcgc ttttctttt cgcatcgtag | 4800 |
| ttgatcaaag tccaagtcaa gcgagctatt tgtgctatag ctcggtggct ataatcagta | 4860 |
| cagcttagag aggctgtaaa ggtatgatac cacagcagta ttcgcgctat aagcggcact | 4920 |
| cctagactaa ttgttacggt ctacagaagt aggtaataaa agcgttaatt gttctaaata | 4980 |
| ctagaggcac ttagagaagc tatctaaata tatattgacc ctagcttatt atccctatta | 5040 |
| gtaagttagt tagctctaac ctatagatag gatcagagac catcaagctt atcgataccg | 5100 |
| tcgacctcga gggggggccc ggtacccagc ttttgttccc tttagtgagg gttaattgcg | 5160 |
| cgcttggcgt aatcatggtc atagctgttt cctgtgtgaa attgttatcc gctcacaatt | 5220 |
| ccacacaaca tacgagccgg gagcataaag tgtaaagcct ggggtgccta atgagtgagc | 5280 |
| taactcacat taattgcgtt gcgctcactg cccgctttcc agtcgggaaa cctgtcgtgc | 5340 |
| cagctgcatt aatgaatcgg ccaacgcgcg gggagaggcg gtttgcgtat tgggcgctct | 5400 |
| tccgcttcct cgctcactga ctcgctgcgc tcggtcgttc ggctgcggcg agcggtatca | 5460 |
| gctcactcaa aggcggtaat acggttatcc acagaatcag gggataacgc aggaaagaac | 5520 |
| atgtgagcaa aaggccagca aaaggccagg aaccgtaaaa aggccgcgtt gctggcgttt | 5580 |
| ttccataggc tccgcccccc tgacgagcat cacaaaaatc gacgctcaag tcagaggtgg | 5640 |
| cgaaacccga caggactata aagataccag gcgtttcccc ctggaagctc cctcgtgcgc | 5700 |
| tctcctgttc cgaccctgcc gcttaccgga tacctgtccg ccttctcccc ttcgggaagc | 5760 |
| gtggcgcttt ctcatagctc acgctgtagg tatctcagtt cggtgtaggt cgttcgctcc | 5820 |
| aagctgggct gtgtgcacga accccccgtt cagcccgacc gctgcgcctt atccggtaac | 5880 |
| tatcgtcttg agtccaaccc ggtaagacac gacttatcgc cactggcagc agccactggt | 5940 |

```
aacaggatta gcagagcgag gtatgtaggc ggtgctacag agttcttgaa gtggtggcct    6000
aactacggct acactagaag aacagtattt ggtatctgcg ctctgctgaa gccagttacc    6060
ttcggaaaaa gagttggtag ctcttgatcc ggcaaacaaa ccaccgctgg tagcggtggt    6120 tttttttgttt gcaagcagca gattacgcgc agaaaaaaag gatctcaaga agatcctttg    6180
atctttctta cggggtctga cgctcagtgg aacgaaaact cacgttaagg gattttggtc    6240
atgagattat caaaaaggat cttcacctag atccttttaa attaaaaatg aagttttaaa    6300
tcaatctaaa gtatatatga gtaaacttgg tctgacagtt accaatgctt aatcagtgag    6360
gcacctatct cagcgatctg tctatttcgt tcatccatag ttgcctgact ccccgtcgtg    6420
tagataacta cgatacggga gggcttacca tctggcccca gtgctgcaat gataccgcgt    6480 gaccccccgct caccggctcc agatttatca gcaataaacc agccagccgg aagggccgag    6540
cgcagaagtg gtcctgcaac tttatccgcc tccatccagt ctattaattg ttgccgggaa    6600
gctagagtaa gtagttcgcc agttaatagt ttgcgcaacg ttgttgccat tgctacaggc    6660
atcgtggtgt cacgctcgtc gtttggtatg gcttcattca gctccggttc ccaacgatca    6720
aggcgagtta catgatcccc catgttgtgc aaaaaagcgg ttagctcctt cggtcctccg    6780
atcgttgtca gaagtaagtt ggccgcagtg ttatcactca tggttatggc agcactgcat    6840
aattctctta ctgtcatgcc atccgtaaga tgcttttctg tgactggtga gtactcaacc    6900
aagtcattct gagaatagtg tatgcggcga ccgagttgct cttgcccggc gtcaatacgg    6960
gataataccg cgccacatag cagaacttta aaagtgctca tcattggaaa acgttcttcg    7020
gggcgaaaac tctcaaggat cttaccgctg ttgagatcca gttcgatgta acccactcgt    7080
gcacccaact gatcttcagc atcttttact ttcaccagcg tttctgggtg agcaaaaaca    7140
ggaaggcaaa atgccgcaaa aaagggaata agggcgacac ggaaatgttg aatactcata    7200
ctcttccttt ttcaatatta ttgaagcatt tatcagggtt attgtctcat gagcggatac    7260
atatttgaat gtatttagaa aaataaacaa ataggggttc cgcgcacatt tccccgaaaa    7320
gtgccaccta aattgtaagc gttaatattt tgttaaaatt cgcgttaaat ttttgttaaa    7380
tcagctcatt ttttaaccaa taggccgaaa tcggcaaaat cccttataaa tcaaaagaat    7440
agaccgagat agggttgagt gttgttccag tttggaacaa gagtccacta ttaaagaacg    7500
tggactccaa cgtcaaaggg cgaaaaaccg tctatcaggg cgatggccca ctacgtgaac    7560
catcacccta atcaagtttt ttggggtcga ggtgccgtaa agcactaaat cggaacccta    7620
aagggagccc ccgatttaga gcttgacggg gaaagccggc gaacgtggcg agaaaggaag    7680
ggaagaaagc gaaaggagcg ggcgctaggg cgctggcaag tgtagcggtc acgctgcgcg    7740
taaccaccac acccgccgcg cttaatgcgc cgctacaggg cgcgtcccat tcgccattc    7799
```

<210> SEQ ID NO 34
<211> LENGTH: 3382
<212> TYPE: DNA
<213> ORGANISM: artificial
<220> FEATURE:
<223> OTHER INFORMATION: CloneNAT expression cassette

<400> SEQUENCE: 34

```
ctaaattgta agcgttaata ttttgttaaa attcgcgtta aattttttgtt aaatcagctc      60 attttttaac caataggccg aaatcggcaa atcccttat aaatcaaaag aatagaccga      120
gatagggttg agtggccgct acagggcgct cccattcgcc attcaggctg cgcaactgtt      180
```

-continued

```
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg agctcattta aatgaattcg aagttcctat actttctaga aataggaac    420 ttccgttaac tgatattgaa ggagcatttt ttgggcttgg ctggagctag tggaggtcaa    480
caatgaatgc ctattttggt ttagtcgtcc aggcggtgag cacaaaattt gtgtcgtttg    540
acaagatggt tcatttaggc aactggtcag atcagcccca cttgtagcag tagcggcggc    600
gctcgaagtg tgactcttat tagcagacag gaacgaggac attattatca tctgctgctt    660
ggtgcacgat aacttggtgc gtttgtcaag caaggtaagt ggacgacccg gtcataccttt   720 cttaagttcg cccttcctcc ctttatttca gattcaatct gacttaccta ttctacctaa    780
gcattcatgg ccaccctcga tgacacggct taccgctacc gtaccagcgt ccccggcgac    840
gccgaagcca tcgaggccct ggatggtctt ttcaccacgg ataccgtctt tcgcgttacc    900
gctaccggtg acggcttcac gctccgtgag gtgcccgtcg accctcccct gaccaaggtt    960
ttccctgatg acgaatctga cgatgaatcc gacgatggcg aggacggcga tcccgactct   1020
cgcacgttcg tcgcttacgg cgatgacggt gacctggccg gctttgtcgt tgtgtcctat   1080
tccggttgga accgtcgcct gaccgtcgaa gacatcgagg ttgccccccga gcatcgcggc   1140 cacggtgtcg gccgcgctct catgggtctc gccacggagt tcgcccgtga gcgcggcgcc   1200
ggtcacctct ggctggaggt taccaatgtc aacgctcccg ccattcacgc ctaccgtcgc   1260 atgggctttta ccctctgcgg cctggatacc gctctctacg atggcaccgc ctccgatggc   1320
gagcaggccc tctatatgag catgccttgc ccctgagaag ttcctatact ttctagagaa    1380
taggaacttc gggcccattt aaatggtacc ctgggcctca tgggccttcc gctcactgcc    1440
cgctttccag tcgggaaacc tgtcgtgcca gctgcattaa catggtcata gctgtttcct    1500
tgcgtattgg gcgctctccg cttcctcgct cactgactcg ctgcgctcgg tcgttcgggt    1560
aaagcctggg gtgcctaatg agcaaaaggc cagcaaaagg ccaggaaccg taaaaaggcc    1620
gcgttgctgc cgttttttcca taggctccgc cccctgacg agcatcacaa aaatcgacgc    1680
tcaagtcaga ggtggcgaaa cccgacagga ctataaagat accaggcgtt tccccctgga    1740
agctccctcg tgcgctctcc tgttccgacc ctgccgctta ccggatacct gtccgccttt    1800
ctcccttcgg gaagcgtggc gctttctcat agctcacgct gtaggtatct cagttcggtg    1860
taggtcgttc gctccaagct gggctgtgtg cacgaacccc ccgttcagcc cgaccgctgc    1920
gccttatccg gtaactatcg tcttgagtcc aacccggtaa gacacgactt atcgccactg    1980
gcagcagcca ctggtaacag gattagcaga gcgaggtatg taggcggtgc tacagagttc    2040
ttgaagtggt ggcctaacta cggctacact agaagaacag tatttggtat ctgcgctctg    2100
ctgaagccag ttaccttcgg aaaaagagtt ggtagctctt gatccggcaa acaaaccacc    2160
gctggtagcg gtggtttttt tgtttgcaag cagcagatta cgcgcagaaa aaaggatct    2220 caagaagatc ctttgatctt ttctacgggg tctgacgctc agtggaacga aaactcacgt    2280
taagggattt tggtcatgag attatcaaaa aggatcttca cctagatcct ttaaattaa    2340 aaatgaagtt ttaaatcaat ctaaagtata tatgagtaaa cttggtctga cagttaccaa    2400
tgcttaatca gtgaggcacc tatctcagcg atctgtctat ttcgttcatc catagttgcc    2460
tgactccccg tcgtgtagat aactacgata cgggagggct taccatctgg ccccagtgct    2520
gcaatgatac cgcgagaacc acgctcaccg gctccagatt tatcagcaat aaaccagcca    2580
```

```
gccggaaggg ccgagcgcag aagtggtcct gcaactttat ccgcctccat ccagtctatt   2640
aattgttgcc gggaagctag agtaagtagt tcgccagtta atagtttgcg caacgttgtt   2700
gccattgcta caggcatcgt ggtgtcacgc tcgtcgtttg gtatggcttc attcagctcc   2760
ggttcccaac gatcaaggcg agttacatga tcccccatgt tgtgcaaaaa agcggttagc   2820
tccttcggtc ctccgatcgt tgtcagaagt aagttggccg cagtgttatc actcatggtt   2880
atggcagcac tgcataattc tcttactgtc atgccatccg taagatgctt ttctgtgact   2940
ggtgagtact caaccaagtc attctgagaa tagtgtatgc ggcgaccgag ttgctcttgc   3000
ccggcgtcaa tacgggataa taccgcgcca catagcagaa ctttaaaagt gctcatcatt   3060
ggaaaacgtt cttcggggcg aaaactctca aggatcttac cgctgttgag atccagttcg   3120
atgtaaccca ctcgtgcacc caactgatct tcagcatctt ttactttcac cagcgtttct   3180
gggtgagcaa aaacaggaag gcaaaatgcc gcaaaaaagg aataagggc gacacggaaa   3240 tgttgaatac tcatactctt cctttttcaa tattattgaa gcatttatca gggttattgt   3300
ctcatgagcg gatacatatt tgaatgtatt tagaaaaata aacaaatagg ggttccgcgc   3360
acatttcccc gaaaagtgcc ac                                           3382

<210> SEQ ID NO 35
<211> LENGTH: 9710
<212> TYPE: DNA
<213> ORGANISM: artificial
<220> FEATURE:
<223> OTHER INFORMATION: pMBL71[pyr5]

<400> SEQUENCE: 35
ctgcaggcat cgtggtgtca cgctcgtcgt ttggtatggc ttcattcagc tccggttccc     60
aacgatcaag gcgagttaca tgatccccca tgttgtgcaa aaaagcggtt agctccttcg    120
gtcctccgat cgttgtcaga agtaagttgg ccgcagtgtt atcactcatg gttatggcag    180
cactgcataa ttctcttact gtcatgccat ccgtaagatg cttttctgtg actggtgagt    240
actcaaccaa gtcattctga gaatagtgta tgcggcgacc gagttgctct tgcccggcgt    300
caacacggga taataccgcg ccacatagca gaactttaaa agtgctcatc attggaaaac    360
gttcttcggg gcgaaaactc tcaaggatct taccgctgtt gagatccagt tcgatgtaac    420
ccactcgtgc acccaactga tcttcagcat ctttactttt caccagcgtt tctgggtgag    480
caaaaacagg aaggcaaaat gccgcaaaaa agggaataag ggcgacacgg aaatgttgaa    540
tactcatact cttccttttt caatattatt gaagcattta tcagggttat tgtctcatga    600
gcggatacat atttgaatgt atttagaaaa ataaacaaat aggggttccg cgcacatttc    660
cccgaaaagt gccacctgac gtctaagaaa ccattattat catgacatta acctataaaa    720
ataggcgtat cacgaggccc tttcgtcttc aagaattatg gtaccataat tctcatgttt    780
gacagcttat catcgataag cttgagatct ggccaagggc caccttgaag tggtcggcat    840
ctgacagtaa ccgtcagcat agccccattg ccgcatcatg tagcctccaa atccgtttcc    900
ttcaggcgtg agggcgta ccatatagga tgttcatcaa atcgcggtgg aaggggtgct    960
gatccgtcaa cacggggaag ctcgagatga tggcgccaaa tttctcgctg catgtctcct   1020
gtgtaaatct gagcaccggg gttagtgccg agtccgaaat cgaatcatca ccagcttcgt   1080
cgcaaacggt gtggtggaat ctggggagat ttgaatcgat gagccgggat caccgacttg   1140
actttgcggg tgtaaaacgc cctaattctg ctaactgttc attgagcgtc agaaaatgtc   1200
```

```
tgcgacctcg agcagtaatt cgggaggcac atactcttga atccgggacg gactgtaatg    1260
gtgttctagg tcagccagca tcccaccact ccgtcaaaac atccaacata ctctgagtcg    1320
gcagtcgcct ctgtgtccgc ctgcggaacg tcagcctttc tcgtcttgca acctttataa    1380
cctagccttc aaacttacga aaggatgatg tcgataaact cctgtgccct gtacgaaaat    1440
gatcagctta gttcaggaaa ggaacagcat atatacgaat tgaacccttta cgtaggcaca    1500 ggcgcgatat ccttccaggc catggcaggc aacgcgcagg gtgctgtccg aatttggcga    1560
tgggggtgtt tgggagttgt cagatagggda gcacctggcg gggcggtgtc gatttgccgt    1620
ccccaagtcg cccgaaataa tttttcgcgg agagcacaaa atgataagat aaggcaggcg    1680
gtgtgcgtta tcaaaatatc ccaagcccag ctcgagaagc attgcaagtg gggtacgacg    1740
tacggagtac tgtgtaactc cgtagacata caaaaaagtt taacgaccct tgggccccac    1800
catgaatcca accccaccaa gaaattcgcg atggagggc tctcttcagc tctgcgatag    1860
ggggacgttt gacaaaactc cctcatttct ttttttcgaa tcttcaccag gagttccctc    1920
cggtaacaaa taaacttcca gcccaagaac ccgtaagaca cgtacgaacc gacagacatg    1980
gccccactcg cttcttacaa agccgacttc ctccgggcgg ccatcgccgg caacatcctc    2040
aagtttggca gcttcgagct caagtcgaag cgcatctcgc cctacttctt caacgcggga    2100
gacttctacc gggccgatct gctcgaggcg ctcgcgacgg cgtacgcgca cgccatcatc    2160
gaggcgcacc ggagcggcgc gatccagttc gacatcgtct tcggcccggc ctacaagggg    2220
atcccgttgg cgacggcggc caccattcgg ctgggccagc tggatccggc cacgtacggc    2280
cataccacgt gctactcgtt cgaccgcaag gaggcaaagg accacggtga gggcggcaac    2340
attgtggggg cgccgctcaa gggcaagagg gtgcttatcg tggatgatgt gatcacggct    2400
ggcacggcga agcgtgaggc gatcgccaag attgagaagg agggcggtat cgtagccggc    2460
atcgtggtcg cgctggaccg catggagaag ctgccttcgc cggatggcga cgatagcaag    2520
ccgatgccga gcgcgatcgg tgagctccgg aaggagtatg gtctgcccat ctttgcgatt    2580
ctcaccttgg acgacatcat cgagggtatc aagggctcg catccgagga ggacatcagg    2640
aggacggagg agtaccgggc caagtacaag gcgaccgact aggcgggagg aacaaatcta    2700
gattgtgcaa accgctctgt gaatacaaaa aaaaaaaaaa aaagggcgt cggggtagtg    2760 accccacgcc tgattcgggg gtaaagcgct gtgtagccta gcgctacttt ggtaagtgca    2820
tcttctgatt ggaaaggctc gacccccaat gtaaagcaca aagaggcaag tccagagtag    2880
aaagcgccca ttattacgtg gcgccaccac ccagagacgg cggcccccaa gggctacgaa    2940
atcaattcgg cggtagcgca tagccgtcga gattcccagt cacggccggt tggccgaggt    3000
gaaatcaact tctcatctgc tcatgtacgt ccgatccaga attcggttga ccagggccga    3060
tgtccccaga accccgcctt gtttgtttcg gggcttcttt gcttccgtgc tctcgttcta    3120
ggaaagtggc gtcttggttt ggcgtggcaa atcgtagacc tggagatggt gagatagtct    3180
gtaacagcat gcacgggtag tcccggccct acacccgagg cgtaggtcaa gagctcttac    3240
catgtcatgc cacccgcccc ctccaaactg cgccttgctc ggcccgaggt gcgtgaaccc    3300
cagccgctca tagtaagaca cgaggtgcta cagacatggc tcgtcagcca gcagatcccc    3360
cctaaccaat ccttaggggc agagagggta gtagtcactc acatcctgac aaatcagtgc    3420
cacccggtcc accaggccgc aattcttcat ctggtccaaa aaggctttga taatcatttg    3480
cccgattcca catcgctgta ggcgcgggag cacagcgaga gagtgcaacc cgacggtacg    3540
cccggcctcc tgatggccga cgctcttgtc aacggtgcgt gcggcggggt tgcgccactc    3600
```

```
cttcgggtac gccatgtcgg cgtcggtgac gacgtcccg cggcatcgtg tcgagatgac    3660
gtgggcgagc aggacgctca cggcgccgtc ggcgcggccc gtctcgaccg gcttggaggt    3720
aggcagcgtc tcgaggccga ggtttgcggc acggtctggg acgacggtga ggaaaacgcc    3780
gagactgagc tcggggcaga cggtgaggcg gtaagcgatc tgtcggggtt gcggttagat    3840
ggttgtcagc gtgtctgttg tgtgctcctt gactggattg ggctgaggat tgcttgcctt    3900
ttcgggcgac gcccgatgtt cgggcttagg gaacgaagca ttttccagct cgatacagga    3960
tgggaggtcg ttgatggtta gcggcctgat attgggtgaa aaggttgaga tgaacgggag    4020
tgccttctgg aggcgagatt ccgggctgtc cttggctgcc ctcctcttct ggcacagcat    4080
ctcttgaagc gaagcaaagt ctccgtcgac gtctgaggac tcgtcaacgg cctggtcagc    4140
ctcttggata ggacaaggac tctgttcctc cgacaggcct ttctcggcgc ctgccataac    4200
tgcgccgagt cgggtgtgtt ctttcgcgac tgcagctagc taagagatcg ggccgtcgag    4260
ccaaaggagc ttaggttgac cggatcaatg atcgcgctag gtgtgccaaa aaccgttacc    4320
gtctcttgaa taatttaata tgcagctcgg ggctgaaacc cttgctgcaa acccggaagt    4380
attgtttcct gggctagcc gggttctcaa cggcttcgtt gccacacagc tcgctgtccg    4440
taatcggcgt ggagctttta ggcgtctaaa ggttggacgt ccaggctatg cactcagaga    4500
aacgagatgt gcgcgtagag atccagtggc gaggttgcgc cgcgagatgc tggcgagctg    4560
gaacgagaag ctgtgttacc gtagtgctgg aacggtagtg tagaatcgaa tggggctagg    4620
agtaggagcc aaggtgcaat tccccgccgc gctgcacgtc tcgccgtgtt aggaaatgct    4680
acctgcaggt cacaaggctg ccgggtagca tgccgtgggt gcccaagcaa cctatcggta    4740
tatggagccg ggcagccggc cagtcgggca gccgggcacg ccggggtatt ttgaaagcct    4800
acctcaacct caattacttg attagaaccg aagttcaggt taagggtgtt aggtgtggct    4860
atgggattat ggcgtgagaa atcagaattt aactcttctt tctacccttg catctccccg    4920
gtactggtct cgaccattcc tgatgacgtg cgctggaaat actaaatggc atagtacctt    4980
tcgacctctg ccagcctcca aggaaagccc caaaagcgtt ctagcagtag gcccatggcg    5040
ggccgtcgct tcgcaactcg cggcccccgt tgaagctctg tggcggggca aagttgccca    5100
gcccctcctg acgtcaccgg caagtgggta ctgaatttcg tttgaacctc atcttcagaa    5160
gacggaatac ttcgttcaga ttgcacatac acggtagctg taccttcttc cccggcagct    5220
ccccgatcgc tagggcgttg agcttggaat atgatcaaag tcgtatgtat gtacatacat    5280
tgtaggactc tcactgtccg cgaacagtta cagtgaaaca agaatggccg cgtcaagtcg    5340
taggcacaag aagcgacggc aagaaacaac ctcgagcagg ggtatgattt tctccgtact    5400
gctgtcagac atttgctgca ccatttgaga tgattctacc gcgtgatagg agcctagtgt    5460
tttggccgag tcggatagaa gtaacaaatt tcgattgctg cagcatggaa tcgctgaggg    5520
tcaactgaat atccgcccga actagagttc ccgttgtgg tttcaccggt caacgccccc    5580
tggcggatct ctattggatt gcactgcaaa atctgcaca cgtagactgc tgctgcacca    5640
accggtggtc gagcgggttg aaaaggaact tctgacgcca accgcaaata gaacagtcac    5700
ccaacacgaa gctgttcaga atgggcgcat gcagggtgaa gatggaagcc agatcagatg    5760
gatcctcaga gtccttcaca tgtgcggggc agagcctccg cgatggcttc tctcgcctac    5820
tcaaccttac ctactaccca cctagggaag ttatcagatg taatacctta aggtaccttc    5880
tctgtagggt aaacgcttcc ggatggaggg ttacttggag tcgtttgaga tcacacatcc    5940
```

```
cgcagccaat tggtcagcaa aactctcccc gtctctatgc agatgggagc agttgaagtc    6000
ttgccgcagt cggggcaaaa ggatactcca agctgcgtaa atacttgaca agacagcaag    6060
acagtcagtg cttcattcgc gtgatgtgtc gatgaagcgt acctgaggtt gtctcgccgc    6120
caaagggtcc cagtacttct gactgcctcg tgctgaaggt gcgttaaaaa aaaaggtggc    6180
taccgtatcc ggccattgtc cgttgcccag acttctaggg cccctccgct cgtcgctccg    6240
cttcttcatc ccgaacttgc cgcatgcgtg tggctactca aacagtgcat cttacctagg    6300
tagaaatttt gctgacaccg gttgctcggc aagtcttcca gagtgttcca ttgaaaagtg    6360
gccgaggaga tagaatgccc gcatctcgcc attggcatgc aggcacactg tttgggctct    6420
gtcgtcgtta ccctgttgtt ctacactaat tgtaggccga tctacccccac gtcagccccc   6480 tgcctagatt acaggtagtg gggtggcaat agccgacagc gattcctcgc ggtggcctag    6540
acccaattac gtgcaggagg gtagtgatcc ttgcagcctc agaatgctgg gtagcagcat    6600
acttcagcct tcttgaaagc cacccgtggt ccctggatct atttgcacct tattatataa    6660
cctctggagc cctcatcact cggacctcga tacagaggga cgcattcgtg cttgcataac    6720
cgcacaatcc aggcgcggat gagactcggg ccttcttggt tctcttctac aataccgcaa    6780 cacccctcc cccaccccga aacttccaac agatactggg catattccgg ccatccttcc    6840
cttccctccc tcctgcaaac caacgagacc gccccgagaa gcacaccaaa atgtacgcga    6900
aaatccgacg ccctgatgtt tcagatcgaa gcctgagtac tgactctccg agctcaggcg    6960
catcacgctc agtattacca attcggagcc ccagagcgac gaccaggacc tgctgtccct    7020
ggaagtgtac cccgagatga cgatcgagac cttgcgcagt tccatacaag ccgaaaccac    7080
ccaccacccc agcgcccaac acctctacca caatggccag ctggtcagcg acaactccaa    7140
gaccctggcc gagctcggcg tgactgacgg cgacatgctc gccctccacg tccgcgacat    7200
gaggggcagc acgacggttc cggcaggggg gggcaggtca ggacgtcccg cggcgcgcca    7260
gcaccagccg gtgcaggatc ccgaagtgat ccgtttgcag attctgggcg accccaacct    7320
gaggggcgag ttggccaggt cgcggcccga cttggtggcg gcactggagg accccccagag   7380 gttcgcacgc ctgttcgccg acagcctgga ccggagcgg agggagcgcg aggagcgcca    7440
gcgacagatt cagctgctga attcggaccc gttcgatgtc gaggctcagg cgaaaatcga    7500
ggagatcatc cgccaggagc gggtcatgga gaacttgcag aatgccatgg agcacaaccc    7560
cgaaggtaac acagggaaac atagcctcgc accgcacgac gtggtcccctt ccaaacccgc   7620 gctaatccgc ccgcttccca gttttttggta ccgtgcacat gctgtatatc gaggtcgaag    7680
tcaacggata caaggtcaag gcgttggtcg actcgggcgc gcaagccacc atcatgagcc    7740
cccagtgcgc cgaggcctgc ggcatcatgc ggctcgtcga caagcgcttt gccggcatcg    7800 cacgggggcgt gggaacggcc aacatcatcg gccgcgtgca ctcggccccg atcaagatcg    7860 gaccctctt ccttccttgc agcttcaccg tcatggaggg caagcaggtg gaactgctgc    7920
tcggcctcga catgctgaag cgtcaccagg cgtgcatcga tcttgccaag acaagctga    7980 ttatccaggg agccgaggtg ccgttcctgg gcccggccga cattccgacc gagaccgagg    8040
aggcctatca gcaggagccg accgtccctg ggccggcggg cacgacgatc ggccagcgct    8100
ccggtgccgt gcatgcgccg agcgcggcag ctcatgcggc ccagtcgagc ggtggtggtc    8160
cctcaggtcc gcaaagtgca gcgagaccgt cgttccccag agaacacatc gaccaattga    8220
tggcgctagg ggcctccgag cagagagcca ttcaggcgct ggaggcaacc ggcgggaacg    8280
tcgagtatgc ggccagtctg attttccagg actgatgcta ttcaacatcc tctggcccat    8340
```

```
ggcttgagac gacgttaacg ggttacgaac ttctctctga atgcggaacg ggttataaag    8400
aaaagatttc taggcacgac ctcgaaagca gctccgcatg gcatttctgg accatagcta    8460
agagtcggct ctgagactac gccgagagtt cgtctggtaa cagattggtg gacggatacc    8520
aaaaaaacta ctgctaaggt gtgtgaaggg tagtttagag ggcacccggg accggccagc    8580
gcatagccta gaattgacag atctccagct gaattcccga gccgcgttgc tggcgttttt    8640
ccataggctc cgccccctg acgagcatca caaaaatcga cgctcaagtc agaggtggcg    8700
aaacccgaca ggactataaa gataccaggc gtttccccct ggaagctccc tcgtgcgctc    8760
tcctgttccg accctgccgc ttaccggata cctgtccgcc tttctccctt cgggaagcgt    8820
ggcgctttct catagctcac gctgtaggta tctcagttcg gtgtaggtcg ttcgctccaa    8880
gctgggctgt gtgcacgaac cccccgttca gcccgaccgc tgcgccttat ccggtaacta    8940
tcgtcttgag tccaacccgg taagacacga cttatcgcca ctggcagcag ccactggtaa    9000
caggattagc agagcgaggt atgtaggcgg tgctacagag ttcttgaagt ggtggcctaa    9060
ctacggctac actagaagga cagtatttgg tatctgcgct ctgctgaagc cagttacctt    9120
cggaaaaaga gttggtagct cttgatccgg caaacaaacc accgctggta gcggtggttt    9180
ttttgtttgc aagcagcaga ttacgcgcag aaaaaaagga tctcaagaag atcctttgat    9240
cttttctacg gggtctgacg ctcagtggaa cgaaaactca cgttaaggga ttttggtcat    9300
gagattatca aaaaggatct tcacctagat ccttttaaat taaaaatgaa gttttaaatc    9360
aatctaaagt atatatgagt aaacttggtc tgacagttac caatgcttaa tcagtgaggc    9420
acctatctca gcgatctgtc tatttcgttc atccatagtt gcctgactcc ccgtcgtgta    9480
gataactacg atacgggagg gcttaccatc tggccccagt gctgcaatga taccgcgaga    9540
cccacgctca ccggctccag atttatcagc aataaaccag ccagccggaa gggccgagcg    9600
cagaagtggt cctgcaactt tatccgcctc catccagtct attaattgtt gccgggaagc    9660
tagagtaagt agttcgccag ttaatagttt gcgcaacgtt gttgccattg                9710
```

<210> SEQ ID NO 36
<211> LENGTH: 5488
<212> TYPE: DNA
<213> ORGANISM: artificial
<220> FEATURE:
<223> OTHER INFORMATION: pMT122-Dclr1-A

<400> SEQUENCE: 36

```
ggccgctcga tttaaatctc gagaggcctg acgtcgggcc cggtaccacg cgtcatatga      60
ctagttcgga cctagggata tcgtcgacat cgatgctgca actaccagtg ttcgttagtc     120 aagggggtgat tcattcgaag gactgcgggcg tggcaggcgc tcgacgccat tcacacctat     180
catcatgcca tactagtact tgtatttcct atcgcccaga ggatagggta cgcgaggtct     240
tttagcgccc aagcccgccc gtcaacacac caccgttgc tgagcgacat gatcggcgga     300
ccaaggatgt cacctagagg aggttggatg gaatgctcgg acctctacat ggatagggcc     360
ggcttctctt tgcagttctc gcttccacca ctcaccaatc ccttcgcgag ctgaaaggct     420
cacttctgtg ttacgaaacg aatccagaat tgggacccga cgatgagacg gtgaattatg     480
ggaaataatg tccttaaact cggcgacgta acttcgaagg gaagacagga gagttgactg     540
atggcagcgg gaagctgcgg acctcgaccc aaaaaaaaag tggcccagtg atcgctgcga     600
gcggttcgaa tcggaaaccc cacccccgcg ttttttttggt tggcatgctc tccttcattt     660
```

```
gcttctctcc gcacacccaa acttcctgac ccaccatttc tcatgccggc ctggcctggg    720
cgtgccattt tcgccctctg caaccgaggt agctaatgtg aaaaacacca cttcgtacat    780
acctctactg tgtacactac ggcggtagta tcagcagtcg gtggctcgtt gcccatttgc    840
caacaatgac acgccgcccc cctgatcgcg ttgtgcagct ccccagaatt ttcaagggcg    900
tggcaggtct ttcgtgatag ctatttggtc tggtggagaa ggaccacagt tgtttcggtt    960
tggcgcgcga accattgcag tctcttttg gccccacccc tactccgaag tgtactagta   1020
ctatgtagtg taggcatctc cacgttcgga gcagggcgag agacaaaaac ccaggagaaa   1080
agcgacattt gaagcacccc acaatgcatc ttctttcgaa gcgtccatgc aaccctcggc   1140
aagggccttt cgtgcgcaac cgcagtcgtc tcctcacccc ggtcggcact agtgcattct   1200 accccctgctc cccgccgccc gccctccgtt agactatggc aggctttccc ggcttccttc   1260
tcagttaaca ggtccaggcg cctcccccg cagagactcg ccgttttcgt tagcacagta   1320
caagtgccta ccccagacac gcgccagccc ttgcctgctg tggttcaggg tacattggcc   1380
cgggaagctc agcgtccaat tcgagcctctg tacagtgacc ggtgactctt tctggcatgc   1440
ggagagacgg acggacgcag agagaagggc tgagtaataa gcgccactgc gccagacagc   1500
tctggcggct ctgaggtgca gtggatgatt attaatccgg gaccggccgc ccctccgccc   1560
cgaagtggaa aggctggtgt gcccctcgtt gaccaagaat ctattgcatc atcggagaat   1620
atggagcttc atcgaatcac cggcagtaag cgaaggagaa tgtgaagcca ggggtgtata   1680
gccgtcggcg aaatagcatg ccattaacct aggtacagaa gtccaattgc ttccgatctg   1740 gtaaagatt cacgagatag taccttctcc gaagtaggta gagcgagtac ccggcgcgta   1800
agctccctaa ttggcccatc cggcatctgt agggcgtcca aatatcgtgc ctctcctgct   1860
ttgcccggtg tatgaaaccg gaaaggccgc tcaggagctg gccagcggcg cagaccggga   1920
acacaagctg gcagtcgacc catccggtgc tctgcactcg acctgctgag gtccctcagt   1980
ccctggtagg cagcttttgcc ccgtctgtcc gccggtgtg tcggcggggt tgacaaggtc   2040
gttgcgtcag tccaacattt gttgccatat ttcctgctc tccccaccag ctgctctttt   2100
cttttctctt tcttttccca tcttcagtat attcatcttc ccatccaaga acctttattt   2160
cccctaagta agtactttgc tacatccata ctccatcctt cccatccctt attcctttga   2220
acctttcagt tcgagctttc ccacttcatc gcagcttgac taacagctac cccgcttgag   2280
cagacatcac catgcctcaa tcctgggaag aactggccgc tgataagcgc gcccgcctcg   2340
caaaaaccat ccctgatgaa tggaaagtcc agacgctgcc tgcggaagac agcgttattg   2400
atttcccaaa gaaatcgggg atcctttcag aggccgaact gaagatcaca gaggcctccg   2460
ctgcagatct tgtgtccaag ctggcggccg gagagttgac ctcggtggaa gttacgctag   2520
cattctgtaa acgggcagca atcgcccagc agttagtagg gtcccctcta cctctcaggg   2580
agatgtaaca acgccacctt atgggactat caagctgacg ctggcttctg tgcagacaaa   2640
ctgcgcccac gagttcttcc ctgacgccgc tctcgcgcag gcaagggaac tcgatgaata   2700
ctacgcaaag cacaagagac ccgttggtcc actccatggc ctccccatct ctctcaaaga   2760
ccagcttcga gtcaaggtac accgttgccc ctaagtcgtt agatgtccct tttgtcagc   2820 taacatatgc caccagggct acgaaacatc aatgggctac atctcatggc taaacaagta   2880
cgacgaaggg gactcggttc tgacaaccat gctccgcaaa gccggtgccg tcttctacgt   2940
caagacctct gtcccgcaga ccctgatggt ctgcgagaca gtcaacaaca tcatcgggcg   3000
caccgtcaac ccacgcaaca agaactggtc gtgcggcggc agttctggtg gtgagggtgc   3060
```

```
gatcgttggg attcgtggtg gcgtcatcgg tgtaggaacg gatatcggtg gctcgattcg    3120
agtgccggcc gcgttcaact tcctgtacgg tctaaggccg agtcatgggc ggctgccgta    3180
tgcaaagatg gcgaacagca tggaggcggc cgctacggga tttaaatcgc tagcgggctg    3240
ctaaaggaag cggaacacgt agaaagccag tccgcagaaa cggtgctgac cccggatgaa    3300
tgtcagctac tgggctatct ggacaaggga aaacgcaagc gcaaagagaa agcaggtagc    3360
ttgcagtggg cttacatggc gatagctaga ctgggcggtt ttatggacag caagcgaacc    3420
ggaattgcca gctggggcgc cctctggtaa ggttgggaag ccctgcaaag taaactggat    3480
ggctttcttg ccgccaagga tctgatggcg caggggatca agatctgatc aagagacagg    3540
atgaggatcg tttcgcatga ttgaacaaga tggattgcac gcaggttctc cggccgcttg    3600
ggtggagagg ctattcggct atgactgggc acaacagaca atcggctgct ctgatgccgc    3660
cgtgttccgg ctgtcagcgc aggggcgccc ggttctttt gtcaagaccg acctgtccgg    3720
tgccctgaat gaactgcagg acgaggcagc gcggctatcg tggctggcca cgacgggcgt    3780
tccttgcgca gctgtgctcg acgttgtcac tgaagcggga agggactggc tgctattggg    3840
cgaagtgccg gggcaggatc tcctgtcatc tcaccttgct cctgccgaga aagtatccat    3900
catggctgat gcaatgcggc ggctgcatac gcttgatccg gctacctgcc cattcgacca    3960
ccaagcgaaa catcgcatcg agcgagcacg tactcggatg gaagccggtc ttgtcgatca    4020
ggatgatctg gacgaagagc atcaggggct cgcgccagcc gaactgttcg ccaggctcaa    4080
ggcgcgcatg cccgacggcg aggatctcgt cgtgacccat ggcgatgcct gcttgccgaa    4140
tatcatggtg gaaaatggcc gcttttctgg attcatcgac tgtggccggc tgggtgtggc    4200
ggaccgctat caggacatag cgttggctac ccgtgatatt gctgaagagc ttggcggcga    4260
atgggctgac cgcttcctcg tgctttacgg tatcgccgct cccgattcgc agcgcatcgc    4320
cttctatcgc cttcttgacg agttcttctg agcgggactc tggggttcga atgaccgac    4380 caagcgacgc ccaacctgcc atcacgagat ttcgattcca ccgccgcctt ctatgaaagg    4440
ttgggcttcg gaatcgtttt ccgggacgcc ggctggatga tcctccagcg cggggatctc    4500
atgctggagt tcttcgccca cgctagcggc gcgccggccg gccggtgtg aaataccgca    4560 cagatgcgta aggagaaaat accgcatcag gcgctcttcc gcttcctcgc tcactgactc    4620
gctgcgctcg gtcgttcggc tgcggcgagc ggtatcagct cactcaaagg cggtaatacg    4680
gttatccaca gaatcagggg ataacgcagg aaagaacatg tgagcaaaag gccagcaaaa    4740
ggccaggaac cgtaaaaagg ccgcgttgct ggcgtttttc cataggctcc gcccccctga    4800
cgagcatcac aaaaatcgac gctcaagtca gaggtggcga aacccgacag gactataaag    4860
ataccaggcg tttccccctg gaagctccct cgtgcgctct cctgttccga ccctgccgct    4920
taccggatac ctgtccgcct ttctcccttc gggaagcgtg gcgctttctc atagctcacg    4980
ctgtaggtat ctcagttcgg tgtaggtcgt tcgctccaag ctgggctgtg tgcacgaacc    5040
ccccgttcag cccgaccgct gcgccttatc cggtaactat cgtcttgagt ccaacccggt    5100
aagacacgac ttatcgccac tggcagcagc cactggtaac aggattagca gagcgaggta    5160
tgtaggcggt gctacagagt tcttgaagtg gtggcctaac tacggctaca ctagaaggac    5220
agtatttggt atctgcgctc tgctgaagcc agttaccttc ggaaaaagag ttggtagctc    5280
ttgatccggc aaacaaacca ccgctggtag cggtggtttt tttgtttgca agcagcagat    5340
tacgcgcaga aaaaaggat ctcaagaaga tcctttgatc ttttctacgg ggtctgacgc    5400
```

<210> SEQ ID NO 37
<211> LENGTH: 5305
<212> TYPE: DNA
<213> ORGANISM: artificial
<220> FEATURE:
<223> OTHER INFORMATION: pMT120-Dclr1-B

<400> SEQUENCE: 37

```
tcagtggaac gaaaactcac gttaagggat tttggtcatg agattatcaa aaaggatctt      5460
cacctagatc cttttaaagg ccggccgc                                         5488 gatccacatc cagtgcgaac gcctaacgtc ccgcccagag cttcctgcca ggacacttgt        60
tctaaggcat cgacgatgca cgctaccaac agtcaaacat cacgcgatag ccccggcatc       120
cctgaccggc accctcgcaa ccaagtgctg gggcacagcg gaggtttcgg cggtctacga       180
catcagctgc gaaactgcgc gcctggtttt cctgtgagcc ggtttccgtg ctcaagatgt       240
ggacaaaaga gctggcacgt cggaaaagca cacggatg cttcccctgt ctccctgtcc         300
ctgttcctga aaaagtgggc tggcagtttc aagtgggaag tgtgtccggc aaaacgcag        360
actgctgagc atctgcaggc ttggttctgg ggttgcacac tctgtttgcc gcagcgagtc       420
acaatttggc ctcttgttga gcaaggctgc ggatgacctt tggggtgcgg agaagccggc       480
ccgagctgcc gcttcccacc tttccattcc ccgctccccg cattctcttc ttgatgcgct       540
ccctgctcgg gacataatcc gaacgggac gcgttcctct ttttttttgt tgcatcttag        600
ccctccgggg ctggttccta acgtcaagta cgaaaacttg gagggggggg gttcaaaatc       660
ggcatgggat acaccgacca ccgtttggcg ttgggatgga gtgccttttgt gaggacatgc      720
tagctacgtt tcggatgttt cagttggatt ttcattgcgg tactatctca ttaagatgct       780
ggatatatcc ccgggcttat accattcaat atgtattcaa gggtatggtg atcgagccgt       840
atgagttacg ttgcctgaaa aaaaaaaaaa aacaatctcc ccaaattcca tccgttgtac       900
tggtgaaccg tttaggtcgt gatcgaatct cctgaacaac tggtgatggt ctttgcgtcc      960
atgagatcaa gccacaacaa tgaggcccgt cggcggcatt tgggtcctat atctggtcat     1020
ggcttaagtg gttcgcttcc tctgcctgta tgatccatct cggcccacca caacggtgca     1080
gcatggcggg gcgtgctgct cgaacaagat tccttatatc ccctttcgaa agaaagaaag     1140
atactacgaa ggaaatcgcg atgatccttt taacacattt catgtcgtgt actatggaag     1200
cctaccacca cttaacctg taggtacccg atttggtgca gatgtggaag tactaggtat     1260
gtaccgtcga cgatatccct aggtccgaac tagtcatatg acgcgtggta ccgggcccga    1320
cgtcaggcct ctcgagattt aaatcgagcg gccgcggccg gccttaaaaa ggatctaggt    1380
gaagatcctt tttgataatc tcatgaccaa aatcccttaa cgtgagtttt cgttccactg    1440
agcgtcagac ccgtagaaaa agatcaaagg atcttcttga atcctttttt ttctgcgcgt    1500
aatctgctgc ttgcaaacaa aaaaaccacc gctaccagcg gtggtttgtt tgccggatca    1560
agagctacca actctttttc cgaaggtaac tggcttcagc agagcgcaga taccaaatac    1620
tgtccttcta gtgtagccgt agttaggcca ccacttcaag aactctgtag caccgcctac    1680
atacctcgct ctgctaatcc tgttaccagt ggctgctgcc agtggcgata agtcgtgtct    1740
taccgggttg gactcaagac gatagttacc ggataaggcg cagcggtcgg gctgaacggg    1800
gggttcgtgc acacagccca gcttggagcg aacgacctac accgaactga gatacctaca    1860
gcgtgagcta tgagaaagcg ccacgcttcc gaagggagaa aaggcggaca ggtatccggt    1920
aagcggcagg gtcggaacag gagagcgcac gagggagctt ccagggggaa acgcctggta    1980
```

```
tctttatagt cctgtcgggt ttcgccacct ctgacttgag cgtcgatttt tgtgatgctc  2040 gtcaggggg cggagcctat ggaaaaacgc cagcaacgcg gccttttac ggttcctggc    2100 cttttgctgg cctttgctc acatgttctt tcctgcgtta tccctgatt ctgtggataa    2160 ccgtattacc gcctttgagt gagctgatac cgctcgccgc agccgaacga ccgagcgcag  2220
cgagtcagtg agcgaggaag cggaagagcg cctgatgcgg tattttctcc ttacgcatct  2280
gtgcggtatt tcacaccggg ccggccggcg cgccgctagc gtgggcgaag aactccagca  2340
tgagatcccc gcgctggagg atcatccagc cggcgtcccg gaaaacgatt ccgaagccca  2400
acctttcata gaaggcggcg gtggaatcga aatctcgtga tggcaggttg ggcgtcgctt  2460
ggtcggtcat ttcgaacccc agagtcccgc tcagaagaac tcgtcaagaa ggcgatagaa  2520
ggcgatgcgc tgcgaatcgg gagcggcgat accgtaaagc acgaggaagc ggtcagccca  2580
ttcgccgcca agctcttcag caatatcacg ggtagccaac gctatgtcct gatagcggtc  2640
cgccacaccc agccggccac agtcgatgaa tccagaaaag cggccatttt ccaccatgat  2700
attcggcaag caggcatcgc catgggtcac gacgagatcc tcgccgtcgg gcatgcgcgc  2760
cttgagcctg gcgaacagtt cggctggcgc gagcccctga tgctcttcgt ccagatcatc  2820
ctgatcgaca agaccggctt ccatccgagt acgtgctcgc tcgatgcgat gtttcgcttg  2880
gtggtcgaat gggcaggtag ccggatcaag cgtatgcagc cgccgcattg catcagccat  2940
gatggatact ttctcggcag gagcaaggtg agatgacagg agatcctgcc ccggcacttc  3000
gcccaatagc agccagtccc ttcccgcttc agtgacaacg tcgagcacag ctgcgcaagg  3060
aacgcccgtc gtggccagcc acgatagccg cgctgcctcg tcctgcagtt cattcagggc  3120 accgacagg tcggtcttga caaaaagaac cgggcgcccc tgcgctgaca gccgaacac   3180 ggcggcatca gagcagccga ttgtctgttg tgcccagtca tagccgaata gcctctccac  3240
ccaagcggcc ggagaacctg cgtgcaatcc atcttgttca atcatgcgaa acgatcctca  3300
tcctgtctct tgatcagatc ttgatcccct gcgccatcag atccttggcg gcaagaaagc  3360
catccagttt actttgcagg gcttcccaac cttaccagag ggcgccccag ctggcaattc  3420
cggttcgctt gctgtccata aaaccgccca gtctagctat cgccatgtaa gcccactgca  3480
agctacctgc tttctctttg cgcttgcgtt ttcccttgtc cagatagccc agtagctgac  3540
attcatccgg ggtcagcacc gtttctgcgg actggctttc tacgtgttcc gcttccttta  3600
gcagcccgct agcgatttaa atcccgtagc ggccgcaagg ggactcggtt ctgacaacca  3660
tgctccgcaa agccggtgcc gtcttctacg tcaagacctc tgtcccgcag accctgatgg  3720
tctgcgagac agtcaacaac atcatcgggc gcaccgtcaa cccacgcaac aagaactggt  3780 cgtgcggcg cagttctggt ggtgagggtg cgatcgttgg gattcgtggt ggcgtcatcg   3840
gtgtaggaac ggatatcggt ggctcgattc gagtgccggc cgcgttcaac ttcctgtacg  3900
gtctaaggcc gagtcatggg cggctgccgt atgcaaagat ggcgaacagc atggagggtc  3960
aggagacggt gcacagcgtt gtcgggccga ttacgcactc tgttgagggt gagtccttcg  4020
cctcttcctt cttttcctgc tctataccag gcctccactg tcctcctttc ttgctttta   4080 tactatatac gagaccggca gtcactgatg aagtatgtta gacctccgcc tcttcaccaa  4140
atccgtcctc ggtcaggagc catggaaata cgactccaag gtcatcccca tgccctggcg  4200
ccagtccgag tcgacatta ttgcctccaa gatcaagaac ggcgggctca atatcggcta   4260
ctacaacttc gacggcaatg tccttccaca ccctcctatc ctgcgcggcg tggaaaccac  4320
```

```
cgtcgccgca ctcgccaaag ccggtcacac cgtgaccccg tggacgccat acaagcacga   4380
tttcggccac gatctcatct cccatatcta cgcggctgac ggcagcgccg acgtaatgcg   4440
cgatatcagt gcatccggcg agccggcgat tccaaatatc aaagacctac tgaacccgaa   4500
catcaaagct gttaacatga acgagctctg ggacacgcat ctccagaagt ggaattacca   4560
gatggagtac cttgagaaat ggcgggaggc tgaagaaaag gccgggaagg aactggacgc   4620
catcatcgcg ccgattacgc ctaccgctgc ggtacggcat gaccagttcc ggtactatgg   4680
gtatgcctct gtgatcaacc tgctggatttt cacgagcgtg gttgttccgg ttacctttgc   4740
ggataagaac atcgataaga agaatgagag tttcaaggcg gttagtgagc ttgatgccct   4800
cgtgcaggaa gagtatgatc cggaggcgta ccatgggggca ccggttgcag tgcaggttat   4860
cggacggaga ctcagtgaag agaggacgtt ggcgattgca gaggaagtgg ggaagttgct   4920
gggaaatgtg gtgactccat agctaataag tgtcagatag caatttgcac aagaaatcaa   4980
taccagcaac tgtaaataag cgctgaagtg accatgccat gctacgaaag agcagaaaaa   5040
aacctgccgt agaaccgaag agatatgaca cgcttccatc tctcaaagga agaatccctt   5100
cagggttgcg tttccagtct agacacgtat aacggcacaa gtgtctctca ccaaatgggt   5160
tatatctcaa atgtgatcta aggatggaaa gcccagaata ttggctgggt tgatggctgc   5220
ttcgagtgca gtctcatgct gccacaggtg actctggatg gccccatacc actcaaccca   5280
tgcgtgcgag gtcccgggtc tagag                                         5305
```

METHOD OF PRODUCING PROTEINS IN FILAMENTOUS FUNGI WITH DECREASED CLR2 ACTIVITY

CROSS-REFERENCE TO RELATED APPLICATIONS

This application is a National Stage application of PCT/EP2016/079526, filed on Dec. 2, 2016, which claims priority to European Application No. 15197497.9, filed on Dec. 2, 2015. Each patent application identified above is incorporated herein by reference.

REFERENCE TO AN ELECTRONIC SEQUENCE LISTING

The contents of the electronic sequence listing (SequenceListing.txt; Size: 254,157 bytes; and Date of Creation: May 25, 2018) is herein incorporated by reference in its entirety.

FIELD OF THE INVENTION

The present invention relates to a method of producing a recombinant polypeptide in a filamentous fungus which is genetically modified to decrease or eliminate the activity of cellulase regulator 2 (CLR2) and to express said recombinant polypeptide. The method further relates to a filamentous fungus *Myceliophthora thermophila*, which is genetically modified to decrease or eliminate the activity of CLR2 and to the use of this filamentous fungus in the production of a recombinant polypeptide.

BACKGROUND

Filamentous fungi have been shown to be excellent hosts for the production of a variety of proteins. Fungal strains such as *Aspergillus, Trichoderma, Penicillium* and *Myceliophthora* have been applied in the industrial production of a wide range of enzymes, since they can secrete large amounts of protein into the fermentation broth. The protein-secreting capacity of these fungi makes them preferred hosts for the targeted production of specific enzymes or enzyme mixtures. However, typically, these hosts secrete a mixture of many different enzymes, making the crude protein product undefined and requiring complex purification schemes for the desired protein. Even in cases where the gene encoding the target enzyme is overexpressed by genetic modification, the target enzyme will only constitute a minor part of the total secreted protein.

Hence, it is highly desirable to provide a fungal production system which is able to secrete high amounts of a specific enzyme without the presence of high levels of other proteins.

Such a production system would enable the production of a relatively pure enzyme and a simplified large scale purification of the desired enzyme. The produced enzyme can be used for different applications, e.g. in food and feed applications, in detergents or homecare as well as for plant biomass hydrolysis (biofuels and chemicals), textile finishing and in paper and pulp industry.

WO 2010/107303 A2 describes the UV-induced mutagenesis of a *Myceliophthora thermophila* strain leading to isolates which produce low amounts of endogenous cellulase and proteases. Visser et al. (2011) Industrial Biotechnology 7(3): 214-223 disclose a *Myceliophthora thermophila* strain called LC (low-cellulase) strain which has lost almost all of its ability to produce cellulase.

Nevertheless, there is still a need for an efficient method for producing a recombinant polypeptide in filamentous fungi.

OBJECTS AND SUMMARY OF THE INVENTION

This need is addressed by the present invention. The present inventors have surprisingly found that a decrease in cellulase regulator 2 (CLR2) activity in a filamentous fungus such as *Myceliophthora thermophila* leads to a strain with the ability to produce a recombinant polypeptide with increased purity.

Accordingly, in one aspect, the present invention provides a method of producing a recombinant polypeptide in a filamentous fungus which is genetically modified to decrease or eliminate the activity of CLR2 compared to a filamentous fungus not having the genetic modification which is cultured under the same conditions as the genetically modified filamentous fungus and which is further genetically modified to express said recombinant polypeptide, wherein the recombinant polypeptide is expressed under the control of a promoter which is not activatable by CLR2, said method comprising:
(i) growing said genetically modified filamentous fungus in a culture medium which does not contain cellulose or a cellulose derivative thereof which is capable of inducing CLR2 activity; and
(ii) isolating the recombinant polypeptide from the culture medium.

In another aspect, the present invention provides a method of producing a recombinant polypeptide in a filamentous fungus which is genetically modified to decrease or eliminate the activity of CLR2 compared to the filamentous fungus not having the genetic modification which is cultured under the same conditions as the genetically modified filamentous fungus and which is further genetically modified to express said recombinant polypeptide, wherein the recombinant polypeptide is expressed under the control of a promoter which is not activatable by CLR2, said method comprising:
(i) growing said genetically modified filamentous fungus in a culture medium which does not contain cellulose or a cellulose derivative thereof which is capable of inducing CLR2 activity; and
(ii) isolating the recombinant polypeptide from the culture medium.

The filamentous fungus may be *Myceliophthora thermophila*.

In another aspect, the present invention relates to a filamentous fungus *Myceliophthora thermophila*, which is genetically modified to decrease or eliminate the activity of CLR2 in said filamentous fungus in comparison to a filamentous fungus not having the genetic modification which is cultured under the same conditions as the genetically modified filamentous fungus, and which is further genetically modified to express a recombinant polypeptide, wherein the recombinant polypeptide is expressed under the control of a promoter which is not activatable by CLR2.

In another aspect, the present invention relates to a filamentous fungus *Myceliophthora thermophila*, which is genetically modified to decrease or eliminate the activity of CLR2 in said filamentous fungus in comparison to the filamentous fungus not having the genetic modification which is cultured under the same conditions as the genetically modified filamentous fungus and which is further genetically modified to express a recombinant polypeptide, wherein the recombinant polypeptide is expressed under the control of a promoter which is not activatable by CLR2.

The recombinant polypeptide may be a heterologous polypeptide.

In one embodiment of the method or the filamentous fungus of the present invention the recombinant polypeptide is a hydrolase.

In one embodiment said genetically modified filamentous fungus is capable of accumulating the recombinant polypeptide in a higher purity than said filamentous fungus not having the genetic modification which is cultured under the same conditions as the genetically modified filamentous fungus.

The decrease or elimination of activity of CLR2 may be due to the reduction or elimination of the expression of a nucleic acid molecule encoding the CLR2 protein.

In one embodiment the nucleic acid molecule encoding the CLR2 protein comprises a nucleic acid sequence selected from the group consisting of:
(a) the nucleic acid sequence according to SEQ ID No. 1 or 2 or a functional part thereof;
(b) a nucleic acid sequence encoding the polypeptide according to SEQ ID No. 3 or a functional part thereof; and
(c) a nucleic acid sequence encoding a polypeptide having CLR2 activity and having at least 70% sequence identity to the nucleic acid sequence according to SEQ ID No. 1 or 2.

The filamentous fungus may comprise at least one additional genetic modification.

The at least one additional genetic modification may decrease or eliminate the activity of a transcription factor other than CLR2, preferably of xylanase regulator 1 (XYR1), Additionally or alternatively the at least one additional genetic modification may decrease or eliminate the activity of a protease, preferably of alkaline protease 1 (ALP1).

In another aspect, the present invention relates to the use of a nucleic acid construct which decreases or eliminates the activity of CLR2 for increasing the purity and/or the amount of a recombinant polypeptide produced in a filamentous fungus.

The activity of CLR2 may be decreased by the reduction of the expression of a nucleic acid molecule encoding the CLR2 protein.

In one embodiment the nucleic acid molecule encoding the CLR2 protein comprises a nucleic acid sequence selected from the group consisting of:
(a) the nucleic acid sequence according to SEQ ID No. 1 or 2 or a functional part thereof;
(b) a nucleic acid sequence encoding the polypeptide according to SEQ ID No. 3 or a functional part thereof; and
(c) a nucleic acid sequence encoding a polypeptide having CLR2 activity and having at least 70% sequence identity to the nucleic acid sequence according to SEQ ID No. 1 or 2.

In still another aspect, the present invention relates to the use of a filamentous fungus as defined herein for the production of a recombinant polypeptide.

DETAILED DESCRIPTION OF THE INVENTION

Figure 1:
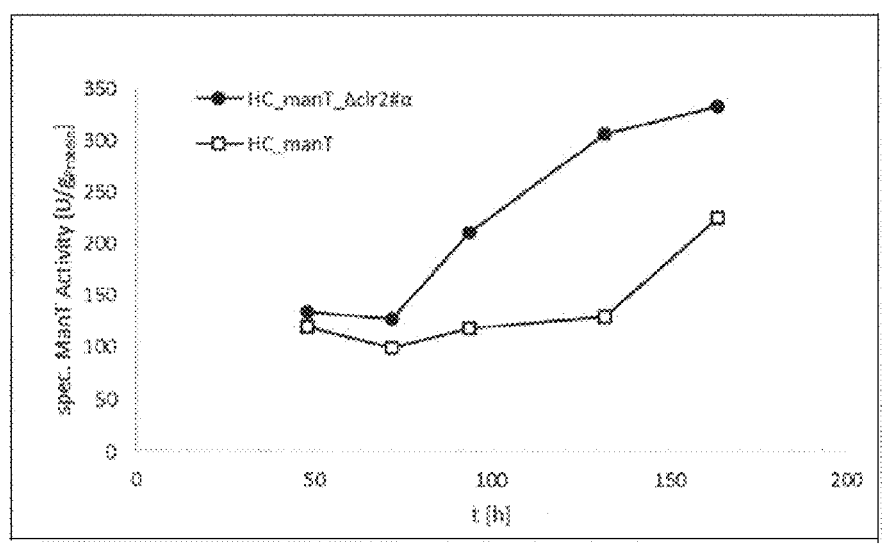
FIG. 1 shows the total specific mannanase activity in U/mg protein of the parent strain (HC-manT; open squares) and the strain in which the clr2 gene is deleted (HC_manT_Δclr2 #α; filled circles), wherein the protein is obtained at different timepoints during the cultivation.

The present invention relates to improved means and methods allowing to produce recombinant polypeptides in a filamentous fungus which is genetically modified to decrease or eliminate the activity of CLR2 and to express the recombinant polypeptide.

Although the present invention will be described with respect to particular embodiments, this description is not to be construed in a limiting sense.

Before describing in detail exemplary embodiments of the present invention, definitions important for understanding the present invention are given. As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used to distinguish between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method of producing a recombinant polypeptide in a filamentous fungus which is genetically modified to decrease or eliminate the activity of CLR2 compared to a filamentous fungus not having the genetic modification which is cultured under the same conditions as the genetically modified filamentous fungus and which is further genetically modified to express said recombinant polypeptide, said method comprising:

(i) growing said genetically modified filamentous fungus in a suitable culture medium; and
(ii) isolating the recombinant polypeptide from the culture medium.

The term "recombinant polypeptide" as used herein refers to any polypeptide which is produced in a host cell by recombinant means, i.e. by transformation of the host cell with a nucleic acid molecule which governs the expression of the recombinant polypeptide encoded by the nucleic acid molecule. In one aspect, the recombinant polypeptide is a polypeptide which is naturally expressed by the cell used for its production, but is expressed in a higher amount than in the non-transformed host cell. Such a polypeptide is also called "homologous polypeptide". In another aspect, the recombinant polypeptide is not naturally expressed by the cell used for its production so that it is only detectable in the transformed host cell. Such a polypeptide is also called "heterologous polypeptide". Preferably, the recombinant polypeptide is a heterologous polypeptide.

Within the present invention, the recombinant polypeptide may be a recombinant hydrolase. A hydrolase is an enzyme which catalyzes the hydrolysis of a chemical bond. Examples of hydrolases are esterases, lipases, phosphatases and peptidases and include nucleases, glycosidases and proteases. Lipases hydrolyse ester bonds between a carboxylic acid and an alcohol in lipids and phosphatases act analogously upon phosphates. Nucleases are phosphatases that hydrolyze nucleic acids. Glycosidases hydrolyse bonds between sugar molecules in carbohydrates. Proteases hydrolyze peptide bonds between the carboxylic acid group of one amino acid and the amino group of another within protein molecules.

Glycosidases include glucosidases which catalyze the hydrolysis of glucosides and xylanases which catalyze the cleavage of the xylose based homopolymer xylan. Particular embodiments of glucosidases include mannanase, lactase, laminaridase, amylase, glucoamylase, chitinase, sucrase, maltase, neuraminidase, invertase, hyaluronidase, lysozyme, cellulase and hemicellulase.

In one embodiment, the recombinant polypeptide is a hydrolase other than a cellulase.

In one embodiment, the recombinant polypeptide is expressed under the control of a promoter, i.e. the nucleic acid sequence encoding the recombinant polypeptide is operably linked to said promoter, which promoter is functional in the genetically modified filamentous fungus and which is not activatable by CLR2. Genes which are activated by CLR2 so that the promoters of these genes are not suitable for regulating the expression of the recombinant polypeptide within the present invention are disclosed in Table 1A of WO 2013/022594 A1 as genes which showed no induction in dr mutants. The genes disclosed in Table 1A of WO 2013/022594 A1 include genes involved in amino acid metabolism, genes encoding cellulases and hemicellulases and other enzymes involved in oligosaccharide and polysaccharide degradation, genes encoding deltaaminolevulinic acid dehydratase, 5-aminolevulinate synthase, pyridoxamine phosphate oxidase, galactokinase, lipases, nuclear segregation protein, dolichylphosphate beta-glucosyltransferase, mitochondrial DNA replication protein YHM2, mitochondrial inner membrane protease subunit 2, nuclear elongation and deformation protein 1, clock-controlled pheromone CCG-4, calcium homeostasis protein Regucalcin endothiapepsin, genes involved in nucleotide metabolism, protein folding, protein modification, rRNA production, translocation and transport, transcription factors.

The skilled person can also easily determine whether a promoter is activated by CLR2 or not. To this end, the promoter to be tested can be operably linked to a nucleic acid sequence encoding a reporter protein such as luciferase, green fluorescence protein or beta-glucuronidase and be transformed into a clr2-deficient host cell. If the expression of the reporter protein is reduced by less than 50% in the clr2-deficient host cell, the promoter is not activated by CLR2 and therefore may be used to express the recombinant polypeptide in the genetically modified host cell. If the expression of the reporter protein is reduced by more than 50% in the clr2-deficient host cell, the promoter is activated by CLR2 and therefore is not suitable for expressing the recombinant polypeptide in the genetically modified host cell.

Genes the expression of which is not activated by CLR2 are listed in Table 1. The promoters of these genes can be used for expression of the recombinant polypeptide. Genes the expression of which is activated by CLR2 are listed in Table 2. The promoters of these genes are not suitable for expression of the recombinant polypeptide within the present invention.

TABLE 1

| Identifier | Annotation |
| --- | --- |
| XP_003662453.1 | Small secreted protein |
| XP_003663544.1 | 42 kDa endochitinase |
| XP_003662414.1 | Subtilisin-like protease CPC735_003880 |
| XP_003662959.1 | GPI anchored serine-rich protein |
| XP_003660173.1 | Elongation factor 1-alpha |
| XP_003663751.1 | H+-transporting ATP synthase |
| XP_003667081.1 | Histone H3 |
| XP_003665420.1 | Histone H2A |
| XP_003658355.1 | WGS project CABT00000000 data, contig 2.1 |
| XP_003667289.1 | 40S ribosomal protein S25 |
| XP_003665767.1 | 4-coumarate:coenzyme a ligase |
| XP_003658782.1 | WGS project CABT00000000 data, contig 2.1 |
| XP_003664932.1 | Putative transporter protein |
| XP_003664979.1 | 40S ribosomal protein S27a |
| XP_003665421.1 | Histone H2B.5 |
| XP_003664809.1 | CRP7 |
| XP_003660671.1 | Eukaryotic translation initiation factor 5A |
| XP_003662326.1 | 60S acidic ribosomal protein p1 |
| XP_003664349.1 | Podospora anserina S mat+ genomic DNA chromosome 4, supercontig 4 |
| XP_003664322.1 | Exo-beta 1, 3 glucanase |
| XP_003659916.1 | Putative uncharacterized protein |
| XP_003659607.1 | 40S ribosomal protein S15 |
| XP_003658626.1 | Rotamase H |
| XP_003665258.1 | Ubiquitin-conjugating enzyme E2-16 kDa |
| XP_003660223.1 | Putative uncharacterized protein |
| XP_003659588.1 | SUN domain-containing protein |
| XP_003658479.1 | 60S ribosomal protein L18a |

TABLE 1-continued

| Identifier | Annotation |
|---|---|
| XP_003661167.1 | Clock-controlled protein 6 |
| XP_003658970.1 | Podospora anserina S mat+ genomic DNA chromosome 1, supercontig 1 |
| XP_003663354.1 | Histone H4 |
| XP_003659986.1 | Woronin body major protein |
| XP_003660094.1 | Whole genome shotgun sequence assembly, scaffold_77, strain Mel28 |
| XP_003661488.1 | 60S ribosomal protein L38 |
| XP_003666882.1 | Podospora anserina S mat+ genomic DNA chromosome 3, supercontig 2 |
| XP_003663354.1 | Histone H4 |
| XP_003659614.1 | 60S acidic ribosomal protein P2-B |
| XP_003659345.1 | 40S ribosomal protein S11 |
| XP_003661611.1 | 40S ribosomal protein S1 |
| XP_003659402.1 | Gentiobiase btgE |
| XP_003658662.1 | Putative uncharacterized protein |
| XP_003662338.1 | 60S ribosomal protein L10 |
| XP_003662432.1 | 40S ribosomal protein S24 |
| XP_003666960.1 | 40S ribosomal protein S6 |
| XP_003658918.1 | L41 |
| XP_003662061.1 | 60S ribosomal protein L28-like protein |
| XP_003662627.1 | Ribosomal protein L34 |
| XP_003662769.1 | 40S ribosomal protein S12 |
| XP_003667290.1 | 40S ribosomal protein S5 |
| XP_003663260.1 | Uncharacterized protein |
| XP_003659536.1 | Ribosomal protein L6 |
| XP_003660224.1 | 60S ribosomal protein L21 |
| XP_003663310.1 | 60S ribosomal protein L8-2 |
| XP_003662159.1 | Actin-3-sub 2 |
| XP_003664978.1 | Putative 40S ribosomal protein S26E |
| XP_003661200.1 | GTP-binding protein EsdC |
| XP_003662777.1 | Translationally-controlled tumor protein homolog |
| XP_003660285.1 | Putative uncharacterized protein |
| XP_003662578.1 | Carbohydrate-binding module family 52 protein |
| XP_003662603.1 | 40S ribosomal protein S19 |
| XP_003659696.1 | 40S ribosomal protein S13 |
| XP_003664271.1 | 60S ribosomal protein L7A |
| XP_003667236.1 | Related to spore coat protein SP96 |
| XP_003658830.1 | 40S ribosomal protein S16 |
| XP_003664979.1 | Ubiquitin |
| XP_003658685.1 | 60S ribosomal protein L33 |
| XP_003664427.1 | Putative uncharacterized protein |
| XP_003665392.1 | Putative 40S ribosomal protein S2 |
| XP_003659932.1 | 60S ribosomal protein L14-B |
| XP_003665947.1 | CRP3 |
| XP_003659547.1 | 60S ribosomal protein L35 |
| XP_003660275.1 | Uncharacterized protein |
| XP_003664636.1 | Translational activator GCN1 |
| XP_003660039.1 | Superoxide dismutase [Cu-Zn] |
| XP_003666816.1 | NAD(P)-dependent glyceraldehyde-3-phosphate dehydrogenase |
| XP_003667288.1 | Uncharacterized protein |
| XP_003662768.1 | 40S ribosomal protein S15a-2 |
| XP_003662043.1 | Uncharacterized protein |
| XP_003666871.1 | 40S ribosomal protein S10b |
| XP_003658492.1 | WGS project CABT00000000 data, contig 2.20 |
| XP_003667045.1 | ATP synthase subunit beta |
| XP_003660747.1 | Podospora anserina S mat+ genomic DNA chromosome 3, supercontig 2 |
| XP_003666573.1 | 60S ribosomal protein L26 |
| XP_003664641.1 | Uncharacterized protein |
| XP_003664442.1 | 40S ribosomal protein S28 |
| XP_003661762.1 | Bys1 family protein |
| XP_003659216.1 | 60S acidic ribosomal protein P0 |
| XP_003662606.1 | 60S ribosomal protein 17 |
| XP_003662895.1 | 60S ribosomal protein L23a |
| XP_003664133.1 | Ubiquitin |
| XP_003662569.1 | Glucan 1,3-beta-glucosidase |
| XP_003666958.1 | 40S ribosomal protein S8 |
| XP_003659548.1 | 60S ribosomal protein L6 |
| XP_003659945.1 | 60S ribosomal protein L24 |
| XP_003662337.1 | 60S ribosomal protein L30-2 |
| XP_003663818.1 | Uncharacterized protein |
| XP_003662273.1 | Putative uncharacterized protein |
| XP_003662019.1 | 60S ribosomal protein L17 |
| XP_003665369.1 | Peroxiredoxin-like protein DDB_G0282517, mitochondrial |
| XP_003664773.1 | Alkaline serine protease |

TABLE 1-continued

| Identifier | Annotation |
|---|---|
| XP_003666989.1 | Large subunit ribosomal protein L3 |
| XP_003662607.1 | 40S ribosomal protein S14 |
| XP_003659946.1 | Thioredoxin reductase |
| XP_003662691.1 | Ribosomal L28e protein |
| XP_003659072.1 | RplA |
| XP_003658742.1 | Ran-related GTP binding protein |
| XP_003659986.1 | Woronin body major protein |
| XP_003667317.1 | Pc22g10000 protein |
| XP_003661900.1 | 60S ribosomal protein L16-B |
| XP_003666937.1 | Ribosomal protein L15 |
| XP_003666685.1 | 40S ribosomal protein S0 |
| XP_003663180.1 | Ribosomal protein S3 |
| XP_003659068.1 | ATP synthase alpha chain |
| XP_003664400.1 | 60S ribosomal protein L13 |
| XP_003661512.1 | Podospora anserina S mat+ genomic DNA chromosome 2, supercontig 2 |
| XP_003658715.1 | 60S ribosomal protein L36 |

TABLE 2

| Identifier | annotation |
|---|---|
| XP_003660789.1 | Exoglucanase B |
| XP_003662435.1 | Endo-1,4-beta-glucanase 6B |
| XP_003666549.1 | Similar to glycoside hydrolase family 61 protein |
| XP_003665516.1 | Similar to glycoside hydrolase family 61 protein |
| XP_003666507.1 | Exocellobiohydrolase |
| XP_003661661.1 | Similar to endoglucanase II |
| XP_003661032.1 | Exocellobiohydrolase 6A |
| XP_003663414.1 | Endoglucanase ii |
| XP_003661887.1 | Endoglucanase II |
| XP_003664565.1 | Endo-1,4-beta-glucanase |
| XP_003663382.1 | Cellobiose-quinone oxidoreductase |
| XP_003664855.1 | Galactose mutarotase-like protein |
| XP_003659323.1 | Endoglucanase V |
| XP_003661261.1 | Endoglucanase-4 |
| XP_003662402.1 | Glycosyl hydrolase family 11 |
| XP_003660474.1 | Similar to 3-carboxymuconate cyclase-like protein |
| XP_003659754.1 | Similar to endoglucanase II |
| XP_003661787.1 | Glycoside hydrolase-61 |
| XP_003665777.1 | Xyloglucanendohydrolase A |
| XP_003662704.1 | Putative uncharacterized protein |
| XP_003666502.1 | Glycosyl hydrolase family 61 |
| XP_003661910.1 | Endoglucanase-4 |
| XP_003664543.1 | Cellobiose-quinone oxidoreductase |
| XP_003664847.1 | GDSL-like Lipase/Acylhydrolase |
| XP_003666179.1 | Arabinoxylan arabinofuranohydrolase axhA-2 |
| XP_003667321.1 | Beta-glucanase |
| XP_003660327.1 | WGS project CABT00000000 data, contig 2.1 |
| XP_003662562.1 | Putative fungistatic metabolite |
| XP_003665081.1 | Similar to glycoside hydrolase family 61 protein |
| XP_003665518.1 | Carbohydrate-binding module family 1 protein |
| XP_003660610.1 | PVX |
| XP_003665702.1 | Glycoside hydrolase family 10 protein |
| XP_003663588.1 | Gentiobiase |
| XP_003662967.1 | Putative uncharacterized protein |
| XP_003664605.1 | WGS project CABT00000000 data, contig 2.76 |
| XP_003663441.1 | Endo-1,4-beta-glucanase |
| XP_003664172.1 | Cel74a |
| XP_003664438.1 | WGS project CABT00000000 data, contig 2.10 |
| XP_003667406.1 | Putative uncharacterized protein |
| XP_003664606.1 | Cellulase B |
| XP_003663683.1 | WGS project CABT00000000 data, contig 2.9 |
| XP_003664579.1 | Pectate lyase |
| XP_003667133.1 | WGS project CABT00000000 data, contig 2.3 |
| XP_003667376.1 | Carbohydrate-binding module family 50 protein |
| XP_003664821.1 | Putative uncharacterized protein |
| XP_003659137.1 | GPI anchored protein |
| XP_003660241.1 | Gentiobiase J |
| XP_003663843.1 | Probable pectate lyase B |
| XP_003658911.1 | 1,4-beta-D-xylan xylanohydrolase |
| XP_003660992.1 | Uncharacterized protein |
| XP_003658951.1 | Uncharacterized protein |
| | Podospora anserina S mat+ genomic DNA chromosome 1, supercontig 1 |

TABLE 2-continued

| Identifier | annotation |
|---|---|
| XP_003664710.1 | Glycoside hydrolase family 18 protein |
| XP_003663492.1 | Acetylxylan esterase A |
| XP_003664441.1 | Probable rhamnogalacturonate lyase A |
| XP_003661220.1 | Uncharacterized protein |
| XP_003661913.1 | Podospora anserina S mat+ genomic DNA chromosome 2, supercontig 2 |
| XP_003661061.1 | Putative uncharacterized protein |
| XP_003665705.1 | Acetylxylan esterase |
| XP_003664525.1 | Exoglucanase 3 |
| XP_003664825.1 | WGS project CABT00000000 data, contig 2.1 |
| XP_003659079.1 | WGS project CABT00000000 data, contig 2.6 |
| XP_003659962.1 | GDSL-like Lipase/Acylhydrolase |
| XP_003665588.1 | Podospora anserina S mat+ genomic DNA chromosome 6, supercontig 3 |
| XP_003659608.1 | Endo-1,4-beta-galactanase |
| XP_003662813.1 | Pc21g20520 protein |
| XP_003661881.1 | Taurine catabolism dioxygenase TauD |
| XP_003667407.1 | Pc13g11940 protein |
| XP_003666322.1 | Xylosidase/arabinosidase |
| XP_003658941.1 | Podospora anserina S mat+ genomic DNA chromosome 1, supercontig 1 |
| XP_003664814.1 | Methyltransferase type 11 |
| XP_003663984.1 | Probable pectate lyase B |
| XP_003666142.1 | Endo-beta-1,4-mannanase A |
| XP_003664909.1 | Pectate lyase B |
| XP_003662067.1 | Glycoside hydrolase family 16 protein |
| XP_003662543.1 | Uncharacterized protein |
| XP_003665722.1 | Beta-glucosidase/beta-xylosidase |
| XP_003660976.1 | Pc22g09680 protein |
| XP_003663268.1 | Esterase/lipase |
| XP_003660526.1 | Ubiquitin-conjugating enzyme |
| XP_003665113.1 | Nhl repeat-containing protein |
| XP_003665690.1 | WGS project CABT00000000 data, contig 2.46 |
| XP_003664826.1 | Short chain dehydrogenase/reductase family protein |
| XP_003658694.1 | Lipase GDSL |
| XP_003663565.1 | WGS project CABT00000000 data, contig 2.31 |
| XP_003659022.1 | Secreted protein |
| XP_003666822.1 | ThiJ/PfpI family protein |
| XP_003658915.1 | Mannan endo-1,4-beta-mannosidase |
| XP_003665747.1 | Cip1 |
| XP_003664164.1 | Arabinosidase |
| XP_003661636.1 | Putative uncharacterized protein BofuT4_P151850.1 |

Suitable promoters which can be used to express the recombinant polypeptide include the promoter of the chi1 gene according to SEQ ID No. 14 and the promoter of the elongation factor 1-alpha gene according to SEQ ID No. 15. Other suitable promoters are disclosed in WO 2010/107303 A2 and include the hex1 promoter, the his2a promoter and the gla promoter. All the foregoing promoters are not activatable by CLR2.

The skilled person knows also other suitable promoters which can typically be used to express recombinant polypeptides. These promotes include promoters derived from other filamentous fungi, like the gpd (glyceraldehyde-3-phosphate dehydrogenase), pdc (pyruvate decarboxylase), eno (enolase), trpC (Tryptophan biosynthesis protein), pda (pyruvate dehydrogenase), glaA (glucoamylase), tpi (triose phosphate isomerase), icl (isocitrate lyase), teff (elongation factor 1) and kdh (ketoglutarate dehydrogenase) promoters from filamentous fungi such as *Aspergillus, Fusarium, Humicola, Myceliophthora, Neurospora, Penicillium, Talaromyces*, and *Trichoderma*.

The expression construct used for expressing the recombinant protein may contain further elements such as a nucleic acid sequence encoding a signal peptide which enables the secretion of the recombinant polypeptide into the culture medium and one or more terminators which are functional in filamentous fungi.

The host cell may comprise more than one copy of the nucleic acid sequence encoding said recombinant polypeptide in the genome.

The expression of the recombinant polypeptide may, in a further embodiment, be conveyed by an optimization of the codon usage, e.g. by an adaptation of the codon usage of the nucleic acid sequence encoding the recombinant polypeptide to the codon usage of the genes which are transcribed or expressed most often in the organism, or which are most highly expressed (in comparison to housekeeping genes such as beta-actin or beta-tubulin). Examples of such codon usage of highly expressed genes may comprise the codon usage of a group of the 5, 10, 15, 20, 25 or 30 or more most highly expressed genes of a filamentous fungus, preferably of *Myceliophthora thermophila*.

An over-expression may further be achieved by optimizing the codon usage with respect to the overall codon usage in all or almost all, or 90% or 80% or 75%, or 70% of the transcribed genes of a filamentous fungus, preferably of *Myceliophthora thermophila*. Such an approach may involve an inspection of the codon usage of the gene and a comparison with the overall codon usage as derivable from a genomic sequence of a filamentous fungus, preferably of *Myceliophthora thermophila*, in particular an annotated genomic sequence of the organism.

The expression of the recombinant polypeptide in the genetically modified filamentous fungus can be detected and quantified by any method known in the art, including Western Blot, Northern Blot and RT-PCR. If the recombinant polypeptide is an enzyme, its expression can also be detected by measuring the enzyme activity. Suitable assays for determining phytase and mannanase activity are described in the Examples section herein.

The term "filamentous fungus" as used herein refers to eukaryotic microorganisms that include all filamentous forms of the subdivision Eumycotina and Oomycota (as defined by Hawksworth et al *Ainsworth & Bisby's Dictionary of the Fungi*. 8th edn. CAB International, Wallingford). The filamentous fungi are characterized by a mycelial wall composed of chitin, cellulose, glucan, chitosan, mannan, and other complex polysaccharides. Vegetative growth takes place by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete, Podospora, Pycnoporus, Rhizopus, Schizophyllum, Sordaria, Talaromyces, Rasamsonia, Thermoascus, Thielavia, Tolypocladium, Trametes* and *Trichoderma*. Preferred filamentous fungal strains that may be used in the present invention belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae* and *Myceliophtora thermophila* (formerly known as *Chrysosporium lucknowense*). Most preferably, the filamentous fungus is *Myceliophtora thermophila*.

The term "genetically modified filamentous fungus" as used herein refers to a modification of a wild-type species of a filamentous fungus by mutagenesis and selection and/or genetic engineering, or to the further modification of an already genetically modified organism, e.g. a filamentous fungus strain which was previously engineered with one or more genes other than the clr2 gene. The genetic modification of the present invention is the modification to decrease or eliminate CLR2 activity.

The term "a filamentous fungus not having the genetic modification" as used herein refers to a filamentous fungus which is not genetically modified to decrease or eliminate the activity of CLR2 and which, apart from that, has the same genetic constitution as the genetically modified filamentous fungus used in the present invention, i.e. the only genetic difference to the genetically modified filamentous fungus of the present invention is the genetic modification of the present invention to decrease or eliminate CLR2 activity. Hence, the filamentous fungus not having the genetic modification is the parental strain into which the genetic modification to decrease or eliminate the activity of CLR2 is introduced within the present invention. The parental strain comprises at least the further genetic modification to express the recombinant polypeptide, but may also comprise additional genetic modifications.

The filamentous fungus may further comprise genetic modifications to enable the selection of transformed cells. Examples of such modifications include the deletion of the pyr4 gene encoding an orotidine 5'-phosphate decarboxylase and the pyr5 gene encoding uridine 5' monophosphate synthase. Both genes are involved in the biosynthesis of uracil so that cells with a deletion of any of these genes cannot grow on media lacking uracil and uridine unless they are genetically modified to complement this deficiency. Another genetic modification of the filamentous fungus may be the deletion of the gene encoding Ku70 which is involved in non-homologous end-joining (NHEJ)-mediated repair The term "growing said genetically modified filamentous fungus in a suitable culture medium" as used herein refers to the use of any suitable means and methods known to the person skilled in the art, which allows the growth of the filamentous fungus as defined herein and which is suitable for the production of the recombinant polypeptide. The growing may be carried out as batch or fed-batch process or in a continuous fermentation process. Preferably, the culture medium does not contain cellulose or any derivative thereof which is capable of inducing CLR2 activity.

Methods for carrying out batch, fed-batch or continuous fermentation processes are well known to the person skilled in the art and are described in the literature. The culturing may be carried out under specific temperature conditions, e.g. between 15° C. and 50° C., preferably between 20° C. and 47° C., more preferably between 32° C. and 45° C. and most preferably between 38° C. and 42° C. The culturing may be carried out at a pH of between pH 5 and pH 8.5, preferably between pH 5.5 and 7.5, more preferably between pH 6 and 7 and most preferably between 6 and 6.7.

A suitable medium for fermentation comprises a carbon source, nitrogen source, phosphate, sulfur and trace elements as known in the art, but not limited to the following components:

As a carbon source mono-, di- and polysaccharides like glucose, dextrose, fructose, xylose, sucrose, maltose, lactose could be used. Complex carbon sources like cellulose, whey, corn starch, wheat bran, starch malt extract, sugar beet molasses, blackstrap molasses, cane molasses, fatty acids or soy bean oil can also be used. Any complex suitable nitrogen source as known in the art including, but not limited to, corn steep liquor/solids, dried distillers solubles, yeast, fish or bone meal, meat or yeast extracts, corn germ or gluten meal, protein peptones, hydrolysates and digests of casein, yeast, cottonseed, milk proteins or soy proteins, soy bean meal, peanut meal, rice bran or pharmamedia could be applied. Alternatively, inorganic nitrogen sources such as ammonia or salts thereof, organic nitrogen sources like urea and/or amino acids could be used. In addition to the carbon source and nitrogen source the medium can be provided with a variety of organic or inorganic compounds which provide sulfur, phosphorus, iron, magnesium, zinc and other elements essential for cell growth, viability and production of desired protein. A suitable medium is also described in the Examples below.

The wording "isolating the recombinant polypeptide from the culture medium" as used herein refers to any suitable method for separating the recombinant polypeptide from cell debris and ingredients of the culture medium. Suitable separation techniques known in the art include, but are not limited to, filtration, microfiltration, ultrafiltration, centrifugation, extraction, spray drying, evaporation, freeze drying and precipitation. The recombinant polypeptide may further be purified by a variety of procedures known in the art including, but not limited to, ammonium sulfate precipitation or other protein precipitation methods, ion exchange chromatography, affinity chromatography, hydrophobic interaction chromatography, size exclusion chromatography or electrophoretic procedures.

The term "genetically modifying the filamentous fungus" or "genetically modified filamentous fungus" as used herein means that a filamentous fungus is altered by any suitable genetic means and methods known to the skilled person. Similarly the term "filamentous fungus which is genetically modified" as used herein means that a filamentous fungus has been modified or altered by any suitable genetic means and methods known to the skilled person such that the activity of CLR2 is decreased or eliminated and a recombinant polypeptide is expressed.

Methods for genetically modifying filamentous fungi are known to the person skilled in the art and are described in the literature. They comprise commonly used methods for introducing genetic elements or material into filamentous fungi so as to be contained in the filamentous fungi, integrated into the chromosome or extrachromosomally, or the removal or destruction, or modification, of genetic elements or sequences naturally present in the genome of a filamentous fungus.

The term "genetic element" as used herein means any molecular unit which is able to transport genetic information. It accordingly relates to a gene, preferably to a native gene, a chimeric gene, a foreign gene or a transgene. The term "gene" refers to a nucleic acid molecule or fragment thereof that expresses a specific protein or polypeptide, preferably it refers to nucleic acid molecules including regulatory sequences upstream (5' non-coding sequences) and downstream (3' non-coding sequences) of the coding sequence. The term "native gene" refers to a gene as found in nature, e.g. in a wild-type filamentous fungus, with its own regulatory sequences. The term "chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature such that the regulatory sequences and the coding sequences are derived from different genes of the same organism. According to the present invention a "foreign gene" refers to a gene not normally found in the filamentous fungus, but that is introduced into the filamentous fungus by genetic manipulation. Foreign genes can comprise genes which are native in an organism other than the one into which they are introduced, or chimeric genes. The term "transgene" refers to a gene that has been introduced into the genome by a transformation procedure.

The term "coding sequence" refers to a DNA sequence which codes for a specific amino acid sequence. The term "regulatory sequence" refers to a nucleotide sequence located upstream (5' non-coding sequences), within, or downstream (3' non-coding sequences) of a coding sequence, and which influences the transcription, RNA processing or stability, or translation of the associated coding sequence. Regulatory sequences may include promoters, enhancers, translation leader sequences, introns, polyadenylation recognition sequences, RNA processing sites, effector binding sites and stem-loop structures.

The term "promoter" refers to a DNA sequence capable of controlling the expression of a coding sequence or functional RNA. Typically, a coding sequence is located 3' to a promoter sequence. Promoters may be derived in their entirety from a native gene, or be composed of different elements derived from different promoters found in nature, or even comprise synthetic DNA segments. Typically, since the exact boundaries of regulatory sequences have not been completely defined, DNA fragments of different lengths may have identical promoter activity. It is understood by a person skilled in the art that different promoters may direct the expression of a gene at different stages of development, or in response to different environmental or physiological conditions. Promoters that cause a gene to be expressed in most cell types at most times are commonly referred to as constitutive promoters. On the other hand, promoters that cause a gene to be expressed in specific contexts only, e.g. based on the presence of specific factors, growth stages, temperatures, pH or the presence of specific metabolites etc., are understood as regulatable promoters.

The term "3' non-coding sequences" refers to DNA sequences located downstream of a coding sequence. It includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' non-coding sequences can influence the transcription, i.e. the presence of RNA transcripts, the RNA processing or stability, or translation of the associated coding sequence. The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. The term "mRNA" refers to messenger RNA, i.e. RNA that is without introns and that can be translated into protein by the cell.

The term "operably linked" refers to the association of nucleic acid sequences on a single nucleic acid fragment so that the function of one is affected by the other. In the context of a promoter the term means that the coding sequence is under the transcriptional control of the promoter.

Within a central embodiment of the present invention, the genetic modification of the filamentous fungus decreases or eliminates the activity of CLR2.

The term "CLR2" refers to a zinc binuclear cluster transcription factor which binds to the promoter region of certain genes and stimulates gene expression.

In preferred embodiments of the present invention the CLR2 activity is provided by a polypeptide comprising, essentially consisting of or consisting of the amino acid sequence of SEQ ID NO: 3 or functional parts or fragments thereof, or is encoded by a nucleic acid comprising, essentially consisting of or consisting of the nucleotide sequence of SEQ ID NO: 1 or 2 or functional parts or fragments thereof, or is provided by a polypeptide comprising, essentially consisting of or consisting of an amino acid sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 3 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 1 or 2 or functional parts or fragments thereof, and encoding a polypeptide having essentially the same activity as the polypeptide with SEQ ID No.3, i.e. CLR2 activity, which means binding to the DNA within promoter regions of target genes and activating transcription.

The sequence according to SEQ ID No. 1 is the cDNA sequence of the clr2 gene and the sequence according to SEQ ID No. 2 is a genomic region comprising the clr2 gene. In a preferred embodiment only the genomic region coding for CLR2 is used which corresponds to nucleotides 3001 to 5570 of SEQ ID No. 2. Hence, the above values for the percentage sequence identity also apply to the sequence comprising nucleotides 3001 to 5570 of SEQ ID No. 2.

The term "functional fragment" or "functional part" is intended to refer to a smaller, contiguous part of the polypeptide having essentially the same activity as the polypeptide with SEQ ID No.3, i.e. CLR2 activity, which means binding to the DNA within promoter regions of target genes and activating transcription.

The functional fragment of the amino acid sequence of SEQ ID No. 3 has a length of at least 250 or 300 amino acids, preferably of at least 350 or 400 amino acids, more preferably of at least 450, 500 or 550 amino acids, even more preferably of at least 600, 650 or 700 amino acids and most preferably of at least 750 to 800 amino acids. The zinc(2)-cysteine(6) binuclear cluster domain is located at positions 49 to 85 of SEQ ID No. 3 and is shown in SEQ ID No. 4. Hence, the functional fragment as defined above is preferably located between amino acids 20 to 270 or amino acids to 320, more preferably between amino acids 20 to 370 or amino acids 20 to 420, even more preferably between amino acids 20 to 470, amino acids 20 to 520 or amino acids 20 to 570, even more preferably between amino acids 20 to 620 or 20 to 670 or 20 to 720 and most preferably between amino acids 20 to 770 or amino acids 20 to 820.

In an alternative embodiment, the polypeptide providing the CLR2 activity comprises, essentially consists of or consists of an amino acid sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 3 and comprising the amino acid sequence according to SEQ ID No. 4 at a position corresponding to positions 49 to 85 of SEQ ID No. 3.

Within the meaning of the present invention, "sequence identity" denotes the degree of conformity with regard to the 5'-3' sequence within a nucleic acid molecule in comparison to another nucleic acid molecule. The sequence identity may be determined using a series of programs, which are based on various algorithms, such as BLASTN, ScanProsite, the laser gene software, etc. As an alternative, the BLAST program package of the National Center for Biotechnology Information (www.ncbi.nlm.nih.gov/) may be used with the default parameters. In addition, the program Sequencher (Gene Codes Corp., Ann Arbor, Mich., USA) using the "dirtydata"-algorithm for sequence comparisons may be employed.

The identity between two protein or nucleic acid sequences is defined as the identity calculated with the program needle in the version available in April 2011. Needle is part of the freely available program package EMBOSS, which can be downloaded from the website emboss.sourceforge.net/. The standard parameters used are: gapopen 10.0 ("gap open penalty"), gapextend 0.5 ("gap extension penalty"), datafile EBLOSUM62 (matrix) in the case of protein and datafile EONAFULL (matrix) in the case of ONA.

The sequence identity refers to the degree of sequence identity over a length of 700, 800 or 900 nucleotides, preferably 1000, 1100, 1200, 1300 or 1400 nucleotides, more preferably 1500, 1600, 1700, 1800 or 1900 nucleotides and most preferably the whole length of the nucleic acid sequence according to SEQ ID No. 1 or 2.

The sequence identity refers to the degree of sequence identity over a length of 300, 350 or 400 amino acids, preferably 450, 500 or 550 amino acids, more preferably 600, 630, 660 or 680 amino acids and most preferably the whole length of the amino acid sequence according to SEQ ID No. 3.

The activity of a CLR2 variant as discussed above, i.e. a functional fragment of the protein according to SEQ ID No. 3 or a protein having a sequence identity of at least 70% to the amino acid sequence according to SEQ ID No. 3, can be measured with suitable tests or assays, which are known to the skilled person or can be derived from suitable literature sources. For example, a promoter which is known to contain binding sites for CLR2 such as a cellulase promoter can be operably linked to a reporter gene which encodes a protein such as green fluorescent protein (GFP), beta-glucuronidase (GUS) or luciferase and transfected into a suitable host cell together with a nucleic acid molecule encoding the CLR2 variant the activity of which is to be tested or the wild-type CLR2 protein. Then the expression of the reporter gene can be compared in cells transfected with the variant with that in cells transfected with the wild-type protein. As discussed above, promoters which are activated by CLR2 are disclosed in Table 2 above and in WO 2013/022594 A1.

The term "essentially the same activity" refers to polypeptides which have at least 50% or 55%, preferably at least 60, 65 or 70%, more preferably at least 75, 80, 85 or 90% and most preferably at least 92, 94, 96, 98 or 99% of the CLR2 activity of the polypeptide according to SEQ ID NO. 3, i.e. the amount of the reporter protein produced by incubating a reporter construct as described above with the variant is at least 50% or 55%, preferably at least 60, 65 or 70%, more preferably at least 75, 80, 85 or 90% and most preferably at least 92, 94, 96, 98 or 99% or more of the amount of the reporter protein produced by incubating the same reporter construct with the polypeptide according to SEQ ID NO. 3.

The term "decrease of activity" or "decrease of amount" as used herein refers to any modification of the genetic element encoding the CLR2 protein, e.g. on a molecular basis, the transcript expressed by the genetic element or the protein or activity encoded by said genetic element, which leads to a decrease of said CLR2 activity, a decrease of the concentration of said CLR2 activity in the cell and/or a decrease of the functioning of said CLR2 activity.

The term "eliminated activity" as used herein refers to any modification of the genetic element encoding the CLR2 which leads to a complete abolishment of CLR2 activity, i.e. no reporter protein can be detected when the reporter gene construct is incubated with the protein or an extract from cells having the genetic modification to eliminate the activity under conditions discussed herein.

A modification of the genetic element encoding an activity may, for example, lead to a decrease of CLR2 activity of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, such decrease of activity is represented by, comprises, essentially consists of, or consists of the amino acid sequence of SEQ ID NO: 3, or variants thereof as defined herein above.

In specific embodiments, the decrease of activity is due to the reduced or eliminated expression of the genetic element whose expression yields the activity as mentioned above. The term "expression" as used herein refers to the transcription and accumulation of sense strand (mRNA) derived from nucleic acid molecules or genes as mentioned herein. More preferably, the term also refers to the translation of mRNA into a polypeptide or protein and the corresponding provision of such polypeptides or proteins within the cell. The term "reduced expression" relates to a decreased number of transcripts and/or a decreased number of polypeptides or proteins than upon the expression an endogenous copy of the genetic element which gives rise to said polypeptide or protein in the context of the same organism.

In a particularly preferred embodiment the decrease of the CLR2 activity is due to the reduced expression of a nucleic acid molecule encoding the CLR2 protein.

In preferred embodiments, the decreased expression as mentioned above may lead to a decrease in the transcription rate of a gene of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, such decrease of in the transcription rate of a gene may be provided for the transcript of the nucleotide sequence of SEQ ID NO: 1 or 2, or variants thereof as defined herein above.

In further preferred embodiments, the decreased expression may lead to a decrease in the amount of mRNA of a gene of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, such decrease in the amount of mRNA of a gene may be provided for the transcript of the nucleotide sequence of SEQ ID NO: 1 or 2, or variants thereof as defined herein above. In preferred embodiments, the amount of mRNA which is decreased refers to mRNA comprising, essentially consisting of, or consisting of the nucleotide sequence of SEQ ID NO: 1 or 2 or variants thereof as defined herein above.

In yet another preferred embodiment, the decreased expression may lead to a decrease in the amount of CLR2 polypeptide or protein of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, the polypeptide whose amount is decreased is represented by, comprises, essentially consists of, or consists of the amino acid sequence of SEQ ID NO: 3 or variants thereof as defined herein above.

The term "control organism" as used herein is intended to include both a wild-type organism, i.e. an organism which does not have any genetic modification, and an organism having one or more genetic modifications other than the genetic modification of the present invention, i.e. the genetic modification to decrease or eliminate CLR2 activity.

In one embodiment, the expression of CLR2 may be reduced by replacing the promoter of the endogenous clr2 gene with a weak promoter. Promoters envisaged by the present invention, which may be used for the decreased expression of genes, may either be constitutive promoters or regulatable promoters. It is preferred that the promoters are endogenous *Myceliophthora* promoters. In specific embodiments, the promoters may also be heterologous promoters or synthetic promoters, e.g. a weak heterologous promoter or a regulatable heterologous promoter. A promoter may be operably linked to a coding sequence such as the nucleic acid sequence encoding CLR2. In a preferred embodiment, the term "promoter" refers to DNA sequence capable of controlling the expression of a coding sequence, which DNA sequence is active in a filamentous fungus, more preferably in *Myceliophthora thermophila*.

Within the meaning of the present invention, the term "weak promoter" is intended to refer to a promoter the activity of which is lower than the activity of the promoter which is operably linked to the nucleic acid molecule to be expressed in a wild-type organism, i.e. a promoter with a lower activity than the promoter of the endogenous clr2 gene. Preferably, the activity of the weak promoter is about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% lower than the activity of the promoter which is operably linked to the nucleic acid molecule to be expressed in a wild-type organism, i.e. the activity of the promoter of the endogenous clr2 gene.

The skilled person knows how to determine the promoter activity and to compare the activities of different promoters. For this purpose, the promoters are typically operably linked to a nucleic acid sequence encoding a reporter protein such as luciferase, green fluorescence protein or beta-glucuronidase and the activity of the reporter protein is determined. Alternatively or additionally, the mRNA levels of the endogenous genes can be compared with each other, e.g. by quantitative real time PCR or Northern Blot. In these assays, weak promoters which are suitable for use in the present invention will lead to a lower expression of the marker protein or a lower mRNA level than the promoter of the endogenous clr2 gene.

In a further embodiment the CLR2 activity may be decreased by the functional disruption of the clr2 gene, preferably by deletion of nucleotides. The deletion may encompass any region of two or more residues in a coding (ORF) or non-coding portion of the genetic element, e.g. from two residues up to the entire gene or locus.

In specific embodiments deletions may affect smaller regions, such as domains, protein sub-portions, repeated sequences or fragments of less than about 50 consecutive base pairs, although larger deletions are preferred. The deletion or functional disruption preferably takes place within the coding sequence or ORF of the clr2 gene. Particularly preferred is the deletion of the complete clr2 coding sequence according to SEQ ID No.1 or 2 or a variant thereof as defined above. Also preferred is the deletion of a functional part of the coding sequence of the clr2 gene, i.e. a part which is required for the CLR2 activity. As discussed above, the zinc(2)cysteine(6) binuclear cluster domain is located at positions 49 to 85 of SEQ ID No. 3. Hence, the deletion of a functional part of the coding sequence of the clr2 gene comprises the deletion of a part of the sequence encoding the zinc(2)-cysteine(6) binuclear cluster domain, i.e. a part of the sequence according to SEQ ID No. 3 comprising amino acids 49 to 85 of SEQ ID No. 3. Also envisaged is a functional disruption in the 3' non-coding sequence of the clr2 gene, as defined herein above, in the promoter sequence (also 5' non coding region) of the clr2 gene, as defined herein above, or in a regulatory sequence associated with the clr2 gene, as defined herein above. Such functional disruptions or modifications may lead, for example, to a decrease of expression or an instability of the transcript, difficulties in transcription initiation etc. thus providing a reduced amount or complete absence of the enzymatic activity.

For deleting part or all of the endogenous clr2 gene, preferably the coding sequence of SEQ ID No.1 or 2 or a variant as defined herein, from the genome of a filamentous fungus, preferably from the genome of *Myceliophthora thermophila*, a construct containing a coding sequence for a suitable selection marker flanked by sequences which are homologous to sequences of the endogenous clr2 gene may be generated. The homologous sequences may have a length of about 1000 to 2000 bp. However, also smaller or larger sequences can in principle be used. Upon introduction of the construct into the cells the homologous sequences will recombine with the corresponding sequences of the endogenous gene, leading to the replacement of the endogenous gene with the sequence encoding the selection marker. The strains carrying the deletion of the clr2coding sequence can then be identified using the selection marker. The construct may further contain sequences located between the homologous sequences and the coding sequence for the selection marker which sequences enable the deletion of the selection marker coding sequence after its introduction into the genome, such as lox or FRT sites. Optionally, the coding sequence for the selection marker may be split so that the 5' part of the gene encoding the selection marker is carried by a first plasmid and the 3' part of said gene is carried by the second plasmid. When both plasmids are present within a cell, the overlapping parts of the coding sequence encoding the selection marker will recombine so that the selection marker becomes functional. The first plasmid will also carry the 5' flanking region of the clr2 gene and the second plasmid will also carry the 3' flanking region of the clr2 gene.

In further embodiments, the inactivation may also be due to a mutation, rearrangement and/or insertion in the coding (ORF) and/or non-coding region of the genetic elements of clr2. Mutations may, for example, be point mutations or 2- or 3-nucleotide exchanges, which lead to a modification of the encoded amino acid sequence, or the introduction of one or more frame-shifts into the ORF, or the introduction of premature stop codons, or the removal of stop codons from the ORF, and/or the introduction of recognition signals for cellular machineries, e.g. the polyadenylation machinery or the introduction of destruction signals for protein degradation machineries etc. Such modified sequence portions may give rise to proteins which do no longer provide the activity of the protein's wildtype version. The proteins may accordingly, for example, have substitutions in regions required for their activity, leading to a loss of functioning, or may be composed of different amino acids (due to frameshifts) and thus be unable to function properly. The modified sequence portions may further give rise to unstable transcripts, which are prone to degradation. Furthermore, the targeting of the proteins may be compromised.

One technique for introducing point mutations into the genome of a filamentous fungal cells, preferably of *Myceliophthora thermophila* cells, is the CRISPR (clustered regularly interspaced short palindromic repeats)/Cas (CRISPR-associated) system which has been shown to facilitate RNA-guided site-specific DNA cleavage and which can be used for genomic engineering (see, e.g., Sander and Young (2014) Nature Biotechnol. 32: 347-355). This system uses Cas9 as a nuclease which is guided by a crRNA and tracrRNA to cleave specific DNA sequences. The mature crRNA:tracrRNA complex directs Cas9 to the target DNA via base-pairing between the spacer on the crRNA and the protospacer on the target DNA next to the protospacer adjacent motif (PAM). Cas9 then mediates the cleavage of the target DNA to create a double-strand break within the protospacer. Instead of crRNA and tracrRNA a guide RNA may be designed to include a hairpin which mimics the tracrRNA-crRNA complex (Jinek et al. (2012) Science 337(6096): 816-821).

In still another embodiment the endogenous clr2 coding sequence may be replaced with a mutant version of the coding sequence, i.e. a coding sequence which upon transcription and translation yields a protein with one or more amino acid deletions, insertions or substitutions compared to the original CLR2 protein and a lower activity than the original CLR2 protein. As discussed above, the region between amino acids 49 to 85 of SEQ ID No. 3 within the CLR2 protein is conserved. Substitution or deletion of one or more amino acids within this region will lead to a decreased or eliminated activity. Hence, in one embodiment of the present invention the endogenous clr2 coding sequence is replaced with a mutant version of the clr2 coding sequence having mutations on five, six, seven or eight, preferably on nine, ten, eleven or twelve, more preferably on 13, 14, 15, 16, 17 or 18 and most preferably on 19, 20, 21, 22, 23, 24, 25, 26, 27, 28, 29, 30 or 31 positions coding for amino acid residues corresponding to amino acids 49 to 85 of SEQ ID No. 3 in the genome of said organism.

In still another embodiment the endogenous clr2 coding sequence may be replaced with another coding region which uses codons which are less preferred in the filamentous fungus, preferably *Myceliophthora thermophila*, which is genetically modified. The skilled person knows that depending on the tRNA pool present in a cell, some codons coding for a specific amino acid are less preferred than other codons coding for the same amino acid. By using the less preferred codons the expression of the gene can therefore be decreased.

The genetic modification in order to decrease the activity of CLR2, e.g. the modification leading to a decreased expression of genes as mentioned herein above, or below, may be performed by any suitable approach known to the skilled person.

A typical approach which may be used in this context is targeted homologous recombination. For example, a modified version of the clr2 gene, e.g. a version comprising a weak promoter instead of the original promoter, or a coding sequence for a selection marker may be flanked by DNA homologous to the target endogenous polynucleotide sequence (e.g. the coding regions or regulatory regions of a gene) at whose location the insertion should take place. Such a construct may be used with or without a selectable marker and/or with or without a negative selectable marker, to transform cells of a filamentous fungus, in particular *Myceliophthora thermophila*. Insertion of the DNA construct via targeted homologous recombination may result in the insertion of a modified version of the targeted gene at the locus of the original gene, or the deletion of the endogenous gene.

The term "transformation" refers to the transfer of a genetic element, typically of a nucleic acid molecule, e.g. a specific cassette comprising a construct for homologous recombination, or of extrachromosomal elements such as vectors or plasmids into the cells of a filamentous fungus, in particular *Myceliophthora thermophila*, wherein said transfer results in a genetically stable inheritance. Conditions for transformation of filamentous fungi and corresponding techniques are known to the person skilled in the art. These techniques include chemical transformation, preferably a polyethylene glycol mediated transformation of protoplasts, lithium acetate transformation, electroporation of spores or germinating conidia, *Agrobacterium*-mediated transformation, protoplast fusion, ballistic impact transformation, microinjection, or any other method that introduces the gene or nucleic acid molecule of interest into the fungal cell.

Preferably, the transformed cell may be identified by selection for a marker contained on the introduced genetic element. Alternatively, a separate marker construct may be co-transformed with the desired genetic element. Typically, transformed cells may be selected for their ability to grow on selective media. Selective media may incorporate an antibiotic or lack a factor necessary for growth of the untransformed cell, such as a nutrient or growth factor. An introduced marker gene may confer antibiotic resistance, or encode an essential growth factor or enzyme, thereby permitting growth on selective media when expressed in the transformed host. If the expressed marker protein can be detected either directly or indirectly, the transformed cell may be selected by detecting the marker protein.

The marker protein may be expressed alone or as a fusion to another protein. The marker protein may be detected, for example, by its enzymatic activity. Alternatively, antibodies may be used to detect the marker protein or a molecular tag on, for example, a protein of interest. Cells expressing the marker protein or tag can be selected, for example, visually, or by techniques such as FACS or panning using antibodies. Preferably, any suitable marker that functions in cells of a filamentous fungus, as known to the person skilled in the art, may be used. More preferably markers which provide resistance to kanamycin, hygromycin, the amino glycoside G418, or nourseothricin (also called NTC or ClonNAT), as well as the ability to grow on media lacking nitrogen, uracil, leucine, histidine, methionine, lysine or tryptophane may be employed. When using a selection marker as mentioned above, e.g. acetamidase or a G418 or ClonNAT resistance marker, or any other suitable marker, recombinase recognition sequences such as those of the Cre-lox system may be used which flank both ends of the marker. Upon expression of the corresponding recombinase recognizing the recognition sequences this system allows an elimination and subsequent reuse of the selection marker after the insertion of the construct. Also envisaged is the use of other, similar recombinase systems which are known to the skilled person.

In specific embodiments, markers may also be combined with target sites for site specific nucleases, e.g. ZINC finger nucleases (ZFNs) or meganucleases which are capable of cleaving specific DNA target sequences in vivo. A specific example of such a system is the TALEN (Transcription Activator-Like Effector Nuclease) system, i.e. an artificial restriction enzyme, which is generated by fusing the TAL effector DNA binding domain to a DNA cleavage domain. TAL effectors are proteins which are typically secreted by *Xanthomonas* bacteria or related species, or which are derived therefrom and have been modified. The DNA binding domain of the TAL effector may comprise a highly conserved sequence, e.g. of about 33-34 amino acids, with the exception of the 12th and 13th amino acids which are highly variable (Repeat Variable Diresidue or RVD) and typically show a strong correlation with specific nucleotide recognition. On the basis of this principle, DNA binding domains may be engineered by selecting a combination of repeat segments containing Repeat Variable Diresidue corresponding to a target gene DNA sequence. The TALEN DNA cleavage domain may be derived from suitable nucleases. For example, the DNA cleavage domain from the FokI endonuclease or from FokI endonuclease variants may be used to construct hybrid nucleases. TALENs may preferably be provided as separate entities due to the peculiarities of the FokI domain, which functions as a dimer.

In specific embodiments, the number of amino acid residues between the TALEN DNA binding domain and the FokI cleavage domain and the number of bases between the two individual TALEN binding sites may be modified or optimized according to the sequence of the construct to be inserted into the genome of a filamentous fungus, preferably *Myceliophthora thermophila*, in order to provide high levels of activity. TALENs or TALEN components may be engineered or modified in order to target any desired DNA sequence, e.g. a DNA sequence comprising a selection marker between homologous ends of a gene to be inserted into the genome of the organism. The enzymatic activity which is required for the recombination may either be provided as such, or it may be provided together with the selection cassette on the construct, leading to its removal upon the start of the nuclease activity. The engineering may be carried out according to suitable methodologies, e.g. as described in Zhang et al. (2011) Nature Biotechnol. 29: 143-148 or Reyon et al. (2012) Nature Biotechnol. 30: 460-465.

Another system for removing the marker sequences from the genome of the filamentous fungal cells, preferably *Myceliophthora thermophila* cells, is the CRISPR (clustered regularly interspaced short palindromic repeats)/Cas (CRISPR-associated) system discussed above.

In a preferred embodiment of the present invention, the homologous recombination may be carried out as described in the Examples herein below. Particularly preferred is the use of transformation cassettes comprising a split acetamidase gene from *Aspergillus nidulans* enabling growth on a nitrogen-free medium as described below.

Typically, the genetic elements may be introduced into the filamentous fungal cell, preferably the *Myceliophthora thermophila* cell, with the help of a transformation cassette or an expression cassette. In accordance with the present invention the term "transformation cassette" refers to a specific vector containing a foreign gene and having elements in addition to the foreign gene that facilitate transformation of filamentous fungal cells, preferably *Myceliophthora thermophila* cells. The term "expression cassette" refers to a specific vector containing a foreign gene and having elements in addition to the foreign gene that allow for expression of that gene in a foreign host, in particular in filamentous fungal cells, preferably in *Myceliophthora thermophila* cells.

The nucleic acid sequences leading to a decrease of CLR2 activity as defined herein may accordingly be provided on genetic elements in the form of expression cassettes or transformation cassettes as defined herein above, in particular expression cassettes or transformation cassettes which are prepared for genomic integration via homologous recombination. Also envisaged is the provision on plasmids or vectors. The terms "plasmid" and "vector" refer to an extrachromosomal element often carrying genes that are not part of the central metabolism of the cell, and usually in the form of circular double-stranded DNA fragments. More preferably, the term plasmid refers to any plasmid suitable for transformation of filamentous fungal cells, preferably *Myceliophthora thermophila* cells, known to the person skilled in the art and in particular to any plasmid suitable for expression of proteins in filamentous fungal cells, preferably *Myceliophthora thermophila* cells, e.g. plasmids which are capable of autonomous replication in other organisms, preferably in bacteria, in particular *E. coli*, and which can be prepared, e.g. digested, for genomic insertional transformation of filamentous fungal cells, preferably *Myceliophthora thermophila* cells.

The functional disruption or deletion of genetic elements, as well as the introduction of point mutations in these genetic elements as outlined above may be performed by any suitable approach known to the skilled person, e.g. by homologous recombination as described herein above.

In further specific embodiments, the inactivation may be due to specific inactivation processes taking place on the level of RNA transcripts. Such inactivation may be due to sequence specific recognition of RNA transcripts of the clr2 gene and a subsequent degradation of these transcripts. For this approach RNA interference or antisense methods as known from higher eukaryotes may be used. The RNAi pathway in filamentous fungi is discussed for example in Liu (2010) Cell Mol. Life Sci. 67(22): 3849-3863. Accordingly, the present invention envisages the provision of siRNA species which are specific for the clr2 transcript.

The term "siRNA" refers to a particular type of antisense-molecules, i.e. small inhibitory RNA double strands that induce the RNA interference (RNAi) pathway. These molecules can vary in length and may be between about 18-28 nucleotides in length, e.g. have a length of 18, 19, 20, 21, 22, 23, 24, 25, 26, 27 or 28 nucleotides.

Preferably, the molecule has a length of 21, 22 or 23 nucleotides. The siRNA molecule according to the present invention may contain varying degrees of complementarity to their target mRNA, preferably in the antisense strand. siRNAs may have unpaired overhanging bases on the 5' or 3' end of the sense strand and/or the antisense strand. The term "siRNA" includes duplexes of two separate strands, as well as single strands that can form hairpin structures comprising a duplex region. Preferably the siRNA may be double-stranded wherein the double-stranded siRNA molecule comprises a first and a second strand, each strand of the siRNA molecule is about 18 to about 23 nucleotides in length, the first strand of the siRNA molecule comprises a nucleotide sequence having sufficient complementarity to the target RNA via RNA interference, and the second strand of said siRNA molecule comprises a nucleotide sequence that is complementary to the first strand. The production of such interference molecules may further be controlled and regulated via the production of siRNAs from regulable promoters.

In yet another specific embodiment of the present invention, the inactivation may be due to specific inactivation processes taking place on the level of proteins or enzymes. This inactivation may be due to a binding of specifically binding molecules such as small molecules to the CLR2 protein.

A "small molecule" in the context of the present invention refers to a small organic compound that is preferably biologically active, i.e. a biomolecule, but is preferably not a polymer. Such an organic compound may have any suitable form or chemical property. The compound may be a natural compound, e.g. a secondary metabolite, or an artificial compound, which has been designed and generated de novo. In one embodiment of the present invention a small molecule is capable of blocking the binding of CLR2 to the promoter region of a target gene, or is capable of blocking the transcriptional activity of CLR2. For example, a small molecule may bind to CLR2 and thereby induce a tight or irreversible interaction between the molecule and the protein, thus leading to a loss or decrease of the normal (wild-type) function of the protein or enzyme, e.g. if the enzymatic core or binding pocket is involved. Methods and techniques for the identification and preparation of such small molecules as well as assays for the testing of small molecules are known to the person skilled in the art and also envisaged herein.

In specific embodiments the genetic elements may comprise microbial expression systems. Such expression systems and expression vectors may contain regulatory sequences that direct high level expression of foreign proteins.

In a preferred embodiment of the present invention a genetically modified organism as defined herein above, e.g. an organism which comprises a modification to decrease or eliminate the activity of CLR2 in said organism, e.g. an organism from whose genome the endogenous nucleic acid molecule encoding CLR2 is deleted, or in which the coding sequence of clr2 is operably linked to a weak promoter, is capable of accumulating more recombinant polypeptide than a control organism without the genetic modification of the present invention. The term "control organism" as used herein refers to an organism with the same or a very similar genetic background as the organism which is used as starting organism for the genetic modification and which is genetically modified to express the recombinant polypeptide. Preferably, a control organism may be an organism used for the genetic modifications as described herein.

The present invention leads to an increase in the purity of the recombinant polypeptide produced by the genetically modified filamentous fungus compared to a filamentous fungus which is not genetically modified to decrease or eliminate the CLR2 activity. The term "increased purity" means that the amount of the recombinant polypeptide is at least about 50% of the total protein produced by the filamentous fungus, preferably at least 55 or 60% of the total protein produced by the filamentous fungus, more preferably at least 65% or 70% of the total protein produced by the filamentous fungus and most preferably at least 75%, 77% or 80% of the total protein produced by the filamentous fungus.

If the recombinant polypeptide is an enzyme, the increase in purity of the recombinant polypeptide leads to an increase in the specific enzyme activity per amount of total protein produced by the genetically modified filamentous fungus which specific enzyme activity may be expressed in units of enzyme activity per gram of protein. Hence, the purity of the recombinant protein can be measured by determining the specific activity of the recombinant enzyme. The specific enzyme activity per amount of total protein is increased by at least about 30% or 40%, preferably by at least 50%, 60% or 70%, more preferably by at least 70%, 80% or 90%, and most preferably by at least 100%, 120% or 150% wherein the enzyme activity is determined after the genetically modified filamentous fungus has been cultured for a period of 80 to 240 hours.

The genetic modification to decrease or eliminate the activity of CLR2 as described herein may lead to an increase of the amount of recombinant polypeptide produced or accumulated by the organism compared to the amount in an organism not having said genetic modification decreasing or eliminating CLR2 activity which organism is cultured under the same conditions. The increase may, in specific embodiments, depend on the genetic background of the organism in which the modifications are performed, and/or on the number of modifications, and/or the technique by which the activity is decreased or eliminated and/or other factors such as the culture conditions, culture medium conditions etc., or on a combination of any of the above parameters and factors. In specific embodiments, the increase of the amount of recombinant polypeptide produced or accumulated by the organism may be at least 0.3%, 0.5%, 0.7%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300% or more than 300% compared to an organism not having the genetic modification of the present invention to decrease or eliminate CLR2 activity, but being genetically modified to express the recombinant polypeptide, which organism is cultured under the same conditions as the genetically modified organism of the present invention.

The determination of the production or accumulation of the recombinant polypeptide and thus also of the increase of this production in the modified organisms in comparison to control organisms may be performed as described above.

In a further embodiment the present invention relates to a genetically modified organism as defined herein above or a method for the production of a recombinant polypeptide using said genetically modified organism, wherein said organism comprises a genetic modification which leads to a decrease or elimination of the activity of CLR2, preferably as defined in detail herein above and a genetic modification to express the recombinant polypeptide, and wherein said organism comprises at least one additional genetic modification.

The term "additional genetic modification" as used herein refers to any further genetic or biochemical modification of an organism as defined above, e.g. a modification such as a deletion of a gene or genomic region, the over-expression of a gene or gene fragment etc. in addition to the genetic modification of the present invention. This additional genetic modification may already be present in the organism which is genetically modified according to the present invention or may be introduced after the organism has been genetically modified according to the present invention.

In a preferred embodiment, the additional genetic modification of an organism as defined above concerns elements which have an influence on the purity and/or amount of said recombinant polypeptide. Such elements include transcription factors involved in the expression of genes which are highly expressed in filamentous fungi, preferably in *Myceliophthora thermophila*, and proteases which are involved in the degradation of endogenous and recombinant polypeptides.

One example of such a transcription factor is XYR1 (xylanase regulator 1) which is involved in the regulation of xylanase expression (Rauscher et al. (2006) Eukaryote Cell 5(3): 447-456). Another example is CLR1 which is involved in the regulation of cellulase expression.

Proteases which can be used in the present invention include the ALP1 protease and the proteases disclosed in WO 2012/048334 A2 and WO 2013/048661 A1.

Accordingly, the additional genetic modifications may preferably be carried out with one or more of the genes xyr1, clr1 or alp1 of filamentous fungi, preferably of *Myceliophthora thermophila*.

In further preferred embodiments, the additional genetic modification may result in at least one of the following alterations: (i) the XYR1 activity is decreased or eliminated; and/or (ii) the CLR1 activity is decreased or eliminated; and/or (iii) the ALP1 activity is decreased or eliminated.

In further preferred embodiments, the activity of XYR1 is provided by a polypeptide comprising, essentially consisting of or consisting of the amino acid sequence of SEQ ID NO: 7 or functional parts or fragments thereof, or is encoded by a nucleic acid comprising, essentially consisting of or consisting of the nucleotide sequence of SEQ ID NO: 5 or 6 or functional parts or fragments thereof, or is provided by a polypeptide comprising, essentially consisting of or consisting of an amino acid having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 7 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 5 or 6 or functional parts or fragments thereof.

The sequence according to SEQ ID No. 5 is the cDNA sequence of the xyr1 gene and the sequence according to SEQ ID No. 6 is a genomic region comprising the xyr1 gene. In a preferred embodiment only the genomic region coding for XYR1 is used which corresponds to nucleotides 3001 to 6016 of SEQ ID No. 6. Hence, the above values for the percentage identity also apply to a sequence comprising nucleotides 3001 to 6016 of SEQ ID No. 6.

In further preferred embodiments, the activity of CLR1 is provided by a polypeptide comprising, essentially consisting of or consisting of the amino acid sequence of SEQ ID NO: 10 or functional parts or fragments thereof, or is encoded by a nucleic acid comprising, essentially consisting of or consisting of the nucleotide sequence of SEQ ID NO: 8 or 9 or functional parts or fragments thereof, or is provided by a polypeptide comprising, essentially consisting of or consisting of an amino acid having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 10 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 8 or 9 or functional parts or fragments thereof.

The sequence according to SEQ ID No. 8 is the cDNA sequence of the clr1 gene and the sequence according to SEQ ID No. 9 is a genomic region comprising the clr1 gene. In a preferred embodiment only the genomic region coding for CLR1 is used which corresponds to nucleotides 3001 to 5245 of SEQ ID No. 9. Hence, the above values for the percentage sequence identity also apply to the sequence comprising nucleotides 3001 to 5245 of SEQ ID No. 9.

In further preferred embodiments, the activity of ALP1 is provided by a polypeptide comprising, essentially consisting of or consisting of the amino acid sequence of SEQ ID NO: 13 or functional parts or fragments thereof, or is encoded by a nucleic acid comprising, essentially consisting of or consisting of the nucleotide sequence of SEQ ID NO: 11 or 12 or functional parts or fragments thereof, or is provided by a polypeptide comprising, essentially consisting of or consisting of an amino acid sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 13 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 11 or 12 or functional parts or fragments thereof.

The sequence according to SEQ ID No. 11 is the cDNA sequence of the alp1 gene and the sequence according to SEQ ID No. 12 is a genomic region comprising the alp1 gene. In a preferred embodiment only the genomic region coding for ALP1 is used which corresponds to nucleotides 5001 to 6547 of SEQ ID No. 12. Hence, the above values for the percentage identity also apply to a sequence comprising nucleotides 5001 to 6547 of SEQ ID No. 12.

The term "functional parts or fragments thereof" as used in the context of sequences described herein refers to contiguous sections or parts of the polypeptide and the encoding nucleotide sequence, which are able to provide essentially the same activity as the full-length polypeptide or which encode a polypeptide which is able to provide essentially the same activity as the full-length polypeptide, respectively. The activity of the functional part or fragment of a polypeptide is at least 10%, 20%, 30% or 40%, preferably at least 45%, 50%, 55% or 60%, more preferably at least 65%, 70%, 75% or 80%, even more preferably at least 82%, 85%, 88% or 90% and most preferably at least 92%, 94%, 96%, 98% or 100% of the activity of the full-length polypeptide. If the polypeptide is a transcriptional activator such as CLR1, CLR2 and XYR1, the functional part or fragment of this polypeptide has essentially the same transcription-activating activity as the full-length polypeptide. If the polypeptide is a protease such as ALP1, the functional part or fragment of this polypeptide has essentially the same proteolytic activity as the full-length polypeptide.

In specific embodiments, the CLR2 activity and the XYR1 activity may be decreased or eliminated by any of the techniques discussed above, preferably by homologous recombination.

In other specific embodiments, the CLR2 activity and the ALP1 activity may be decreased or eliminated by any of the techniques discussed above, preferably by homologous recombination.

In other specific embodiments, the CLR2 activity, the ALP1 activity and the XYR1 activity may be decreased or eliminated by any of the techniques discussed above, preferably by homologous recombination.

In other specific embodiments, the CLR2 activity, the CLR1 activity and the XYR1 activity may be decreased or eliminated by any of the techniques discussed above, preferably by homologous recombination.

In other specific embodiments, the CLR2 activity, the CLR1 activity, the ALP1 activity and the XYR1 activity may be decreased or eliminated by any of the techniques discussed above, preferably by homologous recombination.

If the filamentous fungus, preferably *Myceliophthora thermophila*, is genetically modified to decrease or increase the activity of more than one protein by separate replicating vectors, it is desirable that each vector or plasmid has a different means of selection and should lack homology to the other constructs to maintain stable expression and prevent reassortment of elements among constructs.

The present invention further envisages the use of a nucleic acid construct for decreasing or eliminating the activity of CLR2 for increasing the purity and/or the amount of a recombinant polypeptide in a filamentous fungus expressing said recombinant polypeptide. The nucleic acid construct may be used such that the encoded CLR2 polypeptide and activity may be provided in a decreased amount or concentration in the cells. The activity of CLR2 may preferably be decreased by substituting the endogenous clr2 promoter with a weak promoter or by the deletion of the gene encoding CLR2 or a functional part thereof from the genome of the organism. Promoters and methods for the deletion of genes etc. have been described herein above.

In further specific embodiments, additional genes may be used for increasing the purity and/or amount of a recombinant polypeptide in a filamentous fungus. These genes may include clr1, xyr1, alp1 and proteases other than alp1. It is particularly preferred that clr1 is inactivated so that the CLR1 activity is decreased or eliminated; that xyr1 is inactivated so that the XYR1 activity is decreased or eliminated; and/or that alp1 and/or one or more other proteases is inactivated so that the ALP1 activity and/or the activity of one or more other proteases is decreased or eliminated. In specific embodiments, these genes may be inactivated as described herein above.

The organism may be any filamentous fungus as described herein above, preferably *Myceliophthora thermophila*. The use of a filamentous fungus and in particular *Myceliophthora thermophila* for increasing the purity and/or amount of a recombinant polypeptide may comprise the use of suitable fermentation environments, nutrition, protein extraction from the fermentation vessels etc. The present invention accordingly envisages a corresponding method for the production of a recombinant polypeptide as defined herein above. In further embodiments, the filamentous fungus may be an organism which is has been genetically modified. The genetic modification may be a modification as described herein, e.g. have a direct influence on the purity and/or amount of the recombinant polypeptide, or may have different effects, e.g. in other pathways, or concern the production of other biochemical entities in addition to the recombinant polypeptide, concern the possibilities of using certain carbon sources, concern the possibilities of using certain nitrogen sources etc., concern the stability of the genome or of genomic regions, allow for or improve steps of homologous recombination, allow for the expression of heterologous genes or promoters etc., improve culture behavior of the cells such as filamentation, mycel fragmentation, pH tolerance, density tolerance, use of salts, salt tolerance, concern the generation rate of the cells, concern the resistance towards antibiotics or any other trait which could be advantageous for the production of the recombinant polypeptide.

In a further aspect the present invention relates to the use of an organism as defined herein above, in particular a genetically modified organism comprising the above mentioned genetic modification leading to a decrease or elimination of CLR2 activity and optionally further genetic modifications such as modifications to the genes clr1, xyr1, alp1 and/or encoding proteases other than ALP1 as defined herein above, for the production of a recombinant polypeptide.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

Transformation of *Myceliophthora thermophila*

Several methods for the transformation of *M. thermophila* protoplast are described in the literature (WO 00/20555, US 2012/0005812, Verdoes et al. (2007) Industrial Biotechnology 3(1): 48-57).

Protoplasts of *M. thermophila* strains were prepared by inoculating 100 ml of a standard fungal growth media with $10^6$ spores/ml in a 250 ml shake flask for 24 h at 35° C. and 250 rpm. The mycelium was harvested by filtration through a sterile Myracloth filter (Calbiochem) and washed with 100 ml 1700 mosmol $NaCl/CaCl_2$. The washed mycelium was transferred into a 50 ml tube and weighed. 3 ml fresh prepared Caylase (Cayla, France) solution (20 mg/ml Caylase in 1700 mosmol $NaCl/CaCl_2$)) were combined with 3 g of mycelium and 15 ml of 1700 mosmol $NaCl/CaCl_2$ and mixed. The mycelium suspension was incubated at 37° C. and 70 rpm for 2-4 h until protoplasts are visible under the microscope. Harvesting of protoplasts was done by filtration through a sterile Myracloth filter into a sterile 50 ml tube. After the addition of 25 ml ice cold STC solution (1.2 M sorbitol, 50 mM $CaCl_2$, 35 mM NaCl, 10 mM Tris/HCl pH7.5) to the flow through, the protoplast were harvested by centrifugation (2500 rpm, 10 min, 4° C.). The protoplast were washed again in 50 ml STC and resuspended in 1 ml STC.

For transformation, 5-10 µg of linearized DNA (in case of co-transformation of two DNA fragments, a ratio of 1:5 was used for marker fragment and expression cassette fragment, while a ratio of 1:1 was used for the two fragments of a split marker construct), 1 µl aurintricarboxylic acid (ATA) and 100 µl of protoplast suspension were mixed and incubated for 25 min at room temperature. Then 1.7 ml of PEG solution (60% PEG4000 [polyethylenglycol], 50 mM $CaCl_2$, 35 mM NaCl, 10 mM Tris/HCl pH7.5) was added and mixed gently. After incubation for 20 min at room temperature, the tube was filled with STC solution, centrifuged (10 min, 4° C., 2500 rpm) and the supernatant discarded. The pellet was re-suspended in the remaining STC and plated on selective media plates (composition depends on the used marker) as known in the art. After incubation of the plates for 3-6 days at 37° C., transformants were picked and re-streaked on selective media.

Selective Media Plates

Enriched minimal medium without additional nitrogen source supplemented with 20 mM acetamide is used to select positive transfomants when using amdS as selection marker. If the pyr4 or pyr5 gene is used as selection marker, enriched minimal medium without uridine and uracil is used to select positive transformants. If the nourseothricin resistance selection marker is used, the medium contains nourseothricin. Selection of clones with lost acetamidase functionality is carried out by cultivation on FAC-medium agar plates.

Enriched Minimal Media for amdS selection:

| | |
|---|---|
| Glucose | 10 g/l |
| Sucrose | 229.3 g/l |
| $Mg_2SO_4$ | 0.24 g/l |
| KCl | 0.52 g/l |
| $KH_2PO_4$ | 0.22 g/l |
| $CuSO_4*5H_2O$ | 1.6 mg/l |
| $FeSO_4*7H_2O$ | 5 mg/l |
| $ZnSO_4*7H_2O$ | 22 mg/l |
| $MnSO_4*H_2O$ | 4.3 mg/l |
| $CoCl_2*6H_2O$ | 1.6 mg/l |
| $Na_2MoO_4*2H_2O$ | 1.5 mg/l |
| $H_3BO_3$ | 11 mg/l |
| EDTA | 50 mg/l |
| Uracil | 1.12 g/l |
| Uridine | 2.44 g/l |
| CsCl | 2.52 g/l |
| Penicillin | 20 mg/l |
| Streptomycin | 50 mg/l |
| Acetamide | 0.6 g/l |
| Agar | 16 g/l |

Enriched Minimal Media for pyr4 or pyr5 selection:

| | | |
|---|---|---|
| Glucose | 10 g/l | |
| Sucrose | 229.3 g/l | |
| $Mg_2SO_4$ | 0.24 g/l | |
| KCl | 0.52 g/l | |
| $KH_2PO_4$ | 0.22 g/l | |
| $NaNO_3$ | 1.4 g/l | |
| $CuSO_4*5H_2O$ | 1.6 mg/l | |
| $FeSO_4*7H_2O$ | 5 mg/l | |
| $ZnSO_4*7H_2O$ | 22 mg/l | |
| $MnSO_4*H_2O$ | 4.3 mg/l | |
| $CoCl_2*6H_2O$ | 1.6 mg/l | |
| $Na_2MoO_4*2H_2O$ | 1.5 mg/l | |
| $H_3BO_3$ | 11 mg/l | |
| EDTA | 50 mg/l | |
| Penicillin | 20 mg/l | |
| Streptomycin | 50 mg/ | |
| Casaminoacids | 0.1% (w/v) | |
| Agar | 16 g/l | set pH to 6.5 |

Enriched Minimal Media for nourseothricin selection:

| | | |
|---|---|---|
| Glucose | 10 g/l | |
| Sucrose | 229.3 g/l | |
| $Mg_2SO_4$ | 0.24 g/l | |
| KCl | 0.52 g/l | |
| $KH_2PO_4$ | 0.22 g/l | |
| $NaNO_3$ | 1.4 g/l | |
| $CuSO_4*5H_2O$ | 1.6 mg/l | |
| $FeSO_4*7H_2O$ | 5 mg/l | |
| $ZnSO_4*7H_2O$ | 22 mg/l | |
| $MnSO_4*H_2O$ | 4.3 mg/l | |
| $CoCl_2*6H_2O$ | 1.6 mg/l | |
| $Na_2MoO_4*2H_2O$ | 1.5 mg/l | |
| $H_3BO_3$ | 11 mg/l | |
| EDTA | 50 mg/l | |
| Uracil | 1.12 g/l | |
| Uridine | 2.44 g/l | |
| CsCl | 2.52 g/l | |
| Penicillin | 20 mg/l | |
| Streptomycin | 50 mg/l | |
| Casaminoacids | 0.1% (w/v) | |
| Nourseothricin | 100 mg/l | |
| Agar | 16 g/l | set pH to 6.5 |

FAC-Medium for selection of amdS marker removal

| | |
|---|---|
| Glucose | 10 g/l |
| Sucrose | 229.3 g/l |
| $Mg_2SO_4$ | 0.24 g/l |
| KCl | 0.52 g/l |
| $KH_2PO_4$ | 0.22 g/l |
| $CuSO_4*5H_2O$ | 1.6 mg/l |
| $FeSO_4*7H_2O$ | 5 mg/l |
| $ZnSO_4*7H_2O$ | 22 mg/l |
| $MnSO_4*H_2O$ | 4.3 mg/l |
| $CoCl_2*6H_2O$ | 1.6 mg/l |
| $Na_2MoO_4*2H_2O$ | 1.5 mg/l |
| $H_3BO_3$ | 11 mg/l |
| EDTA | 50 mg/l |
| Uracil | 1.12 g/l |
| Uridine | 2.44 g/l |
| CsCl | 2.52 g/l |
| Penicillin | 20 mg/l |
| Streptomycin | 50 mg/ |
| Urea | 0.3 g/l |
| Fluoracetamide | 5 g/l |
| Agar | 16 g/l |

Selection for amdS Marker Removal

Positive tested clones carrying the correct integration of the amdS gene flanked by the repeated 5'-sequences for marker removal at the deleted gene locus were selected for amdS marker removal. Using the amdS-flanking 5'-sequences, the amdS knock-out cassettes will be removed by homologous recombination leaving scarless adjacent non-coding 5'- and 3'-sequences of the deleted gene locus. Selection of clones with lost acetamidase functionality is carried out by cultivation on FAC-medium agar plates. Acetamidase expressing clones will convert fluoracetamide into the toxic compound fluoroacetate that prevents growth. Clones able to grow on FAC-medium were tested for loss of growth on Enriched Minimal Media for amdS selection. Positive tested clones were analyzed by PCR for the correct recombination event at the deleted gene locus leading to the loss of the amdS marker. Clones with the correct marker removal were selected for further knock-outs using the amdS split marker constructs.

Example 2

Generation of Deletion Constructs

The split-marker method, known in the art, was used for the production of knock-out mutants of the different genes. 1000-2000 bp of the 5' and 3' homologous regions ("flank_A" and "flank_B") of the gene to be disrupted were amplified by PCR from the genomic DNA of *Myceliophthora thermophila* and cloned into plasmids carrying a part of the split marker gene using standard methods known in the art. Each marker fragment is not functional on its own, but becomes functional after recombination of the overlapping part of the two marker fragments split on the two plasmids. The amdS gene encoding the acetamidase from *Aspergillus nidulans* which is well known in the art was used as a selection marker.

Optionally, the deletion plasmid carrying the C-terminal part of the amdS split marker was constructed in a slightly different way. Instead of flank_B, which targets the deletion cassette, the plasmid contained flank_A and flank_B in direct contact. The usage of this construct led to a duplication of flank_A in the genome after targeted homologous integration of both parts of the split marker system. In this case, the amdS marker cassette could optionally be removed via a second homologous recombination step and selection with fluoracetamide as known in the art.

The general amdS split marker deletion plasmids pDB40-amdS-5' (SEQ ID NO: 16) and pDB41-amdS-3' (SEQ ID NO: 17) were cloned based on the vector pH305 (SEQ ID NO: 18) and pGBAAS-1 (SEQ ID No. 19) as template for the PCR amplification of the amdS marker fragments using standard molecular biology techniques known in the art.

Construction of amdS Split Marker Vector Construct

Using standard techniques known in the art, approx. 1.8 kb containing the *Aspergillus nidulans* gpdA-Promoter and the N-terminal part of the amdS split marker were PCR amplified using the plasmid pGBAAS-1 (for construction details see WO 98/46772 and EP 0 635 574 (pGBLA50 is identical to pGBAAS-1)) (SEQ ID NO: 19) as a template and cloned into the plasmid pH305 (SEQ ID NO: 18). The resulting plasmid pDB40-amdS-5' (SEQ ID NO: 16) contained the gpdA-Promoter from bases 142-1044 and the N-terminal part of the amdS split marker from bases 1045-1959.

In the analogous way, approx. 1.7 kb containing the C-terminal part of C-terminal amdS split marker and the amdS terminator were PCR amplified using the plasmid pGBAAS-1 (SEQ ID NO: 19) as a template and cloned into the plasmid pH305 (SEQ ID NO: 18). The resulting plasmid pDB41-amdS-3' (SEQ ID NO: 17) contained the C-terminal part of the amdS split marker from bases 321-1626 and the amdS terminator from bases 1627-1976.

clr2 Deletion Plasmids

Using standard techniques known in the art, approx. 1.6 kb of the 5'-flanking region (clr2_flank_A) of the clr2 gene were PCR amplified and cloned into the plasmid pDB40-amdS-5' (SEQ ID NO: 16) carrying the gpdA-promotor and N-terminal part of the amdS split marker. The resulting plasmid pMT121-Dclr2-A (SEQ ID NO: 20) contained clr2_flank_A from bases 5-1557 and the marker fragment containing the gpda-promoter and the 5'-amdS sequence from bases from bases 1565-3382.

In an analogous way, approx. 1.7 kb of the 3'-flanking region (clr2_flank_B) of the clr2 gene were PCR amplified and cloned into the plasmid pDB41-amdS-3' (SEQ ID NO: 17) carrying the C-terminal part and the terminator region of the amdS split marker. The resulting plasmid pMT147-Dclr2-B (SEQ ID NO: 21) contained the marker fragment from bases 176-1831 and clr2_flank_B from bases 1867-3539. Also a second version of the deletion plasmid carrying the C-terminal part of the amdS split marker, allowing the later removal of the marker, was constructed. Using standard PCR fusion technology with overlapping primers, an approx. 3.2 kb clr2_flank_A/flank_B fusion fragment was amplified using the PCR fragments of the 5'- and the 3'-flanking regions as template and cloned into the plasmid pDB41-amdS-3' (SEQ ID NO: 17) carrying the C-terminal part and the terminator region of the amdS split marker. The resulting plasmid pMT189_Dclr2_AB (SEQ ID NO: 22) contained the marker fragment from bases 153-1808 and clr2_flank_A/flank_B from bases 1841-5072.

All plasmids were digested with SwaI to remove the vector backbone and the fragments containing the deletion cassettes were isolated from an agarose gel. Only the isolated DNA fragments were later used for transformation.

Xyr1 Deletion Plasmids

Using standard techniques known in the art, approx. 1.5 kb of the 5'-flanking region (xyr_flank_A) of the xyr1 gene were PCR amplified and cloned into the plasmid pDB40-amdS-5' (SEQ ID NO: 16) carrying the gpdA-promotor and N-terminal part of the amdS split marker. The resulting plasmid pDB45_Dxyr1_A (SEQ ID NO: 23) contained xyr1_flank_A from bases 66-1593 and the marker fragment from bases 1601-3418.

In an analogous way, approx. 1.5 kb of the 3'-flanking region (xyr1_flank_B) of the xyr1 gene were PCR amplified. Using standard PCR fusion technology with overlapping primers, an approx. 3 kb xyr1_flank_A/flank_B fusion fragment was amplified using the PCR fragments of the 5'- and the 3'-flanking regions as template and cloned into the plasmid pDB41-amdS-3' (SEQ ID NO: 17) carrying the C-terminal part and the terminator region of the amdS split marker. The resulting plasmid pDB58_Dxyr1_AB (SEQ ID NO: 24) contained the marker fragment from bases 321-1976 and xyr1_flank_A/flank_B from bases 2055-5100.

Both plasmids were digested with SwaI to remove the vector backbone and the fragments containing the deletion cassettes were isolated from an agarose gel. Only the isolated DNA fragments were later used for transformation.

Alp1 Deletion Plasmid

The plasmid pDalp1-amdS (SEQ ID NO: 25) was used for the deletion of a major protease (ALP1) in the supernatant of *M. thermophila*. A detailed description of the plasmid is provided in WO 2010/107303 and Visser et. al. (2011) Industrial Biotechnology 7(3): 214-223. The plasmid contained the amdS marker gene, flanked by a short repetitive DNA fragment derived from the cbh locus. This direct repeat could be used for the removal of the amdS gene via homologous recombination and selection with fluoracetamide as known in the art. This deletion marker cassette is flanked by larger genomic fragments (1.6 and 3.6 kb) of the alp1 gene for a targeted integration at the alp1 locus. Transformation with this deletion cassette will remove 0.7 kb of the 5'-coding region and 0.2 kb of the 5'-UTR of the alp1 gene and will therefore inactivate the protease.

The plasmid was digested with HindIII and NotI to remove the vector backbone. The fragment containing the deletion cassettes was isolated from an agarose gel and used for transformation.

Ku70 Deletion Plasmids

Using standard techniques known in the art, approx. 1 kb of the 5'-flanking region (ku70_flank_A) of the ku70 gene (Identifier XP_003660551.1) were PCR amplified and cloned into the plasmid pDB40-amdS-5' (SEQ ID NO: 16) carrying the gpdA-promotor and N-terminal part of the amdS split marker. The resulting plasmid pMT123-Dku70-A (SEQ ID NO: 26) contained ku70_flank_A from bases 269-1291 and the marker fragment containing the gpda-promoter and the 5'-amdS sequence from bases from bases 1299-3116.

In an analogous way, approx. 1.1 kb of the 3'-flanking region (ku70_flank_B) of the ku70 gene were PCR amplified. Using standard PCR fusion technology with overlapping primers, an approx. 2.1 kb ku70_flank_A/flank_B fusion fragment was amplified using the PCR fragments of the 5'- and the 3'-flanking regions as template and cloned into the plasmid pDB41-amdS-3' (SEQ ID NO: 17) carrying the C-terminal part and the terminator region of the amdS split marker. The resulting plasmid pMT124_Dku70_AB (SEQ ID NO: 27) contained the marker fragment from bases 366-2021 and ku70_flank_A/flank_B from bases 2015-4150.

All plasmids were digested with SwaI to remove the vector backbone and the fragments containing the deletion cassettes were isolated from an agarose gel. Only the isolated DNA fragments were later used for transformation.

Ctr1 Deletion Plasmids

Using standard techniques known in the art, approx. 1.3 kb of the 5'-flanking region (clr1_flank_A) of the clr1 gene were PCR amplified and cloned into the plasmid pDB40-amdS-5' (SEQ ID NO: 16) carrying the gpdA-promoter and N-terminal part of the amdS split marker. The resulting plasmid pMT122-Dclr1-A (SEQ ID NO: 36) contained clr1_flank_A from bases 95-1378 and the marker fragment including the gpda-promoter and the 5'-amdS sequence from bases 1389-3206.

In an analogous way, approx. 1.3 kb of the 3'-flanking region (clr1_flank_B) of the clr1 gene were PCR amplified and cloned into the plasmid pDB41-amdS-3' (SEQ ID NO: 17) carrying the C-terminal part and the terminator region of the amdS split marker. The resulting plasmid pMT120-Dclr1-B (SEQ ID NO: 37) contained the marker fragment from bases 3637-5292 and the clr1_flank_B from bases 6-1260 and.

The plasmids were digested with SwaI to remove the vector backbone and the fragments containing the deletion cassettes were isolated from an agarose gel. Only the isolated DNA fragments were later used for transformation.

Example 3

Generation of Enzyme Expression Cassettes
a) manT Expression Plasmid

The codon adapted synthetic gene (GeneArt, ThermoFisher Scientific Inc., USA) manT (SEQ ID No. 28) encodes for an engineered and truncated variant of a mannanase (SEQ ID No. 29) originally derived from *Trichoderma reesei*, which lacks the CBM domain and where the native signal peptide is replaced by the signal peptide from a cellulase of *M. thermophila*.

For the overexpression of the mannanase manT the general expression vector pPchi(1.8)-Tcbh1_NotI was used. The plasmid uses the promotor of the chi1 gene and the terminator of the cbh1 gene from *M. thermophila* to drive the expression of the gene of interest. A detailed description of the plasmid is given in WO 2010/107303. Using standard cloning techniques, the manT expression plasmid pChi1-manT (SEQ ID NO: 30) was constructed. The plasmid contained the promotor sequence Pchi from bases 6871-1813, the manT coding sequence including the signal sequence from bases 1815-2930 and the cbh1 terminator sequence from bases 2938-3961.

The plasmid was digested with SmaI and NotI to remove the vector backbone and the fragment containing the manT expression cassette was isolated from an agarose gel. Only the isolated DNA fragment was later used for transformation.

b) Phytase Expression Plasmid

A synthetic gene (GeneArt, ThermoFisher Scientific Inc., USA) (SEQ ID NO: 31) encoding a synthetic phytase from bacterial origin (disclosed in WO 2012/143862 as phytase PhV-99; SEQ ID NO. 32) was used for the construction of a phytase expression plasmid. For the secretion of the phytase, a signal sequence encoding for a signal peptide derived from *M. thermophila* was added to the mature sequence of the phytase. A promotor sequence amplified from the upstream region of the TEF (elongation factor 1-alpha) encoding gene and a terminator sequence amplified from the downstream region of the Cbh1 encoding gene from *M. thermophila* were used as regulatory elements to drive the expression of the phytase. Using standard PCR fusion and cloning techniques, the expression plasmid pMT873 (SEQ ID NO: 33) was constructed based on the *E. coli* standard cloning vector pBSK+(colE1 origin, amp resistance, lacZ for blue/white screening). The plasmid contained the promotor sequence Ptef (promotor of the elongation factor 1-alpha) from bases 255-2733, the phytase including a signal sequence from bases 2734-4076 and the cbh1 terminator sequence from bases 4077-5070.

The plasmid was digested with EcoRI, SacI and XhoI to remove the vector backbone and the fragment containing the phytase expression cassette was isolated from an agarose gel. Only the isolated DNA fragment was later used for transformation.

Example 4

Generation of Selection Marker Expression Cassettes

CloneNat Marker Plasmid

The synthetic gene cassette PtrpC-Pcnat1 was assembled from synthetic oligonucleotides and/or PCR products by the GENEART AG (Regensburg, Germany) (SEQ ID NO: 34). The cassette contains the *Streptomyces noursei* nat1 gene (Krugel et al. (1993) Gene 127: 127-131), codon optimized for filamentous fungi, under the control of the trpC promoter of *Aspergillus nidulans* and is flanked by FRT sites that can be used for FLP-mediated recombination. The fragment was cloned into standard plasmid MA-RQ (GENEART AG, Regensburg, Germany) using SfiI/SfiI cloning sites. This plasmid contains the Col E1 origin of replication and the ampicillin resistance gene. The plasmid contains the *A. nidulans* promoter sequence trpC (indole-3-glycerol-phosphate synthase) from bases 370-787 and the nourseothricin acetyltransferase including terminator region from bases 787-1410. The plasmid was digested with SacI and KpnI to remove the vector backbone and the fragment containing the nourseothricin acetyltransferase expression cassette was isolated from an agarose gel. Only the isolated DNA fragment was later used for transformation.

Example 5

Construction of a manT Expressing *M. thermophila* Strain

The *M. thermophila* host strain UV18 #100.f Δpyr5 Δalp1 from the C1 lineage, a strain with uracil auxotrophy and reduced protease activity, as described in detail in WO 2008/073914, was co-transformed as described in example 1 with the SmaI and NotI digested and isolated manT (see example 3) expression construct from plasmid pChi1-manT (SEQ ID NO: 30) and an isolated pyr5 marker construct. The pyr5 marker fragment was isolated from the plasmid pMBL71[pyr5] (SEQ ID NO: 35), a genomic library clone constructed from C1 genomic DNA and a standard *E. coli* cloning vector. The 8 kb BglII fragment contained the pyr5 gene including promotor and terminator sequences.

The transformants were incubated for 3-6 days at 37° C. on Enriched Minimal Media for pyr4/5 selection to select for restored uracil prototrophy by complementing the pyr5 deletion with the co-transformed pyr5 marker as known in the art. Colonies were re-streaked and checked for the co-integration of the manT expression cassette using PCR with primer pairs specific for the manT expression cassette as known in the art. A transformant tested positive for the manT expression construct was selected and named HC_manT.

Deletion of clr-2

Different *M. thermophila* host strains were co-transformed as described in example 1 with the two isolated SwaI fragments from plasmids pMT121-Dclr2-A (SEQ ID NO. 20) and pMT147-Dclr2-B (SEQ ID No. 21) in a ratio of 1:1. Enriched Minimal Media for amdS selection was used for incubation. After re-streaking, the transformants were analyzed by PCR for the correct integration of the deletion cassettes in the targeted clr-2 locus and for the disappearance of the intact clr-2 gene. Positive tested clones were selected for further characterization.

In that way, clr-2 was deleted in the *M. thermophila* C1 strains UV18-25, UV18 #100.f (construction described in detail in WO 2008/073914), UV18 #100f Δpyr5 Δalp1 Δku70 and HC_manT, creating the strains UV18-25_Δclr2 #α, UV18 #100.f Δclr2 #α, UV18 #100f Δpyr5 Δalp1 Δku70 Δclr2 #α and HC_manT_Δclr2 #α.

In an analogous way, different C1 host strains were co-transformed as described in example 1 with the two isolated SwaI fragments from plasmids pMT121-Dclr2-A (SEQ ID NO. 20) and pMT189_Dclr2_AB (SEQ ID No. 22) in a ratio of 1:1 to allow the later removal of the marker. Enriched Minimal Media for amdS selection was used for incubation. After re-streaking, the transformants were analyzed by PCR for the correct integration of the deletion cassettes in the targeted clr2 locus and for the disappearance of the intact clr2 gene. Positive tested clones were selected for further characterization.

In that way, clr2 was deleted in the *M. thermophila* C1 strains UV18-25, UV18 #100.f (construction described in detail in WO 2008/073914), UV18 #100f Δpyr5 Δalp1 Δku70 and HC_manT, creating the strains UV18-25_Δclr2 #β, UV18 #100.f Δclr2 #β, UV18 #100f Δpyr5 Δalp1 Δku70 Δclr2 #β and HC_manT_Δclr2 #β.

Deletion of ku70

Strains with impaired non-homologous end joining (NHEJ) repair system have higher rates of homolgous recombination and could be obtained by deletion of Ku70. Ku70 deletion mutants of the host strain *M. thermophila* are obtainable by co-transformation with the two isolated SwaI fragments from plasmids pMT123-Dku70-A (SEQ ID No. 26) and pMT124_Dku70_AB (SEQ ID NO. 27) in a ratio of 1:1. Enriched Minimal Media for amdS selection was used for incubation. After re-streaking, the transformants could be analyzed by PCR for the correct integration of the deletion cassettes in the targeted ku70 locus and for the disappearance of the intact ku70 gene. Positive tested clones are selected for removal of the amdS marker gene cassette by counter selection with FAC.

The marker recycled Δku70 mutant of the selected starting host strain could be used for further genetic modifications.

Deletion of xyr1

The *M. thermophila* host strain UV18 #100f Δpyr5 Δalp1 Δku70 was co-transformed as described in example 1 with the two isolated SwaI fragments from plasmids pDB45_Dxyr1_A (SEQ ID No. 23) and pDB58_Dxyr1_AB (SEQ ID NO. 24) in a ratio of 1:1 to allow the later removal of the marker. Enriched Minimal Media for amdS selection was used for incubation. After re-streaking, the transformants were analyzed by PCR for the correct integration of the deletion cassettes in the targeted xyr1 locus and for the disappearance of the intact xyr1 gene. Positive tested clones were denoted as UV18 #100f Δpyr5 Δalp1 Δku70 Δxyr1 #β and selected for further characterization as well as for marker removal.

Deletion of Clr2 in Xyr1 Knock Out Strain

The successful marker removal of the amdS selection marker from UV18 #100f Δpyr5 Δalp1 Δku70 Δxyr1 #β resulted in the *M. thermophila* strain UV18 #100f Δpyr5 Δalp1 Δku70 Δxyr1, which was co-transformed as described in example 1 with the two isolated SwaI fragments from plasmids pMT121-Dclr2-A (SEQ ID No. 20) and pMT189_Dclr2_AB (SEQ ID No. 22) in a ratio of 1:1. Enriched Minimal Media for amdS selection was used for incubation. After re-streaking, the transformants were analyzed by PCR for the correct integration of the deletion cassettes in the targeted clr2 locus and for the disappearance of the intact clr2 gene. Positive tested clones were denoted as UV18 #100f Δpyr5 Δalp1 Δku70 Δxyr1 Δclr2 #β and were selected for further characterization.

Deletion of Clr1 in Clr2 Knock Out Strains

After successful marker removal of the amdS selection marker in the *M. thermophila* strains UV18-25 Δclr2 #β, UV18 #100.f Δclr2 #β and HC_manT Δclr2 #β, the resulting *M. thermophila* strains are called UV18-25 Δclr2, UV18 #100.f Δclr2 and HC_manT Δclr2. These strains were co-transformed as described in example 1 with the two isolated SwaI fragments from plasmids pMT122-Dclr1-A (SEQ ID No. 36) and pMT120-Dclr1-B (SEQ ID No. 37) in a ratio of 1:1. Enriched Minimal Media for amdS selection was used for incubation. After re-streaking, the transformants were analyzed by PCR for the correct integration of the deletion cassettes in the targeted clr1 locus and for the disappearance of the intact clr1 gene. Positive tested clones were denoted as UV18-25 Δclr2 Δclr1 #α, UV18 #100.f Δclr2 Δclr1 #α and HC_manT Δclr2 Δclr1 #α.

Example 6

Generation of Phytase Producing *M. thermophila* Strains

For the expression of a phytase, different *M. thermophila* strains were co-transformed as described in example 1 with the EcoRI, ScaI and XhoI-digested and isolated phytase (s. example 3) expression construct from plasmid pMT873 (SEQ ID NO: 33) and an SacI and KpnI-digested and isolated nat1 marker expression construct from plasmid PtrpC-Pcnat1 (SEQ ID NO: 34). The transformants were incubated for 3-6 days at 37° C. on Enriched Minimal Media for nourseothricin selection to select for nourseothricin resistance as known in the art. Colonies were re-streaked and checked for the co-integration of the phytase expression cassette using PCR with primer pairs specific for the phytase expression cassette as known in the art. A transformant tested positive for the phytase expression construct was selected for further characterization.

Example 7

Assays for Enzyme Activity a) Phytase Activity Assay

The phytase activity is determined in microtiter plates. The phytase containing supernatant is diluted in reaction buffer (250 mM Na acetate, 1 mM $CaCl_2$, 0.01 Tween 20, pH 5.5 such that the measurement stays within the linear range of the assay. 10 µl of the enzyme solution are incubated with 140 µl substrate solution (6 mM Na phytate (Sigma P3168) in reaction buffer) for 1 h at 37° C. The reaction is quenched by adding 150 µl of trichloroacetic acid solution (15% w/w). To detect the liberated phosphate, 20 µl of the quenched reaction solution are treated with 280 µl of freshly made-up color reagent (60 mM L-ascorbic acid (Sigma A7506), 2.2 mM ammonium molybdate tetrahydrate, 325 mM $H_2SO_4$), and incubated for 25 min at 50° C., and the absorption at 820 nm is subsequently determined. For the blank value, the substrate buffer on its own is incubated at 37° C. and the 10 µl of enzyme sample are only added after quenching with trichloroacetic acid. The color reaction is performed analogously to the remaining measurements. The amount of liberated phosphate is determined via a calibration curve of the color reaction with a phosphate solution of known concentration.

b) Mannanase Activity Assay

Mannanase activity was defined as liberation of reducing sugars from galactomannan as known in the art. In detail, a dilution series of mannanase containing samples in 50 mM NaOAc, 0.5 mg/mL BSA, pH 5.0 was prepared to measure at least two samples within the linear range of the assy. A 1 galactomannan carob (low viscosity, Megazyme), 50 mM NaOAc, pH 5.0 solution was prepared. 17 µl diluted enzyme, 76.5 µl galactomannnan solution and 15.3 µl buffer (250 mM NaOAc pH5.0, 0.025% Triton-X-100) were mixed and incubated for 2 h at 50° C. A sample, where the diluted enzyme is added after the incubation step and immediately before the detection step with the dinitrosalicylic acid solution served as a blank for the calculation of the mannanase activity.

Subsequent to the incubation step the amount of reducing sugar was determined as follows. One part of the galactomannan assay or a defined mannose dilution series, which was used for calibration, was mixed with one part of a solution containing 1% (w/v) dinitrosalicylic acid (DNSA), 30% (w/v) potassium sodium tartrate and 0.4 M NaOH. The mixture was incubated for 10 min at 99° C. and 5 min a 4° C. Finally the absorption was measured at 540 nm. Reducing sugar equivalents (as mannose equivalents) were calculated by plotting the absorption data for the mannose standard samples against the mannose concentration. The amount of reducing sugar equivalents for the samples was calculated using equations that were generated by appropriate curve fitting of the data for the mannose standard samples.

Example 8

Production of manT by Cultivation of M. thermophila in a Stirred Tank Reactor

Pre-cultures of M. thermophila were prepared by inoculation of 175 mL of pre-culture medium with $10^4$ spores/mL in a 1 L shaking flask and incubated for 72 h at 35° C. and 250 rpm. Alternatively, pre-cultures can be inoculated by frozen mycelial stocks of M. thermophila without any influence on process performance or protein yields. For detailed pre-culture media composition, see table 3.

TABLE 3

| pre-culture medium | |
|---|---|
| Component | Concentration [g/kg] |
| Glucose × $H_2O$ | 8.80 |
| $(NH_4)_2SO_4$ | 4.66 |
| $MgSO_4$ × 7 $H_2O$ | 0.49 |
| KCl | 0.52 |
| $CaCl_2$ × 2 $H_2O$ | 0.40 |
| $KH_2PO_4$ | 10.2 |
| Biotin stock solution (6 mg/L) | 1.0 |
| Casaminoacids | 1.0 |
| Pen/Strep solution ( 2 g/L Penicillin G/5 g/L Streptomycin) | 1.0 |
| Trace element solution | 1.0 |

TABLE 4

| Trace element solution | |
|---|---|
| Component | Concentration [g/kg] |
| EDTA | 50.0 |
| $ZnSO_4$ × 7 $H_2O$ | 20.05 |
| $H_3BO_3$ | 10.03 |
| $MnSO_4$ × $H_2O$ | 3.92 |
| $FeSO_4$ × 7 $H_2O$ | 4.56 |
| $CoCl_2$ × 6 $H_2O$ | 1.55 |
| $CuSO_4$ × 5 $H_2O$ | 1.46 |
| $Na_2MoO_4$ × $2H_2O$ | 1.37 |

Extended fed-batch cultivations were carried out in a 5 L working volume glass reactor (Sartorius BiostatB). The pre-cultures were aseptically transferred to the stirred tank reactor. The inoculum volume typically used was 5-10% of the starting volume of 3.5 L. The media composition used for fed-batch cultivation is given in table 5.

| Component | Concentration [g/kg] |
|---|---|
| $(NH_4)_2SO_4$ | 10.1 |
| $MgSO_4$ × 7 $H_2O$ | 0.53 |
| $CaCl_2$ × 2 $H_2O$ | 0.43 |
| $KH_2PO_4$ | 1.64 |
| KCl | 0.56 |
| Glucose × $H_2O$ | 26.4 |
| Trace element solution | 1.0 |
| Biotin stock solution (6 mg/L) | 1.0 |
| Pen/Strep solution ( 2 g/L Penicillin G/5 g/L Streptomycin) | 1.0 |
| Antifoam Adekanol LG109 | 1.0 |

Cultivations were performed at a temperature of 38° C., initial stirrer speed of 300 rpm, gassing with air, 1 vvm (volume air per volume broth and minute). DOT (Dissolved oxygen tension) was controlled at >20% by adjusting the stirrer speed. The pH can be varied between pH 6.0 and pH 6.7 and was controlled using 25% $NH_4OH$ solution. Feeding of 50% (w/w) glucose solution started at the end of the of batch phase when the pH increased up to pH=7.0. The feeding rate was set to 3-5 g/L/h calculated for the initial starting volume.

Broth samples were withdrawn throughout the fermentation. Cell free supernatant was obtained by filtration of the broth with 0.22 μm filters and was used to analyze protein concentrations and mannanase activities. Protein concentrations were determined using the method of Bradford as known in the art with bovine serum albumin as the standard. Mannanase activity was determined as described above.

As can be seen in FIG. 1 deletion of clr2 provides fermentation broth with mannanase of higher purity (higher specific activity) compared to the parental strain. The specific ManT activities produced in the cultivations of the HC_manT_Δclr2 strain were 1.5-fold higher compared to the HC_manT parent strain and reached a maximum of 335 $U/g_{Protein}$ after 164 h.

Figure 2:
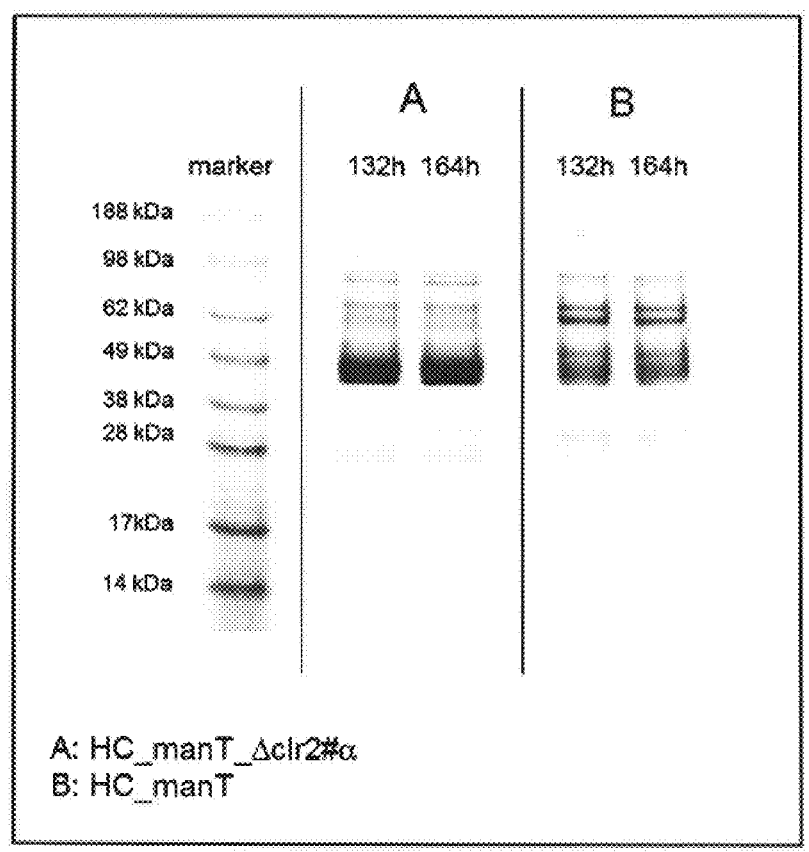
FIG. 2 shows an SDS-PAGE analysis of supernatant from fermentation samples of the clr2 deletion strain HC_manT_Δclr2 #α (A) and the parent strain HC_manT (B). Equal amounts of total protein were loaded.

Cell free supernatants from two different time points were analyzed by SDS-PAGE. The SDS-PAGE was loaded in all cases with equal amount of protein, as determined by measuring the protein concentration. The gel was stained with Coomassie Blue (FIG. 2). The clear shift to a better mannanase (broad protein band of the glycosylated mannanase at approx. 50 kDa) to background protein ratio is shown for the clr2 deletion strain.

Example 9

Analysis of Protein Expression

Generated mutant strains were fermented in small scale cultivation and the supernatants were analyzed. *M. thermophila* strains were inoculated in 1 ml cultivation medium as shown in Table 6 in a 48 well microtiter plate. The strains were fermented at 37° C. on a microtiter plate shaker at 900 rpm and 85% humidity for 3-6 days. Cell free supernatants were harvested at the end of cultivation and equal volumes of supernatants were analyzed by SDS-PAGE. The gel was stained with Coomassie Blue.

Figure 3:
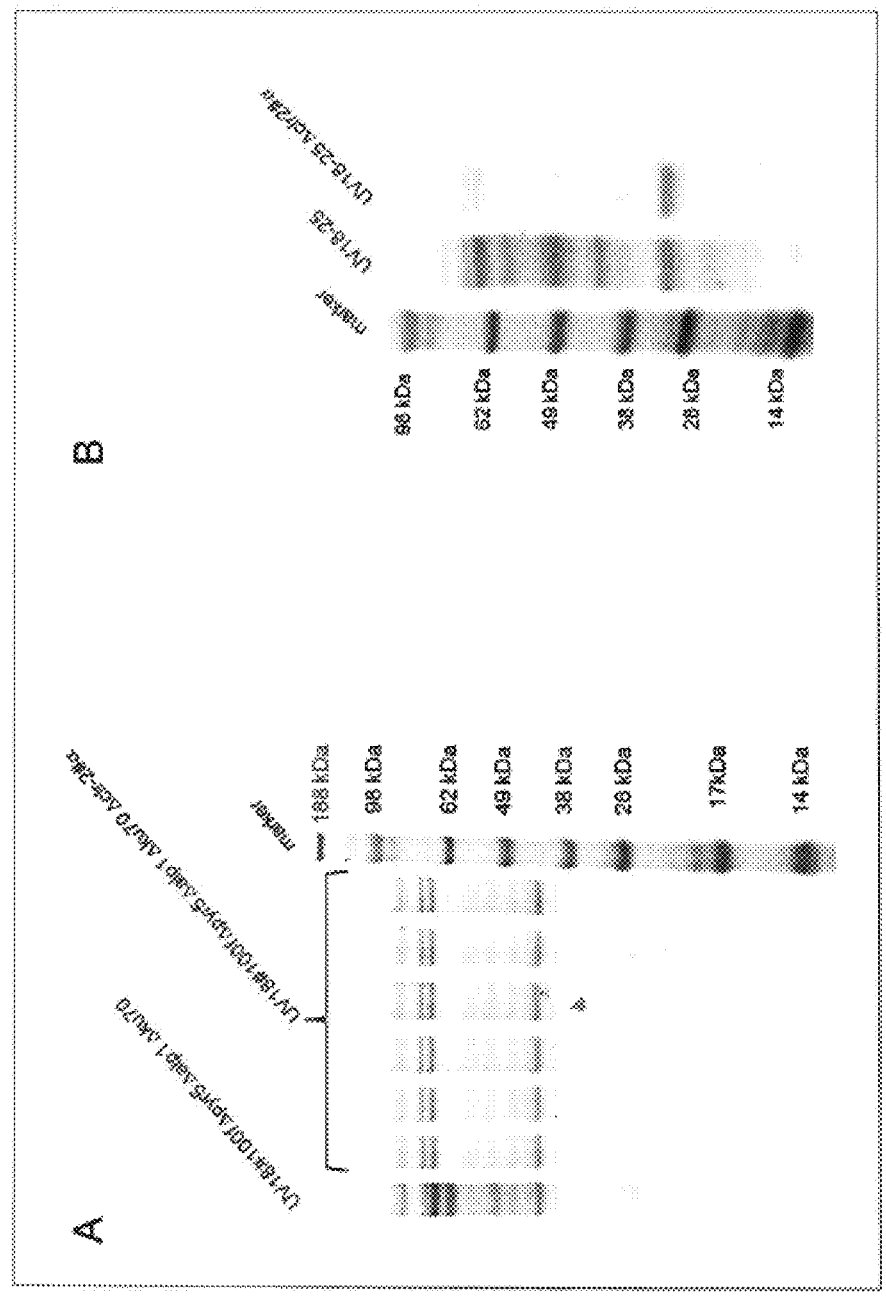
FIG. 3 shows an SDS-PAGE analysis of equal volumes of supernatant from different clr2 deletion strains in comparison to the parental strains. (A) UV18 #100f Δpyr5 Δalp1 Δku70 Δclr2 #α (deletion strain)/UV18 #100f Δpyr5 Δalp1 Δku70 (parent strain); (B) UV18-25_Δclr2 #α (deletion strain)/UV18-25 (parent strain).

It can clearly be seen, that the amount of extracellular protein is drastically reduced in the UV18 #100f Δpyr5 Δalp1 Δku70 Δclr2 #α strains compared to the corresponding parental strain UV18 #100f Δpyr5 Δalp1 Δku70 (FIG. 3A) and in the UV18-25 Δclr2 #α strain compared to the corresponding parental strain UV18-25 (FIG. 3B). This shows that the clr2 deletion strains will be better suited for the production of recombinant protein in high purity.

TABLE 6

| Cultivation medium | |
|---|---|
| Sucrose | 25 g/l |
| $Mg_2SO_4 \cdot 7H_2O$ | 0.57 g/l |
| KCl | 0.6 g/l |
| $KH_2PO_4$ | 1.76 g/l |
| $(NH_4)_2SO_4$ | 10.83 g/l |
| $CuSO_4 \cdot 5H_2O$ | 1.6 mg/l |
| $FeSO_4 \cdot 7H_2O$ | 5 mg/l |
| $ZnSO_4 \cdot 7H_2O$ | 22 mg/l |
| $MnSO_4 \cdot H_2O$ | 4.3 mg/l |
| $CoCl_2 \cdot 6H_2O$ | 1.6 mg/l |
| $Na_2MoO_4 \cdot 2H_2O$ | 1.5 mg/l |
| $H_3BO_3$ | 11 mg/l |

TABLE 6-continued

| Cultivation medium | |
|---|---|
| EDTA | 50 mg/l |
| $CaCl \cdot 2H_2O$ | 0.46 g/l |
| Biotin | 0.6 mg/l |
| Uracil | 1.12 g/l |
| MES | 42.65 g/l |
| α-cellulose | 250 mg/l |

Example 10

Deletion of Xyr1 in Clr2 Knock Out Strain

The successful marker removal of the amdS selection marker from UV18 #100f Δclr2 #β resulted in the *M. thermophila* strain UV18 #100f Δclr2 #α, which was co-transformed as described in example 1 with the two isolated SwaI fragments from plasmids pDB45_Dxyr1_A (SEQ ID No. 23) and pDB58_Dxyr1_AB (SEQ ID NO. 24) in a ratio of 1:1 to allow the later removal of the marker. Enriched Minimal Media for amdS selection was used for incubation. After re-streaking, the transformants were analyzed by PCR for the correct integration of the deletion cassettes in the targeted xyr1 locus and for the disappearance of the intact xyr1 gene. Positive tested clones were denoted as UV18 #100f Δclr2 Δxyr1 #β and were selected for further characterization.

Figure 4:
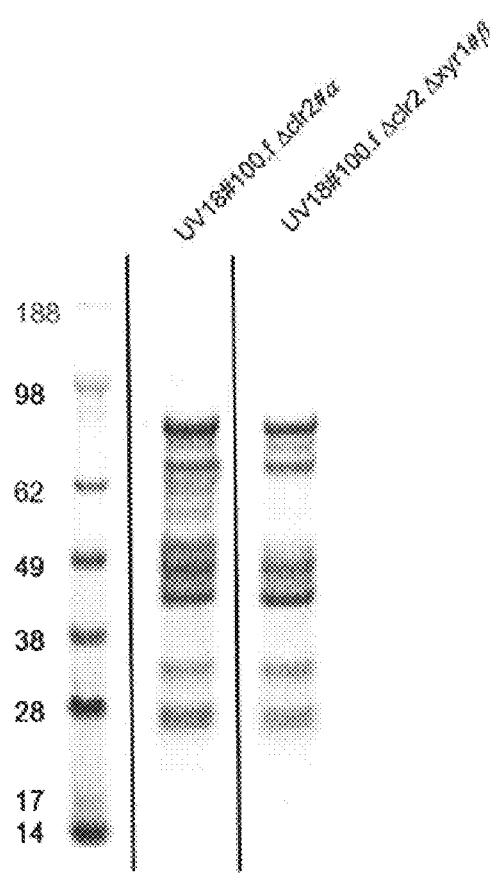
FIG. 4 shows an SDS-PAGE analysis of supernatant from fermentation samples of the clr2 deletion strains UV18 #100.f Δclr2 #α and UV18 #100.f Dclr2 Dxyr1 #β. Equal volumes of cell free supernatant were loaded.

The SDS-PAGE analysis (FIG. 4) of the expressed protein in the supernatant of the UV18 #100f Δclr2 Δxyr1 #p strain showed clearly a further reduction of the extracellular proteins compared to the parental strain UV18 #100f Δclr2 #α after 3 days of cultivation in a stirred reactor according to example 8.

Example 11

Analysis of Protein Expression for Phytase Producing *M. thermophila* Strains

Strain UV18 #100.f Δclr2 #α was transformed with plasmid pMT873 (SEQ ID No: 33) which was generated as described in Example 3. Transformants tested positive for the co-integration of the phytase expression cassette (UV18 #100.f Δclr2 #α phyA) were fermented in a stirred tank reactor for 3 days according to example 8. Cell free supernatants were harvested at the end of cultivation and equal volumes of supernatants were analyzed by SDS-PAGE. The gel was stained with Coomassie Blue.

Figure 5:
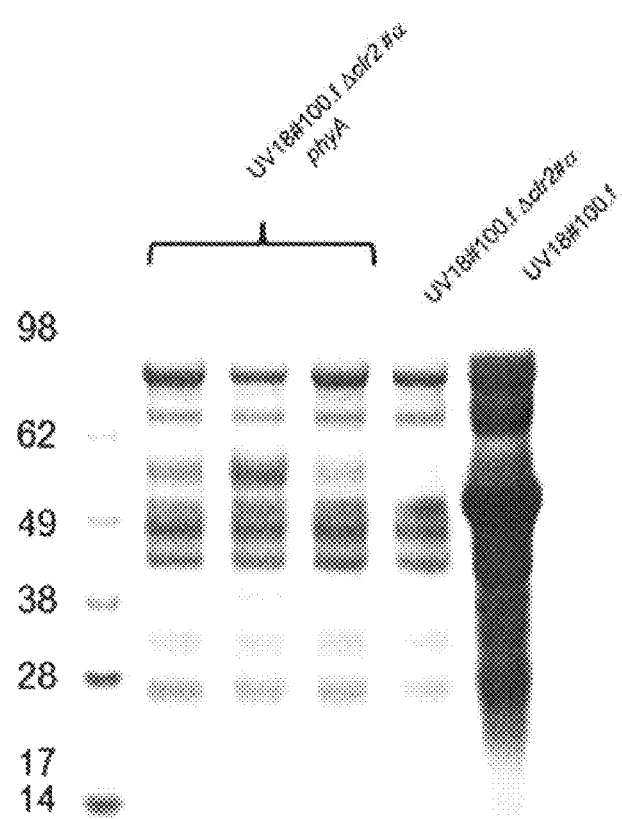
FIG. 5 shows an SDS-PAGE analysis of supernatant from fermentation samples of phytase phyA expressing transformants of the clr2 deletion strain UV18 #100.f Δclr2 #α as well as the parental strains UV18 #100.f Δclr2 #α and UV18 #100.f. Equal volumes of cell free supernatant were loaded.

Compared to the control UV18 #100.f Δclr2 #α the SDS-PAGE analysis of the supernatant of UV18 #100.f Δclr2 #α phyA (FIG. 5) showed clearly visible bands of the phytase protein which run due to glycosylation at approx. 55 kDa. The intensity of the band is different for the individual transformants due to different copy number and integration loci of the randomly integrated phytase expression cassettes. The parental *M. thermophila* strain UV18 #100.f cultivated under the same conditions produced so much secreted protein, that the detection of the same amount of phytase in an SDS-PAGE would have been impossible.

The invention claimed is:

1. A method of producing a recombinant polypeptide in a filamentous fungus which is genetically modified by disruption of the clr2 gene to decrease or eliminate the activity of cellulase regulator 2 (CLR2) and disruption of the xyr1 gene to decrease or eliminate the activity of xylanase regulator 1 (XYR1) compared to the corresponding filamentous fungus not having the genetic modification which is cultured under the same conditions as the genetically modified filamentous fungus, wherein the filamentous fungus is *Myceliophthora thermophila*, wherein the filamentous fungus genetically modified to decrease or eliminate the activity of cellulase regulator 2 (CLR2) has been further genetically modified to express said recombinant polypeptide, wherein the recombinant polypeptide is expressed under the control of a promoter which is not activatable by CLR2, wherein the recombinant polypeptide is a polypeptide which is heterologous to the filamentous fungus, wherein the filamentous fungus genetically modified to decrease or eliminate the activity of cellulose regulator 2 (CLR2) has further been genetically modified by disruption of the alp1 gene to decrease or eliminate the activity of alkaline protease 1 (ALP1), said method comprising:
(i) growing said genetically modified filamentous fungus in a culture medium which does not contain cellulose or any derivative thereof which is capable of inducing CLR2 activity; and
(ii) isolating the recombinant polypeptide from the culture medium.

2. The method of claim 1, wherein the recombinant polypeptide is a hydrolase.

3. The method of claim 1, wherein said genetically modified filamentous fungus is capable of accumulating the recombinant polypeptide in a higher purity than the corresponding filamentous fungus not having the genetic modification which is cultured under the same conditions as the genetically modified filamentous fungus.

4. The method of claim 1, wherein said clr2 gene comprises a nucleic acid sequence selected from the group consisting of:
(a) the nucleic acid sequence of nucleotides 3001 to 5570 of SEQ ID NO: 2 or the sequence of SEQ ID NO: 2 or a part of said nucleic acid sequence encoding a part of the polypeptide of SEQ ID NO: 3 required for CLR2 activity;
(b) a nucleic acid sequence encoding the polypeptide of SEQ ID NO: 3 or a part of said polypeptide having the same CLR2 activity as the polypeptide of SEQ ID NO: 3; and
(c) a nucleic acid sequence encoding a polypeptide having CLR2 activity and having at least 70% sequence identity to the nucleic acid sequence of nucleotides 3001 to 5570 of SEQ ID NO: 2 or the sequence of SEQ ID NO: 2.

5. The method of claim 1, wherein said filamentous fungus which is genetically modified to decrease or eliminate the activity of cellulose regulator 2 (CLR2) further comprises at least one additional genetic modification.

6. The method of claim 5, wherein the at least one additional genetic modification decreases or eliminates the activity of a transcription factor.

7. The method of claim 1, wherein the xyr1 gene is deleted.

* * * * *